United States Patent [19]

Sugai et al.

[11] Patent Number: 5,424,279
[45] Date of Patent: Jun. 13, 1995

[54] PYRAZOLE DERIVATIVES HAVING HERBICIDAL ACTIVITY AND THEIR USE

[75] Inventors: Soji Sugai; Shigeru Mio; Toyokuni Honma; Takashi Sakamoto, all of Shiga, Japan

[73] Assignee: Sankyo Company, Limited, Tokyo, Japan

[21] Appl. No.: 270,401

[22] Filed: Jul. 5, 1994

Related U.S. Application Data

[63] Continuation of Ser. No. 985,361, Dec. 2, 1992, abandoned, which is a continuation of Ser. No. 808,208, Dec. 13, 1991, abandoned.

[30] Foreign Application Priority Data

Dec. 17, 1990 [JP] Japan .................. 2-402675
Mar. 6, 1991 [JP] Japan .................. 3-39784
Aug. 30, 1991 [JP] Japan .................. 3-219620

[51] Int. Cl.$^6$ .................. A01N 43/56; C07D 231/20
[52] U.S. Cl. .................. 504/282; 548/366.7; 548/369.7
[58] Field of Search .................. 548/369.7; 504/282

[56] References Cited

U.S. PATENT DOCUMENTS

| | | | |
|---|---|---|---|
| 4,008,249 | 2/1977 | Fischer et al. | 548/377 |
| 4,298,749 | 11/1981 | Plath et al. | 548/377 |
| 4,316,040 | 2/1982 | Plath et al. | 548/377 |
| 4,331,678 | 5/1982 | De'Auth et al. | 548/375 |

FOREIGN PATENT DOCUMENTS

0007990 2/1980 European Pat. Off. .
0014810 9/1980 European Pat. Off. .
1488285 10/1977 United Kingdom .

OTHER PUBLICATIONS

Chemical Abstracts, vol. 106, No. 9, Mar. 2, 1987, Columbus, Ohio, USA H. Braeuniger et al. "Reactions of 2-cyano-3-(2-cyano-(2-cyano-ethylthio)-3-methyl-thioacrylic acid esters" p. 72, col. 2, abstract No. 61 342s & Wiss. Z. Wilhelm-Pieck-Univ. Rostock, Naturwiss. Reihe 1984, 33(8), 67-74 (Ger.).

Chemical Abstracts, vol. 106, No. 9, Mar. 2, 1987, Columbus, Ohio, USA K. Peseke "Synthesis of substituted pyrazolo (2,3-a) (1,3,5)triazines" p. 581, col. 2, abstract No. 97 217a & Pharmazie 1975, 30(4), 258-9 (Ger.).

Chemical Abstracts, vol. 82, No. 7, Feb. 17, 1975, Columbus, Ohio, USA H. Werbs et al. "Reactions of 4-ethoxycarbonyl-3-amino-2-aminocarbonyl-5-methyl-thiopyrazole with isocyanates and isothiocyanates" p. 426, col. 2, abstract No. 43 249y & Pharmazie 1974, 29(10-11), 687-9 (Ger.).

*Primary Examiner*—Robert W. Ramsuer
*Attorney, Agent, or Firm*—Frishauf, Holtz, Goodman & Woodward

[57] ABSTRACT

Compounds of formula (I):

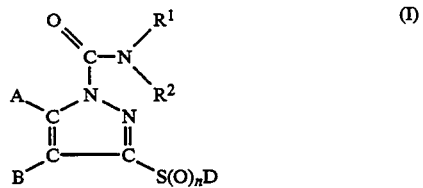

(in which: $R^1$ and $R^2$ are each hydrogen, optionally substituted alkyl, optionally substituted alkenyl, alkynyl, alkoxy, aryl or pyridyl, or $R^1$ and $R^2$ together represent alkylene; A and B are each hydrogen, halogen, optionally substituted alkyl, optionally substituted alkenyl, optionally substituted alkoxy, alkylthio, alkylsulfonyl, dialkylsulfamoyl, aliphatic carboxylic acyl, carboxy, —CONR$^a$R$^b$ where R$^a$ and R$^b$ are each hydrogen or alkyl, formyl or cyano groups; D represents optionally substituted phenyl, benzyl, pyridyl or pyrimidinyl; and n is 0, 1 or 2; and salts and esters thereof) have valuable herbicidal properties, and, since they are totally innocuous to rice plants, are especially useful for the treatment of paddy fields.

31 Claims, No Drawings

PYRAZOLE DERIVATIVES HAVING HERBICIDAL ACTIVITY AND THEIR USE

This application is a Continuation of application Ser. No. 07/985,361, filed Dec. 2, 1992, (abandoned) which is a continuation of Ser. No. 07/808,208 filed Dec. 13, 1991 (abandoned).

BACKGROUND TO THE INVENTION

The present invention relates to a series of new pyrazole derivatives having valuable herbicidal activity and provides methods and compositions using these compounds, as well as processes for preparing them.

The purpose of herbicides in agriculture and horticulture is to kill unwanted plants (weeds), whilst leaving untouched plants which are wanted (crops). A herbicide is of restricted practical use if it is lethal to all plants. Accordingly, for maximum practical effect, it is desirable to target not only specific weeds, but also the desired crop, to ensure that the herbicide is lethal to the weeds and inactive against the crops. We have now discovered a series of pyrazole derivatives which have this effect.

A number of pyrazole derivatives have previously been described and said to have herbicidal activity. For example, UK Patent Specification No. 1 488 285 and U.S. Pat. No. 4,008,249 disclose compounds of this general type which are said to be useful as herbicides, whilst European Patent Specification No. 14 810 discloses such compounds for the protection of plants from "pests", primarily insects. However, the closest prior art to the present invention is believed to be European Patent Specification No. 7 990 (equivalent to U.S. Pat. Nos. 4,316,040 and 4,298,749), which discloses a wide class of compounds (embracing some of those of the present invention) which are said to have herbicidal activity.

In accordance with the present invention, we have now discovered that a limited class of pyrazole compounds has excellent herbicidal activity against a wide range of weeds (better than that of the prior art) whilst exhibiting no harmful effects on crop plants, notably rice.

BRIEF SUMMARY OF INVENTION

It is, therefore, an object of the present invention to provide a series of new pyrazole derivatives having useful herbicidal activity.

It is a further object to provide such pyrazole derivatives, some of which have activities which are very substantially better than those of the prior art.

Other objects and advantages of the invention will become apparent as the description proceeds.

The compounds of the present invention are those compounds of formula (I):

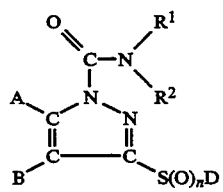

(I)

in which:

$R^1$ and $R^2$ are independently selected from the group consisting of:
hydrogen atoms,
unsubstituted alkyl groups which have from 1 to 6 carbon atoms,
substituted alkyl groups which have from 1 to 6 carbon atoms and which are substituted by at least one substituent selected from the group consisting of substituents (a), defined below,
unsubstituted alkenyl groups having from 2 to 6 carbon atoms,
substituted alkenyl groups which have from 2 to 6 carbon atoms and which are substituted by at least one substituent selected from the group consisting of halogen atoms,
alkynyl groups which have from 2 to 6 carbon atoms,
alkoxy groups which have from 1 to 6 carbon atoms,
carbocyclic aryl groups which have from 6 to 14 ring carbon atoms and which are unsubstituted or are substituted by at least one substituent selected from the group consisting of substituents (b), defined below, and
pyridyl groups which are unsubstituted or are substituted by at least one substituent selected from the group consisting of substituents (b), defined below,
or $R^1$ and $R^2$ together represent an alkylene group having from 4 to 7 carbon atoms;

A and B are independently selected from the group consisting of:
hydrogen atoms,
halogen atoms,
unsubstituted alkyl groups which have from 1 to 6 carbon atoms,
substituted alkyl groups which have from 1 to 6 carbon atoms and which are substituted by at least one substituent selected from the group consisting of substituents (c), defined below,
unsubstituted alkenyl groups which have from 2 to 6 carbon atoms,
substituted alkenyl groups which have from 2 to 6 carbon atoms and which are substituted by at least one substituent selected from the group consisting of halogen atoms,
alkoxy groups which have from 1 to 6 carbon atoms,
substituted alkoxy groups which have from 1 to 6 carbon atoms and which are substituted by at least one substituent selected from the group consisting of substituents (a), defined below,
alkylthio groups which have from 1 to 6 carbon atoms,
alkylsulfonyl groups which have from 1 to 6 carbon atoms,
dialkylsulfamoyl groups in which each alkyl part is independently selected from the group consisting of alkyl groups having from 1 to 4 carbon atoms,
aliphatic carboxylic acyl groups which have from 2 to 7 carbon atoms and which are unsubstituted or are substituted by at least one substituent selected from the group consisting of substituents (a), defined below,
carboxy groups,
groups of formula —$CONR^aR^b$, in which $R^a$ and $R^b$ are independently selected from the group consisting of hydrogen atoms and alkyl groups having from 1 to 4 carbon atoms,
formyl groups, and
cyano groups;

D represents a group of formula (II), (III) or (IV):

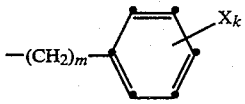  (II)

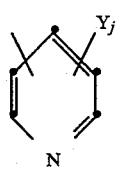  (III)

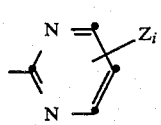  (IV)

in which:

X, Y and Z are independently selected from the group consisting of
halogen atoms,
unsubstituted alkyl groups which have from 1 to 6 carbon atoms,
substituted alkyl groups which have from 1 to 6 carbon atoms and which are substituted by at least one substituent selected from the group consisting of substituents (a), defined below,
alkoxy groups which have from 1 to 6 carbon atoms,
substituted alkoxy groups which have from 1 to 6 carbon atoms and which are substituted by at least one substituent selected from the group consisting of halogen atoms,
alkylthio groups which have from 1 to 6 carbon atoms,
substituted alkylthio groups which have from 1 to 6 carbon atoms and which are substituted by at least one substituent selected from the group consisting of halogen atoms,
alkylsulfonyl groups which have from 1 to 6 carbon atoms,
substituted alkylsulfonyl groups which have from 1 to 6 carbon atoms and which are substituted by at least one substituent selected from the group consisting of halogen atoms,
aryloxy groups in which the aryl part is a carbocyclic aryl group which has from 6 to 14 ring carbon atoms and is unsubstituted or is substituted by at least one substituent selected from the group consisting of substituents (b), defined below,
aralkyl groups in which the alkyl part has from 1 to 4 carbon atoms and the aryl part is a carbocyclic aryl group which has from 6 to 14 ring carbon atoms and which is unsubstituted or are substituted by at least one substituent selected from the group consisting of substituents (b), defined below,
carboxy groups,
nitro groups, and
cyano groups;

$m$ is 0 or 1;
$k$ is 0 or an integer from 1 to 5, and, where $k$ is an integer from 2 to 5, the groups and atoms represented by X may be the same or different;
$j$ is 0 or an integer from 1 to 4, and, where $j$ is an integer from 2 to 4, the groups and atoms represented by Y may be the same or different;
$i$ is 0 or an integer from 1 to 3, and, where $i$ is an integer from 2 to 3, the groups and atoms represented by Z may be the same or different;
$n$ is 0, 1 or 2;

substituents (a) are selected from the group consisting of halogen atoms and alkoxy groups having from 1 to 6 carbon atoms;
substituents (b) are selected from the group consisting of halogen atoms, alkyl groups having from 1 to 6 carbon atoms and alkoxy groups having from 1 to 6 carbon atoms; and
substituents (c) are selected from the group consisting of:
halogen atoms,
hydroxy groups,
alkoxy groups which have from 1 to 6 carbon atoms,
aliphatic acyl groups having from 2 to 7 carbon atoms,
halogenated aliphatic acyl groups having from 2 to 7 carbon atoms,
aromatic acyl groups in which the aryl part is a carbocyclic aryl group which has from 6 to 14 ring carbon atoms and is unsubstituted or is substituted by at least one substituent selected from the group consisting of substituents (b), defined above,
alkoxycarbonyl groups in which the alkoxy part has from 1 to 4 carbon atoms,
alkenyloxycarbonyl groups in which the alkenyl part has from 2 to 4 carbon atoms, and
aralkyloxycarbonyl groups in which the alkyl part has from 1 to 4 carbon atoms and the aryl part is a carbocyclic aryl group which has from 6 to 14 ring carbon atoms and which is unsubstituted or are substituted by at least one substituent selected from the group consisting of substituents (b), defined above;
and salts and esters thereof.

The invention also provides a herbicidal composition comprising an effective amount of a herbicidal agent in admixture with an agriculturally or horticulturally acceptable carrier or diluent, wherein the herbicidal agent is at least one compound selected from the group consisting of compounds of formula (I) and salts and esters thereof.

The invention still further provides a method of destroying weeds by administering a herbicidal agent to a locus including said weeds, wherein the herbicidal agent is at least one compound selected from the group consisting of compounds of formula (I) and salts and esters thereof.

The invention also provides processes for preparing the compounds of the present invention which are described in more detail hereafter.

DETAILED DESCRIPTION OF INVENTION

In the compounds of the present invention, where $R^1$, $R^2$, X, Y or Z represents an alkyl group having from 1 to 6 carbon atoms, this may be a straight or branched chain group having from 1 to 6, preferably from 1 to 5, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl, butyl and isobutyl groups, and most preferably the methyl, ethyl and propyl groups. In the case of Y and Z, we particularly prefer those alkyl groups having 1 or 2 carbon atoms, the methyl and ethyl groups, and most prefer the methyl group.

In the case of A and B, where they represent an alkyl group having from 1 to 6 carbon atoms, this may be a straight or branched chain group, for example the methyl, ethyl, propyl, isopropyl, butyl, isobutyl, sec-butyl, t-butyl, pentyl, isopentyl, 2-methylbutyl, neopentyl and 1-ethylpropyl groups, preferably a straight or branched chain alkyl group having from 1 to 3 carbon atoms, more preferably 1 or 2 carbon atoms.

Such alkyl groups included in the definitions of $R^1$, $R^2$, A, B, X, Y or Z may be unsubstituted or they may be substituted by one or more substituents, selected, in the case of $R^1$, $R^2$, X, Y and Z, from the group consisting of substituents (a), or, in the case of A and B, from the group consisting of substituents (c), both of which are as defined above, and examples of which include: halogen atoms, such as the fluorine, chlorine, bromine and iodine atoms, preferably the fluorine, chlorine or bromine atoms, and most preferably the fluorine or chlorine atoms; alkoxy groups, which may be straight or branched chain groups, having from 1 to 6, preferably from 1 to 4, carbon atoms, such as the methoxy, ethoxy, propoxy, isopropoxy, butoxy, isobutoxy, sec-butoxy and t-butoxy groups, of which we prefer those straight or branched chain alkoxy groups having from 1 to 3 carbon atoms, most preferably the methoxy group; and, in the case of substituents (c), hydroxy groups.

The aliphatic acyl groups, halogenated aliphatic acyl groups, aromatic acyl groups, alkoxycarbonyl groups, alkenyloxycarbonyl groups, and aralkyloxycarbonyl groups which are included in substituents (c) are all as exemplified hereafter in relation to the groups which may be represented by $R^8$.

Where these alkyl groups are substituted, there is no specific limitation upon the number of substituents, except such as may be imposed by the number of substitutable positions or possibly by steric constraints. However, in general, we prefer from 1 to 3 substituents. The same applies likewise to other substituted groups referred to herein where the number of substituents is not otherwise specified.

Where $R^1$, $R^2$, A or B represents an alkenyl group, this may be a straight or branched chain group having from 2 to 6, preferably from 3 to 6, more preferably from 3 to 5 and most preferably 3 or 4, carbon atoms, and examples include the vinyl, allyl, 1-propenyl, isopropenyl, 1-butenyl, 2-butenyl, 3-butenyl, 1-methyl-2-propenyl, 2-methyl-2-propenyl, 1-pentenyl, 2-pentenyl, 3-pentenyl, 4-pentenyl, 2-ethyl-2-propenyl, 1-methyl-2-butenyl, 2-methyl-2-butenyl, 1-methyl-3-butenyl, 2-methyl-3-butenyl, 1-hexenyl, 1-ethyl-2-butenyl, 1-ethyl-3-butenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 2-hexenyl, 3-hexenyl, 4-hexenyl and 5-hexenyl groups, of which the vinyl, allyl, methallyl, 1-propenyl, isopropenyl and butenyl groups are preferred, the allyl (2-propenyl) group being most preferred.

Such groups may be unsubstituted or they may be substituted by one or more halogen atoms, for example as exemplified in relation to substituents (a) and (c). Where they are substituted, there is no specific limitation upon the number of substituents, except such as may be imposed by the number of substitutable positions or possibly by steric constraints. However, in general, we prefer from 1 to 3 substituents. An example of a preferred substituted group is the 2-chloroallyl group.

Where $R^1$ or $R^2$ represents an alkynyl group having from 2 to 6 carbon atoms, this may be a straight or branched chain group having from 2 to 6, preferably from 3 to 6, more preferably from 3 to 5 and most preferably 3 or 4, carbon atoms, and examples include the ethynyl, propargyl (2-propynyl), 1-propynyl, 1-butynyl, 2-butynyl, 3-butynyl, 1-methyl-2-propynyl, 2-methyl-2-propynyl, 1-pentynyl, 2-pentynyl, 3-pentynyl, 4-pentynyl, 2-ethyl-2-propynyl, 1-methyl-2-butynyl, 2-methyl-2-butynyl, 1-ethyl-2-butynyl, 1-methyl-3-butynyl, 2-methyl-3-butynyl, 1-ethyl-3-butynyl, 2-hexynyl, 3-hexynyl, 4-hexynyl, 5-hexynyl 1-methyl-2-pentynyl, 2-methyl-2-pentynyl, 1-methyl-3-pentynyl, 2-methyl-3-pentynyl, 1-methyl-4-pentynyl and 2-methyl-4-pentynyl groups, of which the propynyl and butynyl groups are preferred, the propargyl and 2-butynyl groups being most preferred.

Where $R^1$, $R^2$, A, B, X, Y or Z represents an alkoxy group having from 1 to 6 carbon atoms, this may be a straight or branched chain group having from 1 to 6, preferably from 1 to 4, carbon atoms, and examples include the methoxy, ethoxy, propoxy, isopropoxy, butoxy, isobutoxy, sec-butoxy, t-butoxy, pentyloxy, isopentyloxy, 2-methylbutyloxy, neopentyloxy, hexyloxy, 4-methylpentyloxy, 3-methylpentyloxy, 2-methylpentyloxy, 3,3-dimethylbutyloxy, 2,2-dimethylbutyloxy, 1,1-dimethylbutyloxy, 1,2-dimethylbutyloxy, 1,3-dimethylbutyloxy and 2,3-dimethylbutyloxy groups, of which those straight or branched chain alkoxy groups containing 1 to 4 carbon atoms are preferred, the methoxy and isopropoxy groups being most preferred. In the case of A and B, where they represent one of these groups, the group may be unsubstituted or it may be substituted by one or more (preferably from 1 to 3) substituents selected from the group consisting of substituents (a), defined and exemplified above. In the case of X, Y and Z, where they represent one of these groups, the group may be unsubstituted or it may be substituted by one or more (preferably from 1 to 3) halogen substituents, e.g. as defined and exemplified above.

Where $R^1$ or $R^2$ represents a carbocyclic aryl group, this has from 6 to 14, preferably from 6 to 10, ring carbon atoms and is unsubstituted or is substituted by at least one substituent selected from the group consisting of substituents (b), defined and exemplified above. Examples of the unsubstituted aryl groups are those aromatic hydrocarbon groups containing from 6 to 14 carbon atoms, for example the phenyl, indenyl, naphthyl, phenanthrenyl and anthracenyl groups, preferably the phenyl or naphthyl groups (1- or 2-naphthyl), and more preferably the phenyl group. Such groups may also, if desired be substituted by one or more of substituents (b), defined above. Examples of these substituents include the halogen atoms and alkoxy groups exemplified in relation to substituents (a) and (c), and alkyl groups having from 1 to 6 carbon atoms, such as the methyl, ethyl, propyl, isopropyl, butyl, isobutyl, sec-butyl, t-butyl, pentyl, isopentyl, 2-methylbutyl, neopentyl and 1-ethylpropyl groups, preferably a straight or branched chain alkyl group having from 1 to 3 carbon atoms, more preferably 1 or 2 carbon atoms. There is no specific limitation on the number of substituents, except such as may be imposed by the number of substitutable positions (e.g. 5 in the case of the phenyl group or 7 in the case of the naphthyl group) or possibly by steric constraints. However, in general, from 1 to 3 substituents are preferred. If there are two or more substituents, these may be the same or different. Specific examples of preferred substituted groups include the 2-chlorophenyl, 3-chlorophenyl, 4-chlorophenyl, 2,4-dichlorophenyl, 2,5-dichlorophenyl, 2,4,5-trichlorophenyl, 2-methylphenyl, 3-methylphenyl, 4-methylphenyl, 2,4-dichloro-3-methylphenyl, 4-methoxyphenyl, 3-methoxyphenyl, 2-methoxyphenyl and 3-chloro-4-methoxyphenyl groups.

Where $R^1$ or $R^2$ represents a pyridyl group, this may be the 2-pyridyl, 3-pyridyl or 4-pyridyl group and may be substituted or unsubstituted. If substituted, the substituents are selected from the group consisting of substituents (b), as defined and exemplified above. There is no specific limitation on the number of substituents, except such as may be imposed by the number of substitutable positions (i.e. 4) or possibly by steric constraints. However, in general, from 1 to 3 substituents are preferred. If there are two or more substituents, these may be the same or different. Specific examples of preferred substituted groups include the 3,5-dichloro-2-pyridyl, 4-chloro-5-methyl-2-pyridyl, 4-methoxy-2-pyridyl and 5-chloro-2-pyridyl groups.

Alternatively, $R^1$ and $R^2$ together may represent a straight or branched chain alkylene group having from 4 to 7 carbon atoms, so as to form with the nitrogen atom to which they are attached a nitrogen-containing heterocyclic ring having from 5 to 8 ring atoms and optionally having fewer ring atoms but substituted by one or more lower alkyl groups. Examples of such alkylene groups include the tetramethylene, 1-methyltetramethylene, 2-methyltetramethylene, 3-methyltetramethylene, pentamethylene, 1,4-dimethylpentamethylene, hexamethylene, 1-methylhexamethylene and heptamethylene groups, of which we prefer the straight chain alkylene groups containing 4 or 5 carbon atoms, most preferably the tetramethylene group.

Where A, B, X, Y or Z represents an alkylthio group, this has from 1 to 6 carbon atoms and may be a straight or branched chain group. Examples of such groups include the methylthio, ethylthio, propylthio, isopropylthio, butylthio, isobutylthio, sec-butylthio, t-butylthio, pentylthio, isopentylthio, 2-methylbutylthio, neopentylthio, 1-ethylpropylthio, hexylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio and 2-ethylbutylthio groups, of which we prefer the straight and branched chain alkylthio groups containing from 1 to 3 carbon atoms, and most prefer the methylthio or ethylthio group.

Where A, B, X, Y or Z represents an alkylsulfonyl group, this has from 1 to 6 carbon atoms and may be a straight or branched chain group. Examples of such groups include the methylsulfonyl, ethylsulfonyl, propylsulfonyl, isopropylsulfonyl, butylsulfonyl, isobutylsulfonyl, sec-butylsulfonyl, t-butylsulfonyl, pentylsulfonyl, isopentylsulfonyl, 2-methylbutylsulfonyl, neopentylsulfonyl, 1-ethylpropylsulfonyl, hexylsulfonyl, 4-methylpentylsulfonyl, 3-methylpentylsulfonyl, 2-methylpentylsulfonyl, 1-methylpentylsulfonyl, 3,3-dimethylbutylsulfonyl, 2,2-dimethylbutylsulfonyl, 1,1-dimethylbutylsulfonyl, 1,2-dimethylbutylsulfonyl, 1,3-dimethylbutylsulfonyl, 2,3-dimethylbutylsulfonyl and 2-ethylbutylsulfonyl groups, of which we prefer the straight or branched chain alkylsulfonyl group having from 1 to 3 carbon atoms, and most prefer the methylsulfonyl or ethylsulfonyl group.

In the case of X, Y and Z, the above alkylthio and alkylsulfonyl groups may be unsubstituted or they may have one or more (preferably from 1 to 3) halogen substituents, e.g. as exemplified above, preferably fluorine atoms. Examples of such substituted groups include the trifluoromethylthio and trifluoromethylsulfonyl groups.

Where A or B represents a dialkylsulfamoyl group, this is a group of formula $-SO_2NR^cR^d$, in which $R^c$ and $R^d$, which may be the same or different (although they are preferably the same), each represents an alkyl group having from 1 to 4 carbon atoms. Examples of such groups include the dimethylsulfamoyl, diethylsulfamoyl, N-ethyl-N-propylsulfamoyl, dipropylsulfamoyl, diisopropylsulfamoyl, N-methylpropyl-N-sulfamoyl and N-methyl-N-butylsulfamoyl groups, of which we prefer those groups in which $R^c$ and $R^d$ both represent alkyl groups having from 1 to 3 carbon atoms, and most prefer the dimethylsulfamoyl group.

Where A or B represents an aliphatic carboxylic acyl group, this has, in total, from 2 to 7 carbon atoms and may be a saturated or unsaturated (referring to carbon-carbon bonds) group; it is preferably an alkylcarbonyl group, in which the alkyl part has from 1 to 6 carbon atoms, more preferably from 1 to 4 carbon atoms. Examples of such groups include the acetyl, propionyl, butyryl, isobutyryl, valeryl, isovaleryl, 2-methylbutyryl and pivaloyl groups, of which we prefer those groups having, in total, from 1 to 3 carbon atoms, and most prefer the acetyl group.

Where A, B, X, Y or Z represents a carboxy group, the resulting compound can form esters. There is, in principle, no limitation upon the nature of such esters, provided that, where the compound as such is to be used in agricultural or horticultural treatment, the ester group does not increase the toxicity of the compounds to useful plants or does not do so to an unacceptable extent. Examples of preferred esters include the lower alkyl esters having from 1 to 6, preferably from 1 to 4 carbon atoms, for example, the methyl, ethyl, propyl, isopropyl, butyl, isobutyl, sec-butyl and t-butyl esters, of which we prefer alkyl esters having from 1 to 3 carbon atoms, and most prefer the ethyl esters. However, as is well known in the art, a wide range of esters may be formed using a variety of ester groups which form part of the common general knowledge.

Where A or B represents a group of formula $-CONR^aR^b$, $R^a$ and $R^b$, which may be the same or different, each represents a hydrogen atom or an alkyl group having from 1 to 4 carbon atoms, preferably an alkyl group. These groups are the carbamoyl, alkylcarbamoyl and dialkylcarbamoyl groups, for example the methylcarbamoyl, ethylcarbamoyl, propylcarbamoyl, butylcarbamoyl, dimethylcarbamoyl, diethylcarbamoyl, N-ethyl-N-propylcarbamoyl, dipropylcarbamoyl, diisopropylcarbamoyl, N-methyl-N-propylcarbamoyl and N-methyl-N-butylcarbamoyl groups, of which we prefer the dialkylcarbamoyl groups, especially those having two alkyl groups, which may be the same or different, and each have from 1 to 3 carbon atoms, and most prefer the dimethylcarbamoyl group.

Where X, Y or Z represents an aryloxy group, the aryl part of this may be as defined and exemplified above in relation to the aryl groups which may be represented by $R^1$ or $R^2$, and examples of the unsubstituted groups include the phenoxy, indenyloxy, naphthyloxy (1- or 2-naphthyloxy), phenanthrenyloxy and anthracenyloxy groups, of which we prefer the phenoxy and naphthyloxy groups, and most prefer the phenoxy group. Examples of substituted groups include the aryloxy equivalents of the substituted aryl groups exemplified above in relation to the aryl groups which may be represented by $R^1$ or $R^2$.

Where X, Y or Z represents an aralkyl group, the alkyl part of this group has from 1 to 4 carbon atoms, and the aryl part may be as defined and exemplified above in relation to the aryl groups which may be represented by $R^1$ or $R^2$. Examples of the unsubstituted groups include the benzyl, 2-phenylethyl, 1-phenylethyl, 3-phenylpropyl, 2-phenylpropyl, 1-phenylpropyl, 4-phenylbutyl, 3-phenylbutyl, 2-phenylbutyl, 1-phenylbutyl, α-naphthylmethyl and β-naphthylmethyl groups, of which we prefer those groups in which the alkyl part has from 1 to 3 carbon atoms and the aryl part is a phenyl or naphthyl (preferably phenyl) group, and most prefer the benzyl group, or substituted equivalents as exemplified above in relation to the aryl groups which may be represented by $R^1$ or $R^2$.

When D represents a group of formula (II) and m is 1, this is an optionally substituted benzyl group; and, where m is 0, this is an optionally substituted phenyl group. These groups may be substituted by the groups or atoms represented by X at any free position, for example, at the 2-, 3-, 4-, 2,3-, 2,4-, 2,5-, 2,6-, 3,4-, 3,5-, 2,4,6-, 3,4,6-, 3,4,5-, 2,3,5-, 2,3,4-, 2,3,5,6-, 2,3,4,6- or 2,3,4,5,6- positions. k may be 0 or an integer from 1 to 5, but is preferably 0 or an integer from 1 to 3. Where k is greater than 1, the groups or atoms represented by X may be the same or different.

Where D represents a group of formula (III), this is an optionally substituted pyridyl group, which may be attached to the remainder of the molecule via any of its carbon atoms, i.e. it may be a 2-pyridyl, 3-pyridyl or 4-pyridyl group, preferably a 2-pyridyl or 4-pyridyl group. Where j is an integer of from 1 to 4, the group is substituted by one or more of the groups and atoms defined by Y, and may be substituted at any free position, for example the 3-, 5-, 6- or 3,5- positions. j may be 0 or an integer from 1 to 4, but is preferably 0, 1 or 2. Where j is greater than 1, the groups or atoms represented by Y may be the same or different.

Where D represents a group of formula (IV), this is an optionally substituted pyrimidin-2-yl group. Where i is an integer of from 1 to 3, the group is substituted by one or more of the groups and atoms defined by Z, and may be substituted at any free position, for example the 4-, 5- or 4,6- positions. i may be 0 or an integer from 1 to 3, but is preferably 0, 1 or 2. Where i is greater than 1, the groups or atoms represented by Z may be the same or different.

Of the compounds of the present invention, we prefer those in which each of $R^1$ and $R^2$, which may be the same or different, represents:

an alkyl group having from 1 to 6 carbon atoms;
an alkenyl group having from 3 to 6 carbon atoms;
an alkynyl group having from 3 to 6 carbon atoms; or
an aryl group which has from 6 to 10 carbon atoms and is unsubstituted or has at least one substituent selected from the group consisting of substituents (b), defined above;
or $R^1$ and $R^2$ together represent an alkylene group having from 4 to 6 carbon atoms.

More preferably, each of $R^1$ and $R^2$, which may be the same or different, represents:
an alkyl group having from 1 to 4 carbon atoms;
an alkenyl group having 3 or 4 carbon atoms; or
an alkynyl group having 3 or 4 carbon atoms;
or $R^1$ and $R^2$ together represent an alkylene group having from 4 to 6 carbon atoms.

Most preferably, each of $R^1$ and $R^2$, which may be the same or different, represents:
an alkyl group having from 1 to 4 carbon atoms;
an alkenyl group having 3 or 4 carbon atoms; or
or $R^1$ and $R^2$ together represent an alkylene group having from 4 to 6 carbon atoms.

We also particularly prefer those compounds of the present invention in which A represents:
a hydrogen atom;
a halogen atom;
an alkyl group which has from 1 to 6 carbon atoms and which is unsubstituted or is substituted by at least one substituent selected from the group consisting of substituents (c), defined above;
an alkenyl group having from 3 to 6 carbon atoms; or
a cyano group.

More preferably, A represents:
a hydrogen atom;
a halogen atom;
an alkyl group which has from 1 to 6 carbon atoms and which is unsubstituted or is substituted by from 1 to 3 substituents selected from the group consisting of substituents (a), defined above; or
a cyano group.

Most preferably, A represents a hydrogen atom, a halogen atom or a cyano group.

We also particularly prefer those compounds of the present invention in which B represents:
a hydrogen atom;
a halogen atom;
an alkyl group which has from 1 to 6 carbon atoms and which is unsubstituted or is substituted by at least one substituent selected from the group consisting of substituents (c), defined above;
an alkoxy group which has from 1 to 6 carbon atoms; or
a cyano group.

More preferably, B represents:
a hydrogen atom;
a halogen atom;
an alkyl group which has from 1 to 6 carbon atoms and which is unsubstituted or is substituted by at least one substituent selected from the group consisting of substituents (c), defined above; or
a cyano group.

Most preferably, B represents a hydrogen atom, a halogen atom or a cyano group, in particular a fluorine atom.

Of the groups of formulae (II), (III) and (IV), we prefer that D should represent a group of formula (II) or (III), more preferably a group of formula (II) in which m is 0 or a group of formula (III), and most preferably a group of formula (II) in which m is 0.

In the compounds of formula (I), n can be: 0, in which case the compound is a thio compound; 1, in which case the compound is a sulfinyl compound; or 2, in which case the compound is a sulfonyl compound. We prefer that n should be 0 or 2, most preferably 2.

In the case of the compounds of formula (I) in which D represents a group of formula (II), we prefer that X should represent:
  a halogen atom;
  an alkyl group which has from 1 to 6 carbon atoms and which is unsubstituted or is substituted by at least one substituent selected from the group consisting of substituents (a), defined above;
  an alkoxy group which has from 1 to 6 carbon atoms;
  an alkoxycarbonyl group which has from 2 to 5 carbon atoms; or
  a cyano group.

More preferably, X represents:
  a halogen atom;
  an alkyl group which has from 1 to 6 carbon atoms and which is unsubstituted or is substituted by from 1 to 3 substituents selected from the group consisting of substituents (a), defined above;
  an alkoxy group which has from 1 to 6 carbon atoms; or
  a cyano group.

Most preferably, X represents:
  a halogen atom;
  an alkyl group which has from 1 to 6 carbon atoms and which is unsubstituted or is substituted by from 1 to 3 substituents selected from the group consisting of substituents (a), defined above; or
  an alkoxy group which has from 1 to 6 carbon atoms.

In the case of the compounds of formula (I) in which D represents a group of formula (III), we prefer that Y should represent:
  a halogen atom;
  an alkyl group which has from 1 to 6 carbon atoms and which is unsubstituted or is substituted by at least one substituent selected from the group consisting of substituents (a), defined above; or
  an alkoxy group which has from 1 to 6 carbon atoms.

More preferably Y represents a halogen atom or an alkyl group which has from 1 to 6 carbon atoms and which is unsubstituted or is substituted by from 1 to 3 substituents selected from the group consisting of substituents (a), defined above.

In the case of the compounds of formula (I) in which D represents a group of formula (IV), we prefer that Z should represent: a halogen atom; an alkyl group which has from 1 to 6 carbon atoms; or an alkoxy group which has from 1 to 6 carbon atoms. More preferably Z represents a halogen atom or an alkyl group which has from 1 to 6 carbon atoms, and most preferably Z represents an alkyl group which has from 1 to 6 carbon atoms.

Substituents (a) preferably comprise halogen atoms.

Substituents (b) preferably comprise a halogen atom or an alkyl group which has from 1 to 6 carbon atoms, more preferably a halogen atom.

Substituents (c) preferably comprise a halogen atom or a hydroxy group, more preferably a halogen atom.

The preferred compounds of the present invention are those compounds of formula (I), in which:

$R^1$ and $R^2$ are independently selected from the group consisting of:
  alkyl groups which have from 1 to 6 carbon atoms,
  alkenyl groups which have from 3 to 5 carbon atoms, alkynyl groups which have from 3 to 5 carbon atoms, and
  aryl groups which have from 6 to 10 ring atoms and which are unsubstituted or are substituted by from 1 to 3 substituents selected from the group consisting of halogen atoms and alkyl groups which have from 1 to 4 carbon atoms,
  or $R^1$ and $R^2$ together represent an alkylene group which has from 4 to 7 carbon atoms;

A represents:
  a hydrogen atom,
  a halogen atom,
  an alkyl group which has from 1 to 6 carbon atoms and which is unsubstituted or is substituted by from 1 to 3 substituents selected from the group consisting of halogen atoms and hydroxy groups,
  an alkenyl group which has from 3 to 5 carbon atoms, or
  a cyano group;

B represents:
  a hydrogen atom,
  a halogen atom,
  an alkyl group which has from 1 to 6 carbon atoms and which is unsubstituted or is substituted by from 1 to 3 substituents selected from the group consisting of halogen atoms and hydroxy groups,
  an alkoxy group which has from 1 to 6 carbon atoms, or
  a cyano group;

D represents a group of formula (II):

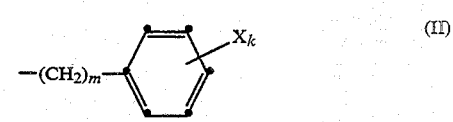

(II)

in which:
  X represents
    a halogen atom,
    an unsubstituted alkyl group which has from 1 to 6 carbon atoms,
    a substituted alkyl group which has from 1 to 6 carbon atoms and which is substituted by from 1 to 3 substituents selected from the group consisting of substituents (a), defined above,
    an alkoxy group which has from 1 to 6 carbon atoms,
    an alkoxycarbonyl group which has from 2 to 7 carbon atoms, or
    a cyano group;
  m is 0 or 1; and
  k is as defined above; or D represents a group of formula (III):

(III)

in which:
  Y represents
    a halogen atom, an unsubstituted alkyl group which has from 1 to 6 carbon atoms,
a substituted alkyl group which has from 1 to 6 carbon atoms and which is substituted by from 1 to 3 substituents selected from the group consisting of substituents (a), defined above,
an alkoxy group which has from 1 to 6 carbon atoms, and
j is as defined above; and
n is 0 or 2;
and salts and esters thereof.

More preferred compounds of the present invention are those compounds of formula (I) in which:
$R^1$ and $R^2$ are the same or different and each represents an alkyl group which has from 1 to 6 carbon atoms, an alkenyl group which has from 3 to 5 carbon atoms or an alkynyl group which has from 3 to 5 carbon atoms, or $R^1$ and $R^2$ together represent an alkylene group which has from 4 to 7 carbon atoms;
A represents a hydrogen atom or a halogen atom;
B represents a hydrogen atom, a halogen atom or a cyano group;
n is 2; and
D represents a group of formula (II):

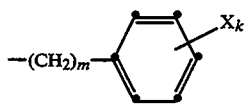

in which:
X represents
a halogen atom,
an unsubstituted alkyl group which has from 1 to 6 carbon atoms,
a substituted alkyl group which has from 1 to 6 carbon atoms and which is substituted by from 1 to 3 halogen substituents,
an alkoxy group which has from 1 to 6 carbon atoms, or
a cyano group;
m is 0; and
k is as defined above; or
D represents a group of formula (III):

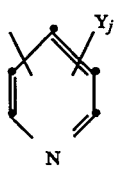

in which:
Y represents
a halogen atom,
an unsubstituted alkyl group which has from 1 to 6 carbon atoms, or
a substituted alkyl group which has from 1 to 6 carbon atoms and which is substituted by from 1 to 3 halogen substituents, and
j is as defined above;
and salts and esters thereof.

The most preferred compounds of the present invention are those compounds of formula (I) in which:
$R^1$ and $R^2$ are the same or different and each represents an alkyl group having from 1 to 6 carbon atoms;
A represents a hydrogen atom;
B represents a hydrogen atom or a halogen atom;
n is 2; and
D represents a group of formula (II):

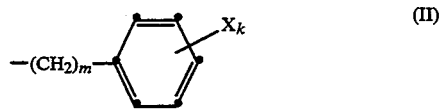

in which:
X represents
a halogen atom,
an unsubstituted alkyl group which has from 1 to 6 carbon atoms,
a substituted alkyl group which has from 1 to 6 carbon atoms and which is substituted by from 1 to 3 halogen substituents, or
an alkoxy group which has from 1 to 6 carbon atoms,;
m is 0; and
k is as defined above;
and salts and esters thereof.

In all of the compounds of the present invention, including the preferred, more preferred and most preferred classes of compounds described above, it is considered especially advantageous that B should represent a fluorine atom, i.e. the 4-fluoropyrazole derivatives are most preferred.

Those compounds of the present invention which contain a carboxy group or a pyridyl or pyrimidinyl group can form salts. There is no particular restriction on the nature of these salts, provided that, where they are intended for agricultural or horticultural use, they are agriculturally or horticulturally acceptable. Where they are intended for non-agricultural or horticultural uses, e.g. as intermediates in the preparation of other, and possibly more active, compounds, even this restriction does not apply. The compounds of the present invention can form salts with bases. Examples of such salts which may be formed by compounds containing a carboxy group include: salts with an alkali metal, such as sodium, potassium or lithium; salts with an alkaline earth metal, such as barium or calcium; salts with another metal, such as magnesium and aluminum; organic base salts, such as a salt with dicyclohexylamine; and salts with a basic amino acid, such as lysine or arginine. Where the compound of the present invention contains a basic group in its molecule, i.e. compounds containing a pyridyl or pyrimidinyl group, it can form acid addition salts. Examples of such acid addition salts include: salts with mineral acids, especially hydrohalic acids (such as hydrofluoric acid, hydrobromic acid, hydroiodic acid or hydrochloric acid), nitric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid or citric acid; and salts with amino acids, such as glutamic acid or aspartic acid.

Specific examples of individual compounds of the present invention are shown in the following formulae (I-1), (I-2) and (I-3):

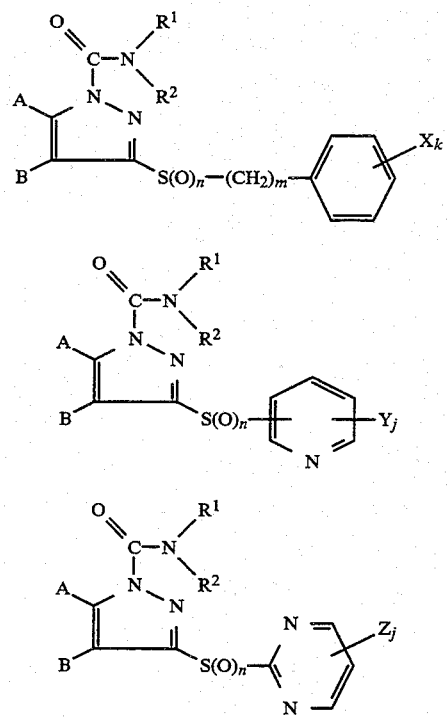

In these formulae, the meanings of $R^1$, $R^2$, n, m, X, k, Y, j, Z and i are as given in the following Tables 1 to 12, in which Tables 1 through 10 relate to formula (I-1), Table 11 relates to formula (I-2) and Table 12 relates to formula (I-3). In the Tables, the following abbreviations are used:

| | |
|---|---|
| All | allyl |
| Bu | butyl |
| sBu | sec-butyl |
| tBu | t-butyl |
| Bz | benzyl |
| Et | ethyl |
| Me | methyl |
| Ph | phenyl |
| Pr | propyl |
| iPr | isopropyl |
| Prg | propargyl (= 2-propynyl) |
| Pyr | pyridyl |

In Compounds No. 4.36 to 4.41, 6.48 to 6.55, 7.60 to 7.74, 9.37 to 9.39 and 10.45, $R^1$ and $R^2$ together represent the alkylene group indicated under their respective columns. In Table 11, the heading "subst. posn." refers to the position on the pyridyl group in formula (I-2) by which it is attached to the group of formula $-S(O)_n-$.

TABLE 1

| Cpd. No. | $R^1$ | $R^2$ | A | B | n | m | $X_k$ |
|---|---|---|---|---|---|---|---|
| 1.1 | Et | Et | H | H | 2 | 0 | not substituted |
| 1.2 | Et | Et | H | H | 0 | 0 | not substituted |
| 1.3 | Et | Et | H | H | 2 | 1 | not substituted |
| 1.4 | Et | Et | H | H | 2 | 0 | 2-F |
| 1.5 | Et | Et | H | H | 0 | 0 | 2-F |
| 1.6 | Et | Et | H | H | 2 | 0 | 2-Cl |
| 1.7 | Et | Et | H | H | 1 | 0 | 2-Cl |

TABLE 1-continued

| Cpd. No. | $R^1$ | $R^2$ | A | B | n | m | $X_k$ |
|---|---|---|---|---|---|---|---|
| 1.8 | Et | Et | H | H | 2 | 0 | 2-Br |
| 1.9 | Et | Et | H | H | 0 | 0 | 2-Br |
| 1.10 | Et | Et | H | H | 2 | 0 | 2-Me |
| 1.11 | Et | Et | H | H | 0 | 0 | 2-Me |
| 1.12 | Et | Et | H | H | 2 | 1 | 2-Me |
| 1.13 | Et | Et | H | H | 0 | 1 | 2-Me |
| 1.14 | Et | Et | H | H | 0 | 0 | 2-Et |
| 1.15 | Et | Et | H | H | 2 | 0 | 2-Et |
| 1.16 | Et | Et | H | H | 2 | 0 | 2-iPr |
| 1.17 | Et | Et | H | H | 2 | 0 | 2-Bz |
| 1.18 | Et | Et | H | H | 0 | 0 | 2-Bz |
| 1.19 | Et | Et | H | H | 2 | 0 | 2-OMe |
| 1.20 | Et | Et | H | H | 0 | 0 | 2-OMe |
| 1.21 | Et | Et | H | H | 2 | 0 | 2-OPh |
| 1.22 | Et | Et | H | H | 0 | 0 | 2-OPh |
| 1.23 | Et | Et | H | H | 2 | 0 | 2-$CF_3$ |
| 1.24 | Et | Et | H | H | 0 | 0 | 2-$CF_3$ |
| 1.25 | Et | Et | H | H | 2 | 0 | 2-$NO_2$ |
| 1.26 | Et | Et | H | H | 0 | 0 | 2-COOEt |
| 1.27 | Et | Et | H | H | 2 | 0 | 2-COOEt |
| 1.28 | Et | Et | H | H | 2 | 0 | 2-SMe |
| 1.29 | Et | Et | H | H | 2 | 0 | 2-$SO_2Me$ |
| 1.30 | Et | Et | CHO | H | 0 | 0 | 2-Bz |
| 1.31 | Me | Me | H | F | 2 | 0 | 2-F |
| 1.32 | Me | Me | H | F | 2 | 0 | 2-Cl |
| 1.33 | Me | Me | H | F | 2 | 0 | 2-Et |
| 1.34 | Me | Me | H | F | 2 | 0 | 2-iPr |
| 1.35 | Me | Me | H | F | 2 | 0 | 2-$CF_3$ |
| 1.36 | Et | Et | H | F | 2 | 0 | 2-F |
| 1.37 | Et | Et | H | F | 2 | 0 | 2-Cl |
| 1.38 | Et | Et | H | F | 2 | 0 | 2-Et |
| 1.39 | Et | Et | H | F | 2 | 0 | 2-iPr |
| 1.40 | Et | Et | H | F | 2 | 0 | 2-$CF_3$ |
| 1.41 | Et | Pr | H | F | 2 | 0 | 2-F |
| 1.42 | Et | Pr | H | F | 2 | 0 | 2-Cl |
| 1.43 | Et | Pr | H | F | 2 | 0 | 2-Et |
| 1.44 | Et | Pr | H | F | 2 | 0 | 2-iPr |
| 1.45 | Et | Pr | H | F | 2 | 0 | 2-$CF_3$ |
| 1.46 | Pr | Pr | H | F | 2 | 0 | 2-F |
| 1.47 | Pr | Pr | H | F | 2 | 0 | 2-Cl |
| 1.48 | Pr | Pr | H | F | 2 | 0 | 2-Et |
| 1.49 | Pr | Pr | H | F | 2 | 0 | 2-iPr |
| 1.50 | Pr | Pr | H | F | 2 | 0 | 2-$CF_3$ |
| 1.51 | All | All | H | F | 2 | 0 | 2-F |
| 1.52 | All | All | H | F | 2 | 0 | 2-Cl |
| 1.53 | All | All | H | F | 2 | 0 | 2-Et |
| 1.54 | All | All | H | F | 2 | 0 | 2-iPr |
| 1.55 | All | All | H | F | 2 | 0 | 2-$CF_3$ |
| 1.56 | Et | Et | H | Cl | 0 | 0 | 2-Cl |
| 1.57 | Et | Et | H | Cl | 2 | 0 | 2-Cl |
| 1.58 | Et | Et | H | Cl | 2 | 0 | 2-Et |
| 1.59 | Et | Et | H | Cl | 0 | 0 | 2-COOEt |
| 1.60 | Et | Et | H | Cl | 2 | 0 | 2-COOEt |
| 1.61 | Et | Et | H | Cl | 2 | 0 | 2-F |
| 1.62 | Et | Et | H | Cl | 2 | 0 | 2-iPr |
| 1.63 | Et | Et | H | Cl | 2 | 0 | 2-$CF_3$ |
| 1.64 | Et | Pr | H | Cl | 2 | 0 | 2-F |
| 1.65 | Et | Pr | H | Cl | 2 | 0 | 2-Cl |
| 1.66 | Et | Pr | H | Cl | 2 | 0 | 2-Et |
| 1.67 | Et | Pr | H | Cl | 2 | 0 | 2-iPr |
| 1.68 | Et | Pr | H | Cl | 2 | 0 | 2-$CF_3$ |
| 1.69 | Pr | Pr | H | Cl | 2 | 0 | 2-F |
| 1.70 | Pr | Pr | H | Cl | 2 | 0 | 2-Cl |
| 1.71 | Pr | Pr | H | Cl | 2 | 0 | 2-Et |
| 1.72 | Pr | Pr | H | Cl | 2 | 0 | 2-iPr |
| 1.73 | Pr | Pr | H | Cl | 2 | 0 | 2-$CF_3$ |
| 1.74 | All | All | H | Cl | 2 | 0 | 2-F |
| 1.75 | All | All | H | Cl | 2 | 0 | 2-Cl |
| 1.76 | All | All | H | Cl | 2 | 0 | 2-Et |
| 1.77 | All | All | H | Cl | 2 | 0 | 2-iPr |
| 1.78 | All | All | H | Cl | 2 | 0 | 2-$CF_3$ |
| 1.79 | Et | Et | H | Br | 2 | 0 | 2-Et |
| 1.80 | Et | Et | H | F | 0 | 0 | 2-$CF_3$ |
| 1.81 | Et | Et | H | F | 2 | 0 | 2-Me |

TABLE 2

| Cpd. No. | R¹ | R² | A | B | n | m | $X_k$ |
|---|---|---|---|---|---|---|---|
| 2.1 | Et | Et | H | H | 2 | 0 | 3-F |
| 2.2 | Et | Et | H | H | 0 | 0 | 3-F |
| 2.3 | Et | Et | H | H | 0 | 0 | 3-Cl |
| 2.4 | Et | Et | H | H | 2 | 0 | 3-Cl |
| 2.5 | Et | Et | H | H | 0 | 0 | 3-Br |
| 2.6 | Et | Et | H | H | 2 | 0 | 3-Br |
| 2.7 | Et | Et | H | H | 2 | 0 | 3-Me |
| 2.8 | Et | Et | H | H | 0 | 0 | 3-Me |
| 2.9 | Et | Et | H | H | 0 | 0 | 3-iPr |
| 2.10 | Et | Et | H | H | 2 | 0 | 3-iPr |
| 2.11 | Et | Et | H | H | 0 | 0 | 3-OMe |
| 2.12 | Et | Et | H | H | 2 | 0 | 3-OMe |
| 2.13 | Et | Et | H | H | 2 | 0 | 3-CN |
| 2.14 | Et | Et | H | H | 0 | 0 | 3-CN |
| 2.15 | Et | Et | H | H | 0 | 0 | 3-CF₃ |
| 2.16 | Et | Et | H | H | 2 | 0 | 3-CF₃ |
| 2.17 | Et | Et | H | H | 2 | 0 | 3-NO₂ |
| 2.18 | Et | Et | H | H | 0 | 0 | 3-COOEt |
| 2.19 | Et | Et | H | H | 2 | 0 | 3-COOEt |
| 2.20 | Et | Et | H | H | 2 | 0 | 3-Me |
| 2.21 | Et | Et | H | H | 0 | 0 | 3-SMe |
| 2.22 | Et | Et | H | H | 2 | 0 | 3-SO₂Me |
| 2.23 | Pr | Pr | H | H | 2 | 0 | 3-F |
| 2.24 | Pr | Pr | H | H | 2 | 0 | 3-CN |
| 2.25 | Pr | Pr | H | H | 2 | 0 | 3-OMe |
| 2.26 | Me | Me | H | H | 2 | 0 | 3-F |
| 2.27 | Me | Me | H | H | 2 | 0 | 3-CN |
| 2.28 | Me | Me | H | H | 2 | 0 | 3-OMe |
| 2.29 | Et | Pr | H | H | 2 | 0 | 3-F |
| 2.30 | Et | Pr | H | H | 2 | 0 | 3-CN |
| 2.31 | Et | Pr | H | H | 2 | 0 | 3-OMe |
| 2.32 | All | All | H | H | 2 | 0 | 3-F |
| 2.33 | All | All | H | H | 2 | 0 | 3-CN |
| 2.34 | All | All | H | H | 2 | 0 | 3-OMe |
| 2.35 | Bu | Me | H | H | 2 | 0 | 3-F |
| 2.36 | Bu | Me | H | H | 2 | 0 | 3-CN |
| 2.37 | Bu | Me | H | H | 2 | 0 | 3-OMe |
| 2.38 | Et | Et | Cl | H | 2 | 0 | 3-F |
| 2.39 | Et | Et | Cl | H | 2 | 0 | 3-CN |
| 2.40 | Et | Et | Cl | H | 2 | 0 | 3-OMe |
| 2.41 | Et | Et | H | Cl | 0 | 0 | 3-F |
| 2.42 | Et | Et | H | Cl | 2 | 0 | 3-F |
| 2.43 | Et | Et | H | Cl | 0 | 0 | 3-Cl |
| 2.44 | Et | Et | H | Cl | 2 | 0 | 3-Cl |
| 2.45 | Et | Et | H | Cl | 2 | 0 | 3-Br |
| 2.46 | Et | Et | H | Cl | 0 | 0 | 3-SMe |
| 2.47 | Et | Et | H | Cl | 0 | 0 | 3-SCF₃ |
| 2.48 | Et | Et | H | Cl | 2 | 0 | 3-SCF₃ |
| 2.49 | Et | Et | H | Cl | 2 | 0 | 3-SO₂CF₃ |
| 2.50 | Et | Et | H | Cl | 2 | 0 | 3-SO₂Me |
| 2.51 | Et | Et | H | Cl | 0 | 0 | 3-CF₃ |
| 2.52 | Et | Et | H | Cl | 2 | 0 | 3-CF₃ |
| 2.53 | Et | Et | H | Cl | 0 | 0 | 3-COOEt |
| 2.54 | Et | Et | H | Cl | 2 | 0 | 3-COOEt |
| 2.55 | Et | Et | H | Cl | 2 | 0 | 3-CN |
| 2.56 | Et | Et | H | Cl | 2 | 0 | 3-OMe |
| 2.57 | Et | Et | H | Cl | 2 | 0 | 3-OCF₃ |
| 2.58 | Et | Et | H | Br | 0 | 0 | 3-F |
| 2.59 | Et | Et | H | Br | 2 | 0 | 3-F |
| 2.60 | Et | Et | H | Br | 0 | 0 | 3-Br |
| 2.61 | Et | Et | H | Br | 2 | 0 | 3-Br |
| 2.62 | Et | Et | H | Br | 2 | 0 | 3-CN |
| 2.63 | Et | Et | H | Br | 2 | 0 | 3-OMe |
| 2.64 | Et | Et | H | F | 2 | 0 | 3-F |
| 2.65 | Et | Et | H | F | 2 | 0 | 3-CN |
| 2.66 | Et | Et | H | F | 2 | 0 | 3-OMe |
| 2.67 | Et | Et | H | F | 2 | 0 | 3-OCF₃ |
| 2.68 | Et | Et | H | F | 2 | 0 | 3-Cl |
| 2.69 | Et | Et | H | F | 2 | 0 | 3-Br |
| 2.70 | Et | Et | H | F | 2 | 0 | 3-CF₃ |
| 2.71 | Me | Me | H | F | 2 | 0 | 3-F |
| 2.72 | Me | Me | H | F | 2 | 0 | 3-CN |
| 2.73 | Me | Me | H | F | 2 | 0 | 3-OMe |
| 2.74 | Et | Pr | H | F | 2 | 0 | 3-F |
| 2.75 | Et | Pr | H | F | 2 | 0 | 3-CN |
| 2.76 | Et | Pr | H | F | 2 | 0 | 3-OMe |
| 2.77 | Pr | Pr | H | F | 2 | 0 | 3-F |
| 2.78 | Pr | Pr | H | F | 2 | 0 | 3-CN |
| 2.79 | Pr | Pr | H | F | 2 | 0 | 3-OMe |
| 2.80 | All | All | H | F | 2 | 0 | 3-F |
| 2.81 | All | All | H | F | 2 | 0 | 3-CN |
| 2.82 | All | All | H | F | 2 | 0 | 3-CMe |
| 2.83 | Et | Et | H | F | 2 | 0 | 3-CF₃ |
| 2.84 | Et | Et | H | Me | 2 | 0 | 3-F |
| 2.85 | Et | Et | H | Me | 2 | 0 | 3-CN |
| 2.86 | Et | Et | H | Me | 2 | 0 | 3-OMe |
| 2.87 | Et | Et | H | CH₂OMe | 2 | 0 | 3-F |
| 2.88 | Et | Et | H | CH₂OMe | 2 | 0 | 3-CN |
| 2.89 | Et | Et | H | CH₂OMe | 2 | 0 | 3-OMe |
| 2.90 | Et | Et | H | CH₂Cl | 2 | 0 | 3-F |
| 2.91 | Et | Et | H | CH₂Cl | 2 | 0 | 3-CN |
| 2.92 | Et | Et | H | CH₂Cl | 2 | 0 | 3-OMe |
| 2.93 | Et | Et | H | CH₂F | 2 | 0 | 3-F |
| 2.94 | Et | Et | H | CH₂F | 2 | 0 | 3-CN |
| 2.95 | Et | Et | H | CH₂F | 2 | 0 | 3-OMe |
| 2.96 | Et | Et | H | CHF₂ | 2 | 0 | 3-F |
| 2.97 | Et | Et | H | CHF₂ | 0 | 0 | 3-Cl |
| 2.98 | Et | Et | H | CHF₂ | 2 | 0 | 3-Cl |
| 2.99 | Et | Et | H | CHF₂ | 2 | 0 | 3-CN |
| 2.100 | Et | Et | H | CHF₂ | 2 | 0 | 3-OMe |
| 2.101 | Et | Et | H | CF₃ | 2 | 0 | 3-F |
| 2.102 | Et | Et | H | CF₃ | 2 | 0 | 3-CN |
| 2.103 | Et | Et | H | CF₃ | 2 | 0 | 3-OMe |
| 2.104 | Et | Et | H | CN | 0 | 0 | 3-F |
| 2.105 | Et | Et | H | CN | 2 | 0 | 3-F |
| 2.106 | Et | Et | H | CN | 2 | 0 | 3-CN |
| 2.107 | Et | Et | H | CN | 2 | 0 | 3-OMe |
| 2.108 | Et | Et | H | COOEt | 2 | 0 | 3-F |
| 2.109 | Et | Et | H | COOEt | 2 | 0 | 3-CN |
| 2.110 | Et | Et | H | COOEt | 2 | 0 | 3-OMe |
| 2.111 | Et | Et | H | SEt | 2 | 0 | 3-F |
| 2.112 | Et | Et | H | SEt | 2 | 0 | 3-CN |
| 2.113 | Et | Et | H | SEt | 2 | 0 | 3-OMe |
| 2.114 | Et | Et | H | SO₂Et | 2 | 0 | 3-F |
| 2.115 | Et | Et | H | SO₂Et | 2 | 0 | 3-CN |
| 2.116 | Et | Et | H | SO₂Et | 2 | 0 | 3-OMe |
| 2.117 | Et | Et | H | OMe | 2 | 0 | 3-F |
| 2.118 | Et | Et | H | OMe | 2 | 0 | 3-CN |
| 2.119 | Et | Et | H | OMe | 2 | 0 | 3-OMe |
| 2.120 | Et | Et | H | F | 0 | 0 | 3-F |
| 2.121 | Et | Et | H | F | 0 | 0 | 3-OMe |

TABLE 3

| Cpd. No. | R¹ | R² | A | B | n | m | $X_k$ |
|---|---|---|---|---|---|---|---|
| 3.1 | Et | Et | H | H | 2 | 0 | 4-F |
| 3.2 | Et | Et | H | H | 0 | 0 | 4-F |
| 3.3 | Et | Et | H | H | 2 | 0 | 4-Cl |
| 3.4 | Et | Et | H | H | 0 | 0 | 4-Cl |
| 3.5 | Et | Et | H | H | 2 | 1 | 4-Cl |
| 3.6 | Et | Et | H | H | 2 | 0 | 4-Br |
| 3.7 | Et | Et | H | H | 0 | 0 | 4-Br |
| 3.8 | Et | Et | H | H | 0 | 0 | 4-Me |
| 3.9 | Et | Et | H | H | 2 | 0 | 4-Me |
| 3.10 | Et | Et | H | H | 0 | 0 | 4-Et |
| 3.11 | Et | Et | H | H | 2 | 0 | 4-Et |
| 3.12 | Et | Et | H | H | 2 | 0 | 4-iPr |
| 3.13 | Et | Et | H | H | 0 | 0 | 4-iPr |
| 3.14 | Et | Et | H | H | 0 | 0 | 4-sBu |
| 3.15 | Et | Et | H | H | 2 | 0 | 4-sBu |
| 3.16 | Et | Et | H | H | 2 | 0 | 4-tBu |
| 3.17 | Et | Et | H | H | 0 | 0 | 4-tBu |
| 3.18 | Et | Et | H | H | 2 | 0 | 4-OPh |
| 3.19 | Et | Et | H | H | 0 | 0 | 4-OPh |
| 3.20 | Et | Et | H | H | 2 | 0 | 4-CN |
| 3.21 | Et | Et | H | H | 0 | 0 | 4-CN |
| 3.22 | Et | Et | H | H | 2 | 0 | 4-NO₂ |
| 3.23 | Et | Et | H | H | 2 | 1 | 4-NO₂ |
| 3.24 | Et | Et | H | H | 2 | 0 | 4-CF₃ |
| 3.25 | Et | Et | H | H | 2 | 1 | 4-CF₃ |
| 3.26 | Et | Et | H | H | 2 | 0 | 4-COOEt |
| 3.27 | Et | Et | H | H | 2 | 0 | 4-SMe |
| 3.28 | Et | Et | H | H | 2 | 0 | 4-SO₂Me |
| 3.29 | Et | Et | CONMe₂ | H | 2 | 0 | 4-OPh |
| 3.30 | Et | Et | CONMe₂ | H | 0 | 0 | 4-OPh |
| 3.31 | Et | Et | COOEt | H | 0 | 0 | 4-tBu |
| 3.32 | Et | Et | COOEt | H | 2 | 0 | 4-tBu |

TABLE 3-continued

| Cpd. No. | $R^1$ | $R^2$ | A | B | n | m | $X_k$ |
|---|---|---|---|---|---|---|---|
| 3.33 | Et | Et | CH₂OMe | H | 2 | 0 | 4-iPr |
| 3.34 | Et | Et | H | Cl | 2 | 1 | 4-Cl |
| 3.35 | Et | Et | H | Cl | 2 | 0 | 4-F |
| 3.36 | Et | Et | H | Cl | 2 | 0 | 4-Me |
| 3.37 | Et | Et | H | Cl | 2 | 0 | 4-iPr |
| 3.38 | Et | Et | H | Cl | 2 | 0 | 4-sBu |
| 3.39 | Et | Et | H | F | 2 | 0 | 4-Cl |
| 3.40 | Et | Et | H | F | 2 | 0 | 4-Me |
| 3.41 | Et | Et | H | F | 2 | 0 | 4-iPr |
| 3.42 | Et | Et | H | F | 2 | 0 | 4-sBu |
| 3.43 | Et | Et | H | F | 2 | 0 | 4-F |

TABLE 4

| Cpd. No. | $R^1$ | $R^2$ | A | B | n | m | $X_k$ |
|---|---|---|---|---|---|---|---|
| 4.1 | Et | Et | H | H | 2 | 0 | 2,3-diCl |
| 4.2 | Et | Et | H | H | 0 | 0 | 2,3-diCl |
| 4.3 | Et | Et | H | H | 2 | 0 | 2-Me,3-Cl |
| 4.4 | Et | Et | H | H | 0 | 0 | 2-Me,3-Cl |
| 4.5 | Et | Et | H | H | 2 | 0 | 2,3-diMe |
| 4.6 | Et | Et | H | H | 0 | 0 | 2,3-diMe |
| 4.7 | Et | Et | H | H | 2 | 0 | 2,3-diF |
| 4.8 | Et | Et | H | H | 0 | 0 | 2,3-diF |
| 4.9 | Et | Et | H | H | 2 | 0 | 2-Cl,3-Me |
| 4.10 | Et | Et | H | H | 2 | 0 | 2-Me,3-OMe |
| 4.11 | Et | Et | H | H | 2 | 0 | 2-OMe,3-Cl |
| 4.12 | Et | Et | H | H | 2 | 0 | 2-Cl,3-COOEt |
| 4.13 | Et | Et | H | H | 2 | 0 | 2-Cl,3-SMe |
| 4.14 | Et | Et | H | H | 2 | 0 | 2-Cl,3-SO₂Me |
| 4.15 | Pr | Pr | H | H | 2 | 0 | 2,3-diCl |
| 4.16 | Pr | Pr | H | H | 2 | 0 | 2-Me,3-Cl |
| 4.17 | Pr | Pr | H | H | 2 | 0 | 2,3-diMe |
| 4.18 | Et | Pr | H | H | 2 | 0 | 2,3-diCl |
| 4.19 | Et | Pr | H | H | 2 | 0 | 2-Me,3-Cl |
| 4.20 | Et | Pr | H | H | 2 | 0 | 2,3-diMe |
| 4.21 | Me | Me | H | H | 2 | 0 | 2,3-diCl |
| 4.22 | Me | Me | H | H | 2 | 0 | 2-Me,3-Cl |
| 4.23 | Me | Me | H | H | 2 | 0 | 2,3-diMe |
| 4.24 | All | All | H | H | 2 | 0 | 2,3-diCl |
| 4.25 | All | All | H | H | 2 | 0 | 2-Me,3-Cl |
| 4.26 | All | All | H | H | 2 | 0 | 2,3-diMe |
| 4.27 | Prg | Prg | H | H | 2 | 0 | 2,3-diCl |
| 4.28 | Prg | Prg | H | H | 2 | 0 | 2-Me,3-Cl |
| 4.29 | Prg | Prg | H | H | 2 | 0 | 2,3-diMe |
| 4.30 | Bu | Me | H | H | 2 | 0 | 2,3-diCl |
| 4.31 | Bu | Me | H | H | 2 | 0 | 2-Me,3-Cl |
| 4.32 | Bu | Me | H | H | 2 | 0 | 2,3-diMe |
| 4.33 | Bu | Et | H | H | 2 | 0 | 2,3-diCl |
| 4.34 | Bu | Et | H | H | 2 | 0 | 2-Me,3-Cl |
| 4.35 | Bu | Et | H | H | 2 | 0 | 2,3-diMe |
| 4.36 | (CH₂)₄ | | H | H | 2 | 0 | 2,3-diCl |
| 4.37 | (CH₂)₄ | | H | H | 2 | 0 | 2-Me,3-Cl |
| 4.38 | (CH₂)₄ | | H | H | 2 | 0 | 2,3-diMe |
| 4.39 | (CH₂)₅ | | H | H | 2 | 0 | 2,3-diCl |
| 4.40 | (CH₂)₅ | | H | H | 2 | 0 | 2-Me,3-Cl |
| 4.41 | (CH₂)₅ | | H | H | 2 | 0 | 2,3-diMe |
| 4.42 | Me | Me | H | Cl | 0 | 0 | 2,3-diF |
| 4.43 | Me | Me | H | Cl | 2 | 0 | 2,3-diF |
| 4.44 | Me | Et | H | Cl | 0 | 0 | 2,3-diF |
| 4.45 | Me | Et | H | Cl | 2 | 0 | 2,3-diF |
| 4.46 | Et | Et | H | Cl | 2 | 0 | 2,3-diF |
| 4.47 | Et | Pr | H | Cl | 0 | 0 | 2,3-diF |
| 4.48 | Et | Pr | H | Cl | 2 | 0 | 2,3-diF |
| 4.49 | Pr | Pr | H | Cl | 0 | 0 | 2,3-diF |
| 4.50 | Pr | Pr | H | Cl | 2 | 0 | 2,3-diF |
| 4.51 | Me | Bu | H | Cl | 0 | 0 | 2,3-diF |
| 4.52 | Me | Bu | H | Cl | 2 | 0 | 2,3-diF |
| 4.53 | Et | 2-ClEt | H | Cl | 2 | 0 | 2,3-diF |
| 4.54 | Et | 2-MeOEt | H | Cl | 2 | 0 | 2,3-diF |
| 4.55 | Et | 2-ClAll | H | Cl | 2 | 0 | 2,3-diF |
| 4.56 | Et | Et | H | Cl | 2 | 0 | 2,3-diCl |
| 4.57 | Et | Et | H | Cl | 2 | 0 | 2-Me,3-Cl |
| 4.58 | Et | Et | H | Cl | 2 | 0 | 2,3-diMe |
| 4.59 | Et | Et | H | Cl | 2 | 0 | 2-CH₂OMe,3-Cl |
| 4.60 | Et | Et | H | Cl | 2 | 0 | 2-Cl,3-Me |
| 4.61 | Et | Et | H | Br | 0 | 0 | 2,3-diCl |
| 4.62 | Et | Et | H | Br | 2 | 0 | 2,3-diCl |
| 4.63 | Et | Et | H | Br | 2 | 0 | 2-Me,3-Cl |
| 4.64 | Et | Et | H | Br | 2 | 0 | 2,3-diMe |
| 4.65 | Et | Et | H | F | 2 | 0 | 2,3-Cl₂ |
| 4.66 | Et | Et | H | F | 2 | 0 | 2-Me,3-Cl |
| 4.67 | Et | Et | H | F | 2 | 0 | 2,3-diMe |
| 4.68 | Et | Et | H | F | 2 | 0 | 2-CH₂OMe,3-Cl |
| 4.69 | Et | Et | H | F | 2 | 0 | 2,3-diF |
| 4.70 | Et | Et | H | F | 2 | 0 | 2-Cl,3-Me |
| 4.71 | Me | Me | H | F | 2 | 0 | 2,3-diCl |
| 4.72 | Me | Me | H | F | 2 | 0 | 2-Me,3-Cl |
| 4.73 | Me | Me | H | F | 2 | 0 | 2,3-diMe |
| 4.74 | Me | Me | H | F | 2 | 0 | 2,3-diF |
| 4.75 | Me | Me | H | F | 2 | 0 | 2-Cl,3-Me |
| 4.76 | Me | Et | H | F | 2 | 0 | 2,3-diCl |
| 4.77 | Me | Et | H | F | 2 | 0 | 2-Me,3-Cl |
| 4.78 | Me | Et | H | F | 2 | 0 | 2,3-diMe |
| 4.79 | Me | Et | H | F | 2 | 0 | 2,3-diF |
| 4.80 | Me | Et | H | F | 2 | 0 | 2-Cl,3-Me |
| 4.81 | Et | Pr | H | F | 2 | 0 | 2,3-diCl |
| 4.82 | Et | Pr | H | F | 2 | 0 | 2-Me,3-Cl |
| 4.83 | Et | Pr | H | F | 2 | 0 | 2,3-diMe |
| 4.84 | Et | Pr | H | F | 2 | 0 | 2,3-diF |
| 4.85 | Et | Pr | H | F | 2 | 0 | 2-Cl,3-Me |
| 4.86 | Pr | Pr | H | F | 2 | 0 | 2,3-diCl |
| 4.87 | Pr | Pr | H | F | 2 | 0 | 2-Me,3-Cl |
| 4.88 | Pr | Pr | H | F | 2 | 0 | 2,3-diMe |
| 4.89 | Pr | Pr | H | F | 2 | 0 | 2,3-diF |
| 4.90 | Pr | Pr | H | F | 2 | 0 | 2-Cl,3-Me |
| 4.91 | All | All | H | F | 2 | 0 | 2,3-diCl |
| 4.92 | All | All | H | F | 2 | 0 | 2-Me,3-Cl |
| 4.93 | All | All | H | F | 2 | 0 | 2,3-diMe |
| 4.94 | All | All | H | F | 2 | 0 | 2,3-diF |
| 4.95 | All | All | H | F | 2 | 0 | 2-Cl,3-Me |
| 4.96 | Et | Et | H | Me | 2 | 0 | 2,3-diCl |
| 4.97 | Et | Et | H | Me | 2 | 0 | 2-Me,3-Cl |
| 4.98 | Et | Et | H | Me | 2 | 0 | 2,3-diMe |
| 4.99 | Et | Et | H | CF₃ | 2 | 0 | 2,3-diCl |
| 4.100 | Et | Et | H | CF₃ | 2 | 0 | 2-Me,3-Cl |
| 4.101 | Et | Et | H | CF₃ | 2 | 0 | 2,3-diMe |
| 4.102 | Et | Et | H | CH₂OH | 2 | 0 | 2-Me,3-Cl |
| 4.103 | Et | Et | H | CH₂OMe | 2 | 0 | 2,3-diCl |
| 4.104 | Et | Et | H | CH₂OMe | 2 | 0 | 2-Me,3-Cl |
| 4.105 | Et | Et | H | CH₂OMe | 2 | 0 | 2,3-diMe |
| 4.106 | Et | Et | H | CH₂F | 2 | 0 | 2,3-diCl |
| 4.107 | Et | Et | H | CH₂F | 2 | 0 | 2-Me,3-Cl |
| 4.108 | Et | Et | H | CH₂F | 2 | 0 | 2,3-diMe |
| 4.109 | Et | Et | H | CHF₂ | 2 | 0 | 2,3-diCl |
| 4.110 | Et | Et | H | CHF₂ | 2 | 0 | 2-Me,3-Cl |
| 4.111 | Et | Et | H | CHF₂ | 2 | 0 | 2,3-diMe |
| 4.112 | Et | Et | H | CHO | 2 | 0 | 2-Me,3-Cl |
| 4.113 | Et | Et | H | COOEt | 2 | 0 | 2,3-diCl |
| 4.114 | Et | Et | H | COOEt | 2 | 0 | 2-Me,3-Cl |
| 4.115 | Et | Et | H | COOEt | 2 | 0 | 2,3-diMe |
| 4.116 | Et | Et | H | SMe | 2 | 0 | 2,3-diCl |
| 4.117 | Et | Et | H | SMe | 2 | 0 | 2-Me,3-Cl |
| 4.118 | Et | Et | H | SMe | 2 | 0 | 2,3-diMe |
| 4.119 | Et | Et | H | SO₂Me | 2 | 0 | 2,3-diCl |
| 4.120 | Et | Et | H | SO₂Me | 2 | 0 | 2-Me,3-Cl |
| 4.121 | Et | Et | H | SO₂Me | 2 | 0 | 2,3-diMe |
| 4.122 | Et | Et | H | OMe | 2 | 0 | 2,3-diCl |
| 4.123 | Et | Et | H | OMe | 2 | 0 | 2-Me,3-Cl |
| 4.124 | Et | Et | H | OMe | 2 | 0 | 2,3-diMe |
| 4.125 | Et | Et | H | OCHF₂ | 2 | 0 | 2,3-diCl |
| 4.126 | Et | Et | H | OCHF₂ | 2 | 0 | 2-Me,3-Cl |
| 4.127 | Et | Et | H | OCH₂OMe | 2 | 0 | 2,3-diCl |
| 4.128 | Et | Et | H | OCH₂OMe | 2 | 0 | 2-Me,3-Cl |
| 4.129 | Et | Et | H | CH₂Cl | 2 | 0 | 2,3-diCl |
| 4.130 | Et | Et | H | CH₂Cl | 2 | 0 | 2-Me,3-Cl |
| 4.131 | Et | Et | H | CH₂Cl | 2 | 0 | 2,3-diMe |
| 4.132 | Et | Et | H | SEt | 2 | 0 | 2-Me,3-Cl |
| 4.133 | Et | Et | H | CN | 0 | 0 | 2,3-diCl |
| 4.134 | Et | Et | H | CN | 2 | 0 | 2,3-diF |
| 4.135 | Et | Et | H | CN | 2 | 0 | 2,3-diCl |
| 4.136 | Et | Et | H | CN | 2 | 0 | 2-Me,3-Cl |
| 4.137 | Et | Et | H | CN | 2 | 0 | 2,3-diMe |
| 4.138 | Et | Et | H | CHO | 0 | 0 | 2-Me,3-Cl |

TABLE 5

| Cpd. No. | R¹ | R² | A | B | n | m | $X_k$ |
|---|---|---|---|---|---|---|---|
| 5.1 | Et | Et | H | H | 2 | 0 | 2,4-diF |
| 5.2 | Et | Et | H | H | 0 | 0 | 2,4-diF |
| 5.3 | Et | Et | H | H | 2 | 0 | 2,4-diCl |
| 5.4 | Et | Et | H | H | 0 | 0 | 2,4-diCl |
| 5.5 | Et | Et | H | H | 2 | 0 | 2,4-diBr |
| 5.6 | Et | Et | H | H | 2 | 0 | 2-F,4-Br |
| 5.7 | Et | Et | H | H | 0 | 0 | 2-CF₃,4-Cl |
| 5.8 | Et | Et | H | H | 2 | 0 | 2-CF₃,4-Cl |
| 5.9 | Et | Et | H | H | 2 | 0 | 2-CF₃,4-Br |
| 5.10 | Et | Et | H | H | 0 | 0 | 2-CF₃,4-Br |
| 5.11 | Et | Et | H | H | 2 | 0 | 2-Cl,4-Me |
| 5.12 | Et | Et | H | H | 0 | 0 | 2-Cl,4-Me |
| 5.13 | Et | Et | H | H | 2 | 0 | 2-Me,4-Cl |
| 5.14 | Et | Et | H | H | 0 | 0 | 2-Me,4-Cl |
| 5.15 | Et | Et | H | H | 2 | 0 | 2,4-diMe |
| 5.16 | Et | Et | H | H | 0 | 0 | 2,4-diMe |
| 5.17 | Et | Et | H | H | 2 | 0 | 2-Me,4-OMe |
| 5.18 | Et | Et | H | H | 0 | 0 | 2-Me,4-OMe |
| 5.19 | Et | Et | H | H | 2 | 0 | 2-Cl,4-Br |
| 5.20 | Et | Et | H | H | 0 | 0 | 2-Cl,4-Br |
| 5.21 | Et | Et | H | H | 2 | 0 | 2-Cl,4-CF₃ |
| 5.22 | Et | Et | H | H | 2 | 0 | 2-Cl,4-tBu |
| 5.23 | Et | Et | H | H | 2 | 0 | 2-NO₂,4-Cl |
| 5.24 | Et | Et | H | H | 2 | 0 | 2-Cl,4-NO₂ |
| 5.25 | Me | Me | H | Cl | 0 | 0 | 2,4-diF |
| 5.26 | Me | Me | H | Cl | 2 | 0 | 2,4-diF |
| 5.27 | Me | Et | H | Cl | 0 | 0 | 2,4-diF |
| 5.28 | Me | Et | H | Cl | 2 | 0 | 2,4-diF |
| 5.29 | Et | Et | H | Cl | 0 | 0 | 2,4-diF |
| 5.30 | Et | Et | H | Cl | 2 | 0 | 2,4-diF |
| 5.31 | Et | Pr | H | Cl | 0 | 0 | 2,4-diF |
| 5.32 | Et | Pr | H | Cl | 2 | 0 | 2,4-diF |
| 5.33 | Pr | Pr | H | Cl | 0 | 0 | 2,4-diF |
| 5.34 | Pr | Pr | H | Cl | 2 | 0 | 2,4-diF |
| 5.35 | Me | Bu | H | Cl | 0 | 0 | 2,4-diF |
| 5.36 | Me | Bu | H | Cl | 2 | 0 | 2,4-diF |
| 5.37 | Et | Et | H | Cl | 0 | 0 | 2-Cl,4-Me |
| 5.38 | Et | Et | H | Cl | 2 | 0 | 2-Cl,4-Me |
| 5.39 | Et | Et | H | Cl | 2 | 0 | 2-Me,4-Cl |
| 5.40 | Et | Et | H | Cl | 2 | 0 | 2-F,4-Br |
| 5.41 | Et | Et | H | Cl | 0 | 0 | 2-CF₃,4-Cl |
| 5.42 | Et | Et | H | Cl | 2 | 0 | 2-CF₃,4-Cl |
| 5.43 | Et | Et | H | Cl | 2 | 0 | 2,4-diMe |
| 5.44 | Et | Et | H | Cl | 2 | 0 | 2,4-diMe |
| 5.45 | Et | Et | H | Cl | 2 | 0 | 2-Cl,4-Br |
| 5.46 | Et | Et | H | Cl | 2 | 0 | 2-Cl,4-CF₃ |
| 5.47 | Pr | Pr | H | Cl | 2 | 0 | 2,4-diF |
| 5.48 | Pr | Pr | H | Cl | 2 | 0 | 2,4-diCl |
| 5.49 | Pr | Pr | H | Cl | 2 | 0 | 2-Me,4-Cl |
| 5.50 | Pr | Pr | H | Cl | 2 | 0 | 2-CF₃,4-Cl |
| 5.51 | Et | Pr | H | Cl | 2 | 0 | 2,4-diF |
| 5.52 | Et | Pr | H | Cl | 2 | 0 | 2,4-diCl |
| 5.53 | Et | Pr | H | Cl | 2 | 0 | 2-Me,4-Cl |
| 5.54 | Et | Pr | H | Cl | 2 | 0 | 2-CF₃,4-Cl |
| 5.55 | All | All | H | Cl | 2 | 0 | 2,4-diF |
| 5.56 | All | All | H | Cl | 2 | 0 | 2,4-diCl |
| 5.57 | All | All | H | Cl | 2 | 0 | 2-Me,4-Cl |
| 5.58 | All | All | H | Cl | 2 | 0 | 2-CF₃,4-Cl |
| 5.59 | Me | 4-ClPh | H | Cl | 2 | 0 | 2-CF₃,4-Cl |
| 5.60 | Me | 2,4-diClPh | H | Cl | 2 | 0 | 2-CF₃,4-Cl |
| 5.61 | Me | 2,5-diClPh | H | Cl | 2 | 0 | 2-CF₃,4-Cl |
| 5.62 | Me | 2,4,5-triClPh | H | Cl | 2 | 0 | 2-CF₃,4-Cl |
| 5.63 | Me | 2,4-diCl-3-MePh | H | Cl | 2 | 0 | 2-CF₃,4-Cl |
| 5.64 | Et | 4-OMePh | H | Cl | 2 | 0 | 2-CF₃,4-Cl |
| 5.65 | Et | 3-Cl-4-OMePh | H | Cl | 2 | 0 | 2-CF₃,4-Cl |
| 5.66 | Me | 3,5-diCl-2-Pyr | H | Cl | 2 | 0 | 2-CF₃,4-Cl |
| 5.67 | Me | 4-Cl-5-Me-2-Pyr | H | Cl | 2 | 0 | 2-CF₃,4-Cl |
| 5.68 | Me | 4-OMe-2-Pyr | H | Cl | 2 | 0 | 2-CF₃,4-Cl |
| 5.69 | Et | Et | H | Br | 0 | 0 | 2,4-diF |
| 5.70 | Et | Et | H | Br | 2 | 0 | 2,4-diF |
| 5.71 | Et | Et | H | Br | 0 | 0 | 2-Cl,4-Me |
| 5.72 | Et | Et | H | Br | 2 | 0 | 2-Cl,4-Me |
| 5.73 | Et | Et | H | Br | 2 | 0 | 2-Me,4-Cl |
| 5.74 | Et | Et | H | F | 2 | 0 | 2-Cl,4-Me |
| 5.75 | Et | Et | H | F | 2 | 0 | 2-CF₃,4-Cl |
| 5.76 | Et | Et | H | F | 2 | 0 | 2,4-diF |
| 5.77 | Et | Et | H | F | 2 | 0 | 2,4-diCl |
| 5.78 | Et | Et | H | F | 2 | 0 | 2-Me,4-Cl |
| 5.79 | Et | Et | H | F | 2 | 0 | 2,4-diMe |
| 5.80 | Et | Et | H | F | 2 | 0 | 2-Cl,4-Br |
| 5.81 | Et | Et | H | F | 2 | 0 | 2-Cl,4-CF₃ |
| 5.82 | Me | Me | H | F | 2 | 0 | 2,4-diCl |
| 5.83 | Me | Me | H | F | 2 | 0 | 2,4-diF |
| 5.84 | Me | Me | H | F | 2 | 0 | 2-Me,4-Cl |
| 5.85 | Me | Me | H | F | 2 | 0 | 2-CF₃,4-Cl |
| 5.86 | Me | Me | H | F | 2 | 0 | 2-Cl,4-Br |
| 5.87 | Me | Et | H | F | 2 | 0 | 2,4-diCl |
| 5.88 | Me | Et | H | F | 2 | 0 | 2,4-diF |
| 5.89 | Me | Et | H | F | 2 | 0 | 2-Me,4-Cl |
| 5.90 | Me | Et | H | F | 2 | 0 | 2-CF₃,4-Cl |
| 5.91 | Me | Et | H | F | 2 | 0 | 2-Cl,4-Br |
| 5.92 | Et | Pr | H | F | 2 | 0 | 2,4-diCl |
| 5.93 | Et | Pr | H | F | 2 | 0 | 2,4-diF |
| 5.94 | Et | Pr | H | F | 2 | 0 | 2-Me,4-Cl |
| 5.95 | Et | Pr | H | F | 2 | 0 | 2-CF₃,4-Cl |
| 5.96 | Et | Pr | H | F | 2 | 0 | 2-Cl,4-Br |
| 5.97 | Pr | Pr | H | F | 2 | 0 | 2,4-diCl |
| 5.98 | Pr | Pr | H | F | 2 | 0 | 2,4-diF |
| 5.99 | Pr | Pr | H | F | 2 | 0 | 2-Me,4-Cl |
| 5.100 | Pr | Pr | H | F | 2 | 0 | 2-CF₃,4-Cl |
| 5.101 | Pr | Pr | H | F | 2 | 0 | 2-Cl,4-Br |
| 5.102 | All | All | H | F | 2 | 0 | 2,4-diCl |
| 5.103 | All | All | H | F | 2 | 0 | 2,4-diF |
| 5.104 | All | All | H | F | 2 | 0 | 2-Me,4-Cl |
| 5.105 | All | All | H | F | 2 | 0 | 2-CF₃,4-Cl |
| 5.106 | All | All | H | F | 2 | 0 | 2-Cl,4-Br |
| 5.107 | Et | Et | H | F | 0 | 0 | 2,4-F₂ |

TABLE 6

| Cpd. No. | R¹ | R² | A | B | n | m | $X_k$ |
|---|---|---|---|---|---|---|---|
| 6.1 | Et | Et | H | H | 2 | 0 | 2-F,5-Me |
| 6.2 | Et | Et | H | H | 0 | 0 | 2-F,5-Me |
| 6.3 | Et | Et | H | H | 2 | 0 | 2,5-diCl |
| 6.4 | Et | Et | H | H | 0 | 0 | 2,5-diCi |
| 6.5 | Et | Et | H | H | 0 | 0 | 2-Cl,5-CF₃ |
| 6.6 | Et | Et | H | H | 2 | 0 | 2-Cl,5-CF₃ |
| 6.7 | Et | Et | H | H | 0 | 0 | 2-Me,5-Cl |
| 6.8 | Et | Et | H | H | 2 | 0 | 2-Me,5-Cl |
| 6.9 | Et | Et | H | H | 0 | 0 | 2,5-diMe |
| 6.10 | Et | Et | H | H | 2 | 0 | 2,5-diMe |
| 6.11 | Et | Et | H | H | 2 | 0 | 2-OMe,5-Me |
| 6.12 | Et | Et | H | H | 0 | 0 | 2-OMe,5-Me |
| 6.13 | Et | Et | H | H | 0 | 0 | 2-OMe,5-Cl |
| 6.14 | Et | Et | H | H | 2 | 0 | 2-OMe,5-Cl |
| 6.15 | Et | Et | H | H | 0 | 0 | 2-Cl,5-OMe |
| 6.16 | Et | Et | H | H | 2 | 0 | 2-Cl,5-OMe |
| 6.17 | Et | Et | H | H | 2 | 0 | 2,5-diBr |
| 6.18 | Et | Et | H | H | 0 | 0 | 2,5-diF |
| 6.19 | Et | Et | H | H | 2 | 0 | 2,5-diF |
| 6.20 | Et | Et | H | H | 2 | 0 | 2-Cl,5-NO₂ |
| 6.21 | Et | Et | H | H | 2 | 0 | 2-Cl,5-COOEt |
| 6.22 | Et | Et | H | H | 2 | 0 | 2-Cl,5-SMe |
| 6.23 | Et | Et | H | H | 2 | 0 | 2-Cl,5-SO₂Me |
| 6.24 | Me | Me | H | H | 2 | 0 | 2,5-diCl |
| 6.25 | Me | Me | H | H | 2 | 0 | 2,5-diMe |
| 6.26 | Me | Me | H | H | 2 | 0 | 2-Cl,5-CF₃ |
| 6.27 | Me | Me | H | H | 2 | 0 | 2-Me,5-Cl |
| 6.28 | Et | Pr | H | H | 2 | 0 | 2,5-diCl |
| 6.29 | Et | Pr | H | H | 2 | 0 | 2,5-diMe |
| 6.30 | Et | Pr | H | H | 2 | 0 | 2-Cl,5-CF |
| 6.31 | Et | Pr | H | H | 2 | 0 | 2-Me,5-Cl3 |
| 6.32 | Pr | Pr | H | H | 2 | 0 | 2,5-diCl |
| 6.33 | Pr | Pr | H | H | 2 | 0 | 2,5-diMe |
| 6.34 | Pr | Pr | H | H | 2 | 0 | 2-Cl,5-CF₃ |
| 6.35 | Pr | Pr | H | H | 2 | 0 | 2-Me,5-Cl |
| 6.36 | All | All | H | H | 2 | 0 | 2,5-diCl |
| 6.37 | All | All | H | H | 2 | 0 | 2,5-diMe |
| 6.38 | All | All | H | H | 2 | 0 | 2-Cl,5-CF₃ |
| 6.39 | All | All | H | H | 2 | 0 | 2-Me,5-Cl |
| 6.40 | Bu | Me | H | H | 2 | 0 | 2,5-diCl |
| 6.41 | Bu | Me | H | H | 2 | 0 | 2,5-diMe |
| 6.42 | Bu | Me | H | H | 2 | 0 | 2-Cl,5-CF₃ |
| 6.43 | Bu | Me | H | H | 2 | 0 | 2-Me,5-Cl |
| 6.44 | Bu | Et | H | H | 2 | 0 | 2,5-diCl |
| 6.45 | Bu | Et | H | H | 2 | 0 | 2,5-diMe |
| 6.46 | Bu | Et | H | H | 2 | 0 | 2-Cl,5-CF₃ |

TABLE 6-continued

| Cpd. No. | R¹ | R² | A | B | n | m | $X_k$ |
|---|---|---|---|---|---|---|---|
| 6.47 | Bu | Et | H | H | 2 | 0 | 2-Me,5-Cl |
| 6.48 | (CH₂)₄ | | H | H | 2 | 0 | 2,5-diCl |
| 6.49 | (CH₂)₄ | | H | H | 2 | 0 | 2,5-diMe |
| 6.50 | (CH₂)₄ | | H | H | 2 | 0 | 2-Cl,5-CF₃ |
| 6.51 | (CH₂)₄ | | H | H | 2 | 0 | 2-Me,5-Cl |
| 6.52 | (CH₂)₅ | | H | H | 2 | 0 | 2,5-diCl |
| 6.53 | (CH₂)₅ | | H | H | 2 | 0 | 2,5-diMe |
| 6.54 | (CH₂)₅ | | H | H | 2 | 0 | 2-Cl,5-CF₃ |
| 6.55 | (CH₂)₅ | | H | H | 2 | 0 | 2-Me,5-Cl |
| 6.56 | Prg | Prg | H | H | 2 | 0 | 2,5-diCl |
| 6.57 | Prg | Prg | H | H | 2 | 0 | 2,5-diMe |
| 6.58 | Prg | Prg | H | H | 2 | 0 | 2-Cl,5-CF₃ |
| 6.59 | Prg | Prg | H | H | 2 | 0 | 2-Me,5-Cl |
| 6.60 | Et | Et | H | F | 2 | 0 | 2,5-diCl |
| 6.61 | Et | Et | H | F | 2 | 0 | 2,5-diMe |
| 6.62 | Et | Et | H | F | 2 | 0 | 2-Cl,5-CF₃ |
| 6.63 | Et | Et | H | F | 2 | 0 | 2-Me,5-Cl |
| 6.64 | Et | Et | H | F | 2 | 0 | 2-Cl,5-OCF₃ |
| 6.65 | Et | Et | H | F | 2 | 0 | 2,5-diF |
| 6.66 | Et | Et | H | F | 2 | 0 | 2-F,5-Me |
| 6.67 | Et | Et | H | F | 2 | 0 | 2-Cl,5-Me |
| 6.68 | Et | Et | H | F | 2 | 0 | 2,5-diBr |
| 6.69 | Et | Et | H | F | 2 | 0 | 2-F,5-Cl |
| 6.70 | Et | Et | H | F | 2 | 0 | 2-Cl,5-OMe |
| 6.71 | Me | Me | H | F | 2 | 0 | 2,5-diCl |
| 6.72 | Me | Me | H | F | 2 | 0 | 2,5-diMe |
| 6.73 | Me | Me | H | F | 2 | 0 | 2-Cl,5-CF₃ |
| 6.74 | Me | Me | H | F | 2 | 0 | 2-Me,5-Cl |
| 6.75 | Me | Me | H | F | 2 | 0 | 2,5-diF |
| 6.76 | Me | Me | H | F | 2 | 0 | 2-F,5-Me |
| 6.77 | Me | Et | H | F | 2 | 0 | 2,5-diCl |
| 6.78 | Me | Et | H | F | 2 | 0 | 2,5-diMe |
| 6.79 | Me | Et | H | F | 2 | 0 | 2-Cl,5-CF₃ |
| 6.80 | Me | Et | H | F | 2 | 0 | 2-Me,5-Cl |
| 6.81 | Me | Et | H | F | 2 | 0 | 2,5-diF |
| 6.82 | Me | Et | H | F | 2 | 0 | 2-F,5-Me |
| 6.83 | Et | Pr | H | F | 2 | 0 | 2,5-diCl |
| 6.84 | Et | Pr | H | F | 2 | 0 | 2,5-diMe |
| 6.85 | Et | Pr | H | F | 2 | 0 | 2-Cl,5-CF₃ |
| 6.86 | Et | Pr | H | F | 2 | 0 | 2-Me,5-Cl |
| 6.87 | Et | Pr | H | F | 2 | 0 | 2,5-diF |
| 6.88 | Et | Pr | H | F | 2 | 0 | 2-F,5-Me |
| 6.89 | Pr | Pr | H | F | 2 | 0 | 2,5-diCl |
| 6.90 | Pr | Pr | H | F | 2 | 0 | 2,5-diMe |
| 6.91 | Pr | Pr | H | F | 2 | 0 | 2-Cl,5-CF₃ |
| 6.92 | Pr | Pr | H | F | 2 | 0 | 2-Me,5-Cl |
| 6.93 | Pr | Pr | H | F | 2 | 0 | 2,5-diF |
| 6.94 | Pr | Pr | H | F | 2 | 0 | 2-F,5-Me |
| 6.95 | All | All | H | F | 2 | 0 | 2,5-diCl |
| 6.96 | All | All | H | F | 2 | 0 | 2,5-diMe |
| 6.97 | All | All | H | F | 2 | 0 | 2-Cl,5-CF₃ |
| 6.98 | All | All | H | F | 2 | 0 | 2-Me,5-Cl |
| 6.99 | All | All | H | F | 2 | 0 | 2,5-diF |
| 6.100 | All | All | H | F | 2 | 0 | 2-F,5-Me |
| 6.101 | Et | Et | H | Cl | 2 | 0 | 2,5-diCl |
| 6.102 | Et | Et | H | Cl | 2 | 0 | 2,5-diMe |
| 6.103 | Et | Et | H | Cl | 2 | 0 | 2-Cl,5-CF₃ |
| 6.104 | Et | Et | H | Cl | 2 | 0 | 2-Me,5-Cl |
| 6.105 | Et | Et | H | Cl | 0 | 0 | 2-Cl,5-OMe |
| 6.106 | Et | Et | H | Cl | 2 | 0 | 2-Cl,5-OMe |
| 6.107 | Et | Et | H | Cl | 2 | 0 | 2-Cl,5-OCF₃ |
| 6.108 | Et | Et | H | Cl | 0 | 0 | 2-F,5-Me |
| 6.109 | Et | Et | H | Cl | 2 | 0 | 2-F,5-Me |
| 6.110 | Et | Et | H | Cl | 0 | 0 | 2,5-diF |
| 6.111 | Et | Et | H | Cl | 2 | 0 | 2,5-diF |
| 6.112 | Et | Et | H | Cl | 2 | 0 | 2-OMe,5-Cl |
| 6.113 | Et | Et | H | Cl | 2 | 0 | 2-F,5-Cl |
| 6.114 | Et | Et | H | Br | 2 | 0 | 2,5-diMe |
| 6.115 | Et | Et | H | Br | 2 | 0 | 2-Cl,5-CF₃ |
| 6.116 | Et | Et | H | Br | 0 | 0 | 2,5-diMe |
| 6.117 | Et | Et | H | Br | 2 | 0 | 2,5-diCl |
| 6.118 | Et | Et | H | Br | 0 | 0 | 2-F,5-Me |
| 6.119 | Et | Et | H | Br | 2 | 0 | 2-F,5-Me |
| 6.120 | Et | Et | H | Br | 0 | 0 | 2-Me,5-Cl |
| 6.121 | Et | Et | H | Br | 2 | 0 | 2-Me,5-Cl |
| 6.122 | Et | Et | H | Me | 2 | 0 | 2,5-diCl |
| 6.123 | Et | Et | H | Me | 2 | 0 | 2,5-diMe |
| 6.124 | Et | Et | H | Me | 2 | 0 | 2-Cl,5-CF₃ |
| 6.125 | Et | Et | H | Me | 2 | 0 | 2-Me,5-Cl |
| 6.126 | Et | Et | H | All | 2 | 0 | 2,5-diCl |
| 6.127 | Et | Et | H | 2-ClAll | 2 | 0 | 2,5-diCl |
| 6.128 | Et | Et | H | CH₂OMe | 2 | 0 | 2,5-diCl |
| 6.129 | Et | Et | H | CH₂OMe | 2 | 0 | 2,5-diMe |
| 6.130 | Et | Et | H | CH₂OMe | 2 | 0 | 2-Cl,5-CF₃ |
| 6.131 | Et | Et | H | CH₂OMe | 2 | 0 | 2-Me,5-Cl |
| 6.132 | Et | Et | H | CH₂F | 2 | 0 | 2,5-diCl |
| 6.133 | Et | Et | H | CH₂F | 2 | 0 | 2,5-diMe |
| 6.134 | Et | Et | H | CH₂F | 2 | 0 | 2-Cl,5-CF₃ |
| 6.135 | Et | Et | H | CH₂F | 2 | 0 | 2-Me,5-Cl |
| 6.136 | Et | Et | H | CHF₂ | 2 | 0 | 2,5-diCl |
| 6.137 | Et | Et | H | CHF₂ | 2 | 0 | 2,5-diMe |
| 6.138 | Et | Et | H | CHF₂ | 2 | 0 | 2-Cl,5-CF₃ |
| 6.139 | Et | Et | H | CHF₂ | 2 | 0 | 2-Me,5-Cl |
| 6.140 | Et | Et | H | CF₃ | 2 | 0 | 2,5-diCl |
| 6.141 | Et | Et | H | CF₃ | 2 | 0 | 2,5-diMe |
| 6.142 | Et | Et | H | CF₃ | 2 | 0 | 2-Cl,5-CF₃ |
| 6.143 | Et | Et | H | CF₃ | 2 | 0 | 2-Me,5-Cl |
| 6.144 | Et | Et | H | CN | 0 | 0 | 2,5-diCl |
| 6.145 | Et | Et | H | CN | 2 | 0 | 2,5-diCl |
| 6.146 | Et | Et | H | CN | 2 | 0 | 2,5-diMe |
| 6.147 | Et | Et | H | CN | 0 | 0 | 2-Cl,5-CF₃ |
| 6.148 | Et | Et | H | CN | 2 | 0 | 2-Cl,5-CF₃ |
| 6.149 | Et | Et | H | CN | 2 | 0 | 2-Me,5-Cl |
| 6.150 | Et | Et | H | COOEt | 0 | 0 | 2,5-diCl |
| 6.151 | Et | Et | H | COOEt | 2 | 0 | 2,5-diCl |
| 6.152 | Et | Et | H | COOEt | 2 | 0 | 2,5-diMe |
| 6.153 | Et | Et | H | COOEt | 2 | 0 | 2-Cl,5-CF₃ |
| 6.154 | Et | Et | H | COOEt | 2 | 0 | 2-Me,5-Cl |
| 6.155 | Et | Et | H | SEt | 2 | 0 | 2,5-diCl |
| 6.156 | Et | Et | H | SEt | 2 | 0 | 2,5-diMe |
| 6.157 | Et | Et | H | SEt | 2 | 0 | 2-Cl,5-CF₃ |
| 6.158 | Et | Et | H | SEt | 2 | 0 | 2-Me,5-Cl |
| 6.159 | Et | Et | H | SMe | 0 | 0 | 2,5-diCl |
| 6.160 | Et | Et | H | SO₂Me | 2 | 0 | 2,5-diCl |
| 6.161 | Et | Et | H | SO₂Et | 2 | 0 | 2,5-diMe |
| 6.162 | Et | Et | H | SO₂Et | 2 | 0 | 2-Cl,5-CF₃ |
| 6.163 | Et | Et | H | SO₂Et | 2 | 0 | 2-Me,5-Cl |
| 6.164 | Et | Et | H | OMe | 2 | 0 | 2,5-diCl |
| 6.165 | Et | Et | H | OMe | 2 | 0 | 2,5-diMe |
| 6.166 | Et | Et | H | OMe | 2 | 0 | 2-Cl,5-CF₃ |
| 6.167 | Et | Et | H | OMe | 2 | 0 | 2-Me,5-Cl |
| 6.168 | Et | Et | H | CH₂Cl | 2 | 0 | 2,5-diCl |
| 6.169 | Et | Et | H | CH₂Cl | 2 | 0 | 2,5-diMe |
| 6.170 | Et | Et | H | CH₂Cl | 2 | 0 | 2-Cl,5-CF₃ |
| 6.171 | Et | Et | H | CH₂Cl | 2 | 0 | 2-Me,5-Cl |
| 6.172 | Et | Et | H | F | 0 | 0 | 2-Cl,5-OMe |
| 6.173 | Et | Et | H | F | 0 | 0 | 2-F,5-Me |

TABLE 7

| Cpd. No. | R¹ | R² | A | B | n | m | $X_k$ |
|---|---|---|---|---|---|---|---|
| 7.1 | Et | Et | H | H | 2 | 0 | 2,6-diF |
| 7.2 | Et | Et | H | H | 2 | 0 | 2-F,6-Cl |
| 7.3 | Et | Et | H | H | 0 | 0 | 2-F,6-Cl |
| 7.4 | Et | Et | H | H | 2 | 0 | 2,6-diCl |
| 7.5 | Et | Et | H | H | 2 | 1 | 2,6-diCl |
| 7.6 | Et | Et | H | H | 2 | 0 | 2,6-diBr |
| 7.7 | Et | Et | H | H | 2 | 0 | 2,6-diMe |
| 7.8 | Et | Et | H | H | 2 | 1 | 2,6-diMe |
| 7.9 | Et | Et | H | H | 0 | 0 | 2,6-diMe |
| 7.10 | Et | Et | H | H | 2 | 0 | 2-Me,6-Et |
| 7.11 | Et | Et | H | H | 2 | 1 | 2-Me,6-Et |

TABLE 7-continued

| Cpd. No. | R¹ | R² | A | B | n | m | $X_k$ |
|---|---|---|---|---|---|---|---|
| 7.12 | Et | Et | H | H | 0 | 0 | 2-Me,6-Et |
| 7.13 | Et | Et | H | H | 0 | 0 | 2-F,6-OMe |
| 7.14 | Et | Et | H | H | 2 | 0 | 2-F,6-OMe |
| 7.15 | Et | Et | H | H | 2 | 0 | 2-Me,6-iPr |
| 7.16 | Et | Et | H | H | 0 | 0 | 2-Me,6-iPr |
| 7.17 | Et | Et | H | H | 2 | 0 | 2-Me,6-Cl |
| 7.18 | Et | Et | H | H | 2 | 1 | 2-Me,6-Cl |
| 7.19 | Et | Et | H | H | 0 | 0 | 2-Me,6-Cl |
| 7.20 | Et | Et | H | H | 2 | 0 | 2-Me,6-OMe |
| 7.21 | Et | Et | H | H | 0 | 0 | 2-Me,6-OMe |
| 7.22 | Et | Et | H | H | 2 | 0 | 2,6-diEt |
| 7.23 | Et | Et | H | H | 0 | 0 | 2,6-diEt |
| 7.24 | Et | Et | H | H | 2 | 0 | 2,6-diiPr |
| 7.25 | Pr | Pr | H | H | 2 | 0 | 2,6-diCl |
| 7.26 | Pr | Pr | H | H | 2 | 0 | 2,6-diMe |
| 7.27 | Pr | Pr | H | H | 2 | 0 | 2-Me,6-Et |
| 7.28 | Pr | Pr | H | H | 2 | 0 | 2,6-diEt |
| 7.29 | Pr | Pr | H | H | 2 | 0 | 2-Me,6-Cl |
| 7.30 | Et | Pr | H | H | 2 | 0 | 2,6-diCl |
| 7.31 | Et | Pr | H | H | 2 | 0 | 2,6-diMe |
| 7.32 | Et | Pr | H | H | 2 | 0 | 2-Me,6-Et |
| 7.33 | Et | Pr | H | H | 2 | 0 | 2,6-diEt |
| 7.34 | Et | Pr | H | H | 2 | 0 | 2-Me,6-Cl |
| 7.35 | Me | Me | H | H | 2 | 0 | 2,6-diCl |
| 7.36 | Me | Me | H | H | 2 | 0 | 2,6-diMe |
| 7.37 | Me | Me | H | H | 2 | 0 | 2-Me,6-Et |
| 7.38 | Me | Me | H | H | 2 | 0 | 2,6-diEt |
| 7.39 | Me | Me | H | H | 2 | 0 | 2-Me,6-Cl |
| 7.40 | Me | Bu | H | H | 2 | 0 | 2,6-diCl |
| 7.41 | Me | Bu | H | H | 2 | 0 | 2,6-diMe |
| 7.42 | Me | Bu | H | H | 2 | 0 | 2-Me,6-Et |
| 7.43 | Me | Bu | H | H | 2 | 0 | 2,6-diEt |
| 7.44 | Me | Bu | H | H | 2 | 0 | 2-Me,6-Cl |
| 7.45 | Et | Bu | H | H | 2 | 0 | 2,6-diCl |
| 7.46 | Et | Bu | H | H | 2 | 0 | 2,6-diMe |
| 7.47 | Et | Bu | H | H | 2 | 0 | 2-Me,6-Et |
| 7.48 | Et | Bu | H | H | 2 | 0 | 2,6-diEt |
| 7.49 | Et | Bu | H | H | 2 | 0 | 2-Me,6-Cl |
| 7.50 | All | All | H | H | 2 | 0 | 2,6-diCl |
| 7.51 | All | All | H | H | 2 | 0 | 2,6-diMe |
| 7.52 | All | All | H | H | 2 | 0 | 2-Me,6-Et |
| 7.53 | All | All | H | H | 2 | 0 | 2,6-diEt |
| 7.54 | All | All | H | H | 2 | 0 | 2-Me,G-Cl |
| 7.55 | Prg | Prg | H | H | 2 | 0 | 2,6-diCl |
| 7.56 | Prg | Prg | H | H | 2 | 0 | 2,6-diMe |
| 7.57 | Prg | Prg | H | H | 2 | 0 | 2-Me,6-Et |
| 7.58 | Prg | Prg | H | H | 2 | 0 | 2,6-diEt |
| 7.59 | Prg | Prg | H | H | 2 | 0 | 2-Me,6-Cl |
| 7.60 | | (CH₂)₄ | H | H | 2 | 0 | 2,6-diCl |
| 7.61 | | (CH₂)₄ | H | H | 2 | 0 | 2,6-diMe |
| 7.62 | | (CH₂)₄ | H | H | 2 | 0 | 2-Me,6-Et |
| 7.63 | | (CH₂)₄ | H | H | 2 | 0 | 2,6-diEt |
| 7.64 | | (CH₂)₄ | H | H | 2 | 0 | 2-Me,6-Cl |
| 7.65 | | (CH₂)₅ | H | H | 2 | 0 | 2,6-diCl |
| 7.66 | | (CH₂)₅ | H | H | 2 | 0 | 2,6-diMe |
| 7.67 | | (CH₂)₅ | H | H | 2 | 0 | 2,Me,6-Et |
| 7.68 | | (CH₂)₅ | H | H | 2 | 0 | 2,6-diEt |
| 7.69 | | (CH₂)₅ | H | H | 2 | 0 | 2-Me,6-Cl |
| 7.70 | | (CH₂)₆ | H | H | 2 | 0 | 2,6-diCl |
| 7.71 | | (CH₂)₆ | H | H | 2 | 0 | 2,6-diMe |
| 7.72 | | (CH₂)₆ | H | H | 2 | 0 | 2-Me,6-Et |
| 7.73 | | (CH₂)₆ | H | H | 2 | 0 | 2,6-diEt |
| 7.74 | | (CH₂)₆ | H | H | 2 | 0 | 2-Me,6-Cl |
| 7.75 | Ph | Me | H | H | 0 | 0 | 2-Me,6-Et |
| 7.76 | Ph | Me | H | H | 2 | 0 | 2-Me,6-Et |
| 7.77 | Ph | Me | H | H | 2 | 0 | 2,6-diCl |
| 7.78 | Ph | Me | H | H | 2 | 0 | 2,6-diMe |
| 7.79 | Ph | Me | H | H | 2 | 0 | 2,6-diEt |
| 7.80 | Ph | Me | H | H | 2 | 0 | 2-Me,6-Cl |
| 7.81 | Ph | Et | H | H | 2 | 0 | 2,6-diCl |
| 7.82 | Ph | Et | H | H | 2 | 0 | 2,6-diMe |
| 7.83 | Ph | Et | H | H | 2 | 0 | 2,6-diEt |
| 7.84 | Ph | Et | H | H | 2 | 0 | 2-Me,6-Et |
| 7.85 | Ph | Et | H | H | 2 | 0 | 2-Me,6-Cl |
| 7.86 | Ph | iPr | H | H | 2 | 0 | 2,6-diCl |
| 7.87 | Ph | iPr | H | H | 2 | 0 | 2,6-diMe |
| 7.88 | Ph | iPr | H | H | 2 | 0 | 2,6-diEt |
| 7.89 | Ph | iPr | H | H | 2 | 0 | 2-Me,6-Cl |
| 7.90 | Et | Et | Me | H | 2 | 0 | 2-Me,6-Cl |
| 7.91 | Et | Et | All | H | 2 | 0 | 2-Me,6-Cl |
| 7.92 | Et | Et | 2-ClAll | H | 2 | 0 | 2-Me,6-Cl |

TABLE 7-continued

| Cpd. No. | R¹ | R² | A | B | n | m | $X_k$ |
|---|---|---|---|---|---|---|---|
| 7.93 | Et | Et | CH₂OMe | H | 2 | 0 | 2,6-diCl |
| 7.94 | Et | Et | CH₂OMe | H | 0 | 0 | 2,6-diF |
| 7.95 | Et | Et | CH₂OMe | H | 2 | 0 | 2,6-diF |
| 7.96 | Et | Et | SMe | H | 0 | 0 | 2-Me,6-Et |
| 7.97 | Et | Et | SO₂Et | H | 2 | 0 | 2-Me,6-Cl |
| 7.98 | Et | Et | SEt | H | 0 | 0 | 2-Me,6-Cl |
| 7.99 | Et | Et | CN | H | 2 | 0 | 2-Me,6-Et |
| 7.100 | Et | Et | CN | H | 2 | 0 | 2-Cl,G-Me |
| 7.101 | Et | Et | Cl | H | 2 | 0 | 2,6-diCl |
| 7.102 | Et | Et | Cl | H | 2 | 0 | 2,6-diMe |
| 7.103 | Et | Et | Cl | H | 2 | 0 | 2-Me,6-Et |
| 7.104 | Et | Et | Cl | H | 2 | 0 | 2,6-diEt |
| 7.105 | Et | Et | Cl | H | 2 | 0 | 2-Me,6-Cl |
| 7.106 | Et | Et | F | H | 2 | 0 | 2,6-diCl |
| 7.107 | Et | Et | F | H | 2 | 0 | 2,6-diMe |
| 7.108 | Et | Et | F | H | 2 | 0 | 2-Me,6-Et |
| 7.109 | Et | Et | F | H | 2 | 0 | 2,6-diEt |
| 7.110 | Et | Et | F | H | 2 | 0 | 2-Me,6-Cl |
| 7.111 | Et | Et | H | F | 2 | 0 | 2,6-diCl |
| 7.112 | Et | Et | H | F | 2 | 0 | 2,6-diMe |
| 7.113 | Et | Et | H | F | 2 | 0 | 2-Me,6-Et |
| 7.114 | Et | Et | H | F | 2 | 0 | 2,6-diEt |
| 7.115 | Et | Et | H | F | 2 | 0 | 2-Me,6-Cl |
| 7.116 | Et | Et | H | F | 2 | 0 | 2-CH₂OMe,6-Cl |
| 7.117 | Et | Et | H | F | 2 | 0 | 2-CH₂OMe,6-Me |
| 7.118 | Et | Et | H | F | 2 | 0 | 2-Me,6-OCF₃ |
| 7.119 | Et | Et | H | F | 2 | 0 | 2,6-diF |
| 7.120 | Et | Et | H | F | 2 | 0 | 2-Me,6-OMe |
| 7.121 | Et | Et | H | F | 2 | 0 | 2-Cl,6-F |
| 7.122 | Et | Et | H | F | 2 | 0 | 2-Me,6-iPr |
| 7.123 | Et | Et | H | F | 2 | 0 | 2-F,6-OMe |
| 7.124 | Et | Et | H | F | 2 | 0 | 2-Cl,6-NO₂ |
| 7.125 | Me | Me | H | F | 2 | 0 | 2,6-diCl |
| 7.126 | Me | Me | H | F | 2 | 0 | 2,6-diMe |
| 7.127 | Me | Me | H | F | 2 | 0 | 2-Me,6-Et |
| 7.128 | Me | Me | H | F | 2 | 0 | 2,6-diEt |
| 7.129 | Me | Me | H | F | 2 | 0 | 2-Me,6-Cl |
| 7.130 | Me | Me | H | F | 2 | 0 | 2,6-diF |
| 7.131 | Me | Me | H | F | 2 | 0 | 2-Me,6-OMe |
| 7.132 | Me | Me | H | F | 2 | 0 | 2-Cl,6-F |
| 7.133 | Me | Et | H | F | 2 | 0 | 2,6-diCl |
| 7.134 | Me | Et | H | F | 2 | 0 | 2,6-diMe |
| 7.135 | Me | Et | H | F | 2 | 0 | 2-Me,6-Et |
| 7.136 | Me | Et | H | F | 2 | 0 | 2,6-diEt |
| 7.137 | Me | Et | H | F | 2 | 0 | 2-Me,6-Cl |
| 7.138 | Me | Et | H | F | 2 | 0 | 2,6-diF |
| 7.139 | Me | Et | H | F | 2 | 0 | 2-Me,6-OMe |
| 7.140 | Me | Et | H | F | 2 | 0 | 2-Cl,6-F |
| 7.141 | Et | Pr | H | F | 2 | 0 | 2,6-diCl |
| 7.142 | Et | Pr | H | F | 2 | 0 | 2,6-diMe |
| 7.143 | Et | Pr | H | F | 2 | 0 | 2-Me,6-Et |
| 7.144 | Et | Pr | H | F | 2 | 0 | 2,6-diEt |
| 7.145 | Et | Pr | H | F | 2 | 0 | 2-Me,6-Cl |
| 7.146 | Et | Pr | H | F | 2 | 0 | 2,6-diF |
| 7.147 | Et | Pr | H | F | 2 | 0 | 2-Me,6-OMe |
| 7.148 | Et | Pr | H | F | 2 | 0 | 2-Cl,6-F |
| 7.149 | Pr | Pr | H | F | 2 | 0 | 2,6-diCl |
| 7.150 | Pr | Pr | H | F | 2 | 0 | 2,6-diMe |
| 7.151 | Pr | Pr | H | F | 2 | 0 | 2-Me,6-Et |
| 7.152 | Pr | Pr | H | F | 2 | 0 | 2,6-diEt |
| 7.153 | Pr | Pr | H | F | 2 | 0 | 2-Me,6-Cl |
| 7.154 | Pr | Pr | H | F | 2 | 0 | 2,6-diF |
| 7.155 | Pr | Pr | H | F | 2 | 0 | 2-Me,6-OMe |
| 7.156 | Pr | Pr | H | F | 2 | 0 | 2-Cl,6-F |
| 7.157 | All | All | H | F | 2 | 0 | 2,6-diCl |
| 7.158 | All | All | H | F | 2 | 0 | 2,6-diMe |
| 7.159 | All | All | H | F | 2 | 0 | 2-Me,6-Et |
| 7.160 | All | All | H | F | 2 | 0 | 2,6-diEt |
| 7.161 | All | All | H | F | 2 | 0 | 2-Me,6-Cl |
| 7.162 | All | All | H | F | 2 | 0 | 2,6-diF |
| 7.163 | All | All | H | F | 2 | 0 | 2-Me,6-OMe |
| 7.164 | All | All | H | F | 2 | 0 | 2-Cl,6-F |
| 7.165 | Et | Et | H | Cl | 2 | 0 | 2,6-diCl |
| 7.166 | Et | Et | H | Cl | 0 | 0 | 2,6-diMe |
| 7.167 | Et | Et | H | Cl | 2 | 0 | 2,6-diMe |
| 7.168 | Et | Et | H | Cl | 2 | 0 | 2-Me,6-Et |
| 7.169 | Et | Et | H | Cl | 0 | 0 | 2-Me,6-Et |
| 7.170 | Et | Et | H | Cl | 2 | 0 | 2-Me,6-iPr |
| 7.171 | Et | Et | H | Cl | 2 | 0 | 2-Cl,6-NO₂ |
| 7.172 | Et | Et | H | Cl | 0 | 0 | 2-Me,6-Cl |
| 7.173 | Et | Et | H | Cl | 2 | 0 | 2-Me,6-Cl |

TABLE 7-continued

| Cpd. No. | R¹ | R² | A | B | n | m | $X_k$ |
|---|---|---|---|---|---|---|---|
| 7.174 | Me | Me | H | Cl | 0 | 0 | 2-Me,6-OMe |
| 7.175 | Me | Me | H | Cl | 2 | 0 | 2-Me,6-OMe |
| 7.176 | Me | Et | H | Cl | 0 | 0 | 2-Me,6-OMe |
| 7.177 | Me | Et | H | Cl | 2 | 0 | 2-Me,6-OMe |
| 7.178 | Et | Et | H | Cl | 0 | 0 | 2-Me,6-OMe |
| 7.179 | Et | Et | H | Cl | 2 | 0 | 2-Me,6-OMe |
| 7.180 | Et | Et | H | Cl | 2 | 0 | 2-Me,6-OCF₃ |
| 7.181 | Et | Pr | H | Cl | 0 | 0 | 2-Me,6-OMe |
| 7.182 | Et | Pr | H | Cl | 2 | 0 | 2-Me,6-OMe |
| 7.183 | Pr | Pr | H | Cl | 0 | 0 | 2-Me,6-OMe |
| 7.184 | Pr | Pr | H | Cl | 2 | 0 | 2-Me,6-OMe |
| 7.185 | Me | Bu | H | Cl | 0 | 0 | 2-Me,6-OMe |
| 7.186 | Me | Bu | H | Cl | 2 | 0 | 2-Me,6-OMe |
| 7.187 | Et | Et | H | Cl | 0 | 0 | 2-F,6-Cl |
| 7.188 | Et | Et | H | Cl | 2 | 0 | 2-F,6-Cl |
| 7.189 | Et | Et | H | Cl | 0 | 0 | 2,6-diF |
| 7.190 | Et | Et | H | Cl | 2 | 0 | 2,6-diF |
| 7.191 | Et | Et | H | Cl | 2 | 0 | 2-F,6-OMe |
| 7.192 | Et | Et | H | Cl | 2 | 0 | 2-CH₂OMe,6-Cl |
| 7.193 | Et | Et | H | Cl | 2 | 0 | 2-CH₂OMe,6-Me |
| 7.194 | Et | Et | H | Cl | 2 | 0 | 2,6-diEt |
| 7.195 | Pr | Pr | H | Cl | 2 | 0 | 2,6-diMe |
| 7.196 | Pr | Pr | H | Cl | 2 | 0 | 2-Me,6-Et |
| 7.197 | Pr | Pr | H | Cl | 2 | 0 | 2,6-diEt |
| 7.198 | Pr | Pr | H | Cl | 2 | 0 | 2-Me,6-Cl |
| 7.199 | Pr | Et | H | Cl | 2 | 0 | 2,6-diCl |
| 7.200 | Pr | Et | H | Cl | 2 | 0 | 2,6-diMe |
| 7.201 | Pr | Et | H | Cl | 2 | 0 | 2-Me,6-Et |
| 7.202 | Pr | Et | H | Cl | 2 | 0 | 2,6-diEt |
| 7.203 | Pr | Et | H | Cl | 2 | 0 | 2-Me,6-Cl |
| 7.204 | Et | 2-ClEt | H | Cl | 2 | 0 | 2-Me,6-Cl |
| 7.205 | Et | 2-ClEt | H | Cl | 2 | 0 | 2-Me,6-Et |
| 7.206 | Et | 2-MeOEt | H | Cl | 2 | 0 | 2-Me,6-Cl |
| 7.207 | Et | 2-MeOEt | H | Cl | 2 | 0 | 2-Me,6-Et |
| 7.208 | Et | 2-ClAll | H | Cl | 2 | 0 | 2-Me,6-Cl |
| 7.209 | Et | 2-ClAll | H | Cl | 2 | 0 | 2-Me,6-Et |
| 7.201 | Et | Et | H | Br | 2 | 0 | 2,6-diCl |
| 7.211 | Et | Et | H | Br | 2 | 0 | 2,6-diMe |
| 7.212 | Et | Et | H | Br | 0 | 0 | 2,6-diMe |
| 7.213 | Et | Et | H | Br | 2 | 0 | 2-Me,6-Et |
| 7.214 | Et | Et | H | Br | 2 | 0 | 2,6-diEt |
| 7.215 | Et | Et | H | Br | 2 | 0 | 2-Me,6-Cl |
| 7.216 | Et | Et | H | Br | 0 | 0 | 2-Me,6-Cl |
| 7.217 | Et | Et | H | Br | 0 | 0 | 2-F,6-Cl |
| 7.218 | Et | Et | H | Br | 2 | 0 | 2-F,6-Cl |
| 7.219 | Et | Et | H | Br | 0 | 0 | 2-Me,6-OMe |
| 7.220 | Et | Et | H | Br | 2 | 0 | 2-Me,6-OMe |
| 7.221 | Et | Et | H | Br | 2 | 0 | 2,6-diF |
| 7.222 | Et | Et | H | I | 0 | 0 | 2-Me,6-iPr |
| 7.223 | Et | Et | H | I | 2 | 0 | 2-Me,6-iPr |
| 7.224 | Et | Et | H | I | 2 | 0 | 2,6-diCl |
| 7.225 | Et | Et | H | I | 2 | 0 | 2,6-diMe |
| 7.226 | Et | Et | H | I | 2 | 0 | 2-Me,6-Et |
| 7.227 | Et | Et | H | I | 2 | 0 | 2,6-diEt |
| 7.228 | Et | Et | H | I | 2 | 0 | 2-Me,6-Cl |
| 7.229 | Et | Et | H | Me | 2 | 0 | 2,6-diCl |
| 7.230 | Et | Et | H | Me | 2 | 0 | 2,6-diMe |
| 7.231 | Et | Et | H | Me | 2 | 0 | 2-Me,6-Et |
| 7.232 | Et | Et | H | Me | 2 | 0 | 2,6-diEt |
| 7.233 | Et | Et | H | Me | 2 | 0 | 2-Me,6-Cl |
| 7.234 | Et | Et | H | Et | 2 | 0 | 2-Me,6-Et |
| 7.235 | Et | Et | H | All | 2 | 0 | 2-Me,6-Cl |
| 7.236 | Et | Et | H | All | 2 | 0 | 2,6-diEt |
| 7.237 | Et | Et | H | All | 2 | 0 | 2-Me,6-Et |
| 7.238 | Et | Et | H | 2-ClAll | 2 | 0 | 2-Me,6-Et |
| 7.239 | Et | Et | H | CH₂OMe | 2 | 0 | 2,6-diCl |
| 7.240 | Et | Et | H | CH₂OMe | 2 | 0 | 2,6-diMe |
| 7.241 | Et | Et | H | CH₂OMe | 2 | 0 | 2-Me,6-Et |
| 7.242 | Et | Et | H | CH₂OMe | 2 | 0 | 2,6-diEt |
| 7.243 | Et | Et | H | CH₂OMe | 2 | 0 | 2-Me,6-Cl |
| 7.244 | Et | Et | H | CF₃ | 2 | 0 | 2,6-diCl |
| 7.245 | Et | Et | H | CF₃ | 2 | 0 | 2,6-diMe |
| 7.246 | Et | Et | H | CF₃ | 0 | 0 | 2-Me,6-Et |
| 7.247 | Et | Et | H | CF₃ | 2 | 0 | 2-Me,6-Et |
| 7.248 | Et | Et | H | CF₃ | 2 | 0 | 2,6-diEt |
| 7.249 | Et | Et | H | CF₃ | 2 | 0 | 2-Me,6-Cl |
| 7.250 | Et | Et | H | CN | 2 | 0 | 2,6-diCl |
| 7.251 | Et | Et | H | CN | 2 | 0 | 2,6-diMe |
| 7.252 | Et | Et | H | CN | 0 | 0 | 2-Me,6-Et |
| 7.253 | Et | Et | H | CN | 2 | 0 | 2-Me,6-Et |
| 7.254 | Et | Et | H | CN | 0 | 0 | 2,6-diEt |

TABLE 7-continued

| Cpd. No. | R$^1$ | R$^2$ | A | B | n | m | X$_k$ |
|---|---|---|---|---|---|---|---|
| 7.255 | Et | Et | H | CN | 2 | 0 | 2,6-diEt |
| 7.256 | Et | Et | H | CN | 0 | 0 | 2-Me,6-Cl |
| 7.257 | Et | Et | H | CN | 2 | 0 | 2-Me,6-Cl |
| 7.258 | Et | Et | H | CN | 0 | 0 | 2-Me,6-OMe |
| 7.259 | Et | Et | H | CN | 2 | 0 | 2-Me,6-OMe |
| 7.260 | Et | Et | H | COOET | 2 | 0 | 2,6-diCl |
| 7.261 | Et | Et | H | COOET | 2 | 0 | 2,6-diMe |
| 7.262 | Et | Et | H | COOET | 0 | 0 | 2-Me,6-Et |
| 7.263 | Et | Et | H | COOET | 2 | 0 | 2-Me,6-Et |
| 7.264 | Et | Et | H | COOET | 0 | 0 | 2,6-diEt |
| 7.265 | Et | Et | H | COOET | 2 | 0 | 2,6-diEt |
| 7.266 | Et | Et | H | COOET | 0 | 0 | 2-Me,6-Cl |
| 7.267 | Et | Et | H | COOET | 2 | 0 | 2-Me,6-Cl |
| 7.268 | Et | Et | H | SMe | 0 | 0 | 2,6-diEt |
| 7.269 | Et | Et | H | SMe | 0 | 0 | 2-Me,6-Et |
| 7.270 | Et | Et | H | SMe | 0 | 0 | 2-Me,6-Cl |
| 7.271 | Et | Et | H | SO$_2$Me | 2 | 0 | 2,6-diEt |
| 7.272 | Et | Et | H | SO$_2$Me | 2 | 0 | 2-Me,6-Et |
| 7.273 | Et | Et | H | SO$_2$Me | 2 | 0 | 2-Me,6-Cl |
| 7.274 | Et | Et | H | SEt | 2 | 0 | 2,6-diCl |
| 7.275 | Et | Et | H | SEt | 2 | 0 | 2,6-diMe |
| 7.276 | Et | Et | H | SEt | 2 | 0 | 2-Me,6-Et |
| 7.277 | Et | Et | H | SEt | 2 | 0 | 2,6-diEt |
| 7.278 | Et | Et | H | SEt | 2 | 0 | 2-Me,6-Cl |
| 7.279 | Et | Et | H | SO$_2$Et | 2 | 0 | 2,6-diCl |
| 7.280 | Et | Et | H | SO$_2$Et | 2 | 0 | 2,6-diMe |
| 7.281 | Et | Et | H | SO$_2$Et | 2 | 0 | 2-Me,6-Et |
| 7.282 | Et | Et | H | SO$_2$Et | 2 | 0 | 2,6-diEt |
| 7.283 | Et | Et | H | SO$_2$Et | 2 | 0 | 2-Me,6-Cl |
| 7.284 | Et | Et | H | OMe | 2 | 0 | 2,6-diCl |
| 7.285 | Et | Et | H | OMe | 2 | 0 | 2,6-diMe |
| 7.286 | Et | Et | H | OMe | 2 | 0 | 2-Me,6-Et |
| 7.287 | Et | Et | H | OMe | 2 | 0 | 2,6-diEt |
| 7.288 | Et | Et | H | OMe | 2 | 0 | 2-Me,6-Cl |
| 7.289 | Et | Et | H | OCHF$_2$ | 2 | 0 | 2-Me,6-Cl |
| 7.290 | Et | Et | H | OCHF$_2$ | 2 | 0 | 2-Me,6-Et |
| 7.291 | Et | Et | H | OCH$_2$OMe | 2 | 0 | 2-Me,6-Cl |
| 7.292 | Et | Et | H | OCH$_2$OMe | 2 | 0 | 2-Me,6-Et |
| 7.293 | Et | Et | H | CH$_2$F | 2 | 0 | 2,6-diCl |
| 7.294 | Et | Et | H | CH$_2$F | 2 | 0 | 2,6-diMe |
| 7.295 | Et | Et | H | CH$_2$F | 2 | 0 | 2-Me,6-Et |
| 7.296 | Et | Et | H | CH$_2$F | 2 | 0 | 2,6-diEt |
| 7.297 | Et | Et | H | CH$_2$F | 2 | 0 | 2-Me,6-Cl |
| 7.298 | Et | Et | H | CHF$_2$ | 2 | 0 | 2,6-diCl |
| 7.299 | Et | Et | H | CHF$_2$ | 2 | 0 | 2,6-diMe |
| 7.300 | Et | Et | H | CHF$_2$ | 0 | 0 | 2-Me,6-Et |
| 7.301 | Et | Et | H | CHF$_2$ | 2 | 0 | 2-Me,6-Et |
| 7.302 | Et | Et | H | CHF$_2$ | 2 | 0 | 2,6-diEt |
| 7.303 | Et | Et | H | CHF$_2$ | 2 | 0 | 2-Me,6-Cl |
| 7.304 | Et | Et | H | SO$_2$NMe$_2$ | 2 | 0 | 2,6-diCl |
| 7.305 | Et | Et | H | SO$_2$NMe$_2$ | 2 | 0 | 2,6-diMe |
| 7.306 | Et | Et | H | SO$_2$NMe$_2$ | 2 | 0 | 2-Me,6-Et |
| 7.307 | Et | Et | H | SO$_2$NMe$_2$ | 2 | 0 | 2,6-diEt |
| 7.308 | Et | Et | H | SO$_2$NMe$_2$ | 2 | 0 | 2-Me,6-Cl |
| 7.309 | Et | Et | H | CONMe$_2$ | 2 | 0 | 2,6-diCl |
| 7.310 | Et | Et | H | CONMe$_2$ | 2 | 0 | 2,6-diMe |
| 7.311 | Et | Et | H | CONMe$_2$ | 0 | 0 | 2-Me,6-Et |
| 7.312 | Et | Et | H | CONMe$_2$ | 2 | 0 | 2-Me,6-Et |
| 7.313 | Et | Et | H | CONMe$_2$ | 2 | 0 | 2,6-diEt |
| 7.314 | Et | Et | H | CONMe$_2$ | 2 | 0 | 2-Me,6-Cl |
| 7.315 | Et | Et | H | COMe | 2 | 0 | 2,6-diCl |
| 7.316 | Et | Et | H | COMe | 2 | 0 | 2,6-diMe |
| 7.317 | Et | Et | H | COMe | 2 | 0 | 2-Me,6-Et |
| 7.318 | Et | Et | H | COMe | 2 | 0 | 2,6-diEt |
| 7.319 | Et | Et | H | COMe | 2 | 0 | 2-Me,6-Cl |
| 7.320 | Et | Et | H | COCH$_2$Cl | 2 | 0 | 2-Me,6-Cl |
| 7.321 | Et | Et | H | COCH$_2$Cl | 2 | 0 | 2-Me,6-Et |
| 7.322 | Et | Et | H | COCH$_2$OMe | 2 | 0 | 2-Me,6-Cl |
| 7.323 | Et | Et | H | COCH$_2$OMe | 2 | 0 | 2-Me,6-Et |
| 7.324 | Et | Et | H | CH$_2$Cl | 2 | 0 | 2,6-diCl |
| 7.325 | Et | Et | H | CH$_2$Cl | 2 | 0 | 2,6-diMe |
| 7.326 | Et | Et | H | CH$_2$Cl | 2 | 0 | 2-Me,6-Et |
| 7.327 | Et | Et | H | CH$_2$Cl | 2 | 0 | 2,6-diEt |
| 7.328 | Et | Et | H | CH$_2$Cl | 2 | 0 | 2-Me,6-Cl |
| 7.329 | Et | Et | SMe | Cl | 2 | 0 | 2-Me,6-Et |
| 7.330 | Et | Et | SEt | Br | 2 | 0 | 2-Me,6-Cl |
| 7.331 | Et | Et | H | F | 0 | 0 | 2,6-diF |
| 7.332 | Et | Et | H | F | 0 | 0 | 2-Cl,6-F |
| 7.333 | Et | Et | H | F | 0 | 0 | 2-iPr,6-Me |
| 7.334 | Et | Pr | H | F | 0 | 0 | 2,6-diMe |
| 7.335 | Pr | Pr | H | F | 0 | 0 | 2,6-diMe |

TABLE 7-continued

| Cpd. No. | R¹ | R² | A | B | n | m | $X_k$ |
|---|---|---|---|---|---|---|---|
| 7.336 | Me | Me | H | Cl | 2 | 0 | 2,6-diF |
| 7.337 | Me | Me | H | Cl | 0 | 0 | 2,6-diF |
| 7.338 | Et | Pr | H | Cl | 2 | 0 | 2,6-diF |
| 7.339 | Et | Pr | H | Cl | 0 | 0 | 2,6-diF |
| 7.340 | Pr | Pr | H | Cl | 2 | 0 | 2,6-diF |
| 7.341 | Et | Et | H | OMe | 2 | 0 | 2-Me,6-Et |
| 7.342 | Et | Et | Me | H | 0 | 0 | 2-Cl,6-Me |

TABLE 8

| Cpd. No. | R¹ | R² | A | B | n | m | $X_k$ |
|---|---|---|---|---|---|---|---|
| 8.1 | Et | Et | H | H | 2 | 0 | 3-Cl,4-F |
| 8.2 | Et | Et | H | H | 0 | 0 | 3-Cl,4-F |
| 8.3 | Et | Et | H | H | 0 | 0 | 3-Cl,4-OMe |
| 8.4 | Et | Et | H | H | 2 | 0 | 3-Cl,4-OMe |
| 8.5 | Et | Et | H | H | 2 | 0 | 3,4-diCl |
| 8.6 | Et | Et | H | H | 0 | 0 | 3,4-diCl |
| 8.7 | Et | Et | H | H | 2 | 0 | 3,4-diMe |
| 8.8 | Et | Et | H | H | 0 | 0 | 3,4-diMe |
| 8.9 | Et | Et | H | H | 2 | 0 | 3-Me,4-Br |
| 8.10 | Et | Et | H | H | 0 | 0 | 3-Me,4-Br |
| 8.11 | Et | Et | H | H | 0 | 0 | 3-CF₃,4-F |
| 8.12 | Et | Et | H | H | 2 | 0 | 3-CF₃,4-F |
| 8.13 | Et | Et | H | H | 2 | 0 | 3,4-diF |
| 8.14 | Et | Et | H | H | 2 | 0 | 3-Cl,4-Me |
| 8.15 | Et | Et | H | H | 2 | 0 | 3-NO₂,4-Cl |
| 8.16 | Et | Et | H | Cl | 0 | 0 | 3,4-diCl |
| 8.17 | Et | Et | H | Cl | 2 | 0 | 3,4-diCl |
| 8.18 | Me | Me | H | Cl | 2 | 0 | 3-CF₃,4-F |
| 8.19 | Me | Et | H | Cl | 2 | 0 | 3-CF₃,4-F |
| 8.20 | Et | Et | H | Cl | 0 | 0 | 3-CF₃,4-F |
| 8.21 | Et | Et | H | Cl | 2 | 0 | 3-CF₃,4-F |
| 8.22 | Et | Et | H | Cl | 0 | 0 | 3-Cl,4-F |
| 8.23 | Et | Et | H | Cl | 2 | 0 | 3-Cl,4-F |
| 8.24 | Et | Et | H | Cl | 2 | 0 | 3,4-diF |
| 8.25 | Et | Et | H | Cl | 2 | 0 | 3,4-diMe |
| 8.26 | Et | Et | H | Br | 0 | 0 | 3-CF₃,4-F |
| 8.27 | Et | Et | H | Br | 2 | 0 | 3-CF₃,4-F |
| 8.28 | Et | Et | H | Br | 0 | 0 | 3,4-diCl |
| 8.29 | Et | Et | H | Br | 2 | 0 | 3,4-diCl |
| 8.30 | Et | Et | H | Br | 0 | 0 | 3-Cl,4-F |
| 8.31 | Et | Et | H | Br | 2 | 0 | 3-Cl,4-F |
| 8.32 | Et | Et | H | F | 2 | 0 | 3-CF₃,4-F |
| 8.33 | Et | Et | H | F | 2 | 0 | 3,4-diF |
| 8.34 | Et | Et | H | F | 2 | 0 | 3,4-diCl |
| 8.35 | Et | Et | H | F | 2 | 0 | 3-Cl,4-F |
| 8.36 | Et | Et | H | F | 2 | 0 | 3,4-diMe |
| 8.37 | Me | Me | H | F | 2 | 0 | 3-CF₃,4-F |
| 8.38 | Me | Me | H | F | 2 | 0 | 3,4-diF |
| 8.39 | Me | Me | H | F | 2 | 0 | 3,4-diCl |
| 8.40 | Me | Me | H | F | 2 | 0 | 3-Cl,4-F |
| 8.41 | Me | Et | H | F | 2 | 0 | 3-CF₃,4-F |
| 8.42 | Me | Et | H | F | 2 | 0 | 3,4-diF |
| 8.43 | Me | Et | H | F | 2 | 0 | 3,4-diCl |
| 8.44 | Me | Et | H | F | 2 | 0 | 3-Cl,4-F |
| 8.45 | Et | Pr | H | F | 2 | 0 | 3-CF₃,4-F |
| 8.46 | Et | Pr | H | F | 2 | 0 | 3,4-diF |
| 8.47 | Et | Pr | H | F | 2 | 0 | 3,4-diCl |
| 8.48 | Et | Pr | H | F | 2 | 0 | 3-Cl,4-F |
| 8.49 | Pr | Pr | H | F | 2 | 0 | 3-CF₃,4-F |
| 8.50 | Pr | Pr | H | F | 2 | 0 | 3,4-diF |
| 8.51 | Pr | Pr | H | F | 2 | 0 | 3,4-diCl |
| 8.52 | Pr | Pr | H | F | 2 | 0 | 3-Cl,4-F |
| 8.53 | All | All | H | F | 2 | 0 | 3-CF₃,4-F |
| 8.54 | All | All | H | F | 2 | 0 | 3,4-diF |
| 8.55 | All | All | H | F | 2 | 0 | 3,4-diCl |
| 8.56 | All | All | H | F | 2 | 0 | 3-Cl,4-F |
| 8.57 | Et | Et | H | F | 0 | 0 | 3-Cl,4-F |

TABLE 9

| Cpd. No. | R¹ | R² | A | B | n | m | $X_k$ |
|---|---|---|---|---|---|---|---|
| 9.1 | Et | Et | H | H | 2 | 0 | 3,5-diCl |
| 9.2 | Et | Et | H | H | 2 | 1 | 3,5-diCl |
| 9.3 | Et | Et | H | H | 0 | 0 | 3,5-diCl |
| 9.4 | Et | Et | H | H | 2 | 0 | 3,5-diBr |
| 9.5 | Et | Et | H | H | 0 | 0 | 3,5-diBr |
| 9.6 | Et | Et | H | H | 2 | 0 | 3,5-diMe |
| 9.7 | Et | Et | H | H | 0 | 0 | 3,5-diMe |
| 9.8 | Et | Et | H | H | 2 | 0 | 3,5-diF |
| 9.9 | Et | Et | H | H | 0 | 0 | 3,5-diF |
| 9.10 | Et | Et | H | H | 0 | 0 | 3,5-diMeO |
| 9.11 | Et | Et | H | H | 2 | 0 | 3,5-diMeO |
| 9.12 | Et | Et | H | H | 2 | 0 | 3-Me,5-Cl |
| 9.13 | Me | H | H | H | 0 | 0 | 3,5-diCl |
| 9.14 | Pr | Pr | H | H | 2 | 0 | 3,5-diCl |
| 9.15 | Pr | Pr | H | H | 2 | 0 | 3,5-diMe |
| 9.16 | Pr | Pr | H | H | 2 | 0 | 3,5-diF |
| 9.17 | Pr | Pr | H | H | 2 | 0 | 3,5-diMeO |
| 9.18 | Et | Pr | H | H | 2 | 0 | 3,5-diCl |
| 9.19 | Et | Pr | H | H | 2 | 0 | 3,5-diMe |
| 9.20 | Et | Pr | H | H | 2 | 0 | 3,5-diF |
| 9.21 | Et | Pr | H | H | 2 | 0 | 3,5-diMeO |
| 9.22 | Me | Me | H | H | 2 | 0 | 3,5-diCl |
| 9.23 | Me | Me | H | H | 2 | 0 | 3,5-diMe |
| 9.24 | Me | Me | H | H | 2 | 0 | 3,5-diF |
| 9.25 | Me | Me | H | H | 2 | 0 | 3,5-diMeO |
| 9.26 | Me | Et | H | H | 2 | 0 | 3,5-diCl |
| 9.27 | Me | Bu | H | H | 2 | 0 | 3,5-diCl |
| 9.28 | Me | Bu | H | H | 2 | 0 | 3,5-diMe |
| 9.29 | Et | Bu | H | H | 2 | 0 | 3,5-diCl |
| 9.30 | Et | Bu | H | H | 2 | 0 | 3,5-diMe |
| 9.31 | Et | 2-ClEt | H | H | 2 | 0 | 3,5-diCl |
| 9.32 | Et | 2-MeOEt | H | H | 2 | 0 | 3,5-diCl |
| 9.33 | Et | 2-ClAll | H | H | 2 | 0 | 3,5-diCl |

TABLE 9-continued

| Cpd. No. | R¹ | R² | A | B | n | m | $X_k$ |
|---|---|---|---|---|---|---|---|
| 9.34 | All | All | H | H | 2 | 0 | 3,5-diCl |
| 9.35 | All | All | H | H | 2 | 0 | 3,5-diMe |
| 9.36 | Prg | Prg | H | H | 2 | 0 | 3,5-diCl |
| 9.37 | | (CH₂)₄ | H | H | 2 | 0 | 3,5-diCl |
| 9.38 | | (CH₂)₅ | H | H | 2 | 0 | 3,5-diCl |
| 9.39 | | (CH₂)₆ | H | H | 2 | 0 | 3,5-diCl |
| 9.40 | Me | 2-MePh | H | H | 2 | 0 | 3,5-diCl |
| 9.41 | Me | 3-MePh | H | H | 2 | 0 | 3,5-diCl |
| 9.42 | Me | 2-ClPh | H | H | 2 | 0 | 3,5-diCl |
| 9.43 | Me | 3-ClPh | H | H | 2 | 0 | 3,5-diCl |
| 9.44 | Me | 4-ClPh | H | H | 2 | 0 | 3,5-diCl |
| 9.45 | Et | 3-ClPh | H | H | 2 | 0 | 3,5-diCl |
| 9.46 | iPr | 4-ClPh | H | H | 2 | 0 | 3,5-diCl |
| 9.47 | Me | 5-Cl-2-Pyr | H | H | 2 | 0 | 3,5-diCl |
| 9.48 | Et | Et | Cl | H | 2 | 0 | 3,5-diCl |
| 9.49 | Et | Et | H | Cl | 2 | 0 | 3,5-diCl |
| 9.50 | Et | Et | H | Cl | 0 | 0 | 3,5-diCl |
| 9.51 | Et | Et | H | Cl | 2 | 0 | 3,5-diMe |
| 9.52 | Et | Et | H | Cl | 0 | 0 | 3,5-diMeO |
| 9.53 | Et | Et | H | Cl | 2 | 0 | 3,5-diMeO |
| 9.54 | Et | Et | H | Cl | 2 | 0 | 3,5-di(CF₃O) |
| 9.55 | Et | Et | H | Cl | 0 | 0 | 3,5-diF |
| 9.56 | Et | Et | H | Cl | 2 | 0 | 3,5-diF |
| 9.57 | Et | Et | H | Cl | 0 | 0 | 3,5-diBr |
| 9.58 | Et | Et | H | Cl | 2 | 0 | 3,5-diBr |
| 9.59 | Me | 2-MePh | H | Cl | 2 | 0 | 3,5-diCl |
| 9.60 | Me | 3-MePh | H | Cl | 2 | 0 | 3,5-diCl |
| 9.61 | Me | 2-ClPh | H | Cl | 2 | 0 | 3,5-diCl |
| 9.62 | Me | 3-ClPh | H | Cl | 2 | 0 | 3,5-diCl |
| 9.63 | Me | 4-ClPh | H | Cl | 2 | 0 | 3,5-diCl |
| 9.64 | Et | 3-ClPh | H | Cl | 2 | 0 | 3,5-diCl |
| 9.65 | iPr | 4-ClPh | H | Cl | 2 | 0 | 3,5-diCl |
| 9.66 | Me | 2,4-diClPh | H | Cl | 2 | 0 | 3,5-diCl |
| 9.67 | Me | 2,5-diClPh | H | Cl | 2 | 0 | 3,5-diCl |
| 9.68 | Me | 2,4,5-triClPh | H | Cl | 2 | 0 | 3,5-diCl |
| 9.69 | Me | 2,4-diCl-3-MePh | H | Cl | 2 | 0 | 3,5-diCl |
| 9.70 | Et | 4-OMePh | H | Cl | 2 | 0 | 3,5-diCl |
| 9.71 | Et | 3-Cl-4-OMePh | H | Cl | 2 | 0 | 3,5-diCl |
| 9.72 | Me | 5-Cl-2-Pyr | H | Cl | 2 | 0 | 3,5-diCl |
| 9.73 | Me | 3,5-diCl-2-Pyr | H | Cl | 2 | 0 | 3,5-diCl |
| 9.74 | Me | 4-Cl-5-Me-2-Pyr | H | Cl | 2 | 0 | 3,5-diCl |
| 9.75 | Me | 4-OMe-2-Pyr | H | Cl | 2 | 0 | 3,5-diCl |
| 9.76 | Et | Et | H | Br | 0 | 0 | 3,5-diCl |
| 9.77 | Et | Et | H | Br | 2 | 0 | 3,5-diCl |
| 9.78 | Et | Et | H | Br | 2 | 0 | 3,5-diMe |
| 9.79 | Et | Et | H | Br | 2 | 0 | 3,5-diMeO |
| 9.80 | Et | Et | H | Br | 0 | 0 | 3,5-diF |
| 9.81 | Et | Et | H | Br | 2 | 0 | 3,5-diF |
| 9.82 | Et | Et | H | Br | 0 | 0 | 3,5-diBr |
| 9.83 | Et | Et | H | Br | 2 | 0 | 3,5-diBr |
| 9.84 | Et | Et | H | F | 2 | 0 | 3,5-diCl |
| 9.85 | Et | Et | H | F | 2 | 0 | 3,5-diMe |
| 9.86 | Et | Et | H | F | 2 | 0 | 3,5-diMeO |
| 9.87 | Et | Et | H | F | 2 | 0 | 3,5-di(CF₃O) |
| 9.88 | Et | Et | H | F | 2 | 0 | 3,5-diF |
| 9.89 | Me | Me | H | F | 2 | 0 | 3,5-diCl |
| 9.90 | Me | Me | H | F | 2 | 0 | 3,5-diMe |
| 9.91 | Me | Me | H | F | 2 | 0 | 3,5-diMeO |
| 9.92 | Me | Me | H | F | 2 | 0 | 3,5-diF |
| 9.93 | Me | Et | H | F | 2 | 0 | 3,5-diCl |
| 9.94 | Me | Et | H | F | 2 | 0 | 3,5-diMe |
| 9.95 | Me | Et | H | F | 2 | 0 | 3,5-diMeO |
| 9.96 | Me | Et | H | F | 2 | 0 | 3,5-diF |
| 9.97 | Et | Pr | H | F | 2 | 0 | 3,5-diCl |
| 9.98 | Et | Pr | H | F | 2 | 0 | 3,5-diMe |
| 9.99 | Et | Pr | H | F | 2 | 0 | 3,5-diMeO |
| 9.100 | Et | Pr | H | F | 2 | 0 | 3,5-diF |
| 9.101 | Pr | Pr | H | F | 2 | 0 | 3,5-diCl |
| 9.102 | Pr | Pr | H | F | 2 | 0 | 3,5-diMe |
| 9.103 | Pr | Pr | H | F | 2 | 0 | 3,5-diMeO |
| 9.104 | Pr | Pr | H | F | 2 | 0 | 3,5-diF |
| 9.105 | All | All | H | F | 2 | 0 | 3,5-diCl |
| 9.106 | All | All | H | F | 2 | 0 | 3,5-diMe |
| 9.107 | All | All | H | F | 2 | 0 | 3,5-diMeO |
| 9.108 | All | All | H | F | 2 | 0 | 3,5-diF |
| 9.109 | Et | Et | H | Me | 2 | 0 | 3,5-diCl |
| 9.110 | Et | Et | H | Me | 2 | 0 | 3,5-diMe |
| 9.111 | Et | Et | H | All | 2 | 0 | 3,5-diCl |
| 9.112 | Et | Et | H | 2-ClAll | 2 | 0 | 3,5-diCl |
| 9.113 | Et | Et | H | CH₂OMe | 2 | 0 | 3,5-diCl |

TABLE 9-continued

| Cpd. No. | R¹ | R² | A | B | n | m | $X_k$ |
|---|---|---|---|---|---|---|---|
| 9.114 | Et | Et | H | CH₂OMe | 2 | 0 | 3,5-diMe |
| 9.115 | Et | Et | H | CH₂F | 2 | 0 | 3,5-diCl |
| 9.116 | Et | Et | H | CH₂F | 2 | 0 | 3,5-diMe |
| 9.117 | Et | Et | H | CHF₂ | 0 | 0 | 3,5-diCl |
| 9.118 | Et | Et | H | CHF₂ | 2 | 0 | 3,5-diCl |
| 9.119 | Et | Et | H | CHF₂ | 2 | 0 | 3,5-diMe |
| 9.120 | Et | Et | H | CF₃ | 2 | 0 | 3,5-diCl |
| 9.121 | Et | Et | H | CF₃ | 2 | 0 | 3,5-diMe |
| 9.122 | Et | Et | H | CN | 0 | 0 | 3,5-diCl |
| 9.123 | Et | Et | H | CN | 2 | 0 | 3,5-diCl |
| 9.124 | Et | Et | H | CN | 2 | 0 | 3,5-diMe |
| 9.125 | Et | Et | H | CN | 0 | 0 | 3,5-diF |
| 9.126 | Et | Et | H | CN | 2 | 0 | 3,5-diF |
| 9.127 | Et | Et | H | COOEt | 2 | 0 | 3,5-diCl |
| 9.128 | Et | Et | H | COOEt | 2 | 0 | 3,5-diMe |
| 9.129 | Et | Et | H | SEt | 2 | 0 | 3,5-diCl |
| 9.130 | Et | Et | H | SEt | 2 | 0 | 3,5-diMe |
| 9.131 | Et | Et | H | SMe | 0 | 0 | 3,5-diCl |
| 9.132 | Et | Et | H | SO₂Me | 2 | 0 | 3,5-diCl |
| 9.133 | Et | Et | H | SO₂Et | 2 | 0 | 3,5-diMe |
| 9.134 | Et | Et | H | OMe | 2 | 0 | 3,5-diCl |
| 9.135 | Et | Et | H | OMe | 2 | 0 | 3,5-diMe |
| 9.136 | Et | Et | H | OCHF₂ | 2 | 0 | 3,5-diCl |
| 9.137 | Et | Et | H | OCH₂OMe | 2 | 0 | 3,5-diCl |
| 9.138 | Et | Et | H | Me | 2 | 0 | 3,5-diCl |
| 9.139 | Et | Et | H | CH₂Cl | 2 | 0 | 3,5-diMe |
| 9.140 | Et | Et | H | CH₂Cl | 2 | 0 | 3,5-diMeO |
| 9.141 | Et | Et | H | CH₂Cl | 2 | 0 | 3,5-diF |

TABLE 10

| Cpd. No. | R¹ | R² | A | B | n | m | $X_k$ |
|---|---|---|---|---|---|---|---|
| 10.1 | Et | Et | H | H | 2 | 0 | 2,4,6-triMe |
| 10.2 | Et | Et | H | H | 0 | 0 | 2,4,6-triMe |
| 10.3 | Me | Me | H | H | 0 | 0 | 2,4,6-triMe |
| 10.4 | Me | Me | H | H | 2 | 0 | 2,4,6-triMe |
| 10.5 | Et | Et | H | H | 2 | 0 | 2,6-diMe,4-OiPr |
| 10.6 | Et | Et | H | H | 2 | 0 | 2,6-diMe,4-Br |
| 10.7 | Et | Et | H | H | 2 | 0 | 2,6-diMe,4-Cl |
| 10.8 | Et | Et | H | H | 2 | 0 | 2,6-diCl,4-Me |
| 10.9 | Et | Et | H | H | 2 | 0 | 2,6-diMe,4-OMe |
| 10.10 | Et | Et | H | H | 2 | 0 | 2,6-diMeO,4-Me |
| 10.11 | Et | Et | H | H | 2 | 0 | 2,6-diCl,4-tBu |
| 10.12 | Et | Et | H | H | 2 | 0 | 2,4-diMe,6-OMe |
| 10.13 | Et | Et | H | H | 0 | 0 | 2,6-diMe,3-Cl |
| 10.14 | Et | Et | H | H | 2 | 0 | 2,6-diMe,3-Cl |
| 10.15 | Et | Et | H | H | 0 | 0 | 2,6-diMe,3,5-diCl |
| 10.16 | Et | Et | H | H | 2 | 0 | 2,6-diMe,3,5-diCl |
| 10.17 | Et | Et | H | H | 0 | 0 | 2-F,4-Cl,5-OMe |
| 10.18 | Et | Et | H | H | 2 | 0 | 2-F,4-Cl,5-OMe |
| 10.19 | Et | Et | H | H | 2 | 0 | 3,5-diMeO,4-Cl |
| 10.20 | Et | Et | H | H | 2 | 0 | 3,5-diMeO,2-Cl |
| 10.21 | Et | Et | H | H | 2 | 0 | 3,5-diMeO,2-Br |
| 10.22 | Et | Et | H | H | 2 | 0 | 2,4,6-triMe,3-Cl |
| 10.23 | Et | Et | H | H | 2 | 0 | 2,6-diCl,3-Me |
| 10.24 | Et | Et | H | H | 0 | 0 | 2,6-diCl,3-Me |
| 10.25 | Et | Et | H | H | 2 | 0 | 2,3,4,5,6-F₅ |
| 10.26 | Et | Et | H | H | 0 | 0 | 2,3,4,5,6-F₅ |
| 10.27 | Et | Et | H | H | 2 | 0 | 2,3-diMe,6-Cl |
| 10.28 | Et | Et | H | H | 2 | 0 | 2,4-diCl,3-Me |
| 10.29 | Et | Et | H | H | 2 | 0 | 2,5-diCl,3-COOEt |
| 10.30 | Pr | Pr | H | H | 2 | 0 | 2,6-diCl,3-Me |
| 10.31 | Pr | Pr | H | H | 2 | 0 | 2,3-diMe,6-Cl |
| 10.32 | Et | Pr | H | H | 2 | 0 | 2,6-diCl,3-Me |
| 10.33 | Et | Pr | H | H | 2 | 0 | 2,3-diMe,6-Cl |
| 10.34 | Me | Me | H | H | 2 | 0 | 2,6-diCl,3-Me |
| 10.35 | Me | Me | H | H | 2 | 0 | 2,3-diMe,6-Cl |
| 10.36 | Me | Bu | H | H | 2 | 0 | 2,6-diCl,3-Me |
| 10.37 | Me | Bu | H | H | 2 | 0 | 2,3-diMe,6-Cl |
| 10.38 | Et | Bu | H | H | 2 | 0 | 2,6-diCl,3-Me |
| 10.39 | Et | Bu | H | H | 2 | 0 | 2,3-diMe,6-Cl |
| 10.40 | H | Et | H | H | 2 | 0 | 2,4,6-triMe |
| 10.41 | Me | Et | H | H | 2 | 0 | 2,4,6-triMe |
| 10.42 | Et | 2-BrEt | H | H | 2 | 0 | 2,4,6-triMe |
| 10.43 | Et | 2-MeOEt | H | H | 2 | 0 | 2,4,6-triMe |
| 10.44 | Et | 2-ClAll | H | H | 2 | 0 | 2,4,6-triMe |
| 10.45 | (CH₂)₄ | | H | H | 2 | 0 | 2,4,6-triMe |

TABLE 10-continued

| Cpd. No. | R¹ | R² | A | B | n | m | $X_k$ |
|---|---|---|---|---|---|---|---|
| 10.46 | Pr | Pr | H | H | 2 | 0 | 2,4,6-triMe |
| 10.47 | Et | Pr | H | H | 2 | 0 | 2,4,6-triMe |
| 10.48 | Me | Bu | H | H | 2 | 0 | 2,4,6-triMe |
| 10.49 | Et | Bu | H | H | 2 | 0 | 2,4,6-triMe |
| 10.50 | All | All | H | H | 2 | 0 | 2,4,6-triMe |
| 10.51 | Et | Et | H | H | 2 | 0 | 3,5-diMeO,4-I |
| 10.52 | Et | Et | H | H | 2 | 0 | 3,5-diMeO,2-I |
| 10.53 | Me | Me | H | Cl | 2 | 0 | 2,4,6-triMe |
| 10.54 | Me | Et | H | Cl | 2 | 0 | 2,4,6-triMe |
| 10.55 | Et | Et | H | Cl | 0 | 0 | 2,4,6-triMe |
| 10.56 | Et | Et | H | Cl | 2 | 0 | 2,4,6-triMe |
| 10.57 | Et | Pr | H | Cl | 2 | 0 | 2,4,6-triMe |
| 10.58 | Pr | Pr | H | Cl | 2 | 0 | 2,4,6-triMe |
| 10.59 | Me | Bu | H | Cl | 2 | 0 | 2,4,6-triMe |
| 10.60 | Me | OMe | H | Cl | 2 | 0 | 2,4,6-triMe |
| 10.61 | Et | Et | H | Cl | 0 | 0 | 2,6-diMe,3-Cl |
| 10.62 | Et | Et | H | Cl | 2 | 0 | 2,6-diMe,3-Cl |
| 10.63 | Et | Et | H | Cl | 0 | 0 | 2,6-diMe,3,5-diCl |
| 10.64 | Et | Et | H | Cl | 2 | 0 | 2,6-diMe,3,5-diCl |
| 10.65 | Et | Et | H | Cl | 0 | 0 | 2,6-diMe,4-Br |
| 10.66 | Et | Et | H | Cl | 2 | 0 | 2,6-diMe,4-Br |
| 10.67 | Et | Et | H | Cl | 2 | 0 | 2,4,6-triCl |
| 10.68 | Et | Et | H | Cl | 2 | 0 | 2,4,5-triCl |
| 10.69 | Et | Et | H | Cl | 0 | 0 | 2-F,4-Cl,5-OMe |
| 10.70 | Et | Et | H | Cl | 2 | 0 | 2-F,4-Cl,5-OMe |
| 10.71 | Et | Et | H | Cl | 2 | 0 | 2-F,4-Cl,5-OCF₃ |
| 10.72 | Et | Et | H | Cl | 0 | 0 | 2-F,4-Cl,5-OiPr |
| 10.73 | Et | Et | H | Cl | 2 | 0 | 2-F,4-Cl,5-OiPr |
| 10.74 | Et | Et | H | Cl | 2 | 0 | 2,4,6-triMe,3-Cl |
| 10.75 | Et | Et | H | H | 2 | 0 | 2,4,6-triMe,3,5-diCl |
| 10.76 | Et | Et | H | Cl | 2 | 0 | 2,4,6-triMe,3,5-diCl |
| 10.77 | Et | Et | H | Cl | 2 | 0 | 2,6-diCl,3-Me |
| 10.78 | Et | Et | H | Cl | 2 | 0 | 2,3-diMe,6-Cl |
| 10.79 | Et | Et | H | H | 0 | 0 | 2,4,6-triMe,3,5-diCl |
| 10.80 | Et | Et | H | Cl | 0 | 0 | 2,4,6-triMe,3,5-diCl |
| 10.81 | Et | Et | H | Cl | 2 | 0 | 2,6-diMeO,4-Me |
| 10.82 | Et | Et | H | Cl | 2 | 0 | 2,6-diMe,4-OMe |
| 10.83 | Me | Me | H | F | 2 | 0 | 2,4,6-triMe |
| 10.84 | Me | Et | H | F | 2 | 0 | 2,4,6-triMe |
| 10.85 | Et | Et | H | F | 2 | 0 | 2,4,6-triMe |
| 10.86 | Et | Pr | H | F | 2 | 0 | 2,4,6-triMe |
| 10.87 | Et | Et | H | F | 2 | 0 | 2,6-diCl,3-Me |
| 10.88 | Et | Et | H | F | 2 | 0 | 2,3-diMe,6-Cl |
| 10.89 | Et | Et | H | F | 2 | 0 | 2,4,6-triMe,3,5-diCl |
| 10.90 | Et | Et | H | F | 2 | 0 | 2,6-diMe,3-Cl |
| 10.91 | Et | Et | H | F | 2 | 0 | 2-F,4-Cl,5-OCF₃ |
| 10.92 | Et | Et | H | F | 2 | 0 | 2,4,6-triCl |
| 10.93 | Et | Et | H | F | 2 | 0 | 2,6-diMe,4-Br |
| 10.94 | Et | Et | H | F | 2 | 0 | 2-Cl,4-CF₃ |
| 10.95 | Et | Et | H | F | 2 | 0 | 2,6-diMe,4-OMe |
| 10.96 | Me | Me | H | F | 2 | 0 | 2,4,6-triMe |
| 10.97 | Me | Me | H | F | 2 | 0 | 2,6-diCl,3-Me |
| 10.98 | Me | Me | H | F | 2 | 0 | 2,4,6-triCl |
| 10.99 | Me | Me | H | F | 2 | 0 | 2,6-diMe,4-Br |
| 10.100 | Me | Et | H | F | 2 | 0 | 2,4,6-triMe |
| 10.101 | Me | Et | H | F | 2 | 0 | 2,6-diCl,3-Me |
| 10.102 | Me | Et | H | F | 2 | 0 | 2,4,6-triCl |
| 10.103 | Me | Et | H | F | 2 | 0 | 2,6-diMe,4-Br |
| 10.104 | Et | Pr | H | F | 2 | 0 | 2,4,6-triMe |
| 10.105 | Et | Pr | H | F | 2 | 0 | 2,6-diCl,3-Me |
| 10.106 | Et | Pr | H | F | 2 | 0 | 2,4,6-triCl |
| 10.107 | Et | Pr | H | F | 2 | 0 | 2,6-diMe,4-Br |
| 10.108 | Pr | Pr | H | F | 2 | 0 | 2,4,6-triMe |
| 10.109 | Pr | Pr | H | F | 2 | 0 | 2,6-diCl,3-Me |
| 10.110 | Pr | Pr | H | F | 2 | 0 | 2,4,6-triCl |
| 10.111 | Pr | Pr | H | F | 2 | 0 | 2,6-diMe,4-Br |
| 10.112 | All | All | H | F | 2 | 0 | 2,4,6-triMe |
| 10.113 | All | All | H | F | 2 | 0 | 2,6-diCl,3-Me |
| 10.114 | All | All | H | F | 2 | 0 | 2,4,6-triCl |
| 10.115 | All | All | H | F | 2 | 0 | 2,6-diMe,4-Br |
| 10.116 | Et | Et | H | Br | 0 | 0 | 2,4,6-triMe |
| 10.117 | Et | Et | H | Br | 2 | 0 | 2,4,6-triMe |
| 10.118 | Et | Et | H | Br | 2 | 0 | 2,3-diMe,4-Br |
| 10.119 | Et | Et | H | Br | 2 | 0 | 2,4,6-triCl |
| 10.120 | Et | Et | H | Br | 2 | 0 | 2,6-diCl,3-Me |
| 10.121 | Et | Et | H | Br | 2 | 0 | 2,3-diMe,6-Cl |
| 10.122 | Et | Et | H | I | 2 | 0 | 2,4,6-triMe |
| 10.123 | Et | Et | H | I | 2 | 0 | 2,6-diCl,3-Me |
| 10.124 | Et | Et | H | I | 2 | 0 | 2,3-diMe,6-Cl |
| 10.125 | Et | Et | H | Me | 2 | 0 | 2,4,6-triMe |

TABLE 10-continued

| Cpd. No. | R¹ | R² | A | B | n | m | $X_k$ |
|---|---|---|---|---|---|---|---|
| 10.126 | Et | Et | H | Me | 2 | 0 | 2,6-diCl,3-Me |
| 10.127 | Et | Et | H | Me | 2 | 0 | 2,3-diMe,6-Cl |
| 10.128 | Et | Et | H | CH₂Cl | 2 | 0 | 2,4,6-triMe |
| 10.129 | Et | Et | H | CH₂Cl | 2 | 0 | 2,6-diCl,3-Me |
| 10.130 | Et | Et | H | CH₂Cl | 2 | 0 | 2,3-diMe,6-Cl |
| 10.131 | Et | Et | H | CH₂F | 2 | 0 | 2,4,6-triMe |
| 10.132 | Et | Et | H | CHF₂ | 2 | 0 | 2,4,6-triMe |
| 10.133 | Et | Et | H | CH₂F | 2 | 0 | 2,6-diCl,3-Me |
| 10.134 | Et | Et | H | CH₂F | 2 | 0 | 2,3-diMe,6-Cl |
| 10.135 | Et | Et | H | CHF₂ | 2 | 0 | 2,6-diCl,3-Me |
| 10.136 | Et | Et | H | CHF₂ | 2 | 0 | 2,3-diMe,6-Cl |
| 10.137 | Et | Et | H | CF₃ | 2 | 0 | 2,4,6-triMe |
| 10.138 | Et | Et | H | CF₃ | 2 | 0 | 2,6-diCl,3-Me |
| 10.139 | Et | Et | H | CF₃ | 2 | 0 | 2,3-diMe,6-Cl |
| 10.140 | Et | Et | H | CN | 0 | 0 | 2,4,6-triMe |
| 10.141 | Et | Et | H | CN | 2 | 0 | 2,4,6-triMe |
| 10.142 | Et | Et | H | CN | 2 | 0 | 2,6-diCl,3-Me |
| 10.143 | Et | Et | H | CN | 2 | 0 | 2,3-diMe,6-Cl |
| 10.144 | Et | Et | H | COOEt | 2 | 0 | 2,4,6-triMe |
| 10.145 | Et | Et | H | COOEt | 2 | 0 | 2,6-diCl,3-Me |
| 10.146 | Et | Et | H | COOEt | 2 | 0 | 2,3-diMe,6-Cl |
| 10.147 | Et | Et | H | SEt | 2 | 0 | 2,4,6-triMe |
| 10.148 | Et | Et | H | SEt | 2 | 0 | 2,6-diCl,3-Me |
| 10.149 | Et | Et | H | SEt | 2 | 0 | 2,3-diMe,6-Cl |
| 10.150 | Et | Et | H | SO₂Et | 2 | 0 | 2,4,6-triMe |
| 10.151 | Et | Et | H | SO₂Et | 2 | 0 | 2,6-diCl,3-Me |
| 10.152 | Et | Et | H | SO₂Et | 2 | 0 | 2,3-diMe,6-Cl |
| 10.153 | Et | Et | H | OMe | 2 | 0 | 2,4,6-triMe |
| 10.154 | Et | Et | H | OMe | 2 | 0 | 2,6-diCl,3-Me |
| 10.155 | Et | Et | H | OMe | 2 | 0 | 2,3-diMe,6-Cl |
| 10.156 | Et | Et | H | OCHF₂ | 2 | 0 | 2,4,6-triMe |
| 10.157 | Et | Et | H | OCH₂OMe | 2 | 0 | 2,4,6-triMe |
| 10.158 | Et | Et | Cl | Cl | 2 | 0 | 2,4,6-triMe |
| 10.159 | Et | Et | CN | Cl | 2 | 0 | 2,4,6-triMe |
| 10.160 | Et | Et | H | H | 2 | 0 | 2,4,6-triCl |
| 10.161 | Et | Et | H | F | 0 | 0 | 2,4,6-triCl |

TABLE 11

| Cpd. No. | R¹ | R² | A | B | n | subst. posn. | $Y_j$ |
|---|---|---|---|---|---|---|---|
| 11.1 | Et | Et | H | H | 2 | 2 | not substituted |
| 11.2 | Et | Et | H | H | 0 | 2 | not substituted |
| 11.3 | Et | Et | H | H | 2 | 4 | not substituted |
| 11.4 | Et | Et | H | H | 2 | 2 | 5-Cl |
| 11.5 | Et | Et | H | H | 2 | 2 | 3-CF₃,5-Cl |
| 11.6 | Et | Et | H | H | 2 | 2 | 3,5-diCl |
| 11.7 | Et | Et | H | H | 0 | 2 | 5-Br |
| 11.8 | Et | Et | H | H | 2 | 2 | 5-Br |
| 11.9 | Et | Et | H | H | 0 | 2 | 3-Cl |
| 11.10 | Et | Et | H | H | 2 | 2 | 3-Cl |
| 11.11 | Et | Et | H | H | 0 | 2 | 6-Me |
| 11.12 | Et | Et | H | H | 2 | 2 | 6-Me |
| 11.13 | Et | Et | H | H | 0 | 2 | 3-CF₃ |
| 11.14 | Et | Et | H | H | 2 | 2 | 3-CF₃ |
| 11.15 | Et | Et | H | H | 0 | 2 | 5-CF₃ |
| 11.16 | Et | Et | H | H | 2 | 2 | 5-CF₃ |
| 11.17 | Et | Et | H | H | 2 | 2 | 3-Cl,5-CF₃ |
| 11.18 | Et | Et | H | Cl | 0 | 2 | 5-Cl |
| 11.19 | Et | Et | H | Cl | 2 | 2 | 5-Cl |
| 11.20 | Me | Me | H | Cl | 0 | 2 | 3-CF₃ |
| 11.21 | Me | Me | H | Cl | 2 | 2 | 3-CF₃ |
| 11.22 | Me | Et | H | Cl | 0 | 2 | 3-CF₃ |
| 11.23 | Me | Et | H | Cl | 2 | 2 | 3-CF₃ |
| 11.24 | Et | Et | H | Cl | 0 | 2 | 3-CF₃ |
| 11.25 | Et | Et | H | Cl | 2 | 2 | 3-CF₃ |
| 11.26 | Et | Et | H | Cl | 0 | 2 | 5-CF₃ |
| 11.27 | Et | Et | H | Cl | 2 | 2 | 5-CF₃ |
| 11.28 | Et | Et | H | Cl | 0 | 2 | 3-Cl,5-CF₃ |
| 11.29 | Et | Et | H | Cl | 2 | 2 | 3-Cl,5-CF₃ |
| 11.30 | Et | Et | H | Br | 0 | 2 | 3-CF₃ |
| 11.31 | Et | Et | H | Br | 2 | 2 | 3-CF₃ |
| 11.32 | Et | Et | H | Br | 2 | 2 | 3-Cl,5-CF₃ |
| 11.33 | Et | Et | H | F | 2 | 2 | 3-Cl |
| 11.34 | Et | Et | H | F | 2 | 2 | 3-CF₃ |
| 11.35 | Et | Et | H | F | 2 | 2 | 5-Cl |
| 11.36 | Et | Et | H | F | 2 | 2 | 5-CF₃ |
| 11.37 | Me | Me | H | F | 2 | 2 | 3-Cl |
| 11.38 | Me | Me | H | F | 2 | 2 | 5-Cl |
| 11.39 | Me | Me | H | F | 2 | 2 | 3-CF₃ |
| 11.40 | Me | Me | H | F | 2 | 2 | 5-CF₃ |
| 11.41 | Me | Et | H | F | 2 | 2 | 3-Cl |
| 11.42 | Me | Et | H | F | 2 | 2 | 3-CF₃ |
| 11.43 | Me | Et | H | F | 2 | 2 | 5-Cl |
| 11.44 | Me | Et | H | F | 2 | 2 | 5-CF₃ |
| 11.45 | Et | Pr | H | F | 2 | 2 | 3-Cl |
| 11.46 | Et | Pr | H | F | 2 | 2 | 3-CF₃ |
| 11.47 | Et | Pr | H | F | 2 | 2 | 5-Cl |
| 11.48 | Et | Pr | H | F | 2 | 2 | 5-CF₃ |
| 11.49 | Pr | Pr | H | F | 2 | 2 | 3-Cl |
| 11.50 | Pr | Pr | H | F | 2 | 2 | 3-CF₃ |
| 11.51 | Pr | Pr | H | F | 2 | 2 | 5-Cl |
| 11.52 | Pr | Pr | H | F | 2 | 2 | 5-CF₃ |
| 11.53 | All | All | H | F | 2 | 2 | 3-Cl |
| 11.54 | All | All | H | F | 2 | 2 | 3-CF₃ |
| 11.55 | All | All | H | F | 2 | 2 | 5-Cl |
| 11.56 | All | All | H | F | 2 | 2 | 5-CF₃ |
| 11.57 | Et | Et | H | F | 0 | 2 | 3-CF₃ |
| 11.58 | Et | Et | H | F | 0 | 2 | 5-Cl |

TABLE 12

| Cpd. No. | R¹ | R² | A | B | n | $Z_q$ |
|---|---|---|---|---|---|---|
| 12.1 | Et | Et | H | H | 0 | 4,6-diMe |
| 12.2 | Et | Et | H | H | 2 | 4,6-diMe |
| 12.3 | Et | Et | H | H | 2 | 4,6-diCl |
| 12.4 | Et | Et | H | H | 2 | 4,6-diMeO |
| 12.5 | Et | Et | H | H | 2 | not substituted |
| 12.6 | Et | Et | H | F | 2 | 4,6-diMe |
| 12.7 | Et | Et | H | F | 2 | 4,6-diMeO |
| 12.8 | Et | Et | H | F | 2 | 4,6-diCl |
| 12.9 | Et | Et | H | Cl | 2 | 4,6-diMe |
| 12.10 | Et | Et | H | Cl | 2 | 4,6-diCl |

TABLE 12-continued

| Cpd. No. | R¹ | R² | A | B | n | $Z_q$ |
|---|---|---|---|---|---|---|
| 12.11 | Et | Et | H | Cl | 2 | 4,6-diMeO |

Of the compounds listed above, preferred compounds are Compounds No. 1.1, 1.4, 1.6, 1.7, 1.8, 1.10, 1.15, 1.16, 1.19, 1.21, 1.23, 1.57, 1.81, 2.1, 2.4, 2.6, 2.7, 2.10, 2.12, 2.13, 2.16, 2.42, 2.45, 2.50, 2.52, 2.56, 2.59, 2.64, 2.65, 2.68, 2.83, 2.105, 3.1, 3.3, 3.6, 3.9, 3.11, 3.12, 3.15, 3.16, 3.18, 3.20, 4.1, 4.3, 4.5, 4.7, 4.43, 4.45, 4.46, 4.48, 4.50, 4.52, 4.56, 4.58, 4.64, 4.65, 4.66, 4.67, 4.69, 4.134, 5.1, 5.3, 5.5, 5.6, 5.8, 5.9, 5.11, 5.13, 5.15, 5.17, 5.19, 5.26, 5.28, 5.30, 5.32, 5.34, 5.36, 5.38, 5.39, 5.40, 5.42, 5.70, 5.72, 5.74, 5.75, 5.76, 6.1, 6.3, 6.6, 6.8, 6.10, 6.11, 6.14, 6.16, 6.17, 6.19, 6.62, 6.63, 6.66, 6.101, 6.102, 6.104, 6.106, 6.109, 6.111, 6.112, 6.115, 6.119, 6.145, 6.148, 6.160, 7.1, 7.2, 7.4, 7.6, 7.7, 7.10, 7.12, 7.15, 7.17, 7.20, 7.22, 7.24, 7.75, 7.76, 7.91, 7.93, 7.95, 7.96, 7.100, 7.103, 7.112, 7.113, 7.114, 7.115, 7.120, 7.126, 7.142, 7.167, 7.168, 7.169, 7.173, 7.175, 7.177, 7.179, 7.182, 7.188, 7.190, 7.191, 7.213, 7.215, 7.216, 7.218, 7.220, 7.221, 7.222, 7.223, 7.252, 7.257, 7.259, 8.1, 8.4, 8.5, 8.7, 8.9, 8.12, 8.17, 8.21, 8.23, 8.24, 8.27, 8.31, 8.32, 8.35, 9.1, 9.4, 9.6, 9.8, 9.11, 9.18, 9.22, 9.26, 9.27, 9.34, 9.49, 9.56, 9.77, 9.84, 9.85, 9.88, 9.123, 9.126, 10.1, 10.4, 10.6, 10.14, 10.23, 10.25, 10.41, 10.46, 10.47, 10.50, 10.53, 10.54, 10.56, 10.57, 10.58, 10.59, 10.62, 10.66, 10.67, 10.68, 10.70, 10.77, 10.83, 10.84, 10.85, 10.86, 10.87, 10.90, 10.117, 10.118, 10.119, 10.141, 10.160, 11.1, 11.10, 11.14, 11.61, 11.19, 11.21, 11.23, 11.25, 11.27, 11.31 and 12.2.

More preferred compounds are Compounds No. 1.4, 1.6, 1.10, 1.15, 1.23, 1.57, 1.81, 2.1, 2.4, 2.16, 2.42, 2.56, 2.59, 2.64, 2.65, 2.68, 2.83, 2.105, 3.1, 3.3, 3.12, 3.15, 3.16, 4.1, 4.3, 4.5, 4.7, 4.43, 4.45, 4.46, 4.48, 4.50, 4.52, 4.56, 4.58, 4.65, 4.66, 4.67, 4.69, 4.134, 5.3, 5.6, 5.8, 5.11, 5.13, 5.15, 5.28, 5.30, 5.32, 5.34, 5.38, 5.40, 5.72, 5.74, 5.75, 5.76, 6.3, 6.6, 6.8, 6.19, 6.62, 6.63, 6.66, 6.101, 6.104, 6.106, 6.109, 6.111, 6.115, 6.145, 6.148, 7.1, 7.2, 7.4, 7.6, 7.7, 7.10, 7.17, 7.20, 7.22, 7.24, 7.112, 7.113, 7.114, 7.115, 7.120, 7.126, 7.142, 7.165, 7.167, 7.168, 7.173, 7.175, 7.177, 7.179, 7.188, 7.190, 7.191, 7.220, 7.221, 7.257, 7.259, 8.1, 8.5, 8.12, 8.24, 8.32, 8.35, 9.1, 9.4, 9.8, 9.11, 9.18, 9.22, 9.34, 9.49, 9.56, 9.77, 9.84, 9.85, 9.88, 9.126, 10.1, 10.6, 10.23, 10.41, 10.46, 10.50, 10.53, 10.54, 10.56, 10.57, 10.58, 10.59, 10.66, 10.77, 10.83, 10.84, 10.85, 10.86, 10.87, 10.90, 10.160, 11.1, 11.10, 11.14, 11.16 and 11.25.

Still more preferred compounds are Compounds No. 1.81, 2.42, 2.64, 2.65, 2.68, 4.69, 5.76, 6.66, 7.112, 7.113, 7.120, 7.126, 7.142, 7.173, 7.188, 7.190, 8.35, 9.1, 9.56, 10.46 and 10.85.

The most preferred compounds are Compounds No.:

7.112. 1-(diethylcarbamoyl)-3-(2,6-dimethylphenyl-sulfonyl)-4-fluoropyrazole;

7.126. 1-(dimethylcarbamoyl)-3-(2,6-dimethylphenyl-sulfonyl)-4-fluoropyrazole;

7.173. 4-chloro-3-(2-chloro-6-methylphenylsulfonyl)-1-(diethylcarbamoyl)pyrazole;

9.1. 3-(3,5-dichlorophenylsulfonyl)-1-(diethylcarbamoyl)pyrazole;

10.46. 1-(dipropylcarbamoyl)-3-(2,4,6-trimethylphenylsulfonyl)pyrazole;

10.85. 1-(diethylcarbamoyl)-3-(2,4,6-trimethylphenylsulfonyl)-4-fluoropyrazole.

The compounds of the present invention can be prepared by a variety of methods well known in the art for the preparation of compounds of this type. For example, in general terms, the compounds may be prepared by reacting a compound of formula (V):

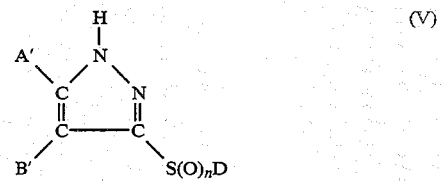

(in which: A' and B' represent any of the groups or atoms represented by A and B, respectively, as defined above, or such a group or atom in which any reactive group is protected, and D and n are as defined above) with a compound of formula (VI):

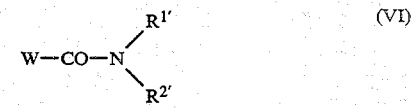

(in which R¹' and R²' represent any of the groups or atoms represented by R¹ and R², respectively as defined above, or such a group or atom in which any reactive group is protected, and W represents a halogen atom);

optionally, where n is 0, oxidising the product to prepare a compound in which 5 is 1 or 2;

optionally, where R¹', R²', A' and/or B' represents a hydrogen atom, converting it to another group or atom represented by R¹, R², A or B;

and optionally removing any protecting group.

Where the compound contains a carboxy group, it may, if desired, then be salified or esterified. Where the compound contains a pyridyl or pyrimidinyl group, it may be salified. Where the compound contains an esterified carboxy group, e.g. an alkoxycarbonyl group, it may be de-esterified.

More specifically, the compounds may be prepared as illustrated in the following Reaction Scheme A:

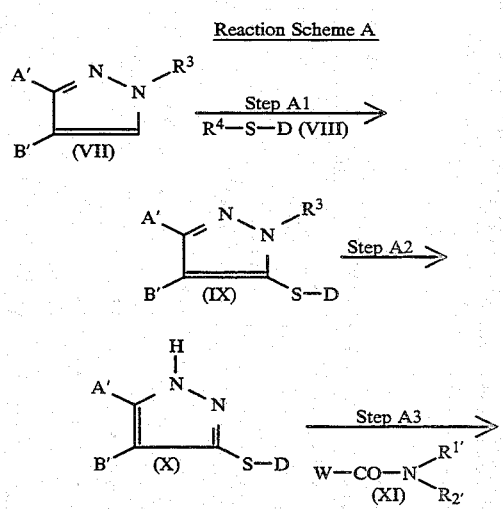

-continued
Reaction Scheme A

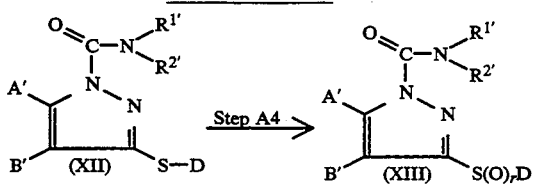

In the above formulae, $R^{1'}$, $R^{2'}$, A' and B' and D are as defined above, $R^3$ represents an amino-protecting group, r is 1 or 2, W represents a halogen atom and $R^4$ represents a leaving group.

Suitable halogen atoms which may be represented by W include the fluorine, chlorine, bromine and iodine atoms, of which the chlorine and bromine atoms are preferred.

The nature of the amino-protecting group represented by $R^3$ is not particularly critical, provided that it can be removed under appropriate conditions and without harming the rest of the molecule. Preferred examples of such protecting groups include: aliphatic acyl groups, such as alkylcarbonyl groups (e.g. the acetyl and propionyl groups) and halogenated alkylcarbonyl groups (e.g. the chloroacetyl, dichloroacetyl, trichloroacetyl and trifluoroacetyl groups); aromatic acyl groups, such as the benzoyl group; lower alkoxycarbonyl groups, in which the alkoxy part preferably has from 1 to 4 carbon atoms, such as the methoxycarbonyl group; lower alkenyloxycarbonyl groups, in which the alkenyl part preferably has from 2 to 4 carbon atoms, such as the vinyloxycarbonyl and allyloxycarbonyl groups; aralkyloxycarbonyl groups, such as the benzyloxycarbonyl group; tri(lower alkyl)silyl groups, in which each alkyl part preferably has from 1 to 4 carbon atoms, such as the trimethylsilyl and t-butyldimethylsilyl groups; di(lower alkyl)sulfamoyl groups, in which each alkyl part preferably has from 1 to 4 carbon atoms, such as the dimethylsulfamoyl group; and (lower alkoxy)-substituted lower alkyl groups, in which the alkyl and alkoxy parts each preferably have from 1 to 4 carbon atoms, such as the methoxymethyl and methoxyethyl groups. Of these, we prefer the aliphatic acyl groups, the lower alkoxycarbonyl groups, the tri(lower alkyl)silyl groups, the di(lower alkyl)sulfamoyl groups and the (lower alkoxy)-substituted lower alkyl groups.

The nature of the leaving group which may be represented by $R^4$ is not particularly critical, provided that it can be eliminated as a nucleophilic residue and any group commonly used in known reactions of this type may equally be used here. Preferred examples of such groups include: halogen atoms, such as the chlorine, bromine and iodine atoms; dicarboximide groups, such as the succinimide and maleimide groups; and groups of formula D—S— or D—SO$_2$— (in which D is as defined above). Of these, we prefer the succinimide group and groups of formula D—S—.

This reaction scheme is particularly useful for the preparation of compounds in which A' and B' are both hydrogen atoms.

In step A1 of this reaction scheme, a compound of formula (IX) is prepared by replacing a hydrogen atom at the 5-position of a pyrazole ring in the compound of formula (VII) with a thioether group using a compound of formula (VIII).

The reaction is carried out in the presence of a base. The nature of the base to be used is not particularly critical, provided that it has the basicity necessary to dissociate a proton at the 5-position of the pyrazole ring, and examples of such bases are well known to those skilled in the art. Examples of preferred bases include organic metal bases, such as butyllithium, sec-butyllithium, lithium diisopropylamide and lithium bis(trimethylsilyl)amide, of which butyllithium and sec-butyllithium are most preferred.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include ethers, such as diethyl ether or tetrahydrofuran.

The reaction can take place over a wide range of temperatures, and the precise reaction temperature is not critical to the invention. In general, we find it convenient to carry out the reaction at a temperature of from −90° C. to 50° C., more preferably from −78° C. to 20° C. The time required for the reaction may also vary widely, depending on many factors, notably the reaction temperature and the nature of the reagents. However, provided that the reaction is effected under the preferred conditions outlined above, a period of from 5 minutes to 4 hours, more preferably from 15 minutes to 1.5 hours, will usually suffice.

In Step A2 a compound of formula (X) is prepared by removing the protecting group represented by $R^3$ from the 1-position of the pyrazole ring in the compound of formula (IX). The nature of the reaction employed to achieve this will depend upon the nature of the protecting group to be removed.

Thus, where the protecting group represented by $R^3$ is a silyl group, such as a tri(lower alkyl)silyl group (in which each alkyl part preferably has from 1 to 4 carbon atoms), or an equivalent group in which one or two of the alkyl groups have been replaced by an aryl (e.g. phenyl) group, it can be removed by treating the compound of formula (IX) with a compound capable of forming a fluoride anion.

There is no particular limitation upon the nature of the compound capable of forming a fluoride anion, provided that it contains a fluorine atom and can give rise to a fluoride anion. Preferred examples of such compounds include: inorganic fluorides, such as inorganic metal fluorides (e.g. lithium fluoride, sodium fluoride, potassium fluoride, rubidium fluoride, cesium fluoride, magnesium fluoride or calcium fluoride) and organic fluorides, such as quaternary ammonium fluorides (e.g. tetrabutylammonium fluoride); we prefer the quaternary ammonium fluorides, especially tetrabutylammonium fluoride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include ethers, such as tetrahydrofuran and dioxane.

The reaction can take place over a wide range of temperatures, and the precise reaction temperature is not critical to the invention. In general, we find it convenient to carry out the reaction at a temperature of from 0° C. to 100° C., preferably at room temperature.

The time required for the reaction may also vary widely, depending on many factors, notably the reaction temperature and the nature of the reagents. However, provided that the reaction is effected under the preferred conditions outlined above, a period of from 1 to 24 hours, more preferably from 2 to 8 hours, will usually suffice.

Where the protecting group represented by $R^3$ is an aliphatic acyl group, an aromatic acyl group, a lower alkoxycarbonyl group, a di(lower alkyl)sulfamoyl group or a (lower alkoxy)-substituted lower alkyl group, it can be removed by treating the compound of formula (IX) with an acid or base in the presence or absence of an aqueous medium.

The nature of the acid to be used is not particularly critical, and any acid commonly used for this type of reaction may equally be used here. Examples of preferred acids include: inorganic acids, such as hydrochloric acid, sulfuric acid, phosphoric acid or hydrobromic acid; organic acids, such as trifluoroacetic acid; and Lewis acids, such as aluminum chloride, zinc chloride or titanium chloride. Of these, we prefer hydrochloric acid, sulfuric acid or trifluoroacetic acid.

The nature of the base to be used is likewise not particularly critical, provided that it has no adverse effect upon other parts of the compound of formula (IX). Examples of preferred bases include: metal, especially alkali metal, alkoxides such as sodium methoxide; alkali metal carbonates, such as sodium carbonate or potassium carbonate; alkali metal hydroxides, such as sodium hydroxide or potassium hydroxide; and amines, such as aqueous ammonia, concentrated methanolic ammonia or hydrazine. Of these, we prefer sodium carbonate, potassium carbonate or hydrazine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent, and any solvent capable of use in a conventional hydrolysis reaction can equally be used here. Examples of suitable solvents include: water; organic solvents, such as alcohols (e.g. methanol, ethanol, propanol or isopropanol), ethers (e.g. tetrahydrofuran or dioxane) and halogenated hydrocarbons, especially halogenated aliphatic hydrocarbons (e.g. methylene chloride, chloroform or dichloroethane); and mixtures of water with any one or more of the above organic solvents. Of these, we prefer methanol, tetrahydrofuran, methylene chloride, chloroform, dichloroethane or a mixture of methanol and water.

The reaction can take place over a wide range of temperatures, and the precise reaction temperature is not critical to the invention. In general, we find it convenient to carry out the reaction at a temperature of from 0° C. to 150° C., more preferably from 30° C. to 80° C., in order to suppress side reactions. The time required for the reaction may also vary widely, depending on many factors, notably the reaction temperature and the nature of the reagents. However, the reaction is normally completed within a period of from 30 minutes to 15 hours, more preferably from 1 to 8 hours, in order to reduce side reactions.

Where the protecting group represented by $R^3$ is a lower alkenyloxycarbonyl group, it can generally be removed by treating the compound of formula (IX) with a base in a similar manner to that described above for the removal of an amino-protecting group when that group is an aliphatic acyl, aromatic acyl or alkoxycarbonyl group. Where the protecting group represented by $R^3$ is an aralkyloxycarbonyl group, it can simply be removed by hydrogenation using palladium and triphenyl phosphine or nickel tetracarbonyl without accompanying side reactions.

At the end of this Step, the compound of formula (X) can, if desired, be subjected to the subsequent reactions without intermediate isolation.

In Step A3, a compound of formula (XII) [a compound of formula (I), in which A and B are A' and B', and preferably each represents a hydrogen atom, and n is 0] is prepared by introducing a carbamoyl group at the 1-position of the pyrazole ring in the compound of formula (X), using a compound of formula (XI). The reaction is carried out in the presence of a base.

The nature of the base used is not particularly critical, and any base commonly used in condensation reactions of this type may equally be used here. Examples of preferred bases include: alkali metal hydroxides, such as sodium hydroxide or potassium hydroxide; alkali metal carbonates, such as sodium carbonate or potassium carbonate; alkali metal hydrides, such as lithium hydride, sodium hydride or potassium hydride; alkali metal alkoxides, such as potassium t-butoxide; organic amines, such as triethylamine, tributylamine, diisopropylethylamine, pyridine, 1,5-diazabicyclo[4.3.0]non-5-ene, 1,4-diazabicyclo[2.2.2]octane (DABCO) or 1,8-diazabicyclo[5.4.0]undec-7-ene (DBU); and organic metal bases, such as butyllithium, sec-butyllithium, lithium diisopropylamide, sodium bis(trimethylsilyl)amide and lithium bis(trimethylsilyl)amide. Of these, we prefer triethylamine, pyridine, 1,4-diazabicyclo[2.2.2]octane (DABCO) or 1,8-diazabicyclo[5.4.0]undec-7-ene (DBU).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, especially halogenated aliphatic or aromatic hydrocarbons, such as methylene chloride, chloroform, carbon tetrachloride, chlorobenzene or dichlorobenzene; esters, such as ethyl acetate; ethers, such as diethyl ether, diisopropyl ether, tetrahydrofuran, dioxane, dimethoxyethane or diethylene glycol dimethyl ether; alcohols, such as t-butanol; nitriles, such as acetonitrile; and ketones, such as acetone, methyl ethyl ketone or methyl isobutyl ketone. Of these, we prefer toluene, methylene chloride, dichloroethane, tetrahydrofuran or acetonitrile.

The reaction can take place over a wide range of temperatures, and the precise reaction temperature is not critical to the invention. In general, we find it convenient to carry out the reaction at a temperature of from 0° C. to 150° C., more preferably from 30° C. to 80° C. The time required for the reaction may also vary widely, depending on many factors, notably the reaction temperature and the nature of the reagents. However, provided that the reaction is effected under the preferred conditions outlined above, a period of from 30 minutes to 12 hours, more preferably from 1 to 4 hours, will usually suffice.

An alternative method of converting a compound of formula (X) to a compound of formula (XII), which may be employed in place of Step A3, involves the chlorocarbonylation of the compound of formula (X) followed by reacting the product with the corresponding secondary amine of formula $HNR^1R^2$.

Examples of reagents which may be employed for chlorocarbonylation include phosgene, trichloromethyl chloroformate and oxalyl chloride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, especially halogenated aliphatic hydrocarbons, such as methylene chloride, chloroform, carbon tetrachloride or dichloroethane; and ethers, such as diethyl ether, tetrahydrofuran or dioxane. Of these, we prefer toluene, chloroform or dichloroethane.

The reaction can take place over a wide range of temperatures, and the precise reaction temperature is not critical to the invention. In general, we find it convenient to carry out the reaction at a temperature of from 0° C. to 150° C., more preferably from 20° C. to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 5 hours will usually suffice.

The chlorocarbonyl compound prepared in this reaction can be used in the subsequent reaction without isolation.

The reaction of this chlorocarbonyl compound with a secondary amine is preferably carried out in the presence of a base. The nature of the base used is not particularly critical provided that it has no adverse effects on the reagents, and any base commonly used in reactions of this type may equally be used here. Examples of suitable bases include organic bases, such as triethylamine, tributylamine, diisopropylethylamine, pyridine, 1,5-diazabicyclo[4.3.0]non-5-ene, 1,4-diazabicyclo[2.2.2]octane (DABCO) and 1,8-diazabicyclo[5.4.0]undec-7-ene (DBU). Of these, we prefer triethylamine or pyridine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform, carbon tetrachloride, dichloroethane, chlorobenzene and dichlorobenzene; esters, such as ethyl acetate; ethers, such as diethyl ether, tetrahydrofuran, dioxane or dimethoxyethane; and nitriles, such as acetonitrile. Of these, we prefer toluene, methylene chloride or tetrahydrofuran.

The reaction can take place over a wide range of temperatures, and the precise reaction temperature is not critical to the invention. In general, we find it convenient to carry out the reaction at a temperature of from 0° C. to 150° C., more preferably from 5° C. to 60° C. The time required for the reaction may also vary widely, depending on many factors, notably the reaction temperature and the nature of the reagents and solvent employed. However, provided that the reaction is effected under the preferred conditions outlined above, a period of from 5 minutes to 24 hours, more preferably from 20 minutes to 4 hours will usually suffice.

In Step A4 the sulfoxide or sulfone compound of formula (XIII) [i.e. a compound of formula (I), wherein both A and B are A' and B', and preferably each represents a hydrogen atom, and n is 1 or 2] may, if desired, be prepared by oxidizing the thioether compound of formula (XII) with an appropriate oxidizing agent in the presence of a solvent.

The nature of oxidizing agent used is not particularly critical, and any compound capable of being used in conventional oxidation reactions of this type may be used, provided that it does not adversely affect the desired compound. Examples of preferred oxidizing agents include: manganese oxides, such as potassium permanganate, sodium permanganate or manganese dioxide; chromic acids, such as potassium chromate, chromic acid/sulfuric acid complex or chromic acid/pyridine complex; a hydrogen peroxide solution; organic peroxides, such as t-butyl hydroperoxide; and organic peracids, such as peracetic acid or 3-chloroperoxybenzoic acid. Of these, we prefer a hydrogen peroxide solution or 3-chloroperoxybenzoic acid.

The amount or nature of the oxidizing agent and the reaction conditions, including reaction time and temperature, may be varied in a manner known per se, in order to produce selectively the sulfone (n=1) or the sulfoxide (n=2).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride, chloroform or dichloroethane; alcohols, such as t-butanol; ketones, such as acetone or methyl ethyl ketone; nitriles, such as acetonitrile; and acetic acid. Of these, we prefer methylene chloride, dichloroethane or acetic acid.

The reaction can take place over a wide range of temperatures, and the precise reaction temperature is not critical to the invention. In general, we find it convenient to carry out the reaction at a temperature of from 20° C. to 150° C., more preferably from 20° C. to 80° C. The time required for the reaction may also vary widely, depending on many factors, notably the reaction temperature and the nature of the reagents and solvent employed. However, provided that the reaction is effected under the preferred conditions outlined above, a period of from 1 to 24 hours, more preferably from 1 to 4 hours, will usually suffice.

Alternatively, as illustrated in Reaction Scheme B, Steps A3 and A4 may be carried out in the reverse order.

Reaction Scheme B

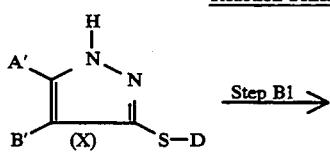

-continued
Reaction Scheme B

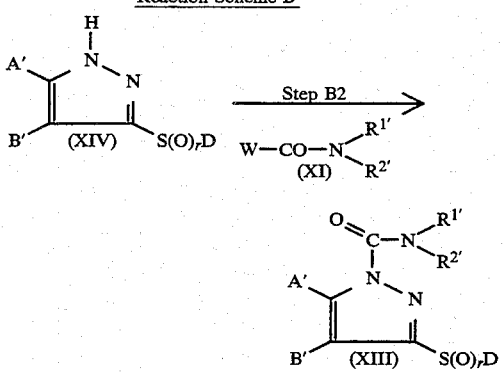

In the above formulae, $R^1$, $R^2$, $A'$, $B'$, $D$, $W$ and $r$ are as defined above.

In this scheme, a compound of formula (XIII) [i.e., the compound of formula (I), wherein A and B are $A'$ and $B'$, and preferably each represents a hydrogen atom, and n is 1 or 2] is prepared by first oxidizing the compound of formula (X), prepared as described in Reaction Scheme A, as shown in Step B1, followed by carbamoylation in Step B2.

Steps B1 and B2 are essentially the same as Steps A4 and A3, respectively, and may be carried out in the same manner and using the same reagents as in those Steps.

A compound of formula (I) having a halogen substituent at the 4-position of the pyrazole ring may be prepared as shown in Reaction Scheme C:

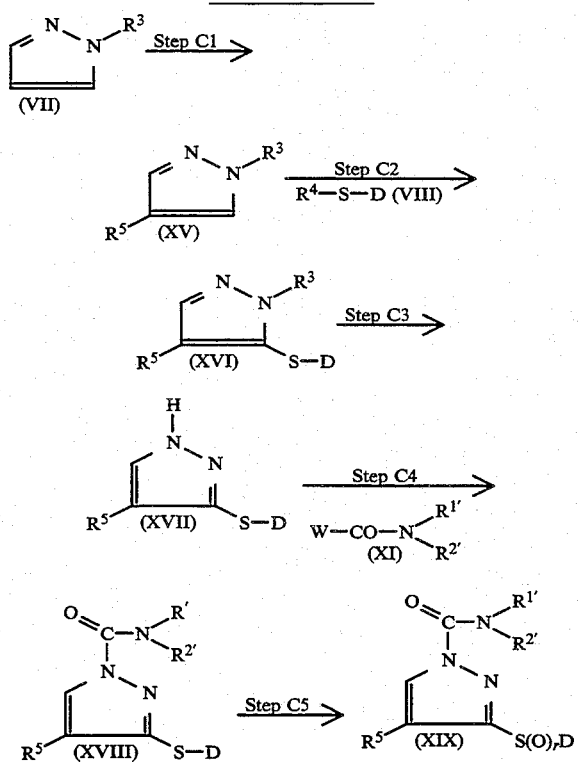

In the above formulae $R^{1'}$, $R^{2'}$, $R^3$, $R^4$, $D$, $W$ and $r$ are as defined above and $R^5$ represents a halogen, e.g. fluorine, chlorine, bromine or iodine, atom.

Reaction Scheme C involves the preparation of a compound of formula (XVIII) [i.e. a compound of formula (I), wherein A represents a hydrogen atom, B represents a halogen, e.g. fluorine, chlorine, bromine or iodine, atom, and n is 0] or a compound of formula (XIX) [i.e. a compound of formula (I), wherein A represents a hydrogen atom, B represents a halogen, e.g. fluorine, chlorine, bromine or iodine, atom, and n is 1 or 2] by introducing a halogen atom at the 4-position of the pyrazole ring in the compound of formula (VII) and then conducting similar reactions to those described in Reaction Scheme A.

In Step C1, a compound of formula (XV) is prepared by introducing a halogen, e.g. fluorine, chlorine, bromine or iodine, atom at the 4-position of the compound of formula (VII).

The reaction is carried out by reacting the compound of formula (VII) with a halogenating agent in the presence of a solvent. Examples of suitable halogenating agents include: N-halosuccinimides, such as N-chlorosuccinimide, N-bromosuccinimide or N-iodosuccinimide; and halogen molecules, such as fluorine, chlorine, bromine or iodine.

There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride, chloroform, dichloroethane or trifluorochloromethane; amides, especially fatty acid amides, such as dimethylformamide or diethylformamide; nitriles, such as acetonitrile; acetic acid; and mixtures of any two or more of the above solvents.

The reaction can take place over a wide range of temperatures, and the precise reaction temperature is not critical to the invention. In general, we find it convenient to carry out the reaction at a temperature of from $-70°$ C. to $150°$ C., more preferably from $-40°$ C. to $110°$ C. The time required for the reaction may also vary widely, depending on many factors, notably the reaction temperature and the nature of the reagents. However, provided that the reaction is effected under the preferred conditions outlined above, a period of from 1 to 24 hours, more preferably from 1 to 10 hours, will usually suffice.

Steps C2, C3, C4 and C5 can be conducted in a similar manner to that described above in respect of Steps A1, A2, A3 and A4, respectively.

An alternative method of preparing a compound of formula (XVI) (prepared in Step C2 of Reaction Scheme C) is shown in Reaction Scheme D:

Reaction Scheme D

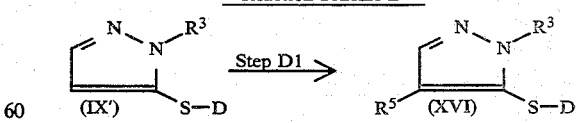

In the above formulae, $R^3$, $R^5$ and $D$ are as defined above.

The reaction consists of the halogenation of the compound of formula (IX'), which may be prepared as shown in Step A1 [formula (IX), $A'$ and $B'$ are both hydrogen]; the reaction may be conducted in a similar manner to that described in Step C1.

Reaction Scheme E shows an alternative method of preparing a compound of formula (XVII) (otherwise prepared in Step C3 of Reaction Scheme C):

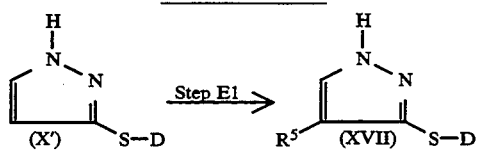

In the above formulae, $R^5$ and D are as defined above.

Reaction Scheme E consists of preparing the compound of formula (XVII) by halogenating the compound of formula (X'), which is a compound of formula (X), in which A' and B' are both hydrogen, prepared as shown in Step A2 of Reaction Scheme A. Step E1 can be carried out in a similar manner to that described in step C1.

Other compounds having a substituent on the 4-position of the pyrazole ring may be prepared as shown in Reaction Scheme F:

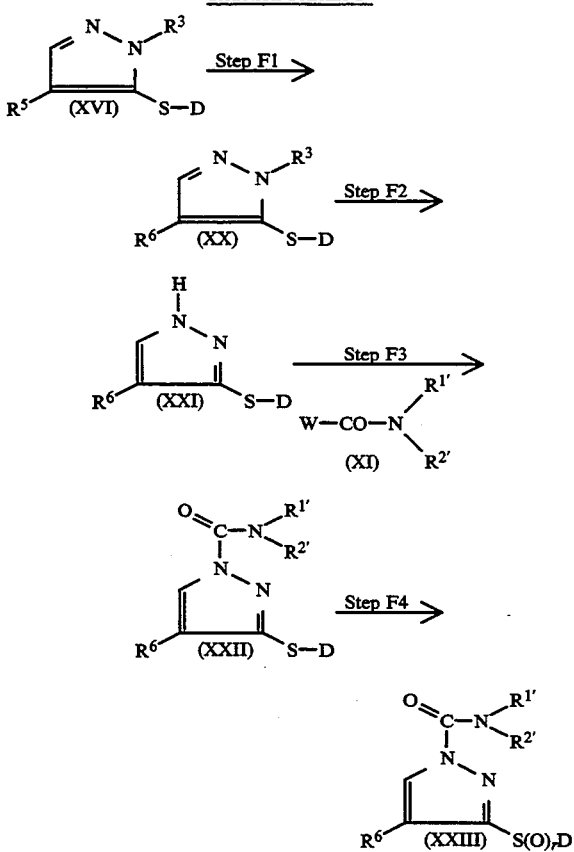

In the above formulae, $R^{1'}$, $R^{2'}$, $R^3$, $R^5$, D, W and r are as defined above and $R^6$ represents:
a hydroxy group,
a fluorine atom,
an unsubstituted alkyl group having from 1 to 6 carbon atoms,
a substituted alkyl group having from 1 to 6 carbon atoms and having at least one, and preferably from 1 to 3, substituents selected from the group consisting of substituents (c), defined above,
an unsubstituted alkenyl group having from 2 to 6 carbon atoms,
a substituted alkenyl group which has from 2 to 6 carbon atoms and which is substituted by at least one substituent selected from the group consisting of halogen atoms,
an alkylthio group having from 1 to 6 carbon atoms,
a dialkylsulfamoyl group, in which each alkyl part has from 1 to 4 carbon atoms,
an aliphatic acyl, preferably alkylcarbonyl, group which has from 2 to 7 carbon atoms and which is unsubstituted or is substituted by at least one substituent selected from the group consisting of substituents (a), defined above,
an alkoxycarbonyl group having from 2 to 7 carbon atoms,
a group of formula —$CONR^a R^b$, in which $R^a$ and $R^b$ are independently selected from the group consisting of hydrogen atoms and alkyl groups having from 1 to 4 carbon atoms,
a formyl group or
a cyano group.

All of the above groups which may be represented by $R^6$ may be as defined and exemplified above in relation to the corresponding groups which may be represented by B.

In Reaction Scheme F, we prepare a compound of formula (XXII) [i.e. a compound of formula (I), wherein A represents a hydrogen atom; B represents any of the groups and atoms defined above for $R^6$; and n is 0] and a compound of formula (XXIII) [i.e. a compound of formula (I), wherein A represents a hydrogen atom; B represents any of the groups and atoms defined above for $R^6$; and n is 1 or 2] by introducing a substituent represented by $R^6$ at the 4-position of the pyrazole ring in the compound of formula (XVI), which may have been prepared as described in Reaction Scheme C, and then treating the product in a similar manner to that described in Reaction Scheme A.

Step F1 involves the preparation of the compound of formula (XX) from a compound of formula (XVI) prepared as described in Step C2 of Reaction Scheme C, either by directly replacing a halogen atom represented by $R^5$ (preferably a chlorine, bromine or iodine atom) at the 4-position of the pyrazole ring by a group or atom $R^6$, or by replacing this halogen atom by a metal atom, and then replacing the metal atom by a group or atom $R^6$. The conditions under which we prefer to carry out this reaction will vary, depending upon the nature of the group or atom $R^6$ which it is wished to introduce.

Thus, where $R^6$ represents a trifluoromethyl group, the desired compound can be prepared by reacting the compound of formula (XVI) with a trifluoromethylating agent, with heating. Examples of trifluoromethylating agents which may be used include: trifluoromethyl metal salts, such as trifluoromethyl silver or trifluoromethyl copper (I); and fluorosulfonyldifluoroacetates, such as methyl fluorosulfonyldifluoroacetate, in the presence of cuprous iodide.

The reaction is normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as dichloroethane, tetrachloroethane, chlorobenzene or dichlorobenzene; ketones, such as methyl ethyl ketone or methyl isobutyl ketone; amides, especially fatty acid amides, such as dimethylformamide or dimethylacetamide; and sulfoxides, such as dimethyl sulfoxide.

The reaction can take place over a wide range of temperatures, and the precise reaction temperature is not critical to the invention. In general, we find it convenient to carry out the reaction at a temperature of from 50° C. to 200° C., more preferably from 80° C. to 150° C. The time required for the reaction may also vary widely, depending on many factors, notably the reaction temperature and the nature of the reagents and solvent employed. However, provided that the reaction is effected under the preferred conditions outlined above, a period of from 1 to 10 hours, more preferably from 1 to 6 hours, will usually suffice.

Where $R^6$ represents a hydroxy group, a fluorine atom, an alkyl group which is unsubstituted or substituted by one or more of substituents (c), an alkenyl group, a haloalkenyl group, an alkylthio group, a dialkylsulfamoyl group, an aliphatic acyl group, an alkoxycarbonyl group, a carbamoyl group, an alkylcarbamoyl group, a dialkylcarbamoyl group, a formyl group or a cyano group, the reaction is preferably initiated by replacing the halogen, preferably chlorine, bromine or iodine, atom at the 4-position of the pyrazole ring in the compound of formula (XVI) with a metal atom. Examples of the reagents which may be used for replacing the halogen atom by a metal atom include organic lithium bases, such as butyllithium, sec-butyllithium or t-butyllithium, and lithium metal.

The reaction is normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include ethers, such as diethyl ether or tetrahydrofuran.

The reaction can take place over a wide range of temperatures, and the precise reaction temperature is not critical to the invention. In general, we find it convenient to carry out the reaction at a relatively low temperature of from −90° C. to 10° C., more preferably from −78° C. to 0° C. The time required for the reaction may also vary widely, depending on many factors, notably the reaction temperature and the nature of the reagents and solvent employed. However, provided that the reaction is effected under the preferred conditions outlined above, a period of from 5 minutes to 1 hour, more preferably from 10 minutes to 1 hour, will usually suffice.

The metal salt prepared in this exchange reaction of a halogen atom with a metal atom can be used in the subsequent reaction with a nucleophilic reagent to introduce the desired group or atom $R^6$ without intermediate isolation. The nature of the nucleophilic agent used will, of course, depend upon the nature of the group or atom $R^6$ which it is desired to introduce.

Thus, for example, when $R^6$ is a hydroxy group, the nucleophilic reagent used is a peroxide, such as trimethylsilyl peroxide.

Where $R^6$ represents a fluorine atom, examples of nucleophilic reagents include N-fluoropyridinium salts, such as N-fluoropyridinium triflate; and N-fluorosulfonimides, such as N-fluorobenzenesulfonimide or N-fluoro-o-benzenedisulfonimide.

Where $R^6$ represents an optionally substituted alkyl group, an optionally substituted alkenyl group, a dialkylsulfamoyl group, an optionally substituted aliphatic acyl group, an alkoxycarbonyl group or a group of formula —$CONR^aR^b$, examples of nucleophilic reagents are the corresponding halides (i.e. the compounds represented by the formula $R^6X'$, wherein $R^6$ is as defined above and X' represents a halogen atom).

Where $R^6$ represents an alkylthio group, examples of nucleophilic reagents include the disulfide or monosulfone compounds equivalent to the corresponding thiol compounds ($R^6$—SH).

Where $R^6$ represents a formyl group, examples of nucleophilic reagents include: formamides, such as dimethylformamide or diethylformamide; formates, such as ethyl formate or t-butyl formate; and mixed formic acid anhydrides, such as formic pivalic anhydride.

Where $R^6$ represents a cyano group, examples of nucleophilic reagents are cyanides, such as trimethylsilyl cyanide or N-toluenesulfonyl cyanide.

The reaction with a nucleophilic reagent can take place over a wide range of temperatures, and the precise reaction temperature is not critical to the invention. In general, we find it convenient to carry out the reaction at a relatively low temperature of from −90° C. to 50° C., more preferably from −78° C. to 20° C. The time required for the reaction may also vary widely, depending on many factors, notably the reaction temperature and the nature of the reagents and solvent employed. However, provided that the reaction is effected under the preferred conditions outlined above, a period of from 10 minutes to 10 hours, more preferably from 10 minutes to 2 hours, will usually suffice.

Steps F2, F3 and F4 involve essentially the same reactions as do Steps A2, A3 and A4, respectively, and can be carried out using the same reagents and reaction conditions.

Those compounds of formulae (XX), (XXI), (XXII) and (XXIII) in which $R^6$ represents a formyl group, prepared as described in Reaction Scheme F, can be reduced to the corresponding compounds having a hydroxymethyl group to produce the corresponding compounds of formulae (XX), (XXI), (XXII) and (XXIII) in which $R^6$ represents a methyl group substituted with a hydroxy group. Examples of the reducing agents which may be used to effect this reduction include: alkali metal aluminum hydrides, such as lithium aluminum hydride, sodium aluminum hydride or sodium aluminum triethoxyhydride; and metal borohydrides, such as sodium borohydride, sodium cyanoborohydride or lithium borohydride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, especially halogenated aliphatic hydrocarbons, such as methylene chloride, chloroform or dichloroethane; ethers, such as diethyl ether, tetrahydrofuran, dimethoxyethane or dioxane; and alcohols, such as methanol, ethanol, propanol or isopropanol.

The reaction can take place over a wide range of temperatures, and the precise reaction temperature is not critical to the invention. In general, we find it convenient to carry out the reaction at a temperature of from −30° C. to 150° C., more preferably from 0° C. to 60° C. The time required for the reaction may also vary widely, depending on many factors, notably the reaction temperature and the nature of the reagents and solvent employed. However, provided that the reaction is effected under the preferred conditions outlined above, a period of from 10 minutes to 15 hours, more preferably from 30 minutes to 2 hours, will usually suffice.

Ester compounds [i.e. B in the compound of formula (I) represents an acyloxymethyl group] can be prepared by reacting a compound in which $R^6$ represents a hydroxymethyl group with a carboxylic acid compound of formula $R^8OH$ or reactive derivative thereof, in which $R^8$ represents: an aliphatic acyl group, such as an alkylcarbonyl group (e.g. an acetyl or propionyl group) or a halogenated alkylcarbonyl group (e.g. a chloroacetyl, dichloroacetyl, trichloroacetyl or trifluoroacetyl group); an aromatic acyl group, such as a benzoyl group; a lower alkoxycarbonyl group, in which the alkoxy part preferably has from 1 to 4 carbon atoms, such as a methoxycarbonyl group; a lower alkenyloxycarbonyl group, in which the alkenyl part preferably has from 2 to 4 carbon atoms, such as a vinyloxycarbonyl or allyloxycarbonyl group; or an aralkyloxycarbonyl group, such as a benzyloxycarbonyl group. The reaction preferably takes place in the presence of a condensing agent, such as dicyclohexylcarbodiimide (DCC) or carbonyldiimidazole. Alternatively, esters may be prepared by reacting a compound in which $R^6$ represents a hydroxymethyl group with an activated acylating agent of formula $R^8Z$ [in which $R^8$ is as defined above and Z represents a leaving group, such as a group of formula $OR^8$, a halogen atom (e g. a chlorine, bromine or iodine atom), a lower alkylcarbonyloxy group, preferably having from 1 to 6 carbon atoms in the alkyl part (e.g. a pivalyloxy group), a lower alkoxycarbonyloxy group, preferably having from 1 to 6 carbon atoms in the alkoxy part (e.g. a methoxycarbonyloxy or ethoxycarbonyloxy group), a lower alkylthio group, preferably having from 1 to 6 carbon atoms in the alkyl part (e.g. a methylthio or ethylthio group), a pyridylthio group (e.g. a 2-pyridylthio group), or a lower alkylsulfonyloxy group, preferably having from 1 to 6 carbon atoms in the alkyl part (e.g. a methanesulfonyloxy or ethanesulfonyloxy group)]. These reactions are preferably carried out in a solvent in the presence of a base.

There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform or carbon tetrachloride; ethers, such as diethyl ether, tetrahydrofuran or dioxane; and esters, such as ethyl acetate.

The nature of the base used is likewise not particularly critical, and any base conventionally used in reactions of this type can equally be used here. Examples of preferred bases include: organic bases, such as triethylamine, tributylamine, diisopropylethylamine, pyridine, 1,5-diazabicyclo[4.3.0]non-5-ene, 1,4-diazabicyclo[2.2.2]octane (DABCO), 1,8-diazabicyclo[5.4.0]undec-7-ene (DBU); and organic metal bases, such as butyllithium, sec-butyllithium, lithium diisopropylamide, sodium bis (trimethylsilyl) amide or lithium bis (trimethylsilyl) amide. Of these, we prefer triethylamine, pyridine, 1,4-diazabicyclo[2.2.2]octane (DABCO) or 1,8-diazabicyclo[5.4.0]undec-7-ene (DBU).

The reaction can take place over a wide range of temperatures, and the precise reaction temperature is not critical to the invention. In general, we find it convenient to carry out the reaction at a temperature of from 0° C. to 100° C., more preferably from 20° C. to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 2 hours, will usually suffice.

If desired, the resulting ester can be converted to the free carboxylic acid by conventional means.

Alternatively, where $R^6$ represents a hydroxymethyl group, it can be converted to a halogenated methyl group, such as a fluoromethyl, chloromethyl, bromomethyl or iodomethyl group, by treating the compound with a halogenating agent.

Any halogenating agent capable of converting a general hydroxy group to halogen atom may be used in this reaction. Examples of preferred halogenating agents include: diethylaminosulfur trifluoride (DAST) for fluorination; thionyl chloride, phosphorus oxychloride or phosphorus pentachloride for chlorination; phosphorus tribromide or phosphorus pentabromide for bromination; and methyltriphenylphosphonium iodide for iodination.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, especially halogenated aliphatic hydrocarbons, such as methylene chloride, chloroform or carbon tetrachloride; ethers, such as diethyl ether, tetrahydrofuran, dioxane or dimethoxyethane; esters, such as ethyl acetate; amides, such as dimethylformamide or hexamethylphosphoric triamide; sulfoxides, such as dimethyl sulfoxide; and ketones, such as acetone or methyl ethyl ketone.

The reaction can take place over a wide range of temperatures, and the precise reaction temperature is not critical to the invention. In general, we find it convenient to carry out the reaction at a temperature of from −20° C. to 150° C., more preferably from 0° C. to 60° C. The time required for the reaction may also vary widely, depending on many factors, notably the reaction temperature and the nature of the reagents and solvent employed. However, provided that the reaction is effected under the preferred conditions outlined above, a period of from 30 minutes to 20 hours, more preferably from 1 to 4 hours, will usually suffice.

The compounds of formula (XX), (XXI), (XXII) and (XXIII), in which $R^6$ represents a formyl group, and which may have been prepared as described in Reaction Scheme F, can be converted to the corresponding compounds in which B represents a difluoromethyl group by using a fluorinating agent such as diethylaminosulfur trifluoride (DAST).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform, dichloroethane or chlorobenzene; ethers, such as diethyl ether, tetrahydrofuran, dioxane or dimethoxyethane; esters, such as ethyl acetate; and nitriles, such as acetonitrile.

The reaction can take place over a wide range of temperatures, and the precise reaction temperature is not critical to the invention. In general, we find it convenient to carry out the reaction at a temperature of from −20° C. to 150° C., more preferably from 0° C. to 60° C. The time required for the reaction may also vary widely, depending on many factors, notably the reaction temperature and the nature of the reagents and solvent employed. However, provided that the reaction is effected under the preferred conditions outlined above, a period of from 1 to 36 hours, more preferably from 1 to 20 hours, will usually suffice.

Compounds, in which $R^6$ represents a lower alkoxy group which may optionally be substituted with at least one, and preferably from 1 to 3, substituents, which may be the same or different, selected from the group consisting of substituents (a), defined and exemplified above, can be prepared by reacting the corresponding compound of formula (XX), (XXI), (XXII) or (XXIII), in which $R^6$ represents a hydroxy group, and which may have been prepared as described in Reaction Scheme F, with various alkylating agents in the presence of a base.

Examples of alkylating agents which may be used in this reaction include: lower alkyl halides, such as iodomethane, iodoethane, iodopropane, 2-iodopropane, bromomethane, bromoethane, bromopropane and 2-bromopropane.

The nature of the base used is not particularly critical, and any base commonly used in conventional reactions of this type may equally be used here. Examples of preferred bases include: alkali metal hydroxides, such as sodium hydroxide or potassium hydroxide; alkali metal carbonates, such as sodium carbonate or potassium carbonate; alkali metal hydrides, such as lithium hydride, sodium hydride or potassium hydride; alkali metal alkoxides, such as potassium t-butoxide; organic bases, such as triethylamine, tributylamine, diisopropylethylamine, pyridine, 1,5-diazabicyclo[4.3.0]non-5-ene, 1,4-diazabicyclo[2.2.2]octane (DABCO) or 1,8-diazabicyclo[5.4.0]undec-7-ene (DBU); and organic metal bases, such as butyllithium, sec-butyllithium, lithium diisopropylamide, sodium bis(trimethylsilyl)amide and lithium bis(trimethylsilyl)amide. Of these, we prefer triethylamine, pyridine, 1,4-diazabicyclo[2.2.2]octane (DABCO) or 1,8-diazabicyclo[5.4.0]undec-7-ene (DBU)

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl acetate; ethers, such as diethyl ether, diisopropyl ether, tetrahydrofuran, dioxane, dimethoxyethane or diethylene glycol dimethyl ether; alcohols, such as methanol, ethanol or isopropyl alcohol; nitriles, such as acetonitrile; formamides, such as dimethylformamide or diethylformamide; sulfoxides, such as dimethyl sulfoxide; and mixtures of water with one or more of the above solvents.

The reaction can take place over a wide range of temperatures, and the precise reaction temperature is not critical to the invention. In general, we find it convenient to carry out the reaction at a temperature of from −90° C. to 150° C., more preferably from −78° C. to 60° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 4 hours, will usually suffice.

Compounds in which $R^6$ represents a lower alkylsulfonyl group can be prepared by oxidizing the corresponding compound of formula (XX), (XXI), (XXII) or (XXIII), in which $R^6$ represents a lower alkylthio group, and which may have been prepared as described in Reaction Scheme F, with various kinds of oxidizing agents.

The reaction is essentially the same as and may be carried out using the same reagents and reaction conditions as described above in relation to Step A4.

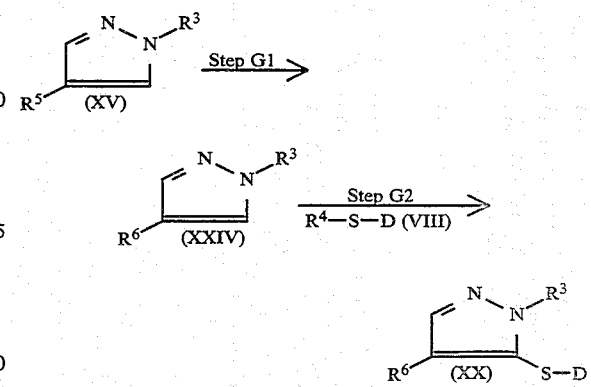

In the above formulae, $R^3$, $R^4$, $R^5$, $R^6$ and D are as defined above.

Reaction Scheme G provides an alternative method of preparation of the compound of formula (XX), which is also prepared as shown in Step F1 of Reaction Scheme F, by exchanging a halogen atom at the 4-position of the pyrazole ring in a compound of formula (XV) (prepared as shown in Step C1 of Reaction Scheme C) with a nucleophilic agent, and then subjecting the resulting compound of formula (XXIV) to thioetherification.

Steps G1 and G2 involve essentially the same reactions as those described in Steps F1 and A1, respectively, and may be carried out using the same reagents and reaction conditions.

Reaction Scheme H

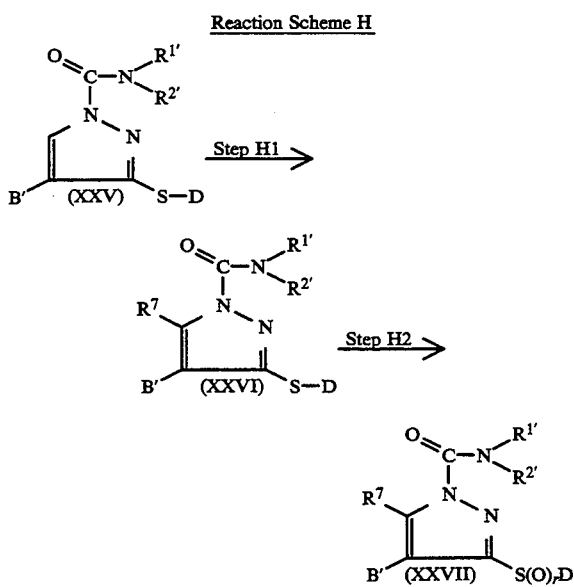

In the above formulae, $R^{1'}$, $R^{2'}$, B', D and r are as defined above and $R^7$ represents:
a hydroxy group,
a halogen atom,
an unsubstituted alkyl group having from 1 to 6 carbon atoms,
a substituted alkyl group having from 1 to 6 carbon atoms and having at least one, and preferably from 1 to 3, substituents selected from the group consisting of substituents (c), defined above,
an unsubstituted alkenyl group having from 2 to 6 carbon atoms,
a substituted alkenyl group which has from 2 to 6 carbon atoms and which is substituted by at least one substituent selected from the group consisting of halogen atoms,
an alkylthio group having from 1 to 6 carbon atoms,
a dialkylsulfamoyl group, in which each alkyl part has from 1 to 4 carbon atoms,
an aliphatic acyl, preferably alkylcarbonyl, group which has from 2 to 7 carbon atoms and which is unsubstituted or is substituted by at least one substituent selected from the group consisting of substituents (a), defined above,
an alkoxycarbonyl group having from 2 to 7 carbon atoms,
a group of formula —$CONR^aR^b$, in which $R^a$ and $R^b$ are independently selected from the group consisting of hydrogen atoms and alkyl groups having from 1 to 4 carbon atoms,
a formyl group or
a cyano group.

All of the above groups which may be represented by $R^7$ may be as defined and exemplified above in relation to the corresponding groups which may be represented by A.

In Reaction Scheme H, a compound of formula (XXVI) [i.e. a compound of formula (I), wherein A represents any one of the groups and atoms defined above in relation to $R^7$, B is B' and n is 0] and a compound of formula (XXVII) [i.e., the compound of formula (I), wherein A represents any one of the groups and atoms defined above in relation to $R^7$, B is B' and n is 1 or 2] may be prepared by introducing a nucleophilic substituent, $R^7$, at the 5-position of the pyrazole ring in a compound of formula (XXV), which may have been prepared as described in any of Reaction Schemes A, C and F.

In Step H1 a compound of formula (XXVI) is prepared by introducing a nucleophilic substituent, $R^7$, at the 5-position of the pyrazole ring in the compound of formula (XXV) [which may be the compound of formula (XII) prepared in Reaction Scheme A, the compound of formula (XVIII) prepared in Reaction Scheme C or the compound of formula (XXII) prepared in Reaction Scheme F].

The substitution reaction of the compound of formula (XXV) can be carried out by deprotonating the hydrogen atom at the 5-position of the pyrazole ring, and then introducing a substituent, $R^7$, using a nucleophilic reagent.

The nature of the deprotonating agent used in the first reaction of this Step is not particularly critical, provided that it has sufficient basicity to dissociate a proton at the 5-position of a pyrazole ring. Examples of suitable deprotonating agents include organic bases, such as butyllithium, sec-butyllithium, t-butyllithium, lithium diisopropylamide or lithium bis(trimethylsilyl)amide, and more preferably butyllithium or sec-butyllithium.

The deprotonation reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include ethers, such as diethyl ether or tetrahydrofuran.

The deprotonation reaction can take place over a wide range of temperatures, and the precise reaction temperature is not critical to the invention. In general, we find it convenient to carry out the reaction at a temperature of from −90° C. to 50° C., more preferably from −78° C. to 20° C. The time required for the reaction may also vary widely, depending on many factors, notably the reaction temperature and the nature of the reagents and solvent employed. However, provided that the reaction is effected under the preferred conditions outlined above, a period of from 5 minutes to 4 hours, more preferably from 15 minutes to 1.5 hours will usually suffice.

The nature of the nucleophilic reagent used will, of course, depend on the nature of the group which it is desired to introduce.

Thus, for example, where $R^7$ represents a hydroxy group, preferred examples of the nucleophilic reagent used for the nucleophilic reaction are peroxides, such as trimethylsilyl peroxide.

Where $R^7$ represents a halogen atom, examples of nucleophilic reagents include: N-halosuccinimides, such as N-chlorosuccinimide or N-bromosuccinimide; halogenated alkanes, such as 1,2-dibromoethane or hexachloroethane; hypochlorites, such as t-butyl hypochlorite; halogen molecules, such as bromine or iodine; N-fluoropyridinium salts, such as N-fluoropyridinium triflate; and N-fluorosulfonimides, such as N-fluoro-o-benzenedisulfonimide.

Where $R^7$ represents an optionally substituted alkyl group, an optionally substituted alkenyl group, a dialkylsulfamoyl group, an optionally substituted aliphatic acyl group, an alkoxycarbonyl group or a group of formula —$CONR^aR^b$, examples of nucleophilic reagents are the corresponding halides (i.e. the compounds represented by the formula R⁷X', wherein R⁷ is as defined above and X' represents a halogen atom).

Where $R^7$ represents an alkylthio group, examples of nucleophilic reagents include the disulfide or monosulfone compounds equivalent to the corresponding thiol compounds ($R^7$—SH).

Where $R^7$ represents a formyl group, examples of nucleophilic reagents include: formamides, such as dimethylformamide or diethylformamide; formates, such as ethyl formate or t-butyl formate; and mixed formic acid anhydrides, such as formic pivalic anhydride.

Where $R^7$ represents a cyano group, examples of nucleophilic reagents are cyanides, such as trimethylsilyl cyanide or N-toluenesulfonyl cyanide.

The reaction with the nucleophilic reagent can take place over a wide range of temperatures, and the precise reaction temperature is not critical to the invention. In general, we find it convenient to carry out the reaction at a relatively low temperature of from −90° C. to 50° C., more preferably from −78° C. to 20° C. The time required for the reaction may also vary widely, depending on many factors, notably the reaction temperature and the nature of the reagents and solvent employed. However, provided that the reaction is effected under the preferred conditions outlined above, a period of from 10 minutes to 10 hours, more preferably from 10 minutes to 2 hours, will usually suffice.

Step H2 involves essentially the same reaction as Step A4 and can be carried out using the same reagents and reaction conditions.

In the compounds of formulae (XXVI) and (XXVII), which may be prepared as described in Reaction Scheme H, a compound having a formyl group represented by $R^7$ can be reduced to a corresponding compound having a hydroxymethyl group. The hydroxymethyl compound thus obtained by reduction can be reacted with various kinds of carboxylic acid compounds to produce the corresponding ester compounds.

Further, the hydroxymethyl group prepared by reduction can be converted to a halogenated methyl group, such as a fluoromethyl, chloromethyl or bromomethyl group, by reaction with a halogenating agents.

Also, in the compounds of formulae (XXVI) and (XXVII), which may have been prepared as described in Reaction Scheme H, a compound having a formyl group represented by $R^7$ can be converted to a corresponding compound having a difluoromethyl group.

A compound in which $R^7$ represents an optionally substituted alkoxy group can be prepared by reacting the compound of formula (XXVI) or (XXVII), wherein $R^7$ represents a hydroxy group, prepared as described in Reaction Scheme H, with various kinds of alkylating agents by conventional means.

All of the above reactions involving the group or atom $R^7$ in the compounds of formulae (XXVI) and (XXVII) prepared as described in Reaction Scheme H can be carried out in a similar manner to those described in relation to $R^6$ in Reaction Scheme F.

A compound having an alkylsulfonyl group represented by $R^7$ can also be prepared by oxidizing the corresponding compound having a lower alkylthio group represented by $R^7$ in the compounds of formulae (XXVI) and (XXVII) with various oxidizing agents by conventional means. This reaction can be conducted in a similar manner to that described in Step A4.

Reaction Scheme I

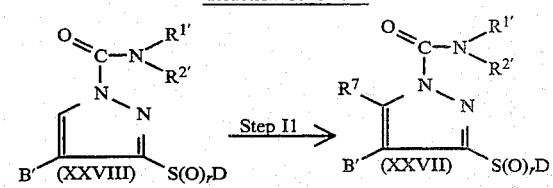

In the above formulae, $R^{1'}$, $R^{2'}$, $R^7$, B', D and r are as defined above.

Reaction Scheme I provides an alternative method of preparing the compound of formula (XXVII) by introducing a nucleophilic substituent represented by $R^7$ at the 5-position of the pyrazole ring in the compound of formula (XXVIII), which may have been prepared as described in Reaction Scheme A, B, C or F.

The reaction of Step I1 involves essentially the same reaction as and may be carried out as described in Step H1.

After completion of each reaction in the above Reaction Schemes A to I, the desired compound from each of the steps can be recovered from the reaction mixture by conventional means. An example of one such technique comprises: neutralizing appropriately the reaction mixture; if insoluble materials exist, filtering them off; adding a water-immiscible solvent; separating the organic phase and washing it with water; and finally distilling off the organic solvent. The product thus obtained can further be purified by conventional means, for example, recrystallization, reprecipitation, or the various chromatography techniques, notably column chromatography or preparative thin layer chromatography.

For use as a herbicide, the compounds of the invention may be applied in admixture with a carrier and, if necessary, with other adjuvants, and may be used in the form of any preparation commonly used for this purpose, for example, as dusts, coarse dusts, fine granules, granules, wettable powders, flowable agents, emulsifiable concentrates, liquids and the like. The carrier with which it may be mixed may be a synthetic or natural inorganic or organic substance, and is incorporated into a herbicide in order to assist the active compound to reach the target plant or in order to facilitate storage, transport or handling of the active compound.

Examples of suitable solid carriers include: clays, such as kaolinites, montmorillonites or attapulgites; inorganic substances, such as talc, mica, agalmatolite, pumice, vermiculite, gypsum, dolomite, diatomaceous earth, magnesium lime, apatite, zeolite, silicic acid anhydride, synthetic calcium silicate, kaolin, bentonite or calcium carbonate; vegetable organic substances, such as soybean flour, tobacco powder, walnut powder, wheat-meal, woodflour, starch or crystalline cellulose; synthetic or natural high molecular weight compounds, such as coumarone resin, petroleum resin, alkyd resin, poly(vinyl chloride), poly(alkylene glycol), ketone resin, ester gum, copal gum or dammar gum; waxes, such as carnauba wax, paraffin wax or beeswax; and urea.

Examples of suitable liquid carriers include: paraffin or naphthene hydrocarbons, such as kerosene, mineral oil, spindle oil or white oil; aromatic hydrocarbons, such as benzene, toluene, xylene, ethylbenzene, cumene or methylnaphthalene; halogenated hydrocarbons, such as carbon tetrachloride, chloroform, trichloroethylene, monochlorobenzene or o-chlorotoluene; ethers, such as dioxane or tetrahydrofuran; ketones, such as acetone, methyl ethyl ketone, diisobutyl ketone, cyclohexanone, acetophenone or isophorone; esters, such as ethyl acetate, amyl acetate, ethylene glycol acetate, diethylene glycol acetate, dibutyl maleate or diethyl succinate; alcohols, such as methanol, hexanol, ethylene glycol, diethylene glycol, cyclohexanol or benzyl alcohol; ether alcohols, such as ethylene glycol ethyl ether, ethylene glycol phenyl ether, diethylene glycol ethyl ether or diethylene glycol butyl ether; polar solvents, such as dimethylformamide or dimethyl sulfoxide; and water.

In order to facilitate emulsification, dispersion, moisturizing, diffusion, spreading, bonding and control of disintegration, to stabilize the active compound, to improve mobility and rust resistance and to accelerate absorption in the plant, the compounds of the present invention may be used in admixture with one or more surface active agents, which may be ionic or non-ionic agents.

Examples of suitable nonionic surface active agents include: for example, fatty acid sucrose esters, addition polymers of ethylene oxide with higher alcohols, such as lauryl alcohol, stearyl alcohol or oleyl alcohol; addition polymers of ethylene oxide with alkylphenols, such as isooctylphenol or nonylphenol; addition polymers of ethylene oxide with alkylnaphthols, such as butylnaphthol or octylnaphthol; addition polymers of ethylene oxide with higher fatty acids, such as palmitic acid, stearic acid or oleic acid; addition polymers of ethylene oxide with mono- or di-alkyl phosphates, such as stearyl phosphate or dilauryl phosphate; addition polymers of ethylene oxide with amines, such as dodecylamine or stearamide; addition polymers of ethylene oxide with higher fatty acid esters of polyhydric alcohols, such as sorbitan; and addition polymers of ethylene oxide with propylene oxide.

Examples of suitable anionic surface active agents include: for example, alkyl sulfates, such as sodium lauryl sulfate or an amine salt of oleyl sulfate; salts of fatty acids, such as sodium dioctyl sulfosuccinate, sodium oleate or sodium stearate; and alkyl arylsulfonates, such as sodium isopropyl naphthalenesulfonate, sodium methylenebisnaphthalenesulfonate, sodium ligninsulfonate or sodium dodecylbenzenesulfonate.

Examples of cationic surface active agents include, for example, higher aliphatic amines, quaternary ammonium salts and alkyl pyridinium salts.

Further, in order to improve the properties of the preparation and to enhance the biological effect, the herbicides of the present invention may be used in combination with high molecular weight polymers, such as gelatin, gum arabic, casein, albumin, glue, sodium alginate, poly(vinyl alcohol), carboxymethyl cellulose, methyl cellulose, and hydroxymethyl cellulose; thixotropic agents, such as sodium polyphosphate or bentonite; or other adjuvants.

These carriers and adjuvants can be used alone or in combination depending upon the purpose of the preparation and the method of application.

The amount of the active compound in the preparation may vary over a wide range, and there is no particular restriction on its concentration. However, the preferred concentration of active compound in the preparation will depend primarily on the nature of the preparation, as well as upon the intended manner of use and the nature of the weeds to be killed. If desired, the preparation may be supplied in a concentrated form intended to be diluted by the user.

Thus, for example, dusts normally comprise from 2 to 10 parts by weight of the active compound, the remainder being a solid carrier.

Wettable powders normally comprise from 10 to 80 parts by weight of the active compound, the remainder being a solid carrier or a dispersing or moistening agent, and, if necessary, a protecting colloidal agent, a thixotropic agent, a defoaming agent or the like.

Granules normally comprise from 0.1 to 10 parts by weight of the active compound, the remainder, for the most part, being a solid carrier. The active compound may be homogeneously mixed with the solid carrier, or adhered on or absorbed by a solid carrier. The particle diameter is preferably in the range of from about 0.2 to 1.5 mm.

Emulsifiable concentrates normally comprise from 1 to 50 parts by weight of the active compound and from 5 to 20 parts by weight of an emulsion, the remainder being a liquid carrier and also, if necessary, a rust-resistant agent.

The herbicide of the present invention may be applied to soil, for example a paddy field or a farm, before or after germination of weeds, preferably in an amount of from 1 to 1000 g, more preferably from 10 to 300 g, of the active compound per 10 ares, in the various forms of preparation mentioned above to eliminate weeds effectively. Furthermore, the compounds may be applied to non-farm areas, such as a road, ground, a building site, a right-of-way or the like, preferably in an amount of from 200 to 1000 g per 10 ares to combat weeds effectively in those locations also.

If desired, the herbicide of the present invention may be used in combination with one or more other herbicides in order to improve a weed-killing spectrum and, in some cases, a synergic effect may be expected.

The herbicide of the invention may be applied in admixture with a plant growth regulator, a bactericide, an insecticide, an acaricide, a nematocide or a fertilizer, if desired, in order to provide a composition for agricultural or horticultural use have a wider field of use.

The compounds of the present invention have herbicidal activity and can be put to herbicidal use. The activity is generally more efficacious against monocotyledons than against dicotyledons. For example, the compounds of the invention can effectively control flourishing weeds in a paddy field, when applied by soil application under flooded conditions to a paddy field before or after germination of the weeds or forbs; in particular, they are effective against: gramineous weeds, such as *Echinochloa oryzicola* Vasing, *Echinochloa crus-galli* (L) Beauv. var. formosensis Ohwi and *Echinochloa crus-galli* subsp. *genuina* var. echinata Honda; perennial weeds which are difficult to exterminate by conventional herbicides, including, cyperaceous weeds, such as *Eleocharis acicularis* (L.) Roem. et Schult. var. longiseta Sven., *Scirpsus juncoides* Roxb. subsp. hotarui (Ohwi) T. Koyama, *Eleocharis kuroguwai* Ohwi and *Cyperus serotinus* Rottb. and alismataceous weeds, such as *Sagittaria pygmaea* Miq. and *Sagittaria trifolia* L. Moreover, they can effectively control broad-leaved weeds, including, scrophulariaceous weeds, such as *Lindernia pyxidaria* L., lythraceous weeds, such as *Rotala indica* (Willd.) Koehne var. uliginosa (Miq) Koehne, *Ammannia multiflora* Roxb. and *Rotala mexicana* Cham et Schltdl. and pontederiaceous weeds, such as

*Monochoria vaginalis* (Burm. f) Presl var. plantaginea (Roxb) Solms-Laub and *Monochoria korsakowii* Regel et Maack.

On the other hand, it has been found that the compounds of the invention show a selective activity, in that they do not harm many useful plants, such as rice, including paddy-rice plant, and have the advantage of a wide range of application for treatment. In a farm, by treating the soil before germination of weeds or forbs, the compounds of the invention can extensively exterminate flourishing weeds or forbs, for example: amaranthaceous weeds, such as *Amaranthus lividus* L., *Amaranthus viridis* L. and *Achyranthes japonica* (Miq) Nakai; portulacaceous weeds, such as *Portulaca oleracea* L.; chenopodiaceous weeds, such as *Chenopodium album* L. var. centrorubrum Makino, *Chenopodium album* L. and *Chenopodium serotinum* L.; commelinaceous weeds, such as *Commelina communis* L.; caryophyllaceous weeds, such as *Stellaria media* (L.) Villars, *Stellaria alsine* Grimm, *Cerastium holosteoides* Fries var. angustifolium (Franch.) Mizushima and *Sagina japonica* (Sw.) Ohwi; euphorbiaceous weeds, such as *Acalypha australis* L. and *Euphorbia supina* Raf.; especially, gramineous weeds, such as *Agropyron tsukushiense* (Honda) Ohwi var. transiens (Hack.), *Digitaria ciliaris* (Retz) Koeler, *Digitaria timorensis* (Kunth) Balansa, *Echinochloa crus-galli* (L.) Beauv. var. crus-galli, *Setaria viridis* (L.) Beauv., *Setaria faberi* Herrm., *Alopecurus aequalis* Sobol. var. amurensis (Komar) Ohwi and *Poa annua* L. Furthermore, the compounds of the invention never cause damage to farm products, such as sweet corn, sugar beet, soybean, cotton plant, radish, tomato, carrot, Chinese cabbage, lettuce or the like.

Further, the compounds of the present invention can be used effectively on non-agricultural areas, forests and the like as a herbicide.

The compounds of the present invention also have the ability to regulate the growth of plants and, when plants are treated with these compounds at the appropriate season and at a proper concentration, the growth of certain types of plants, especially grasses, can be controlled without withering. Thus the compounds of the present invention can be used as a plant growth retardant towards certain plants. Therefore, the term "herbicide" of the present invention covers a plant growth retardant.

In particular, the compounds of the present invention can be used as a lawn grass growth retardant by inhibiting growth of: Japanese lawn grasses, such as lawn grass, sodded lawn grass, Korean lawn grass or the like; and, in particular, American and European lawn grasses, such as Bermuda grass, bent grass, blue grass, fescue grass, ryegrass or the like; they can, as a result, be used in a gardens, public areas of greenery, golf courses and the like.

The preparation of the compounds of the present invention is further illustrated by the following Examples, and the use of these compounds in agricultural and horticultural compositions is illustrated in the subsequent Preparations. The activity of various of these compounds is then shown.

EXAMPLE 1

1-(Diethylcarbamoyl)-3-(2-ethyl-6-methylphenylthio)-pyrazole (Compound No. 7.12)

and 1-(Diethylcarbamoyl)-3-(2-ethyl-6-methylphenylsulfonyl)pyrazole (Compound No. 7.10)

1(1) 1-(Dimethylsulfamoyl)pyrazole 2.80 g of sodium hydride (as a 60% w/w dispersion in mineral oil), and then 10 ml of dimethylsulfamoyl chloride, were added, in turn, to a solution of 4.76 g of pyrazole in 95 ml of tetrahydrofuran, and the resulting mixture was stirred at room temperature for 3 hours. At the end of this time, the reaction mixture was diluted with an excess of water and extracted with ethyl acetate. The extract was washed with water and then dried over anhydrous sodium sulfate, after which it was purified by distillation under reduced pressure. There were obtained 13.10 g (a quantitative yield) of the title compound, boiling at 130° C./0.1 mmHg (13.3 Pa).

Nuclear Magnetic Resonance Spectrum (CDCl$_3$, 200 MHz), δ ppm: 7.98 (1H, doublet, J=2.6 Hz); 7.74 (1H, doublet, J=1.1 Hz); 6.39 (1H, doublet of doublets, J=1.5 & 2.6 Hz); 2.81 (6H, singlet).

1(2) 1-(Dimethylsulfamoyl)-5-(2-ethyl-6-methylphenylthio)pyrazole 2.1 ml of a 1.49M solution of butyllithium in hexane were added, at −78° C. and under an atmosphere of nitrogen, to a solution of 547 mg of 1-(dimethylsulfamoyl)pyrazole [prepared as described in step (1) above] in 16 ml of dry tetrahydrofuran, and the resulting mixture was allowed to stand at the same temperature for 20 minutes. At the end of this time, a solution of 945 mg of 2-ethyl-6-methylphenyl disulfide in 5 ml of tetrahydrofuran was added to the mixture, which was then stirred at the same temperature for 40 minutes. The reaction mixture was then mixed with an aqueous solution of ammonium chloride and extracted with ethyl acetate. The extract was washed with water and dried over anhydrous sodium sulfate, after which it was concentrated by evaporation under reduced pressure. The concentrate was purified by column chromatography through silica gel, eluted with a 10:1 by volume mixture of hexane and ethyl acetate, to give 701 mg (yield 69%) of the title compound as an oil.

Nuclear Magnetic Resonance Spectrum (CDCl$_3$, 200 MHz), δ ppm: 7.44 (1H, doublet, J=1.7 Hz); 7.36–7.18 (3H, multiplet); 5.24 (1H, doublet, J=1.7 Hz); 3.05 (6H, singlet); 2.85 (2H, quartet, J=7.5 Hz); 2.44 (3H, singlet); 1.17 (3H, triplet, J=7.5 Hz).

1(3) 3-(2-Ethyl-6-methylphenylthio)pyrazole 0.9 ml of trifluoroacetic acid was added to a solution of 640 mg of 1-(dimethylsulfamoyl)-5-(2-ethyl-6-methylphenylthio)pyrazole [prepared as described in step (2) above] in 3 ml of methylene chloride, and the resulting mixture was heated at 50° C. for 4 hours. At the end of this time, the reaction mixture was poured into an aqueous solution of sodium hydrogencarbonate and extracted with methylene chloride. The extract was washed with water and dried over anhydrous sodium sulfate. The solvent was removed by distillation under reduced pressure, to give 628 mg (a quantitative yield) of the title compound as an oil.

Nuclear Magnetic Resonance Spectrum (CDCl$_3$, 200 MHz), δ ppm: 7.52 (1H, broad); 7.3–7.1 (4H, multiplet);

7.00 (1H, broad); 2.93 (2H, quartet, J=7.5 Hz); 2.45 (3H, singlet); 1.19 (3H, triplet, J=7.5 Hz).

1(4) 1-(Diethylcarbamoyl)-3-(2-ethyl-6-methylphenylthio)pyrazole 0.41 ml of 1,8-diazabicyclo[5.4.0]undec-7-ene and 0.21 ml of diethylcarbamoyl chloride were added, in turn, to a solution of 299 mg of 3-(2-ethyl-6-methylphenylthio)pyrazole [prepared as described in step (3) above] in 6 ml of acetonitrile, and the resulting mixture was stirred at room temperature for 3 hours. At the end of this time, the reaction mixture was mixed with water and extracted with ethyl acetate. The extract was washed with water and dried over anhydrous sodium sulfate, after which the solvent was removed by distillation under reduced pressure. The resulting residue was purified by column chromatography through silica gel, eluted with a 6:1 by volume mixture of hexane and ethyl acetate, to give 273 mg (yield 63%) of the title compound as an oil.

Nuclear Magnetic Resonance Spectrum (CDCl$_3$, 200 MHz), δ ppm: 8.03 (1H, doublet, J=2.9 Hz); 7.22 (1H, doublet, J=7.0 Hz); 7.16–7.12 (2H, multiplet); 5.94 (1H, doublet, J=2.9 Hz); 3.47 (4H, quartet, J=7.0 Hz); 2.90 (2H, quartet, J=7.5 Hz); 2.44 (3H, singlet); 1.18 (3H, triplet, J=7.5 Hz); 1.09 (6H, broad triplet).

1(5) 1-(Diethylcarbamoyl)-3-(2-ethyl-6-methylphenylsulfonyl)pyrazole 366 mg of 3-chloroperoxybenzoic acid were added to a solution of 245 mg of 1-(diethylcarbamoyl)-3-(2-ethyl-6methylphenylthio)pyrazole [prepared as described in step (4) above] in 4 ml of 1,2-dichloroethane, and the resulting mixture was heated at 50° C. for 1 hour. At the end of this time, the reaction mixture was mixed with an aqueous solution of sodium sulfite, after which it was extracted with methylene chloride. The extract was washed with an aqueous solution of sodium hydrogencarbonate and dried over anhydrous sodium sulfate, and then the solvent was removed by distillation under reduced pressure. The resulting residue was purified by column chromatography through silica gel, eluted with an 8:1 by volume mixture of hexane and ethyl acetate, to give 266 mg (yield 99%) of the title compound as an oil.

Nuclear Magnetic Resonance Spectrum (CDCl$_3$, 270 MHz), δ ppm: 8.20 (1H, doublet, J=2.9 Hz); 7.37 (1H, triplet, J=7.5 Hz); 7.20 (1H, broad doublet, J=7.5 Hz); 7.13 (1H, broad doublet, J=7.5 Hz); 6.89 (1H, doublet, J=2.9 Hz); 3.44 (1H, quartet, J=7.0 Hz); 3.11 (2H, quartet, J=7.5 Hz); 2.67 (3H, singlet); 1.27 (3H, singlet); 1.3–0.9 (6H, broad).

EXAMPLE 2

1-(Dipropylcarbamoyl)-3-(2,4,6-trimethylphenylsulfonyl)pyrazole (Compound No. 10.46)

2(1) 3-(2,4,6-Trimethylphenylthio)pyrazole 9.13 ml of trifluoroacetic acid were added to a solution of 11.59 g of 1-(dimethylsulfamoyl)-5-(2,4,6-trimethylphenylthio)pyrazole [prepared in a similar manner to that described in Example 1(2)] in 58 ml of chloroform, and the resulting mixture was heated at 60° C. for 4 hours. The reaction mixture was then concentrated by evaporation under reduced pressure, and the concentrate was diluted with water and made alkaline by the addition of an aqueous solution of sodium hydrogencarbonate; it was then extracted with ethyl acetate. The extract was washed with water and dried over anhydrous sodium sulfate. The solvent was removed by distillation under reduced pressure, to give 7.77 g (a quantitative yield) of the title compound as an oil.

Nuclear Magnetic Resonance Spectrum (CDCl$_3$, 200 MHz), δ ppm: 7.44 (1H, doublet, J=2.1 Hz); 7.27 (2H, singlet); 5.95 (1H, doublet, J=2.1 Hz); 2.45 (6H, singlet); 2.29 (3H, singlet).

2(2) 3-(2,4,6-Trimethylphenylsulfonyl)pyrazole 7.60 g of 3-chloroperoxybenzoic acid were added to a solution of 3.5 g of 3-(2,4,6-trimethylphenylthio)pyrazole [prepared as described in step (1) above] in 70 ml of 1,2-dichloroethane, and the resulting mixture was stirred at room temperature for 15 hours. At the end of this time, the reaction mixture was washed with an aqueous solution of sodium hydrogencarbonate and with water, in that order, after which it was dried over anhydrous sodium sulfate. The solvent was removed by distillation under reduced pressure, and then the crystalline residue was recrystallized from a mixture of methylene chloride and diisopropyl ether to give 3.70 g (yield 92%) of the title compound, melting at 185°–186° C.

Nuclear Magnetic Resonance Spectrum (CDCl$_3$, 200 MHz), δ ppm: 7.85 (1H, doublet, J=2.4 Hz); 6.96 (2H, singlet); 6.72 (1H, doublet, J=2.4 Hz); 2.66 (6H, singlet); 2.30 (3H, singlet).

2(3) 1-(Dipropylcarbamoyl)-3-(2,4,6-trimethylphenylsulfonyl)pyrazole 2 ml of a 1.98M solution of phosgene in toluene were added to a solution of 200 mg of 3-(2,4,6-trimethylphenylsulfonyl)pyrazole [prepared as described in step (2) above] in 1 ml of toluene, and the resulting solution was heated at 60° C. for 1 hour. The mixture was concentrated by evaporation under reduced pressure, and then 97 mg of triethylamine and 89 mg of diisopropylamine were added, in that order, to the oily residue. The reaction mixture was then stirred at ambient temperature for 20 minutes, after which it was diluted with diethyl ether. The ethereal solution was washed with 1N aqueous hydrochloric acid, with an aqueous solution of sodium hydrogencarbonate and with water, in that order, and was then dried over anhydrous sodium sulfate. The solvent was removed by distillation under reduced pressure, and the resulting residue was purified by column chromatography through silica gel, eluted with a 6:1 by volume mixture of hexane and ethyl acetate, to afford 268 mg (yield 89%) of the title compound, melting at 64°–65° C.

Nuclear Magnetic Resonance Spectrum (CDCl$_3$, 200 MHz), δ ppm: 8.18 (1H, doublet, J=2.8 Hz); 6.94 (2H, singlet); 6.87 (1H, doublet, J=2.8 Hz); 3.38 (4H, broad triplet, J=7.2 Hz); 2.65 (6H, singlet); 2.29 (3H, singlet); 1.8–1.4 (4H, broad); 1.1–0.8 (3H, broad); 0.8–0.6 (3H, broad).

EXAMPLE 3

1-(Diethylcarbamoyl)-4-chloro-3-(3,5-dichlorophenylthio)pyrazole (Compound No. 9.50)

and 1-(Diethylcarbamoyl)-4-chloro-3-(3,5-dichlorophenylsulfonyl)pyrazole (Compound No. 9.49)

3(1) 1-(Dimethylsulfamoyl)-4-chloropyrazole 2.45 g of N-chlorosuccinimide were added to a solution of 2.14 g of 1-(dimethylsulfamoyl)pyrazole [prepared as described in Example 1(1)] in 20 ml of chloroform, and the resulting mixture was heated at 70° C. for 5 hours. At the end of this time, the reaction mixture was diluted with ethyl acetate, and then the ethyl acetate solution was washed with water and dried over anhydrous sodium sulfate. The solvent was then removed by distillation under reduced pressure. The resulting residue was purified by column chromatography through silica gel, eluted with an 8:1 by volume mixture of hexane and ethyl acetate, to give 2.00 g (yield 78%) of the title compound as an oil.

Nuclear Magnetic Resonance Spectrum (CDCl$_3$, 270 MHz), δ ppm: 7.95 (1H, doublet, J=0.8 Hz); 7.65 (1H, doublet, J=0.8 Hz); 2.97 (6H, singlet).

Following the procedure described above, but using N-bromosuccinimide and N-iodosuccinimide, we also produced:

1-(dimethylsulfamoyl)-4-bromopyrazole as an oil.

Nuclear Magnetic Resonance Spectrum (CDCl$_3$, 270 MHz), δ ppm: 7.98 (1H, singlet); 7.68 (1H, singlet); 2.97 (6H, singlet).

1-(dimethylsulfamoyl)-4-iodopyrazole as an oil.

Nuclear Magnetic Resonance Spectrum (CDCl$_3$, 200 MHz), δ ppm: 8.01 (1H, singlet); 7.71 (1H, singlet); 2.96 (6H, singlet.

3(2)    1-(Dimethylsulfamoyl)-4-chloro-5-(3,5-dichlorophenylthio)pyrazole 0.67 ml of a 1.49M solution of butyllithium in hexane was added at −78° C. to a solution of 300 mg of 1-(dimethylsulfamoyl)-4-chloropyrazole [prepared as described in step (1) above] in 15 ml of dry tetrahydrofuran. After 10 minutes, a solution of 449 mg of 3,5-dichlorophenyl disulfide in 7 ml of dry tetrahydrofuran was added to the mixture, which was then stirred at the same temperature for 1 hour. At the end of this time, the reaction mixture was mixed with an aqueous solution of ammonium chloride and extracted with ethyl acetate. The extract was washed with water and dried over anhydrous sodium sulfate; the solvent was then removed by distillation under reduced pressure. The residue thus obtained was purified by column chromatography through silica gel, eluted with a 6:1 by volume mixture of hexane and ethyl acetate, to give 410 mg (yield 74%) of the title compound, melting at 32° C.

Nuclear Magnetic Resonance Spectrum (CDCl$_3$, 200 MHz), δ ppm: 7.72 (1H, singlet); 7.21 (1H, triplet, J=1.8 Hz); 7.11 (2H, doublet, J=1.8 Hz); 3.08 (6H, singlet).

3(3)    1-(Diethylcarbamoyl)-4-chloro-3-(3,5-dichlorophenylthio)pyrazole 195 mg of trifluoroacetic acid were added to a solution of 200 mg of 1-(dimethylsulfamoyl)-4-chloro-5-(3,5-dichlorophenylthio)pyrazole [prepared as described in step (2) above] in 5 ml of chloroform, and the resulting mixture was heated at 50° C. for 2 hours. The mixture was allowed to cool, after which it was diluted with water and neutralized with an aqueous solution of sodium hydrogencarbonate. It was then extracted with ethyl acetate. The extract was washed with water and dried over anhydrous sodium sulfate, and then the solvent was removed by distillation under reduced pressure. The residue was dissolved in 5 ml of acetonitrile, and 89 mg of diethylcarbamoyl chloride and 55 mg of 1,4-diazabicylo[2.2.2]octane were added to the resulting solution. The reaction mixture was then heated at 50° C. for 2 hours, after which it was diluted with ethyl acetate and the solution was washed with 2N aqueous hydrochloric acid, with a 5% w/v aqueous solution of sodium hydroxide and with water, in that order. The organic layer was separated and dried over anhydrous sodium sulfate, and then the solvent was removed by distillation under reduced pressure. There were obtained 163 mg (yield 83%) of the title compound as an oil.

Nuclear Magnetic Resonance Spectrum (CDCl$_3$, 200 MHz), δ ppm: 8.19 (1H, singlet); 7.24 (3H, multiplet); 3.53 (4H, quartet, J=7.0 Hz); 1.22 (6H, triplet, J=7.0 Hz).

3(4)    1-(Diethylcarbamoyl)-4-chloro-3-(3,5-dichlorophenylsulfonyl)pyrazole 125 mg of 3-chloroperoxybenzoic acid were added to a solution of 125 mg of 1-(diethylcarbamoyl)-4-chloro-3-(3,5-dichlorophenylthio)pyrazole [prepared as described in step (3) above] in 3 ml of 1,2-dichloroethane, and the resulting mixture was heated at 50° C. for 2 hours. The reaction mixture was then diluted with ethyl acetate, after which it was washed with an aqueous solution of sodium sulfite, with an aqueous solution of sodium hydrogencarbonate and with water, in that order. The mixture was then dried over anhydrous sodium sulfate, and the solvent was removed by distillation under reduced pressure, after which the residue was purified by column chromatography through silica gel, eluted with an 8:1 by volume mixture of hexane and ethyl acetate, to give 115 mg (yield 85%) of the title compound, melting at 89°–90° C.

Nuclear Magnetic Resonance Spectrum (CDCl$_3$, 200 MHz), δ ppm: 8.16 (1H, singlet); 7.93 (2H, doublet, J=1.9 Hz); 7.63 (1H, triplet, J=1.9 Hz); 3.51 (4H, quartet, J=7.0 Hz); 1.26 (6H, triplet, J=7.0 Hz).

EXAMPLE 4

1-(Diethylcarbamoyl)-4-bromo-5-(2,5-dimethylphenylthio)pyrazole (Compound No. 6.116)

and 1-(Diethylcarbamoyl)-4-bromo-3-(2,5-dimethylphenylsulfonyl)pyrazole (Compound No. 6.114)

4(1)    1-(Dimethylsulfamoyl)-4-bromo-5-(2,5-dimethylphenylthio)pyrazole 1.55 g of N-bromosuccinimide was added to a solution of 2.71 g of 1-(dimethylsulfamoyl)-5-(2,5-dimethylphenylthio)pyrazole [prepared in a similar manner to that described in Example 1(2)] in 27 ml of chloroform, and the resulting mixture was heated at 65° C. for 1.5 hours. At the end of this time, the reaction mixture was poured into an aqueous solution of sodium sulfite and extracted with methylene chloride. The extract was washed with water and dried over anhydrous sodium sulfate, and the solvent was removed by distillation under reduced pressure. The residue was purified by column chromatography through silica gel, eluted with an 8:1 by volume mixture of hexane and ethyl acetate, to afford 2.44 g (yield 72%) of the title compound, melting at 83°–84° C.

Nuclear Magnetic Resonance Spectrum (CDCl$_3$, 200 MHz), δ ppm: 7.72 (1H, singlet); 7.08 (1H, doublet, J=7.7 Hz); 6.9 (1H, doublet, J=7.7 Hz); 6.71 (1H, singlet); 3.05 (6H, singlet); 2.41 (3H, singlet); 2.21 (3H, singlet).

4(2)    1-(Diethylcarbamoyl)-4-bromo-5-(2,5-dimethylphenylthio)pyrazole 1.4 ml of trifluoroacetic acid was added to a solution of 2.39 g of 1-(dimethylsulfamoyl)-4-bromo-5-(2,5-dimethylphenylthio)pyrazole [prepared as described in step (1) above] in 20 ml of methylene chloride, and the resulting mixture was heated at 50° C. for 3 hours. At the end of this time, the reaction mixture was diluted with water and extracted with methylene chloride. The extract was washed with water and dried over anhydrous sodium sulfate; the solvent was then removed by distillation under reduced pressure. The residue thus obtained was dissolved in 20 ml of acetonitrile, and 1.15 g of 1,4-diazabicyclo[2.2.2]octane, followed by 1.47 ml of diethylcarbamoyl chloride, were added to the resulting solution. The resulting mixture was heated at 50° C. for 4 hours, poured into water and then extracted with ethyl acetate. The extract was washed with a saturated aqueous solution of sodium chloride and dried over anhydrous sodium sulfate; the solvent was then removed by distillation under reduced pressure. The resulting residue was purified by column chromatography through silica gel, eluted with a 6:1 by volume mixture of hexane and ethyl acetate, to afford 2.33 g (a quantitative yield) of the title compound.

Nuclear Magnetic Resonance Spectrum (CDCl$_3$, 200 MHz), δ ppm: 8.16 (1H, singlet); 7.23–7.01 (3H, multiplet); 3.44 (4H, quartet, J=7.2 Hz); 2.40 (3H, singlet); 2.27 (3H, singlet); 1.20–0.95 (6H, broad).

4(3) 1-(Diethylcarbamoyl)-4-bromo-5-(2,5-dimethylphenylsulfonyl)pyrazole 398 mg of 3-chloroperoxybenzoic acid were added to a solution of 315 mg of 1-(diethylcarbamoyl)-4-bromo-5-(2,5-dimethylphenylthio)pyrazole [prepared as described in step (2) above] in 7 ml of 1,2-dichloroethane, and the resulting mixture was heated at 50° C. for 2 hours. At the end of this time, the reaction mixture was poured into an aqueous solution of sodium sulfite and extracted with methylene chloride. The extract was washed with an aqueous solution of sodium hydrogencarbonate and with water, in that order, after which it was dried over anhydrous sodium sulfate and the solvent was removed by distillation under reduced pressure. The resulting residue was purified by column chromatography through silica gel, eluted with a 10:1 by volume mixture of hexane and ethyl acetate, to give 283 mg (yield 83%) of the title compound, melting at 82°–83° C.

Nuclear Magnetic Resonance Spectrum (CDCl$_3$, 200 MHz), δ ppm: 8.24 (1H, singlet); 7.4–7.1 (3H, multiplet); 3.44 (4H, quartet, J=7.0 Hz); 2.67 (6H, singlet); 1.35–0.9 (6H, broad).

EXAMPLE 5

1-(Diethylcarbamoyl)-4-chloro-3-(2,4,6-trimethylphenylthio)pyrazole (Compound No. 10.55)

and 1-(Diethylcarbamoyl)-4-chloro-3-(2,4,6-trimethylphenylsulfonyl)pyrazole (Compound No. 10.56)

5(1) 4-Chloro-3-(2,4,6-trimethylphenylthio)pyrazole 306 mg of N-chlorosuccinimide were added to a solution of 500 mg of 3-(2,4,6-trimethylphenylthio)pyrazole [prepared as described in Example 2(1)] in 10 ml of chloroform, and the resulting mixture was heated at 50° C. for 2 hours. The reaction mixture was then diluted with water and extracted with methylene chloride. The extract was washed with water and dried over anhydrous sodium sulfate, after which the solvent was removed by distillation under reduced pressure. The resulting residue was purified by column chromatography through silica gel, eluted with a 5:1 by volume mixture of hexane and ethyl acetate, to afford 516 mg (yield 89%) of the title compound as an oil.

Nuclear Magnetic Resonance Spectrum (CDCl$_3$, 200 MHz), δ ppm: 7.43 (1H, singlet); 6.98 (2H, singlet); 2.43 (6H, singlet); 2.29 (3H, singlet).

5(2) 1-(Diethylcarbamoyl)-4-chloro-3-(2,4,6-trimethylphenylthio)pyrazole 453 mg of 1,4-diazabicyclo[2.2.2]octane and 356 mg of diethylcarbamoyl chloride were added, in that order, to a solution of 510 mg of 4-chloro-3-(2,4,6-trimethylphenylthio)pyrazole [prepared as described in step (1) above] in 5 ml of acetonitrile, and the resulting mixture was stirred at room temperature for 20 minutes. At the end of this time, the reaction mixture was diluted with water and extracted with ethyl acetate. The extract was washed with water and dried over anhydrous sodium sulfate, after which the solvent was removed by distillation under reduced pressure. The residue was purified by column chromatography through silica gel, eluted with a 6:1 by volume mixture of hexane and ethyl acetate, to afford 561 mg (yield 79%) of the title compound, melting at 84°–86° C.

Nuclear Magnetic Resonance Spectrum (CDCl$_3$, 200 MHz), δ ppm: 8.07 (1H, singlet); 6.95 (2H, singlet); 3.34 (4H, quartet, J=7.0 Hz); 2.43 (6H, singlet); 2.28 (3H, singlet); 1.2–0.7 (6H, broad).

5(3) 1-(Diethylcarbamoyl)-4-chloro-3-(2,4,6-trimethylphenylsulfonyl)pyrazole 734 mg of 3-chloroperoxybenzoic acid were added to a solution of 536 mg of 1-(diethylcarbamoyl)-4-chloro-3-(2,4,6-trimethylphenylthio)pyrazole [prepared as described in step (2) above] in 5 ml of 1,2-dichloroethane, and the resulting mixture was heated at 50° C. for 1.5 hours. The reaction mixture was then diluted with water and extracted with ethyl acetate. The extract was washed with an aqueous solution of sodium hydrogencarbonate and with water, in that order, after which it was dried over anhydrous sodium sulfate, and the solvent was removed by distillation under reduced pressure. The resulting residue was purified by column chromatography through silica gel, eluted with an 8:1 by volume mixture of hexane and ethyl acetate, to afford 504 mg (yield 86%) of the title compound, melting at 123°–126° C.

Nuclear Magnetic Resonance Spectrum (CDCl$_3$, 200 MHz), δ ppm: 8.15 (1H, singlet); 6.96 (2H, singlet); 3.47 (4H, quartet, J=7.0 Hz); 2.63 (6H, singlet); 2.31 (3H, singlet); 1.3–0.9 (6H, broad).

EXAMPLE 6

4-Cyano-1-(diethylcarbamoyl)-3-(2-methoxy-6-methylphenylthio)pyrazole (Compound No. 7.258)

and

4-Cyano-1-(diethylcarbamoyl)-3-(2-methoxy-6-methylphenylsulfonyl)pyrazole (Compound No. 7.259)

6(1) 4-Cyano-1-(dimethylsulfamoyl)-5-(2-methoxy-6-methylphenylthio)pyrazole 1.2 ml of a 1.48M solution of t-butyllithium in pentane were added, at −78° C. and under an atmosphere of nitrogen, to a solution of 561 mg of 4-iodo-1-(dimethylsulfamoyl)-5-(2-methoxy-6-methylphenylthio)pyrazole [prepared in a similar manner to that described in Example 7(1)] in 25 ml of dry diethyl ether, and the resulting mixture was stirred for 30 minutes. At the end of this time, a solution of 314 mg of p-toluenesulfonyl cyanide in 3 ml of dry diethyl ether was added to the mixture, and the resulting mixture was stirred for 30 minutes at −78° C. and then at 0° C. for a further 30 minutes. The reaction mixture was then mixed with an aqueous solution of ammonium chloride and extracted with diethyl ether. The extract was washed with water and dried over anhydrous sodium sulfate over anhydrous sodium sulfate, after which the solvent was removed by distillation under reduced pressure. The resulting residue was purified by column chromatography through silica gel, eluted with an 8:1 by volume mixture of hexane and ethyl acetate, to afford 162 mg (yield 37%) of the title compound as an oil.

Nuclear Magnetic Resonance Spectrum (CDCl$_3$, 200 MHz), δ ppm: 7.70 (1H, singlet); 7.40 (1H, triplet, J=8.0 Hz); 6.97 (1H, doublet, J=8.0 Hz); 6.82 (1H, doublet, J=8.0 Hz); 3.82 (3H, singlet); 3.12 (6H, singlet); 3.05 (3H, singlet).

6(2) 4-Cyano-1-(diethylcarbamoyl)-3-(2-methoxy-6-methylphenylthio)pyrazole 0.10 ml of trifluoroacetic acid was added to a solution of 154 mg of 4-cyano-1-(dimethylsulfamoyl)-5(2-methoxy-6-methylphenylthio)pyrazole [prepared as described in step (1) above] in 2 ml of chloroform, and the resulting mixture was heated at 60° C. for 2 hours. At the end of this time, the reaction mixture was diluted with methylene chloride, and the organic layer was separated, washed with a saturated aqueous solution of sodium chloride and dried over anhydrous sodium sulfate. The solvent was removed by distillation under reduced pressure, and then the oily residue thus obtained was dissolved in 4 ml of acetonitrile. 59 mg of 1,4-diazabicyclo[2.2.2]octane and 60 μl of diethylcarbamoyl chloride were added, in that order, to the solution, and the resulting mixture was stirred at room temperature for 2 hours. At the end of this time, the reaction mixture was diluted with ethyl acetate, washed with water and then dried over anhydrous sodium sulfate. It was then concentrated by evaporation under reduced pressure, and the resulting residue was purified by column chromatography through silica gel, eluted with a 6:1 by volume mixture of hexane and ethyl acetate, to afford 145 mg (yield 96%) of the title compound as an oil.

Nuclear Magnetic Resonance Spectrum (CDCl$_3$, 200 MHz), δ ppm: 8.46 (1H, singlet); 7.31 (1H, triplet, J=8.0 Hz); 6.92 (1H, doublet, J=8.0 Hz); 6.80 (1H, doublet, J=8.0 Hz); 3.82 (3H, singlet); 3.47-3.36 (4H, multiplet); 2.49 (3H, singlet); 1.4-0.9 (6H, broad).

6(3) 4-Cyano-1-(diethylcarbamoyl)-3-(2-methoxy-6-methylphenylsulfonyl)pyrazole 175 mg of 3-chloroperoxybenzoic acid were added to a solution of 127 mg of 4-cyano-1-(diethylcarbamoyl)-3-(2-methoxy-6-methylphenylthio)pyrazole [prepared as described in step (2) above] in 4 ml of 1,2-dichloroethane, and the resulting mixture was stirred at room temperature for 2 hours. At the end of this time, an aqueous solution of sodium sulfite was added to the reaction mixture, after which it was extracted with methylene chloride. The extract was washed with an aqueous solution of sodium hydrogencarbonate, dried over anhydrous sodium sulfate and concentrated by evaporation under reduced pressure. The concentrate was purified by column chromatography through silica gel, eluted with a 10:1 by volume mixture of hexane and ethyl acetate, to afford 90 mg (yield 65%) of the title compound as an oil.

Nuclear Magnetic Resonance Spectrum (CDCl$_3$, 200 MHz), δ ppm: 8.56 (1H, singlet); 7.44 (1H, doublet of doublets, J=7.6 & 8.3 Hz); 6.92 (1H, doublet, J=7.6 Hz); 6.83 (1H, doublet, J=8.3 Hz); 3.85 (3H, singlet); 3.49 (4H, broad quartet, J=7.2 Hz); 2.82 (3H, singlet); 1.3-1.1 (6H, broad).

EXAMPLE 7

1-(Diethylcarbamoyl)-3-(2,4,6-trimethylphenylsulfonyl)-4-fluoropyrazole (Compound No. 10.85)

7(1) 1-(Dimethylsulfamoyl)-5-(2,4,6-trimethylphenylthio)-4-iodopyrazole 5.26 g of N-iodosuccinimide were added to a solution of 6.92 g of 1-(dimethylsulfamoyl)-5-(2,4,6-trimethylphenylthio)pyrazole [prepared in a similar manner to that described in Example 1(2)] in 60 ml of chloroform, and the resulting mixture was heated at 60° C. for 20 hours. At the end of this time, the reaction mixture was diluted with an aqueous solution of sodium sulfite and extracted with methylene chloride. The extract was washed with a saturated aqueous solution of sodium chloride and dried over anhydrous sodium sulfate; the solvent was then removed by distillation under reduced pressure. The resulting residue was purified by column chromatography through silica gel, eluted with an 8:1 by volume mixture of hexane and ethyl acetate, to afford 8.34 g (yield 87%) of the title compound, melting at 154°–157° C.

Nuclear Magnetic Resonance Spectrum (CDCl$_3$, 200 MHz), δ ppm: 7.51 (1H, singlet); 6.91 (2H, singlet); 3.11 (6H, singlet); 2.33 (6H, singlet); 2.28 (3H, singlet).

7(2) 1-(Dimethylsulfamoyl)-5-(2,4,6-trimethylphenylthio)-4-fluoropyrazole 0.41 ml of a 1.64M solution of butyllithium in tetrahydrofuran was added at −78° C. to a solution of 277 mg of 1-(dimethylsulfamoyl)-5-(2,4,6-trimethylphenylthio)-4-iodopyrazole [prepared as described in step (1) above] in 9 ml of dry tetrahydrofuran, and the resulting mixture was stirred for 50 minutes. At the end of this time, a solution of 193 mg of N-fluorobenzenesulfonimide in 10 ml of dry tetrahydrofuran was added to the resulting mixture, which was then stirred for 30 minutes. The reaction mixture was then poured into water and extracted with diethyl ether. The extract was washed with a saturated aqueous solution of sodium chloride, dried over anhydrous sodium sulfate and concentrated by evaporation under reduced pressure. The concentrate was purified by column chromatography through silica gel, eluted with a 5:1 by volume mixture of hexane and ethyl acetate, to afford 79 mg (yield 37%) of the title compound as an oil.

Nuclear Magnetic Resonance Spectrum (CDCl$_3$, 200 MHz), δ ppm: 7.42 (1H, doublet, J=4.5 Hz); 6.94 (2H, singlet); 3.08 (6H, singlet); 2.44 (6H, singlet); 2.28 (3H, singlet).

7(3) 1-(Diethylcarbamoyl)-3-(2,4,6-trimethylphenylsulfonyl)-4-fluoropyrazole

43 μl of trifluoroacetic acid were added to a solution of 64 mg of 1-(dimethylsulfamoyl)-5-(2,4,6-trimethylphenylthio)-4-fluoropyrazole [prepared as described in step (2) above] in 1.5 ml of chloroform, and the resulting mixture was heated at 65° C. for 4 hours. At the end of this time, the reaction mixture was poured into water and extracted with methylene chloride. The extract was washed with a saturated aqueous solution of sodium chloride and dried over anhydrous sodium sulfate; the solvent was then removed by distillation under reduced pressure. The residue thus obtained was dissolved in 3 ml of acetonitrile, and 32 mg of 1,4-diazabicyclo[2.2.2]octane, followed by 26 μl of diethylcarbamoyl chloride, were added to the resulting solution; the mixture was then stirred at room temperature for 1 hour. After this, the reaction mixture was diluted with water and extracted with ethyl acetate. The extract was washed with water and dried over anhydrous sodium sulfate, after which the solvent was removed by distillation under reduced pressure. The residue was dissolved in 3 ml of 1,2-dichloroethane, and 89 mg of 3-chloroperoxybenzoic acid were added to the resulting solution, after which it was heated at 50° C. for 2 hours. The reaction mixture was then mixed with an aqueous solution of sodium sulfite and extracted with methylene chloride. The extract was washed with an aqueous solution of sodium hydrogencarbonate and dried over anhydrous sodium sulfate; the solvent was then removed by distillation under reduced pressure. The resulting residue was purified by column chromatography through silica gel, eluted with a 6:1 by volume mixture of hexane and ethyl acetate, to afford 61 mg (yield 89%) of the title compound, melting at 109°–111° C.

Nuclear Magnetic Resonance Spectrum (CDCl$_3$, 200 MHz), δ ppm: 8.00 (1H, doublet, J=4.7 Hz); 6.96 (2H, singlet); 3.6–3.4 (4H, multiplet); 2.66 (6H, singlet); 2.30 (3H, singlet); 1.18 (6H, broad).

EXAMPLE 8

1-(Diethylcarbamoyl)-3-(2-methyl-6-ethylphenylthio)-4-methoxypyrazole (Compound No. 7.341)

and 1-(Diethylcarbamoyl)-3-(2-methyl-6-ethylphenylsulfonyl)-4-methoxypyrazole (Compound No. 7.286)

8(1) 1-(Dimethylsulfamoyl)-5-(2-methyl-6-ethylphenylthio)-4-iodopyrazole 5.53 g of N-iodosuccinimide were added to a solution of 8 g of 1-(dimethylsulfamoyl)-5-(2-methyl-6-ethylphenylthio)pyrazole [prepared as described in Example 1(2)] in 80 ml of chloroform, and the resulting mixture was heated at 60° C. for 8 hours. At the end of this time, the reaction mixture was allowed to cool and was then mixed with 20 ml of an aqueous solution of sodium sulfite, stirred for 5 minutes and extracted with methylene chloride. The extract was washed with water and dried over anhydrous sodium sulfate, after which the solvent was removed by distillation under reduced pressure. The crude product thus obtained was recrystallized from hexane, and further purified by column chromatography through silica gel, eluted with a 10:1 by volume mixture of hexane and ethyl acetate, to give 9.4 g (yield 85%) of the title compound, melting at 102°–104° C.

Nuclear Magnetic Resonance Spectrum (CDCl$_3$, 200 MHz), δ ppm: 7.51 (1H, singlet); 7.24 (1H, doublet, J=7.5 Hz); 7.11 (2H, triplet, J=7.5 Hz); 3.11 (6H, singlet); 2.90 (2H, quartet, J=7.5 Hz); 2.30 (3H, singlet); 1.20 (3H, triplet, J=7.5 Hz).

8(2) 1-(Dimethylsulfamoyl)-5-(2-methyl-6-ethylphenylthio)-4-hydroxypyrazole 1.4 ml of a 1.59M solution of butyllithium in tetrahydrofuran were added at −78° C. to a solution of 826 mg of 1-(dimethylsulfamoyl)-5-(2-methyl-6-ethylphenylthio)-4-iodopyrazole [prepared as described in step (1) above] in 30 ml of dry tetrahydrofuran, and the resulting mixture was allowed to stand for 30 minutes. At the end of this time, a solution of 0.36 g of bistrimethylsilyl peroxide in 2 ml of dry tetrahydrofuran was added to the mixture, which was then stirred at −78° C. for 30 minutes; the temperature was then allowed to rise to 0° C. The reaction mixture was then mixed with an aqueous solution of ammonium chloride and extracted with diethyl ether. The extract was washed with water and dried over anhydrous sodium sulfate; the solvent was then removed by distillation under reduced pressure. The resulting residue was purified by column chromatography through silica gel, eluted with a 5:1 by volume mixture of hexane and ethyl acetate, to afford 103 mg (yield 16%) of the title compound as an oil.

Nuclear Magnetic Resonance Spectrum (CDCl$_3$, 200 MHz), δ ppm: 7.35 (1H, singlet); 7.33–7.15 (3H, multiplet); 3.04 (6H, singlet); 2.97 (2H, quartet, J=7.5 Hz); 2.42 (3H, singlet); 1.22 (3H, triplet, J=7.5 Hz).

8(3) 1-(Dimethylsulfamoyl)-5-(2-methyl-6-ethylphenylthio)-4-methoxypyrazole 25 mg of sodium hydride (as a 50% w/w dispersion in mineral oil), followed by 36 μl of iodomethane, were added at 0° C. to a solution of 98 mg of 1-(dimethylsulfamoyl)-5-(2-methyl-6-ethylphenylthio)-4-hydroxypyrazole [prepared as described in step (2) above] in a mixture of 1.5 ml of dry tetrahydrofuran and 1 ml of dimethylformamide, and the resulting mixture was stirred for 2 hours. At the end of this time, the reaction mixture was poured into water and extracted with diethyl ether. The extract was washed with water and dried over anhydrous sodium sulfate, after which the solvent was removed by distillation under reduced pressure. The resulting residue was purified by column chromatography through silica gel, eluted with an 8:1 by volume mixture of hexane and ethyl acetate, to afford 74 mg (yield 73%) of the title compound as an oil.

Nuclear Magnetic Resonance Spectrum (CDCl$_3$, 200 MHz), δ ppm: 7.41 (1H, singlet); 7.22–7.03 (3H, multiplet); 3.31 (3H, singlet); 3.05 (6H, singlet); 2.96 (2H, quartet, J=7.5 Hz); 2.41 (3H, singlet); 1.17 (3H, triplet, J=7.5 Hz).

8(4) 1-(Diethylcarbamoyl)-3-(2-methyl-6-ethyphenylthio)-4-methoxypyrazole

45 μl of trifluoroacetic acid were added to a solution of 70 mg of 1-(dimethylsulfamoyl)-5-(2-methyl-6-ethylphenylthio)-4-methoxypyrazole [prepared as described in step (3) above] in 1 ml of chloroform, and the resulting mixture was heated at 60° C. for 4 hours. At the end of this time, the reaction mixture was poured into water and extracted with methylene chloride. The extract was washed with a saturated aqueous solution of sodium chloride, dried over anhydrous sodium sulfate and concentrated by evaporation under reduced pressure. The concentrate thus obtained was dissolved in acetonitrile, and 27 mg of 1,4-diazabicyclo[2.2.2]octane and 30 μl of diethylcarbamoyl chloride were added, in that order, to the resulting solution, which was then stirred for 5 hours. After this, the reaction mixture was diluted with water and extracted with ethyl acetate. The extract was washed with a saturated aqueous solution of sodium chloride, dried over anhydrous sodium sulfate and concentrated by evaporation under reduced pressure. The crude product thus obtained was purified by column chromatography through silica gel, eluted with a 6:1 by volume mixture of hexane and ethyl acetate, to afford 66 mg (yield 96%) of the title compound an oil.

Nuclear Magnetic Resonance Spectrum (CDCl$_3$, 200 MHz), δ ppm: 7.68 (1H, singlet); 7.26–7.09 (3H, singlet); 3.81 (3H, singlet); 3.33 (4H, quartet, J=7.0 Hz); 2.92 (2H, quartet, J=7.6 Hz); 2.46 (3H, singlet); 1.18 (3H, triplet, J=7.6 Hz); 1.08–0.8 (6H, broad).

8(5) 1-(Diethylcarbamoyl)-3-(2-methyl-6-ethylphenylsulfonyl)-4-methoxypyrazole 84 mg of 3-chloroperoxybenzoic acid were added to a solution of 62 mg of 1-(diethylcarbamoyl)-3-(2-methyl-6-ethylphenylthio)-4-methoxypyrazole [prepared as described in step (4) above] in 2 ml of 1,2-dichloroethane, and the resulting mixture was stirred at 50° C. for 2 hours. The reaction mixture was then mixed with an aqueous solution of sodium sulfite and extracted with methylene chloride. The extract was washed with an aqueous solution of sodium hydrogencarbonate and with a saturated aqueous solution of sodium chloride, in that order, after which it was dried over anhydrous sodium sulfate and concentrated by evaporation under reduced pressure. The concentrate was purified by column chromatography through silica gel, eluted with a 7:1 by volume mixture of hexane and ethyl acetate, to afford 34 mg (yield 51%) of the title compound as an oil.

Nuclear Magnetic Resonance Spectrum (CDCl$_3$, 200 MHz), $\delta$ ppm: 7.76 (1H, singlet); 7.36 (1H, triplet, J=7.6 Hz); 7.17 (1H, doublet, J=7.6 Hz); 7.10 (1H, doublet, J=7.6 Hz); 3.80 (3H, singlet); 3.10 (2H, quartet, J=7.5 Hz); 3.43 (4H, quartet, J=7.0 Hz); 2.67 (3H, singlet); 1.4–0.9 (6H, broad); 1.23 (3H, triplet, J=7.5 Hz).

EXAMPLE 9

1-(Diethyl carbamoyl)-3-(2-methyl-3-chlorophenylthio)-4-formylpyrazole (Compound No. 4.138)

and 1-(Diethylcarbamoyl)-3-(2-methyl-3-chlorophenylsulfonyl)-4-formylpyrazole (Compound No. 4.112)

9(1)   1-(Dimethylsulfamoyl)-5-(2-methyl-3-chlorophenylthio)-4-formylpyrazole 3.3 ml of a 1.59M solution of butyllithium in tetrahydrofuran were added at −78° C. to a solution of 2.0 g of 1-(dimethylsulfamoyl)-5-(2-methyl-3-chlorophenylthio)-4-iodopyrazole [prepared in a similar manner to that described in Example 7(1)] in 70 ml of dry tetrahydrofuran, and the resulting mixture was stirred at that temperature for 20 minutes, after which 0.51 ml of dimethylformamide was added. The reaction mixture was stirred at the same temperature for 30 minutes, and then the reaction temperature was allowed to rise to 20° C. The reaction mixture was then mixed with an aqueous solution of ammonium chloride and extracted with diethyl ether. The extract was washed with a saturated aqueous solution of sodium chloride, dried over anhydrous sodium sulfate and concentrated by evaporation under reduced pressure. The concentrate was purified by column chromatography through silica gel, eluted with a 10:1 by volume mixture of hexane and ethyl acetate, to afford 1.05 g (yield 66%) of the title compound as an oil.

Nuclear Magnetic Resonance Spectrum (CDCl$_3$, 200 MHz), $\delta$ ppm: 9.63 (1H, singlet); 8.10 (1H, singlet); 7.46–6.92 (3H, multiplet); 3.11 (6H, singlet); 2.56 (3H, singlet).

9(2) 1-(Diethylcarbamoyl)-3-(2-methyl-3-chlorophenylthio)-4-formylpyrazole 0.14 ml of trifluoroacetic acid was added to a solution of 224 mg of 1-(dimethylsulfamoyl)-5-(2-methyl-3-chlorophenylthio)-4-formylpyrazole [prepared as described in step (1) above] in 2.5 ml of chloroform, and the resulting mixture was stirred at 60° C. for 2 hours. At the end of this time, the reaction mixture was diluted with water and extracted with methylene chloride. The extract was washed with an aqueous solution of sodium hydrogencarbonate and with water, in that order, and dried over anhydrous sodium sulfate, after which the solvent was removed by distillation under reduced pressure. The residue was dissolved in 4 ml of acetonitrile, and 104 mg of 1,4-diazabicyclo[2.2.2]octane and 117 μl of diethylcarbamoyl chloride were added, in that order, to the resulting solution. The resulting mixture was then stirred for 2 hours. At the end of this time, the reaction mixture was diluted with water and extracted with ethyl acetate. The extract was washed with water, dried over anhydrous sodium sulfate and concentrated by evaporation under reduced pressure. The concentrate was purified by column chromatography through silica gel, eluted with a 6:1 by volume mixture of hexane and ethyl acetate, to afford 96 mg (yield 44%) of the title compound as an oil.

Nuclear Magnetic Resonance Spectrum (CDCl$_3$, 200 MHz), $\delta$ ppm: 9.99 (1H, singlet); 8.68 (1H, singlet); 7.52 (1H, doublet of doublets, J=0.9 & 8.5 Hz); 7.42 (1H, doublet of doublets, J=0.9 & 7.7 Hz); 7.13 (1H, doublet of doublets, J=7.7 & 8.5 Hz); 3.36 (4H, quartet, J=7.0 Hz); 2.52 (3H, singlet); 1.35–0.6 (6H, broad).

9(3) 1-(Diethylcarbamoyl)-3-(2-methyl-3-chlorophenylsulfonyl)-4-formylpyrazole 0.77 g of 3-chloroperoxybenzoic acid was added to a solution of 0.57 g of 1-(diethylcarbamoyl)-3-(2-methyl-3-chlorophenylthio)-4-formylpyrazole [prepared as described in step (2) above] in 15 ml of 1,2-dichloroethane, and the resulting mixture was stirred at room temperature for 10 hours. The reaction mixture was then mixed with an aqueous solution of sodium sulfite and extracted with methylene chloride. The extract was washed with an aqueous solution of sodium hydrogencarbonate and with a saturated aqueous solution of sodium chloride, in that order, after which it was dried over anhydrous sodium sulfate and concentrated by evaporation under reduced pressure. The concentrate was purified by column chromatography through silica gel, eluted with an 8:1 by volume mixture of hexane and ethyl acetate, to afford 198 mg (yield 32%) of the title compound, melting at 95°–97° C.

Nuclear Magnetic Resonance Spectrum (CDCl$_3$, 200 MHz), $\delta$ ppm: 10.31 (1H, singlet); 8.70 (1H, singlet); 8.20 (1H, doublet of doublets, J=8.0 & 1.4 Hz); 7.40 (1H, triplet, J=8.0 Hz); 3.44 (4H, quartet, J=7.2 Hz); 2.64 (3H, singlet); 1.4–1.0 (6H, broad).

EXAMPLE 10

1-(Diethylcarbamoyl)-3-(2-methyl-3-chlorophenylsulfonyl)-4-hydroxymethylpyrazole (Compound No. 4.102)

11 mg of sodium borohydride were added at 0° C. to a solution of 112 mg of 1-(diethylcarbamoyl)-3-(2-methyl-3-chlorophenylsulfonyl)-4-formylpyrazole [prepared as described in Example 9(3)] in 3.5 ml of methanol, and the resulting mixture was stirred for 30 minutes. At the end of this time, the reaction mixture was poured into water and extracted with ethyl acetate. The extract was washed with a saturated aqueous solution of sodium chloride, dried over anhydrous sodium sulfate and concentrated by evaporation under reduced pressure. The concentrate was purified by column chromatography through silica gel, eluted with a 5:1 by volume mixture of hexane and ethyl acetate, to afford 114 mg (a quantitative yield) of the title compound as an oil.

Nuclear Magnetic Resonance Spectrum (CDCl$_3$, 200 MHz), $\delta$ ppm: 8.17 (1H, singlet); 8.15 (1H, doublet of doublets, J=8.0 & 1.4 Hz); 7.67 (1H, doublet of doublets, J=8.0 & 1.4 Hz); 7.37 (1H, triplet, J=8.0 Hz); 4.73 (2H, singlet); 3.93 (1H, singlet); 3.43 (4H, quartet, J=7.0 Hz); 2.63 (3H, singlet); 1.4–0.9 (6H, broad).

EXAMPLE 11

1-(Diethylcarbamoyl)-3-(2-methyl-3-chlorophenylsulfonyl)-4-fluoromethylpyrazole (Compound No. 4.107)

20 μl of diethylaminosulfur trifluoride were added at 0° C. to a solution of 54 mg of 1-(diethylcarbamoyl)-3-(2-methyl-3-chlorophenylsulfonyl)-4-hydroxymethylpyrazole (prepared as described in Example 10) in 1.8 ml of methylene chloride, and the resulting mixture was stirred for 1 hour. At the end of this time, the reaction mixture was poured into water and extracted with methylene chloride. The extract was washed with a saturated aqueous solution of sodium chloride, dried over anhydrous sodium sulfate and concentrated by evaporation under reduced pressure. The concentrate was purified by column chromatography through silica gel, eluted with an 8:1 by volume mixture of hexane and ethyl acetate, to afford 51 mg (yield 95%) of the title compound as an oil.

Nuclear Magnetic Resonance Spectrum (CDCl$_3$, 200 MHz), δ ppm: 8.27 (1H, doublet, J=2.0 Hz); 8.14 (1H, doublet of doublets, J=8.0 & 1.2 Hz); 7.66 (1H, doublet of doublets, J=8.0 & 1.2 Hz); 7.36 (1H, triplet, J=8.0 Hz); 5.57 (2H, doublet, J=47.3 Hz); 3.46 (4H, quartet, J=7.0 Hz); 2.64 (3H, singlet); 1.4–1.0 (6H, broad).

EXAMPLE 12

1-(Diethylcarbamoyl)-3-(2-methyl-6-ethylphenylthio)-4-trifluoromethylpyrazole (Compound No. 7.246)

and 1-(Diethylcarbamoyl)-3-(2-methyl-6-ethylphenylsulfonyl)-4-trifluoromethylpyrazole (Compound No. 7.247)

12(1) 1-(Dimethylsulfamoyl)-5-(2-methyl-6-ethylphenylthio)-4-trifluoromethylpyrazole 0.22 ml of methyl fluorosulfonyl(difluoro)acetate and 73 mg of cuprous iodide were added to a solution of 346 mg of 1-(dimethylsulfamoyl)-5-(2-methyl-6-ethylphenylthio)-4-iodopyrazole [prepared as described in Example 8(1)] in 5 ml of dimethylformamide, and the resulting mixture was heated at 120° C. for 4 hours. At the end of this time, the reaction mixture was poured into water and extracted with diethyl ether. The extract was washed with water, dried over anhydrous sodium sulfate and concentrated by evaporation under reduced pressure. The concentrate was purified by column chromatography through silica gel, eluted with a 10:1 by volume mixture of hexane and ethyl acetate, to afford 270 mg (yield 90%) of the title compound as an oil.

Nuclear Magnetic Resonance Spectrum (CDCl$_3$, 200 MHz), δ ppm: 7.70 (1H, singlet); 7.28–7.06 (3H, multiplet); 3.16 (6H, singlet); 2.87 (2H, quartet, J=7.6 Hz); 2.30 (3H, singlet); 1.17 (3H, triplet, J=7.6 Hz).

12(2) 1-(Diethylcarbamoyl)-3-(2-methyl-6-ethylphenylthio)-4-trifluoromethylpyrazole 0.12 ml of trifluoroacetic acid was added to a solution of 210 mg of 1-(dimethylsulfamoyl)-5-(2-methyl-6-ethylphenylthio)-4-trifluoromethylpyrazole [prepared as described in step (1) above] in 2 ml of chloroform, and the resulting mixture was heated at 60° C. for 1.5 hours. At the end of this time, the reaction mixture was poured into water and extracted with methylene chloride. The extract was washed with a saturated aqueous solution of sodium chloride and dried over anhydrous sodium sulfate; the solvent was then removed by distillation under reduced pressure. The residue was dissolved in 4 ml of acetonitrile, and 72 mg of 1,4-diazabicyclo[2.2.2]octane and 81 μl of diethylcarbamoyl chloride were added, in that order, to the resulting solution. The resulting mixture was then heated at 50° C. for 2 hours. After this, the reaction mixture was diluted with water and extracted with ethyl acetate. The extract was washed with a saturated aqueous solution of sodium chloride, dried over anhydrous sodium sulfate and concentrated by evaporation under reduced pressure. The concentrate was purified by column chromatography through silica gel, eluted with a 6:1 by volume mixture of hexane and ethyl acetate, to afford 203 mg (yield 99%) of the title compound as an oil.

Nuclear Magnetic Resonance Spectrum (CDCl$_3$, 200 MHz), δ ppm: 8.40 (1H, quartet, J=1.0 Hz); 7.28–7.11 (3H, multiplet); 3.4–3.2 (4H, multiplet); 2.88 (2H, quartet, J=7.5 Hz); 2.43 (3H, singlet); 1.17 (3H, triplet, J=7.5 Hz); 1.35–0.50 (6H, broad).

12(3) 1-(Diethylcarbamoyl)-3-(2-methyl-6-ethylphenylsulfonyl)-4-trifluoromethylpyrazole 189 mg of 3-chloroperoxybenzoic acid were added to a solution of 154 mg of 1-(diethylcarbamoyl)-3-(2-methyl-6-ethylphenylthio)-4-trifluoromethylpyrazole [prepared as described in step (2) above] in 5.0 ml of 1,2-dichloroethane, and the resulting mixture was stirred at room temperature for 10 hours. At the end of this time, the reaction mixture was poured into an aqueous solution of sodium sulfite and extracted with methylene chloride. The extract was washed with an aqueous solution of sodium hydrogencarbonate and with a saturated aqueous solution of sodium chloride, in that order, after which it was dried over anhydrous sodium sulfate and concentrated by evaporation under reduced pressure. The concentrate was purified by column chromatography through silica gel, eluted with an 8:1 by volume mixture of hexane and ethyl acetate, to afford 154 mg (yield 93%) of the title compound as an oil.

Nuclear Magnetic Resonance Spectrum (CDCl$_3$, 200 MHz), δ ppm: 8.53 (1H, multiplet); 7.46–7.12 (3H, multiplet); 3.5–3.2 (4H, broad); 3.05 (2H, quartet, J=7.4 Hz); 2.60 (3H, singlet); 1.24 (3H, triplet, J=7.4 Hz); 1.4–0.6 (6H, broad).

EXAMPLE 13

1-(Diethylcarbamoyl)-3-(3-chlorophenylthio)-4-difluoromethylpyrazole (Compound No. 2.97)

and 1-(Diethylcarbamoyl)-3-(3-chlorophenylsulfonyl)-4-difluoromethylpyrazole (Compound No. 2.98)

13(1) 1-(Dimethylsulfamoyl)-4-formylpyrazole 1.26 ml of a 1.4M solution of t-butyllithium in pentane was added at −78° C. to a solution of 299 mg of 1-(dimethylsulfamoyl)-4-bromopyrazole [prepared as described in Example 3(1)] in 7 ml of dry diethyl ether, and the resulting mixture was stirred for 20 minutes, after which 0.27 ml of dimethylformamide was added to it. After it had been stirred for 50 minutes, the reaction mixture was poured into an aqueous solution of ammonium chloride and extracted with ethyl acetate. The extract was washed with a saturated aqueous solution of sodium chloride, dried over anhydrous sodium sulfate and concentrated by evaporation under reduced pressure. The concentrate was purified by column chromatography through silica gel, eluted with an 8:1 by volume mixture of hexane and ethyl acetate, to afford 128 mg (yield 53%) of the title compound, melting at 86°–88° C.

Nuclear Magnetic Resonance Spectrum (CDCl$_3$, 200 MHz), δ ppm: 9.96 (1H, singlet); 8.47 (1H, singlet); 8.15 (1H, singlet); 3.01 (6H, singlet).

13(2) 1-(Dimethylsulfamoyl)-4-difluoromethylpyrazole 0.83 ml of diethylaminosulfur trifluoride was added to a solution of 847 mg of 1-(dimethylsulfamoyl)-4-formylpyrazole [prepared as described in step (1) above] in 8 ml of methylene chloride, and the resulting mixture was stirred at room temperature for 19 hours. At the end of this time, the reaction mixture was diluted with water and extracted with methylene chloride. The extract was washed with water, dried over anhydrous sodium sulfate and concentrated by evaporation under reduced pressure. The resulting concentrate was purified by column chromatography through silica gel, eluted with a 10:1 by volume mixture of hexane and ethyl acetate, to afford 777 mg (yield 83%) of the title compound as an oil.

Nuclear Magnetic Resonance Spectrum (CDCl$_3$, 200 MHz), δ ppm: 8.14 (1H, singlet); 7.86 (1H, singlet); 6.73 (1H, triplet, J=55.6 Hz); 2.98 (6H, singlet).

13(3) 1-(Dimethylsulfamoyl)-5-(3-chlorophenylthio)-4difluoromethylpyrazole 0.66 ml of a 1.5M solution of butyllithium in hexane was added at −78° C. to a solution of 203 mg of 1-(dimethylsulfamoyl)-4-difluoromethylpyrazole [prepared as described in step (2) above] in 5 ml of tetrahydrofuran, and the resulting mixture was stirred for 30 minutes, after which a solution of 311 mg of 3-chlorophenyl disulfide in 2 ml of dry tetrahydrofuran was added to the mixture. After it had been stirred for 40 minutes, the reaction mixture was poured into an aqueous solution of ammonium chloride and extracted with ethyl acetate. The extract was washed with a saturated aqueous solution of sodium chloride, dried over anhydrous sodium sulfate and concentrated by evaporation under reduced pressure. The concentrate was purified by column chromatography through silica gel, eluted with a 10:1 by volume mixture of hexane and ethyl acetate, to afford 280 mg (yield 84%) of the title compound as an oil.

Nuclear Magnetic Resonance Spectrum (CDCl$_3$, 200 MHz), δ ppm: 7.93 (1H, singlet); 7.23–7.21 (3H, multiplet); 7.15–7.07 (1H, multiplet); 6.65 (1H, triplet, J=54.5 Hz); 3.07 (6H, singlet).

13(4) 1-(Diethylcarbamoyl)-3-(3-chlorophenylthio)-4-difluoromethylpyrazole 0.16 ml of trifluoroacetic acid was added to a solution of 253 mg of 1-(dimethylsulfamoyl)-5-(3-chlorophenylthio)-4-difluoromethylpyrazole [prepared as described in step (3) above] in 5 ml of 1,2-dichloroethane, and the resulting mixture was heated at 50° C. for 2 hours. At the end of this time, the reaction mixture was poured into an aqueous solution of sodium hydrogencarbonate and extracted with methylene chloride. The extract was dried over anhydrous sodium sulfate, and the solvent was removed by distillation under reduced pressure. The residue was dissolved in 4 ml of acetonitrile, and 155 mg of 1,4-diazabicyclo[2.2.2]octane, followed by 0.11 ml of diethylcarbamoyl chloride, were then added to the resulting solution. The reaction mixture was then heated at 50° C. for 1.5 hours, after which it was diluted with water and extracted with ethyl acetate. The extract was washed with water, dried over anhydrous sodium sulfate and concentrated by evaporation under reduced pressure. The concentrate was purified by column chromatography through silica gel, eluted with a 6:1 by volume mixture of hexane and ethyl acetate, to afford 207 mg (yield 83%) of the title compound as an oil.

Nuclear Magnetic Resonance Spectrum (CDCl$_3$, 200 MHz), δ ppm: 8.38 (1H, triplet, J=1.6 Hz); 7.42–7.40 (1H, multiplet); 7.32–7.22 (3H, multiplet); 6.61 (1H, triplet, J=55.1 Hz); 3.53 (4H, quartet, J=6.6 Hz); 1.19 (6H, triplet, J=6.6 Hz).

13(5) 1-(Diethylcarbamoyl)-3-(3-chlorophenylsulfonyl)-4-difluoromethylpyrazole 250 mg of 3-chloroperoxybenzoic acid were added to a solution of 179 mg of 1-(diethylcarbamoyl)-3-(3-chlorophenylthio)-4-difluoromethylpyrazole [prepared as described in step (4) above] in 4 ml of 1,2-dichloroethane, and the resulting mixture was heated at 50° C. for 1.5 hours. At the end of this time, the reaction mixture was poured into an aqueous solution of sodium sulfite and extracted with methylene chloride. The extract was washed with an aqueous solution of sodium hydrogencarbonate and with a saturated aqueous solution of sodium chloride, in that order, after which it was dried over anhydrous sodium sulfate and concentrated by evaporation under reduced pressure. The concentrate was purified by column chromatography through silica gel, eluted with an 8:1 by volume mixture of hexane and ethyl acetate, to afford 170 mg (yield 87%) of the title compound as an oil.

Nuclear Magnetic Resonance Spectrum (CDCl$_3$, 200 MHz), δ ppm: 8.38 (1H, doublet, J=1.6 Hz); 8.02 (1H, triplet, J=1.6 Hz); 7.91 (1H, triplet of doublets, J=1.6 & 7.9 Hz); 7.61 (1H, triplet of doublets, J=1.6 & 7.9 Hz); 7.50 (1H, triplet, J=7.9 Hz); 7.16 (1H, triplet, J=54.9 Hz); 3.48 (4H, quartet, J=7.0 Hz); 1.25 (6H, triplet, J=7.0 Hz).

EXAMPLE 14

4-Cyano-1-(diethylcarbamoyl)-3-(2-ethyl-6-methylphenylthio)pyrazole (Compound No. 7.252)

and

4-Cyano-1-(diethylcarbamoyl)-3-(2-ethyl-6-methylphenylsulfonyl)pyrazole (Compound No. 7.253)

14(1) 4-Cyano-1-(dimethylsulfamoyl)pyrazole 2.03 ml of a 1.48M solution of t-butyllithium in pentane were added, at −78° C. and under an atmosphere of nitrogen, to a solution of 500 mg of 4-bromo-1-(dimethylsulfamoyl)pyrazole prepared as described in Example 3(1)] in 20 ml of dry diethyl ether, and the resulting mixture was stirred for 20 minutes, after which 710 mg of p-toluenesulfonyl cyanide were added. The reaction mixture was then stirred at 0° C. for 1 hour, after which it was poured into ice-water and extracted with ethyl acetate. The extract was dried over anhydrous sodium sulfate and concentrated by evaporation under reduced pressure. The concentrate was then purified by column chromatography through silica gel, eluted with a 10:1 by volume mixture of hexane and ethyl acetate, to afford 245 mg (yield 62%) of the title compound as an oil.

Nuclear Magnetic Resonance Spectrum (CDCl$_3$, 200 MHz), δ ppm: 8.37 (1H, singlet); 7.96 (1H, singlet); 3.07 (6H, singlet).

14(2) 4-Cyano-1-(dimethylsulfamoyl)-5-(2-ethyl-6-methylphenylthio)pyrazole 0.47 ml of a 1.49M solution of butyllithium in hexane was added, at −78° C. and under an atmosphere of nitrogen, to a solution of 138 mg of 4-cyano-1-(dimethylsulfamoyl)pyrazole [prepared as described in step (1) above] in dry tetrahydrofuran, and after 20 minutes, 200 mg of 2-ethyl-6-methylphenyl disulfide were added to the resulting mixture. The reaction mixture was stirred at 0° C. for 15 minutes, after which it was mixed with an aqueous solution of ammonium chloride and extracted with ethyl acetate. The extract was washed with water, dried over anhydrous sodium sulfate over anhydrous sodium sulfate and concentrated by evaporation under reduced pressure. The concentrate was purified by column chromatography through silica gel, eluted with a 10:1 by volume mixture of hexane and ethyl acetate, to afford 120 mg (yield 50%) of the title compound as an oil.

Nuclear Magnetic Resonance Spectrum (CDCl$_3$, 200 MHz), δ ppm: 7.70 (1H, singlet); 7.39 (1H, doublet, J=7.6 Hz); 7.25–7.20 (2H, multiplet); 3.13 (6H, singlet); 2.88 (2H, quartet, J=7.6 Hz); 2.46 (3H, singlet); 1.23 (3H, triplet, J=7.6 Hz).

14(3)  4-Cyano-1-(diethylcarbamoyl)-3-(2-ethyl-6-methylphenylthio)pyrazole 0.13 ml of trifluoroacetic acid was added to a solution of 200 mg of 4-cyano-1-(dimethylsulfamoyl)-5-(2-ethyl-6-methylphenylthio)pyrazole [prepared as described in step (2) above] in 5 ml of 1,2-dichloroethane, and the resulting mixture was stirred at 50° C. for 40 minutes. At the end of this time, the reaction mixture was poured into ice-water and extracted with methylene chloride. The extract was dried over anhydrous sodium sulfate and concentrated by evaporation under reduced pressure. The resulting oily residue was dissolved in 4 ml of acetonitrile, and 90 μl of diethylcarbamoyl chloride and 132 mg of 1,4-diazabicyclo[2.2.2]octane were added, in that order, to the resulting solution. The reaction mixture was then stirred at 50° C. for 50 minutes, after which it was poured into ice-water and extracted with ethyl acetate. The extract was washed with water, dried over anhydrous sodium sulfate and concentrated by evaporation under reduced pressure. The concentrate was purified by column chromatography through silica gel, eluted with a 5:1 by volume mixture of hexane and ethyl acetate, to afford 170 mg (yield 87%) of the title compound as an oil.

Nuclear Magnetic Resonance Spectrum (CDCl$_3$, 200 MHz), δ ppm: 8.48 (1H, singlet); 7.31–7.14 (3H, multiplet); 3.33 (4H, quartet, J=7.0 Hz); 2.88 (2H, quartet, J=7.5 Hz); 2.44 (3H, singlet); 1.88 (3H, triplet, J=7.5 Hz); 1.13–0.74 (6H, broad).

14(4)  4-Cyano-1-(diethylcarbamoyl)-3-(2-ethyl-6-methylphenylsulfonyl)pyrazole 200 mg of 3-chloroperoxybenzoic acid were added to a solution of 150 mg of 4-cyano-1-(diethylcarbamoyl)-3-(2-ethyl-6-methylphenylthio)pyrazole [prepared as described in step (3) above] in 5 ml of 1,2-dichloroethane, and the resulting mixture was heated at 50° C. for 2 hours. At the end of this time, the reaction mixture was poured into an aqueous solution of sodium sulfite and extracted with methylene chloride. The extract was washed with an aqueous solution of sodium hydrogencarbonate, dried over anhydrous sodium sulfate and concentrated by evaporation under reduced pressure. The concentrate was purified by column chromatography through silica gel, eluted with a 6:1 by volume mixture of hexane and ethyl acetate, to afford 153 mg (yield 95%) of the title compound, melting at 101°–102° C.

Nuclear Magnetic Resonance Spectrum (CDCl$_3$, 200 MHz), δ ppm: 8.59 (1H, singlet); 7.43 (1H, triplet, J=7.5 Hz); 7.22–7.16 (2H, multiplet); 3.46 (4H, quartet, J=7.1 Hz); 3.12 (2H, quartet, J=7.4 Hz); 2.70 (3H, singlet); 1.26 (3H, triplet, J=7.4 Hz); 1.27–1.08 (6H, broad).

EXAMPLE 15

1-(Diethylcarbamoyl)-3-(2-chloro-6-methylphenylthio)-5-methylpyrazole (Compound No. 7.342)

and 1-(Diethylcarbamoyl)-3-(2-chloro-6-methylphenylsulfonyl)-5-methylpyrazole (Compound No. 7.90)

15(1)  1-(Diethylcarbamoyl)-3-(2-chloro-6-methylphenylthio)-5-methylpyrazole 0.45 ml of a 1.59M solution of butyllithium in hexane was added at −78° C. to a solution of 211 mg of 1-(diethylcarbamoyl)-3-(2-chloro-6-methylphenylthio)pyrazole (prepared as described in Example 17) in 7 ml of dry tetrahydrofuran, and the resulting mixture was allowed to stand for 45 minutes, after which 0.20 ml of iodomethane was added. The mixture was stirred at the same temperature for 1.5 hours, and then the temperature of the reaction mixture was allowed to rise to 0° C., upon which it was stirred for a further 15 minutes. The reaction mixture was then mixed with an aqueous solution of ammonium chloride and extracted with ethyl acetate. The extract was washed with water, dried over anhydrous sodium sulfate and concentrated by evaporation under reduced pressure. The concentrate was purified by column chromatography through silica gel, eluted with a 6:1 by volume mixture of hexane and ethyl acetate, to afford 190 mg (yield 86%) of the title compound as an oil.

Nuclear Magnetic Resonance Spectrum (CDCl$_3$, 200 MHz), δ ppm: 7.37–7.32 (1H, multiplet); 7.25–7.19 (2H, multiplet); 5.80 (1H, singlet); 3.36 (4H, quartet, J=7.0 Hz); 2.52 (3H, singlet).; 2.35 (3H, singlet); 1.15 (6H, broad).

15(2)  1-(Diethylcarbamoyl)-3-(2-chloro-6-methylphenylsulfonyl)-5-methylpyrazole 252 mg of 3-chloroperoxybenzoic acid were added to a solution of 180 mg of 1-(diethylcarbamoyl)-3-(2-chloro-6-methylphenylthio)-5-methylpyrazole [prepared as described in step (1) above] in 4 ml of 1,2-dichloroethane, and the resulting mixture was heated at 50° C. for 45 minutes. At the end of this time, the reaction mixture was poured into an aqueous solution of sodium sulfite and extracted with methylene chloride. The extract was washed with an aqueous solution of sodium hydrogencarbonate and with water, in that order, after which it was dried over anhydrous sodium sulfate and the solvent was removed by distillation under reduced pressure. The residue was purified by column chromatography through silica gel, eluted with an 8:1 by volume mixture of hexane and ethyl acetate, to afford 195 mg (a quantitative yield) of the title compound as an oil.

Nuclear Magnetic Resonance Spectrum (CDCl$_3$, 270 MHz), δ ppm: 7.35–7.33 (2H, multiplet); 7.25–7.21 (1H, multiplet); 6.71 (1H, singlet); 3.43 (2H, quartet, J=7.0 Hz); 3.13 (2H, quartet, J=7.0 Hz); 2.84 (3H, singlet); 2.46 (3H, singlet); 1.24 (3H, broad); 0.97 (3H, broad).

EXAMPLE 16

4-Chloro-1-(diethylcarbamoyl)-3-(2-ethyl-6-methylphenylsulfonyl)-5-methylthiopyrazole (Compound No. 7.329)

0.11 ml of a 1.49M solution of butyllithium in hexane was added, at −78° C. and under an atmosphere of nitrogen, to a solution of 59 mg of 4-chloro-1-(diethylcarbamoyl)-3-(2-ethyl-6-methylphenylsulfonyl)-pyrazole (prepared as described in Example 18) in 2 ml of dry tetrahydrofuran, and the resulting mixture was stirred for 30 minutes, after which 15 μl of methyl disulfide were added. The resulting reaction mixture was stirred for 30 minutes, and then mixed with an aqueous solution of ammonium chloride and extracted with diethyl ether. The extract was washed with water, dried over anhydrous sodium sulfate and concentrated by evaporation under reduced pressure. The concentrate was purified by column chromatography through silica gel, eluted with a 10:1 by volume mixture of hexane and ethyl acetate, to afford 28 mg (yield 35%) of the title compound as an oil.

Nuclear Magnetic Resonance Spectrum (CDCl$_3$, 200 MHz), δ ppm: 7.43 (1H, triplet, J=7.6 Hz); 7.20 (1H, broad doublet, J=7.6 Hz); 7.14 (1H, broad doublet, J=7.6 Hz); 3.50 (1H, quartet, J=7.2 Hz); 3.16–3.02 (4H, multiplet); 2.68 (3H, singlet); 2.45 (3H, singlet); 1.33–1.19 (6H, multiplet); 1.04 (3H, triplet, J=7.0 Hz).

EXAMPLE 17

1-(Diethylcarbamoyl)-3-(2-chloro-6-methylphenylthio)pyrazole (Compound No. 7.19)

17(1) 1-(Dimethylsulfamoyl)-5-(2-chloro-6-methylphenylthio)pyrazole 32.3 ml of a 1.59M solution of butyllithium in hexane were added, at −78° C. and under an atmosphere of nitrogen, to a solution of 8.18 g of 1-(dimethylsulfamoyl)pyrazole [prepared as described in Example 1(1)] in 250 ml of dry tetrahydrofuran, and the resulting mixture was allowed to stand at the same temperature for 40 minutes. At the end of this time, a solution of 14.73 g of 2-chloro-6-methylphenyl disulfide in 100 ml of tetrahydrofuran was added to the mixture, which was then stirred at the same temperature for 1 hour. The reaction mixture was then mixed with an aqueous solution of ammonium chloride and extracted with ethyl acetate. The extract was washed with water and dried over anhydrous sodium sulfate, after which it was concentrated by evaporation under reduced pressure. The concentrate was purified by column chromatography through silica gel, eluted with a 10:1 by volume mixture of hexane and ethyl acetate, to give 13.70 g (yield 88%) of the title compound as an oil.

Nuclear Magnetic Resonance Spectrum (CDCl$_3$, 200 MHz), δ ppm: 7.48 (1H, doublet, J=1.6 Hz); 7.45–7.27 (3H, multiplet); 5.32 (1H, doublet, J=1.6 Hz); 3.05 (6H, singlet); 2.53 (3H, singlet).

17(2) 1-(Diethylcarbamoyl)-3-(2-chloro-6-methylphenylthio)pyrazole 9.8 ml of trifluoroacetic acid were added to a solution of 12.70 mg of 1-(dimethylsulfamoyl)-5-(2-chloro-6-methylphenylthio)pyrazole [prepared as described in step (1) above] in 60 ml of chloroform, and the resulting mixture was heated at 50° C. for 6 hours. The mixture was allowed to cool, after which it was diluted with water and neutralized with an aqueous solution of sodium hydrogencarbonate. It was then extracted with ethyl acetate. The extract was washed with water and dried over anhydrous sodium sulfate, and then the solvent was removed by distillation under reduced pressure. The residue was dissolved in 110 ml of acetonitrile, and 8.18 ml of diethylcarbamoyl chloride and 9.02 g of 1,4-diazabicyclo[2.2.2]octane were added to the resulting solution. The reaction mixture was then stirred at room temperature for 6 hours, after which it was diluted with ethyl acetate; the resulting solution was washed with 2N aqueous hydrochloric acid, with a 5% w/v aqueous solution of sodium hydroxide and with water, in that order. The organic layer was separated and dried over anhydrous sodium sulfate, and then the solvent was removed by distillation under reduced pressure. The residue thus obtained was purified by column chromatography through silica gel, eluted with a 3:1 by volume mixture of hexane and ethyl acetate, to give 10.29 g (yield 83%) of the title compound melting at 57°–58° C.

Nuclear Magnetic Resonance Spectrum (CDCl$_3$, 200 MHz), δ ppm: 8.06 (1H, doublet, J=2.5 Hz); 7.38–7.32 (1H, multiplet); 7.26–7.18 (2H, multiplet); 6.11 (1H, doublet, J=2.5 Hz); 3.46 (4H, quartet, J=7.0 Hz); 1.09 (6H, broad).

EXAMPLE 18

1-(Diethylcarbamoyl)-4-chloro-3-(2-ethyl-6-methylphenylthio)pyrazole (Compound No. 7.169)

and 1-(Diethylcarbamoyl)-4-chloro-3-(2-ethyl-6methylphenylsulfonyl)pyrazole (Compound No. 7.168)

18(1) 1-(Dimethylsulfamoyl)-4-chloro-5-(2-ethyl-6-methylphenylthio)pyrazole 2.6 ml of a 1.49M solution of butyllithium in hexane were added at −78° C. to a solution of 747 mg of 1-(dimethylsulfamoyl)-4-chloropyrazole [prepared as described in Example 3(1)] in 20 ml of dry tetrahydrofuran. After 20 minutes, a solution of 1.08 g of 2-ethyl-6-methylphenyl disulfide in 12 ml of dry tetrahydrofuran was added to the mixture, which was then stirred at the same temperature for 30 minutes. At the end of this time, the reaction mixture was mixed with an aqueous solution of ammonium chloride and extracted with ethyl acetate. The extract was washed with water and dried over anhydrous sodium sulfate; the solvent was then removed by distillation under reduced pressure. The residue thus obtained was purified by column chromatography through silica gel, eluted with a 4:1 by volume mixture of hexane and ethyl acetate, to give 1.19 g (yield 93%) of the title compound, melting at 68°–72° C.

Nuclear Magnetic Resonance Spectrum (CDCl$_3$, 200 MHz), δ ppm: 7.45 (1H, singlet); 7.21 (1H, doublet, J=7.3 Hz); 7.14–7.06 (2H, multiplet); 3.11 (6H, singlet); 2.92 (2H, quartet, J=7.5 Hz); 2.36 (3H, singlet); 1.19 (3H, triplet, J=7.5 Hz).

18(2) 1-(Diethylcarbamoyl)-4-chloro-3-(2-ethyl-6-methylphenylthio)pyrazole 0.76 ml of trifluoroacetic acid was added to a solution of 1.08 g of 1-(dimethylsulfamoyl)-4-chloro-5-(2-ethyl-6-methylphenylthio)pyrazole [prepared as described in step (1) above] in 5 ml of methylene chloride, and the resulting mixture was stirred for 2 hours. The mixture was then diluted with water and neutralized with an aqueous solution of sodium hydrogencarbonate. It was then extracted with ethyl acetate. The extract was washed with water and dried over anhydrous sodium sulfate, and then the solvent was removed by distillation under reduced pressure. The resulting residue was dissolved in 8 ml of acetonitrile, and 0.19 ml of diethylcarbamoyl chloride and 0.31 ml of 1,8-diazabicylo[5,4,0]undec-7-ene were added to the resulting solution. The reaction mixture was then heated at 50° C. for 2 hours, after which it was diluted with ethyl acetate, and the solution thus obtained was washed with 2N aqueous hydrochloric acid, with a 5% w/v aqueous solution of sodium hydroxide and with water, in that order. The organic layer was separated and dried over anhydrous sodium sulfate, and then the solvent was removed by distillation under reduced pressure. The residue thus obtained was purified by column chromatography through silica gel, eluted with a 6:1 by volume mixture of hexane and ethyl acetate, to give 915 mg (yield 79%) of the title compound as an oil.

Nuclear Magnetic Resonance Spectrum (CDCl$_3$, 200 MHz), δ ppm: 8.08 (1H, singlet); 7.23–7.10 (3H, singlet); 3.30 (4H, quartet, J=7.0 Hz); 2.89 (2H, quartet, J=7.6 Hz); 2.44 (3H, singlet); 1.27–1.14 (9H, multiplet).

18(3) 1-(Diethylcarbamoyl)-4-chloro-3-(2-ethyl-6-methylphenylsulfonyl)pyrazole 0.44 g of 3-chloroperoxybenzoic acid were added to a solution of 288 mg of 1-(diethylcarbamoyl)-4-chloro-3-(2-ethyl-6-methylphenylthio)pyrazole [prepared as described in step (2) above] in 6 ml of 1,2-dichloroethane, and the resulting mixture was heated at 50° C. for 2 hours. The reaction mixture was then diluted with ethyl acetate, after which it was washed with an aqueous solution of sodium sulfite, with an aqueous solution of sodium hydrogencarbonate and with water, in that order. The mixture was then dried over anhydrous sodium sulfate, and the solvent was removed by distillation under reduced pressure, after which the residue was purified by column chromatography through silica gel, eluted with an 8:1 by volume mixture of hexane and ethyl acetate, to give 168 mg (yield 53%) of the title compound as a gum.

Nuclear Magnetic Resonance Spectrum (CDCl$_3$, 200 MHz), δ ppm: 8.16 (1H, singlet); 7.41 (1H, triplet, J=7.6 Hz); 7.21 (1H, broad doublet, J=7.3 Hz); 7.15 (1H, broad doublet, J=7.3 Hz); 3.44 (4H, quartet, J=7.0 Hz); 3.10 (2H, quartet, J=7.4 Hz); 2.67 (3H, singlet); 1.24 (3H, triplet, J=7.4 Hz); 1.5–0.9 (6H, broad).

EXAMPLE 19

1-(Diethylcarbamoyl)-4-fluoro-3-(2,4,6-trichlorophenylthio)pyrazole (Compound No. 10.161)

and 1-(Diethylcarbamoyl)-4-fluoro-3-(2,4,6-trichlorophenylsulfonyl)pyrazole (Compound No. 10.92)

19(1) 1-(Dimethylsulfamoyl)-4-fluoropyrazole 2.1 liters of fluorine gas (10% in N$_2$) were bubbled, at 0°–5° C., into a solution of 11.1 g of 1-(dimethylsulfamoyl)pyrazole [prepared as described in Example 1(1)] and 25.9 g of sodium acetate in 500 ml of a 9:1 by volume mixture of chloroform and acetic acid. The mixture was stirred for 2 hours, after which it was diluted with water. The organic layer was separated, washed with water and dried over anhydrous sodium sulfate. The solvent was then removed by distillation under reduced pressure. The resulting residue was purified by column chromatography through silica gel, eluted with a 5:1 by volume mixture of hexane and ethyl acetate, to give 1.77 g (yield 14%) of the title compound as an oil.

Nuclear Magnetic Resonance Spectrum (CDCl$_3$, 270 MHz), δ ppm: 7.84 (1H, doublet, J=4.8 Hz); 7.63 (1H, doublet, J=4.8 Hz); 2.96 (6H, singlet).

19(2) 1-(Dimethylsulfamoyl)-4-fluoro-5-(2,4,6-trichlorophenylthio)pyrazole 0.30 ml of a 1.64M solution of butyllithium in hexane was added at −78° C. to a solution of 76 mg of 1-(dimethylsulfamoyl)-4-fluoropyrazole [prepared as described in step (1) above] in 3 ml of dry tetrahydrofuran. After 40 minutes, a solution of 201 mg of 2,4,6-trichlorophenyl disulfide in 2.5 ml of dry tetrahydrofuran was added to the mixture, which was then stirred at the same temperature for 1 hour. At the end of this time, the reaction mixture was mixed with an aqueous solution of ammonium chloride and extracted with ethyl acetate. The extract was washed with water and dried over anhydrous sodium sulfate; the solvent was then removed by distillation under reduced pressure. The residue thus obtained was purified by column chromatography through silica gel, eluted with an 8:1 by volume mixture of hexane and ethyl acetate, to give 104 mg (yield 65%) of the title compound as an oil.

Nuclear Magnetic Resonance Spectrum (CDCl$_3$, 200 MHz), δ ppm: 7.50 (1H, doublet, J=4.8 Hz); 7.42 (2H, singlet); 3.07 (6H, singlet).

19(3) 1-(Diethylcarbamoyl-4-fluoro-3-(2,4,6-trichlorophenylthio)pyrazole 0.06 ml of trifluoroacetic acid were added to a solution of 97 mg of 1-(dimethylsulfamoyl)-4-fluoro-5-(2,4,6-dichlorophenylthio)pyrazole [prepared as described in step (2) above] in 2 ml of chloroform, and the resulting mixture was heated at 50° C. for 2 hours. The mixture was then allowed to cool, after which it was diluted with water and neutralized with an aqueous solution of sodium hydrogencarbonate. It was then extracted with ethyl acetate. The extract was washed with water and dried over anhydrous sodium sulfate, and then the solvent was removed by distillation under reduced pressure. The residue was dissolved in 3 ml of acetonitrile, and 34 μl of diethylcarbamoyl chloride and 51 mg of 1,4-diazabicyclo[2.2.2]octane were added to the resulting solution. The reaction mixture was then heated at 50° C. for 2 hours, after which it was diluted with ethyl acetate and the solution was washed with 2N aqueous hydrochloric acid, with a 5% w/v aqueous solution of sodium hydroxide and with water, in that order. The organic layer was separated and dried over anhydrous sodium sulfate, and then the solvent was removed by distillation under reduced pressure. The residue thus obtained was purified by column chromatography, eluted with a 10:1 by volume mixture of hexane and ethyl acetate, to give 73 mg (yield 77%) of the title compound as an oil.

Nuclear Magnetic Resonance Spectrum (CDCl$_3$, 200 MHz), δ ppm: 7.95 (1H, doublet, J=4.8Hz); 7.44 (2H, singlet); 3.43 (2H, quartet, J=7.0 Hz); 1.10 (3H, triplet, J=7.0 Hz).

19(4) 1-(Diethylcarbamoyl)-4-fluoro-3-(2,4,6-trichlorophenylsulfonyl)pyrazole 83 mg of 3-chloroperoxybenzoic acid were added to a solution of 69 mg of 1-(diethylcarbamoyl)-4-fluoro-3-(2,4,6-trichlorophenylthio)pyrazole [prepared as described in step (3) above] in 2 ml of 1,2-dichloroethane, and the resulting mixture was heated at 50° C. for 4 hours. The reaction mixture was then diluted with ethyl acetate, after which it was washed with an aqueous solution of sodium sulfite, with an aqueous solution of sodium hydrogencarbonate and with water, in that order. The mixture was then dried over anhydrous sodium sulfate, and the solvent was removed by distillation under reduced pressure, after which the residue was purified by column chromatography through silica gel, eluted with a 6:1 by volume mixture of hexane and ethyl acetate, to give 65 mg (yield 88%) of the title compound, melting at 89°–90° C.

Nuclear Magnetic Resonance Spectrum (CDCl$_3$, 200 MHz), δ ppm: 8.06 (1H, doublet, J=5.0 Hz); 7.49 (2H, singlet); 3.46 (4H, broad quartet, J=7.0 Hz); 1.40–0.95 (6H, broad).

By using the procedures described in Examples 1 to 19, the following compounds were also prepared.

1-(Diethylcarbamoyl)-3-phenylsulfonylpyrazole (Compound No. 1.1)

Following the procedure of Example 1, there were obtained 194 mg (yield 59.7%) of the title compound, melting at 65°–66.5° C.

1-(Diethylcarbamoyl)-3-phenylthiopyrazole (Compound No. 1.2)

Following the procedure of Example 1, there were obtained 463 mg (yield 60.4%) of the title compound, as an oily substance.

Nuclear Magnetic Resonance Spectrum (CDCl$_3$, 270 MHz), δ ppm: 8.11 (1H, doublet, J=2.6 Hz); 7.44 (2H, doublet of doublets, J=1.4 & 7.8 Hz); 7.34–7.28 (3H, multiplet); 6.25 (1H, doublet, J=2.6 Hz); 3.57 (4H, broad quartet, J=7.0 Hz); 1.21 (6H, broad triplet, J=7.0 Hz).

1-(Diethylcarbamoyl)-3-(2-fluorophenylsulfonyl)-pyrazole (Compound No. 1.4)

Following the procedure of Example 1, there were obtained 185 mg (yield 65.7%) of the title compound, as an oily substance.

Nuclear Magnetic Resonance Spectrum (CDCl$_3$, 270 MHz), δ ppm: 8.19 (1H, doublet, J=2.9 Hz); 8.16 (1H, doublet of triplets, J=1.7 & 8.0 Hz); 7.68–7.60 (1H, multiplet); 7.35 (1H, triplet, J=7.5 Hz); 7.17 (1H, triplet, J=8.0 Hz); 6.96 (1H, doublet, J=2.9 Hz); 3.48 (4H, broad quartet, J=7.0 Hz); 1.18 (6H, broad).

1-(Diethylcarbamoyl)-3-(2-fluorophenylthio)pyrazole (Compound No. 1.5)

Following the procedure of Example 1, there were obtained 627 mg (yield 70.7%) of the title compound, as an oily substance.

Nuclear Magnetic Resonance Spectrum (CDCl$_3$, 270 MHz), δ ppm: 8.12 (1H, doublet, J=2.6 Hz); 7.45–7.10 (4H, multiplet); 6.27 (1H, double t, J=2.6 Hz); 3.53 (4H, broad quartet, J=7.0 Hz); 1.17 (6H, broad triplet, J=7.0 Hz).

1-(Diethyl carbamoyl)-3-(2-chlorophenylsulfonyl)-pyrazole (Compound No. 1.6)

Following the procedure of Example 1, there were obtained 154 mg (yield 57.7%) of the title compound, as an oily substance.

Nuclear Magnetic Resonance Spectrum (CDCl$_3$, 200 MHz), δ ppm: 8.37–8.32 (1H, multiplet); 8.12 (1H, doublet, J=2.8 Hz); 7.59–7.46 (4H, multiplet); 6.99 (1H, doublet, J=2.8 Hz); 3.42 (4H, quartet, J=7.0 Hz); 1.4–0.8 (6H, broad).

1-(Diethylcarbamoyl)-3-(2-chlorophenylsulfinyl)-pyrazole (Compound No. 1.7)

Following the procedure of Example 1, there were obtained 172 mg (yield 61.4%) of the title compound, as an oily substance.

Nuclear Magnetic Resonance Spectrum (CDCl$_3$, 200 MHz), δ ppm: 8.16 (1H, doublet, J=2.8 Hz); 8.12 (1H, doublet of doublets, J=2.0 & 7.6 Hz); 7.61–7.43 (4H, multiplet); 6.51 (1H, doublet, J=2.8 Hz); 3.56–3.44 (4H, multiplet); 1.3–1.1 (6H, broad).

1-(Diethylcarbamoyl)-3-(2-bromophenylsulfonyl)-pyrazole Compound No. 1.8)

Following the procedure of Example 1, there were obtained 203 mg (yield 36.3%) of the title compound, melting at 54°–56° C.

1-(Diethylcarbamoyl)-3-(2-bromophenylthio)pyrazole (Compound No. 1.9)

Following the procedure of Example 1, there were obtained 712 mg (yield 39.0%) of the title compound, as an oily substance.

Nuclear Magnetic Resonance Spectrum (CDCl$_3$, 200 MHz), δ ppm: 8.18 (1H, doublet, J=2.7 Hz); 7.57 (1H, doublet of doublets, J=7.7 & 1.1 Hz); 7.26–7.08 (3H, multiplet); 6.39 (1H, doublet, J=2.7 Hz); 3.57 (4H, quartet, J=7.0 Hz); 1.20 (6H, triplet, J=7.0 Hz).

1-(Diethylcarbamoyl)-3-(2-methylphenylsulfonyl)-pyrazole (Compound No. 1.10)

Following the procedure of Example 1, there were obtained 179 mg (yield 59.3%) of the title compound, as an oily substance.

Nuclear Magnetic Resonance Spectrum (CDCl$_3$, 200 MHz), δ ppm: 8.20–8.17 (1H, multiplet); 8.18 (1H, doublet, J=2.6 Hz); 7.51 (1H, doublet of triplets, J=7.5 & 1.2 Hz); 7.41–7.36 (1H, multiplet); 7.29–7.26 (1H, multiplet); 6.87 (1H, doublet, J=2.6 Hz); 3.45 (4H, broad quartet, J=7.0 Hz); 2.58 (3H, singlet); 1.15 (6H, broad).

1-(Diethylcarbamoyl)-3-(2-methylphenylthio)pyrazole (Compound No. 1.11)

Following the procedure of Example 1, there were obtained 605 mg (yield 69.0%) of the title compound, as an oily substance.

Nuclear Magnetic Resonance Spectrum (CDCl$_3$, 270 MHz), δ ppm: 8.10 (1H, doublet, J=2.9 Hz); 7.41 (1H, broad doublet, J=7.0 Hz); 7.24–7.11 (3H, multiplet); 6.16 (1H, doublet, J=2.9 Hz); 3.54 (4H, broad quartet, J=7.0 Hz); 2.42 (3H, singlet); 1.17 (6H, triplet, J=7.0 Hz).

1-(Diethylcarbamoyl)-3-(2-methylbenzylsulfonyl)-pyrazole (Compound No. 1.12)

Following the procedure of Example 1, there were obtained 151 mg (yield 48.1%) of the title compound, as an oily substance.

Nuclear Magnetic Resonance Spectrum (CDCl$_3$, 200 MHz), δ ppm: 8.16 (1H, doublet, J=2.9 Hz); 7.26–7.12 (4H, multiplet); 6.64 (1H, doublet, J=2.9 Hz); 4.57 (2H, singlet); 3.54 (4H, quartet, J=7.0 Hz); 2.34 (3H, singlet); 1.29 (6H, triplet, J=7.0 Hz).

1-(Diethylcarbamoyl)-3-(2-methylbenzylthio)pyrazole (Compound No. 1.13)

Following the procedure of Example 1, there were obtained 574 mg (yield 56.5%) of the title compound, as an oily substance.

Nuclear Magnetic Resonance Spectrum (CDCl$_3$, 200 MHz), δ ppm: 8.10 (1H, doublet, J=2.9 Hz); 7.29–7.11 (4H, multiplet); 6.22 (1H, doublet, J=2.9 Hz); 4.29 (2H, singlet); 3.60 (4H, quartet, J=7.0 Hz); 2.42 (3H, singlet); 1.28 (6H, triplet, J=7.0 Hz).

1-(Diethylcarbamoyl)-3-(2-ethylphenylthio)pyrazole (Compound No. 1.14)

Following the procedure of Example 1, there were obtained 1.53 g (yield 39.0%) of the title compound, as an oily substance.

Nuclear Magnetic Resonance Spectrum (CDCl$_3$, 200 MHz), δ ppm: 8.09 (1H, doublet, J=2.0 Hz); 7.41 (1H, doublet, J=7.5 Hz); 7.26 (2H, doublet of doublets, J=2.4 & 1.1 Hz); 7.24–7.11 (1H, multiplet); 6.15 (1H, doublet, J=2.0 Hz); 3.54 (4H, quartet, J=7.0 Hz); 2.84 (2H, quartet, J=7.4 Hz); 1.22 (6H, triplet, J=7.0 Hz); 1.18 (3H, triplet, J=7.4 Hz).

1-(Diethylcarbamoyl)-3-(2-ethylphenylsulfonyl)-pyrazole (Compound No. 1.15)

Following the procedure of Example 2, there were obtained 228 mg (yield 39.0%) of the title compound, as an oily substance.

Nuclear Magnetic Resonance Spectrum (CDCl$_3$, 200 MHz), δ ppm: 8.18 (1H, doublet, J=2.6 Hz); 7.57 (1H, triplet of doublets, J=7.4 & 1.5 Hz); 7.38 (2H, multiplet); 6.86 (1H, doublet, J=2.6 Hz); 3.45 (4H, quartet, J=7.4 Hz); 2.99 (2H, quartet, J=7.4 Hz); 1.19 (9H, triplet, J=7.4 Hz).

1-(Diethylcarbamoyl)-3-(2-isopropylphenylsulfonyl)-pyrazole (Compound No. 1.16)

Following the procedure of Example 1, there were obtained 161 mg (yield 17.2%) of the title compound, as an oily substance.

Nuclear Magnetic Resonance Spectrum (CDCl$_3$, 200 MHz), δ ppm: 8.18 (1H, doublet, J=2.7 Hz); 7.63–7.32 (4H, multiplet); 6.85 (1H, doublet, J=2.7 Hz); 3.88 (1H, septet, J=6.8 Hz); 3.45 (4H, quartet, J=7.0 Hz); 1.35–0.98 (6H, broad); 1.11 (6H, doublet, J=6.8 Hz).

1-(Diethylcarbamoyl)-3-(2-benzylphenylsulfonyl)-pyrazole (Compound No. 1.17)

Following the procedure of Example 1, there were obtained 226 mg (yield 37.0%) of the title compound, melting at 72°–73° C.

1-(Diethylcarbamoyl)-3-(2-benzylphenylthio)pyrazole (Compound No. 1.18)

Following the procedure of Example 1, there were obtained 497 mg (yield 37.8%) of the title compound, as an oily substance.

Nuclear Magnetic Resonance Spectrum (CDCl$_3$, 200 MHz), δ ppm: 8.08 (1H, doublet, J=2.9 Hz); 7.48–7.43 (1H, multiplet); 7.31–7.12 (8H, multiplet); 6.12 (1H, doublet, J=2.9 Hz); 4.20 (2H, singlet); 3.53 (4H, quartet, J=7.0 Hz); 1.17 (4H, triplet, J=7.0 Hz).

1-(Diethylcarbamoyl)-3-(2-methoxyphenylsulfonyl)-pyrazole (Compound No. 1.19)

Following the procedure of Example 1, there were obtained 193 mg (yield 69.4%) of the title compound, as an oily substance.

Nuclear Magnetic Resonance Spectrum (CDCl$_3$, 270 MHz), δ ppm: 8.15 (1H, doublet, J=2.9 Hz); 7.59 (1H, doublet of triplets, J=1.7 & 8.7 Hz); 7.12 (1H, triplet, J=7.2 Hz); 6.97–6.94 (1H, multiplet); 6.94 (1H, doublet, J=2.9 Hz); 3.80 (3H, singlet); 3.40 (4H, broad quartet, J=7.0 Hz); 1.15 (6H, broad).

1-(Diethylcarbamoyl)-3-(2-methoxyphenylthio)-pyrazole (Compound No. 1.20)

Following the procedure of Example 1, there were obtained 619 mg (yield 69.4%) of the title compound, as an oily substance.

Nuclear Magnetic Resonance Spectrum (CDCl$_3$, 200 MHz), δ ppm: 8.12 (1H, doublet, J=2.6 Hz); 7.29–7.23 (2H, multiplet); 6.90 (2H, doublet, J=8.0 Hz); 6.26 (1H, doublet, J=2.6 Hz); 3.87 (3H, singlet); 3.57 (4H, broad quartet, J=7.0 Hz); 1.20 (6H, triplet, J=7.0 Hz).

1-(Diethylcarbamoyl)-3-(2-phenoxyphenylsulfonyl)-pyrazole (Compound No. 1.21)

Following the procedure of Example 1, there were obtained 330 mg (yield 67.0%) of the title compound, as an oily substance.

Nuclear Magnetic Resonance Spectrum (CDCl$_3$, 200 MHz), δ ppm: 8.24 (1H, doublet, J=8.1 Hz); 8.11 (1H, doublet, J=2.6 Hz); 7.51 (1H, triplet, J=8.1 Hz); 7.36–7.12 (5H, multiplet); 6.93 (1H, doublet, J=2.6 Hz); 6.87–6.81 (2H, multiplet); 3.47 (4H, quartet, J=6.8 Hz); 1.16–1.08 (6H, multiplet).

1-(Diethylcarbamoyl)-3-(2-phenoxyphenylthio)-pyrazole (Compound No. 1.22)

Following the procedure of Example 1, there were obtained 1.06 g (yield 67.0%) of the title compound, as an oily substance.

Nuclear Magnetic Resonance Spectrum (CDCl$_3$, 200 MHz), δ ppm: 8.14 (1H, doublet, J=2.6 Hz); 7.37–6.89 (9H, multiplet); 6.34 (1H, doublet, J=2.6 Hz); 3.57 (4H, quartet, J=7.0 Hz); 1.21 (6H, triplet, J=7.0 Hz).

1-(Diethylcarbamoyl)-3-(2-trifluoromethylphenylsulfonyl)pyrazole (Compound No. 1.23)

Following the procedure of Example 1, there were obtained 214 mg (yield 46.8%) of the title compound, melting at 67°–68° C.

1-(Diethylcarbamoyl)-3-(2-trifluoromethylphenylthio)-pyrazole (Compound No. 1.24)

Following the procedure of Example 1, there were obtained 864 mg (yield 47.7%) of the title compound, as an oily substance.

Nuclear Magnetic Resonance Spectrum (CDCl$_3$, 200 MHz), δ ppm: 8.14 (1H, doublet, J=2.6 Hz); 7.69 (1H, doublet of doublets, J=2.2 & 7.0 Hz); 7.44–7.30 (3H, multiplet); 6.31 (1H, doublet, J=2.6 Hz); 3.60 (4H, quartet, J=6.9 Hz); 1.37 (3H, triplet, J=6.9 Hz).

Ethyl 2-(1-diethylcarbamoyl-3-pyrazolylthio)benzoate (Compound No. 1.26)

Following the procedure of Example 1, there were obtained 203 mg (yield 55.2%) of the title compound, melting at 47°–49° C.

Ethyl 2-(1-diethylcarbamoyl-3-pyrazolylsulfonyl)benzoate (Compound No. 1.27)

Following the procedure of Example 1, there were obtained 154 mg (yield 55.2%) of the title compound, melting at 59°–61° C.

1-(Diethylcarbamoyl)-3-(2-benzylphenylthio)-5-formyl-pyrazole (Compound No. 1.30)

Following the procedure of Example 15, there were obtained 76 mg (yield 23.8%) of the title compound, as an oily substance.

Nuclear Magnetic Resonance Spectrum (CDCl$_3$, 200 MHz), δ ppm: 10.0 (1H, singlet); 7.49 (1H, doublet, J=6.7 Hz); 7.30–7.10 (8H, multiplet); 6.58 (1H, singlet); 4.20 (2H, singlet); 3.52–3.33 (4H, multiplet); 1.34–1.10 (6H, multiplet).

1-(Diethylcarbamoyl)-3-(2-chlorophenylsulfonyl)-4-fluoropyrazole (Compound No. 1.37)

Following the procedure of Example 19, there were obtained 82 mg (yield 8.5%) of the title compound, as an oily substance.

Nuclear Magnetic Resonance Spectrum (CDCl$_3$, 200 MHz), δ ppm: 8.36–8.31 (1H, multiplet); 8.01 (1H, doublet, J=4.8 Hz); 7.61–7.47 (3H, multiplet); 3.46 (4H, quartet, J=7.0 Hz); 1.29–1.08 (6H, broad).

1-(Diethylcarbamoyl)-3-(2-ethylphenylsulfonyl)-4-fluoropyrazole (Compound No. 1.38)

Following the procedure of Example 19, there were obtained 74 mg (yield 7.8%) of the title compound, as an oily substance.

Nuclear Magnetic Resonance Spectrum (CDCl₃, 200 MHz), δ ppm: 8.20 (1H, doublet, J=7.5 Hz); 8.00 (1H, doublet J=4.8 Hz); 7.59 (1H, triplet of doublets, J=7.5 & 1.4 Hz); 7.40 (2H, triplet of doublets, J=7.5 & 1.4 Hz); 3.49 (4H, broad quartet, J=6.3 Hz); 3.03 (2H, quartet, J=7.4 Hz); 1.22 (6H, triplet, J=6.3 Hz). 1.20 (3H, triplet, J=7.4 Hz).

1-(Diethylcarbamoyl)-3-(2-trifluoromethylphenylsulfonyl)-4-fluoropyrazole (Compound No. 1.40)

Following the procedure of Example 19, there were obtained 26 mg (yield 2.9%) of the title compound, as an oily substance.

Nuclear Magnetic Resonance Spectrum (CDCl₃, 200 MHz), δ ppm: 8.55–8.51 (1H, multiplet); 7.94 (1H, doublet, J=5.7 Hz); 7.88–7.66 (3H, multiplet); 3.43 (4H, quartet, J=7.0 Hz); 1.27–1.05 (6H, broad).

1-(Diethylcarbamoyl)-3-(2-chlorophenylthio)-4-chloropyrazole (Compound No. 1.56)

Following the procedure of Example 3, there were obtained 216 mg (yield 44.7%) of the title compound, as an oily substance.

Nuclear Magnetic Resonance Spectrum (CDCl₃, 200 MHz), δ ppm: 8.19 (1H, singlet); 7.44–7.39 (1H, multiplet); 7.20–7.17 (3H, multiplet); 3.52 (4H, quartet, J=7.0 Hz); 1.66 (6H, triplet, J=7.0 Hz).

1-(Diethylcarbamoyl(-3-(2-chlorophenylsulfonyl)-4-chloropyrazole (Compound No. 1.57)

Following the procedure of Example 3, there were obtained 146 mg (yield 33.1%) of the title compound, melting at 84°–86° C.

1-(Diethylcarbamoyl)-3-(2-ethylphenylsulfonyl)-4-chloropyrazole (Compound No. 1.58)

Following the procedure of Example 5, there were obtained 128 mg (yield 9.8%) of the title compound, melting at 68°–69° C.

Ethyl 2-(1-diethylcarbamoyl-4-chloro-3-pyrazolylthio)benzoate (Compound No. 1.59)

Following the procedure of Example 5, there were obtained 150 mg (yield 44.0%) of the title compound, melting at 113°–117° C.

Ethyl 2-(1-diethylcarbamoyl-4-chloro-3-pyrazolylsulfonyl)benzoate (Compound No. 1.60)

Following the procedure of Example 5, there were obtained 112 mg (yield 40.7%) of the title compound, melting at 54°–58° C.

1-(Diethylcarbamoyl)-3-(2-ethylphenylsulfonyl)-4-bromopyrazole (Compound No. 1.79)

Following the procedure of Example 4, there were obtained 89 mg (yield 10.0%) of the title compound, melting at 65°–67° C.

1-(Diethylcarbamoyl)-3-(2-trifluoromethylphenylthio)-4-fluoropyrazole (Compound No. 1.80)

Following the procedure of Example 19, there were obtained 33 mg (yield 3.9%) of the title compound, as an oily substance.

Nuclear Magnetic Resonance Spectrum (CDCl₃, 200 MHz), δ ppm: 8.02 (1H, doublet, J=5.1 Hz); 7.69 (1H, doublet, J=7.2 Hz); 7.43–7.35 (3H, multiplet); 3.54 (4H, quartet, J=7.0 Hz); 1.20 (6H, triplet J=7.0 Hz).

1-(Diethylcarbamoyl)-3-(2-methylphenylsulfonyl)-4-fluoropyrazole (Compound No. 1.81)

Following the procedure of Example 7, there were obtained 12 mg (yield 1.5%) of the title compound, as an oily substance.

Nuclear Magnetic Resonance Spectrum (CDCl₃, 200 MHz), δ ppm: 8.20 (1H, doublet of doublets, J=7.9 & 1.4 Hz); 8.00 (1H, doublet, J=4.8 Hz); 7.54 (1H, triplet of doublets, J=7.9 & 1.4 Hz); 7.40 (1H, triplet, J=7.9 Hz); 7.30 (1H, doublet, J=7.9 Hz); 3.49 (4H, quartet, J=6.9 Hz); 2.61 (3H, singlet); 1.20 (6H, triplet, J=6.9 Hz).

1-(Diethylcarbamoyl)-3-(3-fluorophenylsulfonyl)-pyrazole (Compound No. 2.1)

Following the procedure of Example 1, there were obtained 219 mg (yield 50.0%) of the title compound, as an oily substance.

Nuclear Magnetic Resonance Spectrum (CDCl₃, 200 MHz), δ ppm: 8.16 (1H, doublet, J=2.7 Hz); 7.83 (1H, multiplet); 7.74 (1H, multiplet); 7.53 (1H, multiplet); 7.33 (1H, multiplet); 6.88 (1H, doublet, J=2.7 Hz); 3.49 (4H, quartet, J=7.0 Hz); 1.23 (6H, triplet, J=7.0 Hz).

1-(Diethylcarbamoyl)-3-(3-fluorophenylthio)pyrazole (Compound No. 2.2)

Following the procedure of Example 1, there were obtained 567 mg (yield 51.0%) of the title compound, as an oily substance.

Nuclear Magnetic Resonance Spectrum (CDCl₃, 200 MHz), δ ppm: 8.15 (1H, doublet, J=2.4 Hz); 7.32–7.11 (3H, multiplet); 6.98 (1H, multiplet); 6.33 (1H, triplet, J=2.4 Hz); 3.58 (4H, quartet, J=7.0 Hz); 1.23 (6H, triplet, J=7.0 Hz).

1-(Diethylcarbamoyl)-3-(3-chlorophenylthio)pyrazole (Compound No. 2.3)

Following the procedure of Example 1, there were obtained 585 mg (yield 72.2%) of the title compound, as an oily substance.

Nuclear Magnetic Resonance Spectrum (CDCl₃, 200 MHz), δ ppm: 8.15 (1H, doublet, J=2.6 Hz); 7.39–7.20 (4H, multiplet); 6.33 (1H, doublet, J=2.6 Hz); 3.57 (4H, quartet, J=7.0 Hz); 1.22 (6H, triplet, J=7.0 Hz).

1-(Diethylcarbamoyl)-3-(3-chlorophenylsulfonyl)-pyrazole (Compound No. 2.4)

Following the procedure of Example 1, there were obtained 217 mg (yield 63.5%) of the title compound, as an oily substance.

Nuclear Magnetic Resonance Spectrum (CDCl₃, 200 MHz), δ ppm: 8.17 (1H, doublet, J=2.9 Hz); 8.03 (1H, triplet, J=1.7 Hz); 7.94–7.89 (1H, multiplet); 7.62–7.57 (1H, multiplet); 7.48 (1H, triplet, J=7.7 Hz); 6.88 (1H, doublet, J=2.9 Hz); 3.49 (4H, quartet, J=7.0 Hz); 1.23 (6H, triplet, J=7.0 Hz).

1-(Diethylcarbamoyl)-3-(3-bromophenylthio)pyrazole (Compound No. 2.5)

Following the procedure of Example 1, there were obtained 747 mg (yield 63.5%) of the title compound, as an oily substance.

Nuclear Magnetic Resonance Spectrum (CDCl₃, 200 MHz), δ ppm: 8.15 (1H, doublet, J=2.7 Hz); 7.55 (1H, triplet, J=1.7 Hz); 7.40–7.30 (2H, multiplet); 7.16 (1H, triplet, J=8.0 Hz); 6.33 (1H, doublet, J=2.7 Hz); 3.57 (4H, quartet, J=7.0 Hz); 1.22 (6H, triplet, J=7.0 Hz).

1-(Diethylcarbamoyl)-3-(3-bromophenylsulfonyl)-pyrazole (Compound No. 2.6)

Following the procedure of Example 1, there were obtained 229 mg (yield 55.9%) of the title compound, as an oily substance.

Nuclear Magnetic Resonance Spectrum (CDCl₃, 200 MHz), δ ppm: 8.10–8.16 (2H, multiplet); 7.99–7.93 (1H, multiplet); 7.78–7.72 (1H, multiplet); 7.42 (1H, triplet, J=7.9 Hz); 6.88 (1H, doublet, J=2.7 Hz); 3.49 (4H, quartet, J=7.0 Hz); 1.23 (6H, triplet, J=7.0 Hz).

1-(Diethylcarbamoyl)-3-(3-methylphenylsulfonyl)-pyrazole (Compound No. 2.7)

Following the procedure of Example 1, there were obtained 367 mg (yield 49.4%) of the title compound, as an oily substance.

Nuclear Magnetic Resonance Spectrum (CDCl₃, 200 MHz), δ ppm: 8.15 (1H, doublet, J=2.8 Hz); 7.85-7.82 (1H, multiplet); 7.44-7.41 (1H, multiplet); 6.86 (1H, doublet, J=2.8 Hz); 3.49 (4H, quartet, J=7.0 Hz); 2.43 (3H, singlet); 1.22 (6H, triplet, J=7.0 Hz).

1-(Diethylcarbamoyl)-3-(3-methylphenylthio)pyrazole (Compound No. 2.8)

Following the procedure of Example 1, there were obtained 2.18 g (yield 49.4%) of the title compound, as an oily substance.

Nuclear Magnetic Resonance Spectrum (CDCl₃, 200 MHz), δ ppm: 8.11 (1H, doublet, J=2.7 Hz); 7.23-7.06 (4H, multiplet); 6.25 (1H, doublet, J=2.7 Hz); 3.68 (4H, quartet, J=7.0 Hz); 2.32 (3H, singlet); 1.22 (6H, triplet, J=7.0 Hz).

1-(Diethylcarbamoyl)-3-(3-isopropylphenylthio)-pyrazole (Compound No. 2.9)

Following the procedure of Example 1, there were obtained 706 mg (yield 54.0%) of the title compound, as an oily substance.

Nuclear Magnetic Resonance Spectrum (CDCl₃, 200 MHz), δ ppm: 8.11 (1H, doublet, J=2.5 Hz); 7.32-7.11 (4H, multiplet); 6.23 (1H, doublet, J=2.5 Hz); 3.57 (4H, quartet, J=7.0 Hz); 2.87 (1H, septet, J=7.0 Hz); 1.23 (6H, doublet, J=7.0 Hz); 1.21 (6H, triplet, J=7.0 Hz).

1-(Diethylcarbamoyl)-3-(3-isopropylphenylsulfonyl)-pyrazole (Compound No. 2.10)

Following the procedure of Example 1, there were obtained 147 mg (yield 48.8%) of the title compound, as an oily substance.

Nuclear Magnetic Resonance Spectrum (CDCl₃, 200 MHz), δ ppm: 8.15 (1H, doublet, J=2.8 Hz); 7.89-7.81 (2H, multiplet); 7.48-7.40 (2H, multiplet); 6.86 (1H, doublet, J=2.8 Hz); 3.49 (4H, quartet, J=6.9 Hz); 2.99 (1H, septet, J=6.9 Hz); 1.27 (6H, doublet, J=6.9 Hz); 1.21 (6H, triplet, J=6.9 Hz).

1-(Diethylcarbamoyl)-3-(3-methoxyphenylthio)-pyrazole (Compound No. 2.11)

Following the procedure of Example 1, there were obtained 615 mg (yield 73.9%) of the title compound, as an oily substance.

Nuclear Magnetic Resonance Spectrum (CDCl₃, 200 MHz), δ ppm: 8.11 (1H, doublet, J=2.6 Hz); 7.21 (1H, triplet, J=7.9 Hz); 7.01-6.95 (2H, multiplet); 6.83-6.77 (1H, multiplet); 6.28 (1H, doublet, J=2.6 Hz); 3.76 (3H, singlet); 3.58 (4H, quartet, J=7.0 Hz); 1.22 (6H, triplet, J=7.0 Hz).

1-(Diethylcarbamoyl)-3-(3-methoxyphenylsulfonyl)-pyrazole (Compound No. 2.12)

Following the procedure of Example 1, there were obtained 169 mg (yield 69.4%) of the title compound, as an oily substance.

Nuclear Magnetic Resonance Spectrum (CDCl₃, 200 MHz), δ ppm: 8.15 (1H, doublet, J=2.7 Hz); 7.63-7.58 (1H, multiplet); 7.52 (1H, triplet, J=2.3 Hz); 7.43 (1H, triplet, J=7.9 Hz); 7.17-7.11 (1H, multiplet); 6.85 (1H, doublet, J=2.7 Hz); 3.85 (3H, singlet); 3.48 (4H, quartet, J=7.0 Hz); 1.22 (6H, triplet, J=7.0 Hz).

1-(Diethylcarbamoyl)-3-(3-cyanophenylsulfonyl)-pyrazole (Compound No. 2.13)

Following the procedure of Example 1, there were obtained 304 mg (yield 48.7%) of the title compound, as an oily substance.

Nuclear Magnetic Resonance Spectrum (CDCl₃, 200 MHz), δ ppm: 8.35-8.23 (2H, multiplet); 8.19 (1H, doublet, J=2.8 Hz); 7.91 (1H, doublet of triplets, J=7.9 & 1.4 Hz); 7.70 (1H, triplet, J=7.9 Hz); 6.91 (1H, doublet, J=2.8 Hz); 3.50 (4H, quartet, J=7.0 Hz); 1.24 (6H, triplet, J=7.0 Hz).

1-(Diethylcarbamoyl)-3-(3-cyanophenylthio)pyrazole (Compound No. 2.14)

Following the procedure of Example 1, there were obtained 808 mg (yield 52.9%) of the title compound, as an oily substance.

Nuclear Magnetic Resonance Spectrum (CDCl₃, 200 MHz), δ ppm: 8.21 (1H, doublet, J=2.7 Hz); 7.66-7.40 (4H, multiplet); 6.38 (4H, quartet, J=7.0 Hz); 1.23 (6H, triplet, J=7.0 Hz).

1-(Diethylcarbamoyl)-3-(3-trifluoromethylphenylthio)-pyrazole (Compound No. 2.15)

Following the procedure of Example 1, there were obtained 633 mg (yield 47.9%) of the title compound, as an oily substance.

Nuclear Magnetic Resonance Spectrum (CDCl₃, 200 MHz), δ ppm: 8.16 (1H, doublet, J=2.8 Hz); 7.67-7.41 (4H, multiplet); 6.35 (1H, doublet, J=2.8 Hz); 3.55 (4H, quartet, J=7.0 Hz); 1.19 (6H, triplet, J=7.0 Hz).

1-(Diethylcarbamoyl)-3-(3-trifluoromethylphenylsulfonyl)pyrazole (Compound No. 2.16)

Following the procedure of Example 1, there were obtained 232 mg (yield 43.1%) of the title compound, as an oily substance.

Nuclear Magnetic Resonance Spectrum (CDCl₃, 200 MHz), δ ppm: 8.33-8.19 (2H, multiplet); 8.18 (1H, doublet, J=2.6 Hz); 7.91-7.88 (1H, multiplet); 7.70 (1H, triplet, J=8.0 Hz); 6.91 (1H, doublet, J=2.6 Hz); 3.48 (4H, quartet, J=7.0 Hz); 1.21 (6H, triplet, J=7.0 Hz).

Ethyl 3-(1-diethylcarbamoyl-3-pyrazolylthio)benzoate (Compound No. 2.18)

Following the procedure of Example 1, there were obtained 279 mg (yield 80.9%) of the title compound, as an oily substance.

Nuclear Magnetic Resonance Spectrum (CDCl₃, 200 MHz), δ ppm: 8.16 (1H, doublet, J=2.7 Hz); 8.13-8.11 (1H, multiplet); 7.96-7.91 (1H, multiplet); 7.62-7.57 (1H, multiplet); 7.40 (1H, triplet, J=7.7 Hz); 6.30 (1H, doublet, J=2.7 Hz); 4.37 (2H, quartet, J=7.1 Hz); 3.56 (4H, broad quartet, J=7.0 Hz); 1.38 (3H, triplet, J=7.0 Hz); 1.20 (6H, triplet, J=7.0 Hz).

Ethyl 3-(1-diethylcarbamoyl-3-pyrazolylsulfonyl)benzoate (Compound No. 2.19)

Following the procedure of Example 1, there were obtained 262 mg (yield 80.9%) of the title compound, as an oily substance.

Nuclear Magnetic Resonance Spectrum (CDCl₃, 200 MHz), δ ppm: 8.68 (1H, triplet, J=1.7 Hz); 8.33-8.19 (2H, multiplet); 8.17 (1H, doublet, J=2.7 Hz); 7.64 (1H, triplet, J=7.8 Hz); 6.90 (1H, doublet, J=2.7 Hz); 4.41 (2H, quartet, J=7.1 Hz); 3.48 (4H, broad quartet, J=7.0 Hz); 1.41 (3H, triplet, J=7.1 Hz); 1.21 (6H, broad triplet, J=7.0 Hz).

1-(Diethylcarbamoyl)-3-(3-methylthiophenylthio)-pyrazole (Compound No. 2.21)

Following the procedure of Example 1, there were obtained 737 mg (yield 60.0%) of the title compound, as an oily substance.

Nuclear Magnetic Resonance Spectrum (CDCl₃, 200 MHz), δ ppm: 8.13 (1H, doublet, J=2.3 Hz); 7.30-7.11 (4H, multiplet); 6.29 (1H, doublet, J=2.3 Hz); 3.58 (4H, quartet, J=7.0 Hz); 2.45 (3H, singlet); 1.23 (6H, triplet, J=7.0 Hz).

1-(Diethylcarbamoyl)-3-(3-methylsulfonylphenylsulfonyl)pyrazole (Compound No. 2.22)

Following the procedure of Example 1, there were obtained 334 mg (yield 60.0%) of the title compound, melting at 133°–135° C.

1-(Diethylcarbamoyl)-3-(3-fluorophenylthio)-4-chloropyrazole (Compound No. 2.41)

Following the procedure of Example 3, there were obtained 242 mg (yield 53.7%) of the title compound, as an oily substance.

Nuclear Magnetic Resonance Spectrum (CDCl$_3$, 200 MHz), δ ppm: 8.17 (1H, singlet); 7.33–7.22 (1H, multiplet); 7.18–7.00 (2H, multiplet); 7.00–6.90 (1H, multiplet); 3.54 (4H, quartet, J=6.9 Hz); 1.20 (6H, triplet, J=6.9 Hz).

1-(Diethylcarbamoyl)-3-(3-fluorophenylsulfonyl)-4-chloropyrazole (Compound No. 2.42)

Following the procedure of Example 3, there were obtained 216 mg (yield 49.4%) of the title compound, as an oily substance.

Nuclear Magnetic Resonance Spectrum (CDCl$_3$, 200 MHz), δ ppm: 8.13 (1H, singlet); 7.87 (1H, doubled doublet of doublets, J=7.8, 2.0 & 1.1 Hz); 7.76 (1H, triplet of doublets, J=2.0 & 8.1 Hz); 7.56 (1H, triplet of doublets, J=8.1 & 5.1 Hz); 7.36 (1H, tripled doublet of doublets, J=8.1, 2.0 & 1.1 Hz); 3.50 (4H, quartet, J=7.0 Hz); 1.24 (6H, triplet, J=7.0 Hz).

1-(Diethylcarbamoyl)-3-(3-chlorophenylthio)-4-chloropyrazole (Compound No. 2.43)

Following the procedure of Example 3, there were obtained 398 mg (yield 33.4%) of the title compound, as an oily substance.

Nuclear Magnetic Resonance Spectrum (CDCl$_3$, 200 MHz), δ ppm: 8.17 (1H, singlet); 7.40–7.22 (4H, multiplet); 3.54 (4H, quartet, J=7.0 Hz); 1.19 (6H, triplet, J=7.0 Hz).

1-(Diethylcarbamoyl)-3-(3-chlorophenylsulfonyl)-4-chloropyrazole (Compound No. 2.44)

Following the procedure of Example 3, there were obtained 354 mg (yield 31.4%) of the title compound, melting at 77°–79° C.

1-(Diethylcarbamoyl)-3-(3-bromophenylsulfonyl)-4-chloropyrazole (Compound No. 2.45)

Following the procedure of Example 4, there were obtained 220 mg (yield 42.0%) of the title compound, as an oily substance.

Nuclear Magnetic Resonance Spectrum (CDCl$_3$, 200 MHz), δ ppm: 8.19 (1H, triplet, J=1.1 Hz); 8.13 (1H, singlet); 8.00 (1H, doublet of triplets, J=8.0 & 1.1 Hz); 7.78 (1H, doublet of triplets, J=8.0 & 1.1 Hz); 7.45 (1H, triplet, J=8.0 Hz); 3.50 (4H, quartet, J=7.0 Hz); 1.24 (6H, triplet, J=7.0 Hz).

1-(Diethylcarbamoyl)-3-(3-methylthiophenylthio)-4-chloropyrazole (Compound No. 2.46)

Following the procedure of Example 3, there were obtained 834 mg (yield 47.7%) of the title compound, as an oily substance.

Nuclear Magnetic Resonance Spectrum (CDCl$_3$, 200 MHz), δ ppm: 8.15 (1H, singlet); 7.30–7.12 (4H, multiplet); 3.52 (4H, quartet, J=6.9 Hz); 2.45 (3H, singlet); 1.18 (6H, triplet, J=6.9 Hz).

1-(Diethylcarbamoyl)-3-(3-methylsulfonylphenylsulfonyl)-4-chloropyrazole (Compound No. 2.50)

Following the procedure of Example 3, there were obtained 331 mg (yield 44.9%) of the title compound, melting at 127°–130° C.

1-(Diethylcarbamoyl)-3-(3-trifluoromethylphenylthio)-4-chloropyrazole (Compound No. 2.51)

Following the procedure of Example 3, there were obtained 186 mg (yield 45.5%) of the title compound, as an oily substance.

Nuclear Magnetic Resonance Spectrum (CDCl$_3$, 200 MHz), δ ppm: 7.70 (1H, singlet); 7.70–7.40 (4H, multiplet); 3.08 (6H, singlet).

1-(Diethylcarbamoyl)-3-(3-trifluoromethylphenylsulfonyl)-4-chloropyrazole (Compound No. 2.52)

Following the procedure of Example 3, there were obtained 146 mg (yield 36.8%) of the title compound, as an oily substance.

Nuclear Magnetic Resonance Spectrum (CDCl$_3$, 200 MHz), δ ppm: 8.34 (1H, singlet); 8.27 (1H, doublet, J=8.0 Hz); 8.15 (1H, singlet); 7.93 (1H, doublet, J=8.0 Hz); 7.74 (1H, doublet, J=8.0 Hz); 3.49 (4H, quartet, J=7.0 Hz); 1.22 (6H, triplet, J=7.0 Hz).

Ethyl 3-(1-diethylcarbamoyl-4-chloro-3-pyrazolylthio)benzoate (Compound No. 2.53)

Following the procedure of Example 4, there were obtained 346 mg (yield 60.9%) of the title compound, as an oily substance.

Nuclear Magnetic Resonance Spectrum (CDCl$_3$, 200 MHz), δ ppm: 8.16 (1H, singlet); 8.13–8.11 (1H, multiplet); 7.95 (1H, doublet of triplets, J=8.0 & 1.5 Hz); 7.58 (1H, doublet of triplets, J=8.0 & 1.5 Hz); 7.39 (1H, triplet, J=8.0 Hz); 4.37 (2H, quartet, J=7.0 Hz); 3.51 (4H, broad quartet, J=7.0 Hz); 1.39 (3H, triplet, J=7.0 Hz); 1.16 (6H, broad triplet, J=7.0 Hz).

Ethyl 3-(1-diethylcarbamoyl-4-chloro-3-pyrazolylsulfonyl)benzoate (Compound No. 2.54)

Following the procedure of Example 4, there were obtained 318 mg (yield 60.9%) of the title compound, as an oily substance.

Nuclear Magnetic Resonance Spectrum (CDCl$_3$, 200 MHz), δ ppm: 8.70 (1H, triplet, J=1.6 Hz); 8.33 (1H, doublet of triplets, J=7.8 & 1.6 Hz); 8.25 (1H, doublet of triplets, J=7.8 & 1.6 Hz); 8.13 (1H, singlet); 7.66 (1H, triplet, J=7.8 Hz); 4.42 (2H, quartet, J=7.1 Hz); 3.49 (4H, broad quartet, J=7.0 Hz); 1.41 (3H, triplet, J=7.1 Hz); 1.22 (6H, broad triplet, J=7.0 Hz).

1-(Diethylcarbamoyl)-3-(3-methoxyphenylsulfonyl-4-chloropyrazole (Compound No. 2.56)

Following the procedure of Example 3, there were obtained 118 mg (yield 14.1%) of the title compound, as an oily substance.

Nuclear Magnetic Resonance Spectrum (CDCl$_3$, 200 MHz), δ ppm: 8.12 (1H, singlet); 7.64 (1H, doublet of doublets, J=8.0 & 1.2 Hz); 7.56 (1H, doublet, J=1.2 Hz); 7.45 (1H, triplet, J=8.0 Hz); 7.17 (1H, doublet of doublets, J=8.0 & 0.9 Hz); 3.86 (3H, singlet); 3.50 (4H, broad quartet, J=7.0 Hz); 1.23 (6H, triplet, J=7.0 Hz).

1-(Diethylcarbamoyl)-3-(3-fluorophenylthio)-4-bromopyrazole (Compound No. 2.58)

Following the procedure of Example 4, there were obtained 203 mg (yield 47.4%) of the title compound, as an oily substance.

Nuclear Magnetic Resonance Spectrum (CDCl$_3$, 200 MHz), δ ppm: 8.20 (1H, singlet); 7.29 (1H, triplet of doublets, J=8.2 & 5.6 Hz); 7.19–7.06 (2H, multiplet); 6.96 (1H, tripled doublet of doublets, J=8.2, 2.4 & 1.1 Hz); 3.53 (4H, quartet, J=7.1 Hz); 1.19 (6H, triplet, J=7.1 Hz).

1-(Diethylcarbamoyl)-3-(3-fluorophenylsulfonyl)-4-bromopyrazole (Compound No. 2.59)

Following the procedure of Example 4, there were obtained 194 mg (yield 46.4%) of the title compound, as an oily substance.

Nuclear Magnetic Resonance Spectrum (CDCl$_3$, 200 MHz), δ ppm: 8.17 (1H, singlet); 7.88 (1H, doubled doublet of doublets, J=7.8, 2.0 & 1.0 Hz); 7.77 (1H, triplet of doublets, J=2.0 & 8.1 Hz); 7.56 (1H, triplet of doublets, J=8.1 & 5.2 Hz); 7.36 (1H, tripled doublet of doublets, J=8.1, 2.0 & 1.0 Hz); 3.49 (4H, quartet, J=6.9 Hz); 1.23 (6H, triplet, J=6.9 Hz).

1-(Diethylcarbamoyl)-3-(3-bromophenylthio)-4-bromopyrazole (Compound No. 2.60)

Following the procedure of Example 4, there were obtained 170 mg (yield 46.7%) of the title compound, melting at 65°-65.5° C.

1-(Diethylcarbamoyl)-3-(3-bromophenylsulfonyl)-4-bromopyrazole (Compound No. 2.61)

Following the procedure of Example 4, there were obtained 78 mg (yield 21.0%) of the title compound, melting at 104°-105° C.

1-(Diethylcarbamoyl)-3-(3-fluorophenylsulfonyl)-4-fluoropyrazole (Compound No. 2.64)

Following the procedure of Example 19, there were obtained 29 mg (yield 3.4%) of the title compound, as an oily substance.

Nuclear Magnetic Resonance Spectrum (CDCl$_3$, 200 MHz), δ ppm: 8.00 (1H, doublet, J=4.7 Hz); 7.88-7.83 (1H, multiplet); 7.78-7.72 (1H, multiplet); 7.62-7.51 (1H, multiplet); 7.41-7.30 (1H, multiplet); 3.51 (4H, quartet, J=7.0 Hz); 1.25 (6H, triplet, J=7.0 Hz).

1-(Diethylcarbamoyl)-3-(3-cyanophenylsulfonyl)-4-fluoropyrazole (Compound No. 2.65)

Following the procedure of Example 19, there were obtained 72 mg (yield 7.4%) of the title compound, as an oily substance.

Nuclear Magnetic Resonance Spectrum (CDCl$_3$, 200 MHz), δ ppm: 8.34-8.26 (2H, multiplet); 8.02 (1H, doublet, J=4.8 Hz); 7.94 (1H, triplet of doublets, J=7.4 & 1.3 Hz); 7.73 (1H, triplet, J=7.4 Hz); 3.51 (4H, broad quartet, J=7.0 Hz); 1.26 (6H, triplet, J=7.0 Hz).

1-(Diethylcarbamoyl)-3-(3-methoxyphenylsulfonyl)-4-fluoropyrazole (Compound No. 2.66)

Following the procedure of Example 19, there were obtained 35 mg (yield 3.8%) of the title compound, as an oily substance.

Nuclear Magnetic Resonance Spectrum (CDCl$_3$, 200 MHz), δ ppm: 7.98 (1H, doublet, J=4.8 Hz); 7.66-7.61 (1H, multiplet); 7.55-7.53 (1H, multiplet); 7.50-7.42 (1H, multiplet); 7.20-7.14 (1H, multiplet); 3.87 (3H, singlet); 3.51 (4H, broad quartet, J=7.0 Hz); 1.25 (6H, triplet, J=7.0 Hz).

1-(Diethylcarbamoyl)-3-(3-chlorophenylsulfonyl)-4-fluoropyrazole (Compound No. 2.68)

Following the procedure of Example 7, there were obtained 15 mg (yield 0.3%) of the title compound, as an oily substance.

Nuclear Magnetic Resonance Spectrum (CDCl$_3$, 200 MHz), δ ppm: 8.04 (1H, triplet, J=1.8 Hz); 8.00 (1H, doublet, J=4.8 Hz); 7.95 (1H, triplet of doublets, J=7.7 & 1.8 Hz); 7.64 (1H, triplet of doublets, J=7.7 & 1.8 Hz); 7.51 (1H, triplet, J=7.7 Hz); 3.51 (4H, quartet, J=7.0 Hz); 1.25 (6H, triplet, J=7.0 Hz).

1-(Diethylcarbamoyl)-3-(3-trifluoromethylphenylsulfonyl)-4-fluoropyrazole (Compound No. 2.83)

Following the procedure of Example 7, there were obtained 12 mg (yield 2.3%) of the title compound, melting at 70°-73° C.

1-(Diethylcarbamoyl)-3-(3-fluorophenylthio)-4-cyanopyrazole (Compound No. 2.104)

Following the procedure of Example 14, there were obtained 190 mg (yield 51.5%) of the title compound, as an oily substance.

Nuclear Magnetic Resonance Spectrum (CDCl$_3$, 200 MHz), δ ppm: 8.54 (1H, singlet); 7.40-7.21 (3H, multiplet); 7.10-7.00 (1H, multiplet); 3.63-3.46 (4H, multiplet); 1.18-1.08 (6H, multiplet).

1-(Diethylcarbamoyl)-3-(3-fluorophenylsulfonyl)-4-cyanopyrazole (Compound No. 2.105)

Following the procedure of Example 14, there were obtained 145 mg (yield 41.2%) of the title compound, melting at 110°-111° C.

1-(Diethylcarbamoyl)-3-(3-fluorophenylthio)-4-fluoropyrazole (Compound No. 2.120)

Following the procedure of Example 19, there were obtained 33 mg (yield 4.1%) of the title compound, as an oily substance.

Nuclear Magnetic Resonance Spectrum (CDCl$_3$, 200 MHz), δ ppm: 8.03 (1H, doublet, J=5.1 Hz); 7.32-6.87 (4H, multiplet); 3.57 (4H, quartet, J=7.1 Hz); 1.24 (6H, triplet, J=7.1 Hz).

1-(Diethylcarbamoyl)-3-(3-methoxyphenylthio)-4-fluoropyrazole (Compound No. 2.121)

Following the procedure of Example 19, there were obtained 43 mg (yield 5.1%) of the title compound, as an oily substance.

Nuclear Magnetic Resonance Spectrum (CDCl$_3$, 200 MHz), δ ppm: 8.01 (1H, doublet, J=5.1 Hz); 7.24-7.17 (1H, multiplet); 6.98-6.93 (2H, multiplet); 6.82-6.76 (1H, multiplet); 3.78 (3H, singlet); 3.57 (4H, quartet, J=7.0 Hz); 1.23 (6H, triplet, J=7.0 Hz).

1-(Diethylcarbamoyl)-3-(4-fluorophenylsulfonyl)-pyrazole (Compound No. 3.1)

Following the procedure of Example 1, there were obtained 193 mg (yield 72.3%) of the title compound, as an oily substance.

Nuclear Magnetic Resonance Spectrum (CDCl$_3$, 270 MHz), δ ppm: 8.16 (1H, doublet, J=2.6 Hz); 8.09-8.03 (2H, multiplet); 7.25-7.19 (2H, multiplet); 6.86 (1H, doublet, J=2.6 Hz); 3.48 (4H, broad quartet, J=6.7 Hz); 1.22 (6H, broad triplet, J=6.7 Hz).

1-(Diethylcarbamoyl)-3-(4-fluorophenylthio)pyrazole (Compound No. 3.2)

Following the procedure of Example 1, there were obtained 700 mg (yield 73.8%) of the title compound, as an oily substance.

Nuclear Magnetic Resonance Spectrum (CDCl$_3$, 200 MHz), δ ppm: 8.10 (1H, doublet, J=2.6 Hz); 7.51-7.43 (2H, multiplet); 7.07-6.98 (2H, multiplet); 6.99 (1H, doublet, J=2.6 Hz); 3.55 (4H, broad quartet, J=7.1 Hz); 1.19 (4H, broad triplet, J=7.1 Hz).

1-(Diethylcarbamoyl)-3-(4-chlorophenylsulfonyl)-pyrazole (Compound No. 3.3)

Following the procedure of Example 1, there were obtained 198 mg (yield 78.7%) of the title compound, as an oily substance.

Nuclear Magnetic Resonance Spectrum (CDCl$_3$, 200 MHz), δ ppm: 8.16 (1H, doublet, J=2.6 Hz); 7.98-7.54 (2H, multiplet); 7.54-7.49 (2H, multiplet); 6.87 (1H, doublet, J=2.6 Hz); 3.48 (4H, broad quartet, J=6.9 Hz); 1.22 (6H, broad triplet, J=6.9 Hz).

1-(Diethylcarbamoyl)-3-(4-chlorophenylthio)pyrazole (Compound No. 3.4)

Following the procedure of Example 1, there were obtained 790 mg (yield 79.5%) of the title compound, as an oily substance.

Nuclear Magnetic Resonance Spectrum (CDCl$_3$, 270 MHz), δ ppm: 8.13 (1H, doublet, J=2.9 Hz); 7.38-7.34

(2H, multiplet); 7.30–7.25 (2H, multiplet); 6.27 (1H, doublet, J=2.9 Hz); 3.56 (4H, broad quartet, J=6.9 Hz); 1.21 (6H, broad triplet, J=6.9 Hz).

1-(Diethylcarbamoyl)-3-(4-chlorobenzylsulfonyl)-pyrazole (Compound No. 3.5)

Following the procedure of Example 1, there were obtained 100 mg (yield 29.6%) of the title compound, melting at 96°–98° C.

1-(Diethylcarbamoyl)-3-(4-bromophenylsulfonyl)-pyrazole (Compound No. 3.6)

Following the procedure of Example 1, there were obtained 204 mg (yield 79.9%) of the title compound, as an oily substance.

Nuclear Magnetic Resonance Spectrum (CDCl$_3$, 270 MHz), δ ppm: 8.16 (1H, doublet, J=2.9 Hz); 7.92–7.87 (2H, multiplet); 7.71–7.67 (2H, multiplet); 6.86 (1H, doublet, J=2.9 Hz); 3.48 (4H, broad quartet, J=7.0 Hz); 1.22 (6H, broad triplet, J=7.0 Hz).

1-(Diethylcarbamoyl)-3-(4-bromophenylthio)pyrazole (Compound No. 3.7)

Following the procedure of Example 1, there were obtained 885 mg (yield 79.9%) of the title compound, as an oily substance.

Nuclear Magnetic Resonance Spectrum (CDCl$_3$, 200 MHz), δ ppm: 8.13 (1H, doublet, J=2.7 Hz); 7.45–7.40 (2H, multiplet); 7.31–7.26 (2H, multiplet); 6.28 (1H, doublet, J=2.7 Hz); 3.56 (4H, broad quartet, J=7.0 Hz); 1.21 (6H, broad triplet, J=7.0 Hz).

1-(Diethylcarbamoyl)-3-(4-methylphenylthio)pyrazole (Compound No. 3.8)

Following the procedure of Example 1, there were obtained 731 mg (yield 72.0%) of the title compound, as an oily substance.

Nuclear Magnetic Resonance Spectrum (CDCl$_3$, 270 MHz), δ ppm: 8.08 (1H, doublet, J=2.9 Hz); 7.37 (2H, doublet, J=8.1 Hz); 7.13 (2H, doublet, J=8.1 Hz); 6.18 (1H, doublet, J=2.9 Hz); 3.57 (4H, broad quartet, J=7.0 Hz); 2.34 (3H, singlet); 1.21 (6H, broad triplet, J=7.0 Hz).

1-(Diethylcarbamoyl)-3-(4-methylphenylsulfonyl)-pyrazole (Compound No. 3.9)

Following the procedure of Example 1, there were obtained 197 mg (yield 70.6%) of the title compound, as an oily substance.

Nuclear Magnetic Resonance Spectrum (CDCl$_3$, 270 MHz), δ ppm: 8.13 (1H, doublet, J=2.9 Hz); 7.91 (2H, doublet, J=7.9 Hz); 7.33 (2H, doublet, J=7.9 Hz); 6.84 (1H, doublet, J=2.9 Hz); 3.48 (4H, broad quartet, J=6.9 Hz); 2.43 (3H, singlet); 1.22 (6H, broad triplet, J=6.9 Hz).

1-(Diethylcarbamoyl)-3-(4-ethylphenylthio)pyrazole (Compound No. 3.10)

Following the procedure of Example 1, there were obtained 813 mg (yield 83.0%) of the title compound, as an oily substance.

Nuclear Magnetic Resonance Spectrum (CDCl$_3$, 200 MHz), δ ppm: 8.90 (1H, doublet, J=2.6 Hz); 7.40 (2H, doublet, J=8.3 Hz); 7.15 (2H, doublet, J=8.3 Hz); 6.20 (1H, doublet, J=2.6 Hz); 3.56 (4H, broad quartet, J=7.0 Hz); 2.64 (2H, quartet, J=7.6 Hz); 1.22 (3H, triplet, J=7.6 Hz); 1.20 (6H, triplet, J=7.0 Hz).

1-(Diethylcarbamoyl)-3-(4-ethylphenylsulfonyl)-pyrazole (Compound No. 3.11)

Following the procedure of Example 1, there were obtained 209 mg (yield 83.0%) of the title compound, as an oily substance.

Nuclear Magnetic Resonance Spectrum (CDCl$_3$, 200 MHz), δ ppm: 8.14 (1H, doublet, J=2.7 Hz); 7.99–7.91 (2H, multiplet); 7.38–7.33 (2H, multiplet); 6.85 (1H, doublet, J=2.7 Hz); 3.48 (4H, broad quartet, J=7.0 Hz); 2.72 (2H, quartet, J=7.6 Hz); 1.29–1.18 (9H, multiplet).

1-(Diethylcarbamoyl)-3-(4-isopropylphenylsulfonyl)-pyrazole (Compound No. 3.12)

Following the procedure of Example 1, there were obtained 1.08 g (yield 44.2%) of the title compound, as an oily substance.

Nuclear Magnetic Resonance Spectrum (CDCl$_3$, 200 MHz), δ ppm: 8.14 (1H, doublet, J=2.8 Hz); 7.94 (2H, doublet, J=8.4 Hz); 7.38 (2H, doublet, J=8.4 Hz); 6.85 (1H, doublet, J=2.8 Hz); 3.48 (4H, quartet, J=7.0 Hz); 2.98 (1H, septet, J=6.7 Hz); 1.26 (6H, doublet, J=6.7 Hz); 1.30–1.12 (6H, broad).

1-(Diethylcarbamoyl)-3-(4-isopropylphenylthio)-pyrazole (Compound No. 3.13)

Following the procedure of Example 1, there were obtained 1.11 g (yield 47.0%) of the title compound, as an oily substance.

Nuclear Magnetic Resonance Spectrum (CDCl$_3$, 200 MHz), δ ppm: 8.09 (1H, doublet, J=2.6 Hz); 7.40 (2H, doublet, J=8.3 Hz); 7.18 (2H, doublet, J=8.3 Hz); 6.21 (1H, doublet, J=2.6 Hz); 3.55 (4H, quartet, J=7.1 Hz); 3.45 (1H, septet, J=6.9 Hz); 1.24 (6H, doublet, J=6.9 Hz); 1.20 (6H, triplet, J=7.1 Hz).

1-(Diethylcarbamoyl)-3-(4-sec-butylphenylthio)-pyrazole (Compound No. 3.14)

Following the procedure of Example 1, there were obtained 987 mg (yield 91.0%) of the title compound, as an oily substance.

Nuclear Magnetic Resonance Spectrum (CDCl$_3$, 200 MHz), δ ppm: 8.01 (1H, doublet, J=2.8 Hz); 7.42–7.37 (2H, multiplet); 7.16–7.11 (2H, multiplet); 6.21 (1H, doublet, J=2.8 Hz); 3.56 (4H, broad quartet, J=7.0 Hz); 2.59 (1H, sextet, J=7.2 Hz); 1.58 (2H, quintet, J=7.2 Hz); 1.24–1.16 (9H, multiplet); 0.81 (3H, triplet, J=7.2 Hz).

1-(Diethylcarbamoyl)-3-(4-sec-butylphenylsulfonyl)-pyrazole (Compound No. 3.15)

Following the procedure of Example 1, there were obtained 201 mg (yield 91.0%) of the title compound, as an oily substance.

Nuclear Magnetic Resonance Spectrum (CDCl$_3$, 200 MHz), δ ppm: 8.15 (1H, doublet, J=2.7 Hz); 7.97–7.91 (2H, multiplet); 7.37–7.31 (2H, multiplet); 6.86 (1H, doublet, J=2.7 Hz); 3.48 (4H, broad quartet, J=7.0 Hz); 2.69 (1H, sextet, J=7.3 Hz); 1.61 (2H, quintet, J=7.3 Hz); 1.26–1.17 (9H, multiplet); 0.81 (3H, triplet, J=7.3 Hz).

1-(Diethylcarbamoyl)-3-(4-t-butylphenylsulfonyl)-pyrazole (Compound No. 3.16)

Following the procedure of Example 1, there were obtained 231 mg (yield 65.6%) of the title compound, as an oily substance.

Nuclear Magnetic Resonance Spectrum (CDCl$_3$, 200 MHz), δ ppm: 8.14 (1H, doublet, J=2.7 Hz); 7.94 (2H, broad doublet, J=8.8 Hz); 7.54 (2H, broad doublet, J=8.8 Hz); 6.85 (1H, doublet, J=2.7 Hz); 3.48 (4H, quartet, J=7.0 Hz); 1.33 (9H, singlet); 1.20 (6H, triplet, J=7.0 Hz).

1-(Diethylcarbamoyl)-3-(4-t-butylphenylthio)pyrazole (Compound No. 3.17)

Following the procedure of Example 1, there were obtained 842 mg (yield 66.2%) of the title compound, as an oily substance.

Nuclear Magnetic Resonance Spectrum (CDCl$_3$, 200 MHz), δ ppm: 8.10 (1H, doublet, J=2.7 Hz); 7.41 (2H, broad doublet, J=8.8 Hz); 7.34 (2H, broad doublet, J=8.8 Hz); 6.22 (1H, doublet, J=2.7 Hz); 3.56 (4H, quartet, J=7.0 Hz); 1.31 (9H, singlet); 1.19 (6H, triplet, J=7.0 Hz).

1-(Diethylcarbamoyl)-3-(4-phenoxyphenylsulfonyl)-pyrazole (Compound No. 3.18)

Following the procedure of Example 1, there were obtained 227 mg (yield 76.6%) of the title compound, as an oily substance.

Nuclear Magnetic Resonance Spectrum (CDCl$_3$, 200 MHz), δ ppm: 8.15 (1H, doublet, J=2.7 Hz); 7.98 (2H, broad doublet, J=6.9 Hz); 7.5–7.0 (7H, multiplet); 6.85 (1H, doublet, J=2.7 Hz); 3.50 (4H, quartet, J=7.0 Hz); 1.23 (6H, triplet, J=7.0 Hz).

1-(Diethylcarbamoyl)-3-(4-phenoxyphenylthio)-pyrazole (Compound No. 3.19)

Following the procedure of Example 1, there were obtained 756 mg (yield 78.2%) of the title compound, as an oily substance.

Nuclear Magnetic Resonance Spectrum (CDCl$_3$, 200 MHz), δ ppm: 8.10 (1H, doublet, J=2.8 Hz); 6.94–7.49 (9H, multiplet); 6.20 (1H, doublet, J=2.8 Hz); 3.59 (4H, quartet, J=7.0 Hz); 1.21 (6H, triplet, J=7.0 Hz).

1-(Diethylcarbamoyl)-3-(4-cyanophenylsulfonyl)-pyrazole (Compound No. 3.20)

Following the procedure of Example 1, there were obtained 216 mg (yield 48.9%) of the title compound, melting at 74°–75° C.

1-(Diethylcarbamoyl-3-(4-cyanophenylthio)pyrazole (Compound No. 3.21)

Following the procedure of Example 1, there were obtained 428 mg (yield 49.9%) of the title compound, as an oily substance.

Nuclear Magnetic Resonance Spectrum (CDCl$_3$, 200 MHz), δ ppm: 8.22 (1H, doublet, J=2.7 Hz); 7.53 (2H, doublet of doublets, J=2.0 & 6.8 Hz); 7.33 (2H, doublet of doublets, J=2.0 & 6.8 Hz); 6.45 (1H, doublet, J=2.7 Hz); 3.59 (4H, quartet, J=7.0 Hz); 1.24 (6H, triplet, J=7.0 Hz).

1-(Diethylcarbamoyl)-3-(4-phenoxyphenylsulfonyl)-5-(dimethylcarbamoyl)pyrazole (Compound No. 3.29)

Following the procedure of Example 15, there were obtained 183 mg (yield 57.3%) of the title compound, melting at 43°–45° C.

1-(Diethylcarbamoyl)-3-(4-phenoxyphenylthio)-5-(dimethylcarbamoyl)pyrazole (Compound No. 3.30)

Following the procedure of Example 15, there were obtained 233 mg (yield 61.0%) of the title compound, as an oily substance.

Nuclear Magnetic Resonance Spectrum (CDCl$_3$, 200 MHz), δ ppm: 7.50–6.93 (9H, multiplet); 6.22 (1H, singlet); 3.47 (4H, quartet, J=7.0 Hz); 3.06 (3H, singlet); 3.01 (3H, singlet); 1.21 (6H, triplet, J=7.0 Hz).

Ethyl 1-(diethylcarbamoyl)-3-(4-t-butylphenylthio)-pyrazole-5-carboxylate (Compound No. 3.31)

Following the procedure of Example 15, there were obtained 72 mg (yield 15.9%) of the title compound, as an oily substance.

Nuclear Magnetic Resonance Spectrum (CDCl$_3$, 200 MHz), δ ppm: 7.39 (2H, doublet, J=9.0 Hz); 7.32 (2H, doublet, J=9.0 Hz); 6.75 (1H, singlet); 4.36 (2H, quartet, J=7.0 Hz); 3.54 (2H, quartet, J=7.0 Hz); 3.20 (2H, quartet, J=7.0 Hz); 1.33 (6H, triplet, J=7.0 Hz); 1.31 (9H, singlet); 1.13 (3H, triplet, J=7.0 Hz).

Ethyl 1-(diethylcarbamoyl)-3-(4-t-butylphenylsulfonyl)pyrazole-5-carboxylate (Compound No. 3.32)

Following the procedure of Example 15, there were obtained 67 mg (yield 14.4%) of the title compound, as an oily substance.

Nuclear Magnetic Resonance Spectrum (CDCl$_3$, 200 MHz), δ ppm: 7.94 (2H, doublet, J=8.7 Hz); 7.53 (2H, doublet, J=8.7 Hz); 7.30 (1H, singlet); 4.35 (2H, quartet, J=7.1 Hz); 3.53 (2H, quartet, J=7.1 Hz); 3.03 (2H, quartet, J=7.1 Hz); 1.33 (9H, singlet); 1.38–1.29 (6H, multiplet); 1.08 (3H, triplet, J=7.1 Hz).

1-(Diethylcarbamoyl)-3-(4-isopropylphenylsulfonyl)-5-(methoxymethyl)pyrazole (Compound No. 3.33)

Following the procedure of Example 16, there were obtained 81 mg (yield 33.6%) of the title compound, melting at 71°–73° C.

1-(Diethylcarbamoyl)-3-(4-chlorobenzylsulfonyl)-4-chloropyrazole (Compound No. 3.34)

Following the procedure of Example 3, there were obtained 127 mg (yield 25.1%) of the title compound, melting at 106°–109° C.

1-(Diethylcarbamoyl)-3-(2,3-dichlorophenylsulfonyl)-pyrazole (Compound No. 4.1)

Following the procedure of Example 1, there were obtained 179 mg (yield 80.8%) of the title compound, melting at 100°–101.5° C.

1-(Diethylcarbamoyl)-3-(2,3-dichlorophenylthio)-pyrazole (Compound No. 4.2)

Following the procedure of Example 1, there were obtained 1.01 g (yield 94.0%) of the title compound, melting at 60°–61.5° C.

1-(Diethylcarbamoyl)-3-(3-chloro-2-methylphenylsulfonyl)pyrazole (Compound No. 4.3)

Following the procedure of Example 1, there were obtained 527 mg (yield 77.1%) of the title compound, melting at 76°–77° C.

1-(Diethylcarbamoyl)-3-(3-chloro-2-methylphenylthio)pyrazole (Compound No. 4.4)

Following the procedure of Example 1, there were obtained 1.28 g (yield 78.7%) of the title compound, as an oily substance.

Nuclear Magnetic Resonance Spectrum (CDCl$_3$, 200 MHz), δ ppm: 8.13 (1H, doublet, J=2.8 Hz); 7.30 (2H, doublet, J=7.6 Hz); 7.06 (1H, triplet, J=7.6 Hz); 6.22 (1H, quartet, J=2.8 Hz); 3.53 (4H, quartet, J=7.0 Hz); 2.51 (3H, singlet); 1.17 (6H, triplet, J=7.0 Hz).

1-(Diethylcarbamoyl)-3-(2,3-dimethylphenylsulfonyl)-pyrazole (Compound No. 4.5)

Following the procedure of Example 1, there were obtained 196 mg (yield 39.4%) of the title compound, melting at 87°–88° C.

1-(Diethylcarbamoyl)-3-(2,3-dimethylphenylthio)-pyrazole (Compound No. 4.6)

Following the procedure of Example 1, there were obtained 981 mg (yield 44.2%) of the title compound, as an oily substance.

Nuclear Magnetic Resonance Spectrum (CDCl$_3$, 200 MHz), δ ppm: 8.09 (1H, doublet, J=2.6 Hz); 7.32 (1H, doublet of doublets, J=1.1 & 7.2 Hz); 7.12 (1H, broad doublet, J=6.2 Hz); 7.04 (1H, triplet, J=7.2 Hz); 6.13 (1H, doublet, J=2.6 Hz); 3.54 (4H, quartet, J=7.0 Hz); 2.88 (3H, singlet); 2.31 (3H, singlet); 1.18 (6H, triplet, J=7.0 Hz).

1-(Diethylcarbamoyl)-3-(2,3-difluorophenylsulfonyl)-pyrazole (Compound No. 4.7)

Following the procedure of Example 1, there were obtained 224 mg (yield 46.0%) of the title compound, as an oily substance.

Nuclear Magnetic Resonance Spectrum (CDCl$_3$, 200 MHz), δ ppm: 8.21 (1H, doublet, J=2.8 Hz); 7.91–7.82

(1H, multiplet); 7.53–7.40 (1H, multiplet); 7.35–7.24 (1H, multiplet); 6.96 (1H, doublet, J=2.8 Hz); 3.48 (4H, quartet, J=7.0 Hz); 1.19 (6H, broad).

1-(Diethylcarbamoyl)-3-(2,3-difluorophenylthio)-pyrazole (Compound No. 4.8)

Following the procedure of Example 1, there were obtained 297 mg (yield 50.1%) of the title compound, as an oily substance.

Nuclear Magnetic Resonance Spectrum (CDCl$_3$, 200 MHz), δ ppm: 8.13 (1H, doublet, J=2.6 Hz); 7.26–7.00 (3H, multiplet); 6.32 (1H, doublet, J=2.6 Hz); 3.53 (4H, quartet, J=7.0 Hz); 1.17 (6H, triplet, J=7.0 Hz).

1-(Dimethylcarbamoyl)-3-(2,3-difluorophenylthio)-4-chloropyrazole (Compound No. 4.42)

Following the procedure of Example 4, there were obtained 236 mg (yield 44.6%) of the title compound, melting at 76°–78° C.

1-(Dimethylcarbamoyl)-3-(2,3-difluorophenylsulfonyl)-4-chloropyrazole (Compound No. 4.43)

Following the procedure of Example 4, there were obtained 192 mg (yield 41.9%) of the title compound, melting at 98°–102° C.

1-(N-Ethyl-N-methylcarbamoyl)-3-(2,3-difluorophenylthio)-4-chloropyrazole (Compound No. 4.44)

Following the procedure of Example 4, there were obtained 228 mg (yield 41.8%) of the title compound, as an oily substance.

Nuclear Magnetic Resonance Spectrum (CDCl$_3$, 200 MHz), δ ppm: 8.14 (1H, singlet); 7.21–6.97 (3H, multiplet); 3.53 (2H, quartet, J=7.1 Hz); 3.11 (3H, singlet); 1.15 (3H, broad).

1-(N-Ethyl-N-methylcarbamoyl)-3-(2,3-difluorophenylsulfonyl)-4-chloropyrazole (Compound No. 4.45)

Following the procedure of Example 4, there were obtained 183 mg (yield 40.1%) of the title compound, melting at 89°–91° C. 1(Diethylcarbamoyl)-3-(2,3-difluorophenylsulfonyl)-4-chloropyrazole (Compound No. 4.46)

Following the procedure of Example 4, there were obtained 121 mg (yield 32.0%) of the title compound, melting at 71°–72° C.

1-(N-Ethyl-N-propylcarbamoyl)-3-(2,3-difluorophenylthio)-4-chloropyrazole (Compound No. 4.47)

Following the procedure of Example 4, there were obtained 256 mg (yield 42.7%) of the title compound, as an oily substance.

Nuclear Magnetic Resonance Spectrum (CDCl$_3$, 200 MHz), δ ppm: 8.15 (1H, singlet); 7.21–7.00 (3H, multiplet); 3.51 (2H, broad quartet, J=6.7 Hz); 3.39 (2H, broad triplet, J=7.5 Hz); 1.68–1.53 (2H, multiplet); 1.14 (3H, broad); 0.84 (3H, broad).

1-(N-Ethyl-N-propylcarbamoyl)-3-(2,3-difluorophenylsulfonyl)-4-chloropyrazole (Compound No. 4.48)

Following the procedure of Example 4, there were obtained 203 mg (yield 41.5%) of the title compound, as an oily substance.

Nuclear Magnetic Resonance Spectrum (CDCl$_3$, 200 MHz), δ ppm: 8.18 (1H, singlet); 7.96–7.87 (1H, multiplet); 7.57–7.44 (1H, multiplet); 7.39–7.28 (1H, multiplet); 3.55–3.38 (4H, multiplet); 1.69 (2H, broad sextet, J=7.6 Hz); 1.22 (3H, broad); 0.92 (3H, broad).

1-(Dipropylcarbamoyl)-3-(2,3-difluorophenylthio)-4-chloropyrazole (Compound No. 4.49)

Following the procedure of Example 4, there were obtained 265 mg (yield 43.2%) of the title compound, as an oily substance.

Nuclear Magnetic Resonance Spectrum (CDCl$_3$, 200 MHz), δ ppm: 8.14 (1H, singlet); 7.19–6.96 (3H, multiplet); 3.42 (4H, broad triplet, J=7.1 Hz); 1.61 (4H, broad); 0.83 (6H, broad).

1-(Dipropylcarbamoyl)-3-(2,3-difluorophenylsulfonyl)-4-chloropyrazole (Compound No. 4.50)

Following the procedure of Example 4, there were obtained 212 mg (yield 42.3%) of the title compound, melting at 41°–46° C.

1-(N-Butyl-N-methylcarbamoyl)-3-(2,3-difluorophenylthio)-4-chloropyrazole (Compound No. 4.51)

Following the procedure of Example 4, there were obtained 248 mg (yield 42.7%) of the title compound, as an oily substance.

Nuclear Magnetic Resonance Spectrum (CDCl$_3$, 200 MHz), δ ppm: 8.14 (1H, singlet); 7.19–6.98 (3H, multiplet); 3.51 (2H, broad triplet, J=6.6 Hz); 3.13 (3H, broad singlet); 1.62–1.51 (2H, multiplet); 1.39–1.15 (2H, multiplet); 0.90 (3H, broad triplet, J=7.1 Hz).

1-(N-Butyl-N-methylcarbamoyl)-3-(2,3-difluorophenylsulfony)-4-chloropyrazole (Compound No. 4.52)

Following the procedure of Example 4, there were obtained 207 mg (yield 42.7%) of the title compound, as an oily substance.

Nuclear Magnetic Resonance Spectrum (CDCl$_3$, 200 MHz), δ ppm: 8.16 (1H, singlet); 7.96–7.87 (1H, multiplet); 7.57–7.44 (1H, multiplet); 7.39–7.27 (1H, multiplet); 3.52 (2H, broad); 3.21–3.11 (3H, multiplet); 1.72–1.57 (2H, multiplet); 1.37–1.25 (2H, multiplet); 0.93 (3H, broad).

1-(Diethylcarbamoyl)-3-(2,3-dichlorophenylsulfonyl)-4-chloropyrazole (Compound No. 4.56)

Following the procedure of Example 4, there were obtained 291 mg (yield 41.8%) of the title compound, melting at 110°–113° C.

1-(Diethylcarbamoyl)-3-(2,3-dimethylphenylsulfonyl)-4-chloropyrazole (Compound No. 4.58)

Following the-procedure of Example 5, there were obtained 38 mg (yield 4.8%) of the title compound, melting at 102°–102.5° C.

1-(Diethylcarbamoyl)-3-(2,3-dichlorophenylthio)-4-bromopyrazole (Compound No. 4.61)

Following the procedure of Example 4, there were obtained 833 mg (yield 43.8%) of the title compound, melting at 67°–70° C.

1-(Diethylcarbamoyl)-3-(2,3-dichlorophenylsulfonyl)-4-bromopyrazole (Compound No. 4.62)

Following the procedure of Example 4, there were obtained 301 mg (yield 40.8%) of the title compound, melting at 109°–112° C.

1-(Diethylcarbamoyl)-3-(2,3-dimethylphenylsulfonyl)-4-bromopyrazole (Compound No. 4.64)

Following the procedure of Example 5, there were obtained 97 mg (yield 10.3%) of the title compound, melting at 94°–96° C.

1-(Diethylcarbamoyl)-3-(2,3-dichlorophenylsulfonyl)-4-fluoropyrazole (Compound No. 4.65)

Following the procedure of Example 19, there were obtained 40 mg (yield 6.3%) of the title compound, melting at 68°–69° C.

1-(Diethylcarbamoyl)-3-(3-chloro-2-methylphenylsulfonyl)-4-fluoropyrazole (Compound No. 4.66)

Following the procedure of Example 7, there were obtained 16 mg (yield 3.7%) of the title compound, melting at 74°–77° C.

1-(Diethylcarbamoyl)-3-(2,3-dimethylphenylsulfonyl)-4-fluoropyrazole (Compound No. 4.67)

Following the procedure of Example 7, there were obtained 14 mg (yield 4.0%) of the title compound, melting at 78°–81° C.

1-(Diethylcarbamoyl)-3-(2,3-difluorophenylsulfonyl)-4-fluoropyrazole (Compound No. 4.69)

Following the procedure of Example 19, there were obtained 70 mg (yield 6.8%) of the title compound, as an oily substance.

Nuclear Magnetic Resonance Spectrum (CDCl$_3$, 200 MHz), δ ppm: 8.04 (1H, doublet, J=4.7 Hz); 7.93–7.84 (1H, multiplet); 7.52–7.43 (1H, multiplet); 7.38–7.27 (1H, multiplet); 3.58–3.44 (4H, broad quartet, J=7.0 Hz); 1.23 (6H, triplet, J=5.6 Hz).

1-(Diethylcarbamoyl)-3-(2,3-difluorophenylthio)-4-cyanopyrazole (Compound No. 4.133)

Following the procedure of Example 14, there were obtained 142 mg (yield 37.4%) of the title compound, as an oily substance.

Nuclear Magnetic Resonance Spectrum (CDCl$_3$, 200 MHz), δ ppm: 8.52 (1H, singlet); 7.38–7.10 (3H, multiplet); 3.46 (4H, quartet, J=7.0 Hz); 1.12 (6H, triplet, J=7.0 Hz).

1-(Diethylcarbamoyl)-3-(2,3-difluorophenylsulfonyl)-4cyanopyrazole (Compound No. 4.134)

Following the procedure of Example 14, there were obtained 125 mg (yield 35.1%) of the title compound, melting at 124°–125° C.

1-(Diethylcarbamoyl)-3-(2,4-difluorophenylsulfonyl)-pyrazole (Compound No. 5.1)

Following the procedure of Example 1, there were obtained 110 mg (yield 73.4%) of the title compound, as an oily substance.

Nuclear Magnetic Resonance Spectrum (CDCl$_3$, 200 MHz), δ ppm: 8.20 (1H, doublet, J=2.5 Hz); 8.16–8.08 (1H, multiplet); 7.12–7.02 (1H, multiplet); 6.95 (1H, doublet, J=2.5 Hz); 6.93–6.88 (1H, multiplet); 3.49 (4H, quartet, J=6.8 Hz); 1.3–1.1 (6H, broad).

1-(Diethylcarbamoyl)-3-(2,4-difluorophenylthio)-pyrazole (Compound No. 5.2)

Following the procedure of Example 1, there were obtained 257 mg (yield 75.7%) of the title compound, as an oily substance.

Nuclear Magnetic Resonance Spectrum (CDCl$_3$, 200 MHz), δ ppm: 8.10 (1H, doublet, J=2.6 Hz); 7.56–7.43 (1H, multiplet); 6.94–6.82 (2H, multiplet); 6.23 (1H, doublet, J=2.6 Hz); 3.51 (4H, quartet, J=7.0 Hz); 1.16 (6H, triplet, J=7.0 Hz).

1-(Diethylcarbamoyl)-3-(2,4-dichlorophenylsulfonyl)-pyrazole (Compound No. 5.3)

Following the procedure of Example 1, there were obtained 120 mg (yield 66.0%) of the title compound, melting at 85°–86° C.

1-(Diethylcarbamoyl)-3-(2,4-dichlorophenylthio)-pyrazole (Compound No. 5.4)

Following the procedure of Example 1, there were obtained 219 mg (yield 66.0%) of the title compound, as an oily substance.

Nuclear Magnetic Resonance Spectrum (CDCl$_3$, 200 MHz), δ ppm: 8.18 (1H, doublet, J=2.8 Hz); 7.42 (1H, singlet); 7.16 (2H, singlet); 6.38 (1H, doublet, J=2.8 Hz); 3.56 (4H, quartet, J=7.1 Hz); 1.12 (6H, triplet, J=7.1 Hz).

1-(Diethylcarbamoyl)-3-(2,4-dibromophenylsulfonyl)-pyrazole (Compound No. 5.5)

Following the procedure of Example 1, there were obtained 86 mg (yield 54.5%) of the title compound, melting at 103°–105° C.

1-(Diethylcarbamoyl)-3-(4-bromo-2-fluorophenylsulfonyl)pyrazole (Compound No. 5.6)

Following the procedure of Example 1, there were obtained 110 mg (yield 58.3%) of the title compound, melting at 96°–97° C.

1-(Diethylcarbamoyl)-3-(4-chloro-2-trifluoromethylphenylthio)pyrazole (Compound No. 5.7)

Following the procedure of Example 1, there were obtained 873 mg (yield 74.4%) of the title compound, as an oily substance.

Nuclear Magnetic Resonance Spectrum (CDCl$_3$, 200 MHz), δ ppm: 8.15 (1H, doublet, J=2.6 Hz); 7.68 (1H, broad singlet); 7.43–7.36 (2H, multiplet); 6.33 (1H, doublet, J=2.6 Hz); 3.55 (4H, broad quartet, J=7.0 Hz); 1.21 (6H, broad triplet, J=7.0 Hz).

1-(Diethylcarbamoyl)-3-(4-chloro-2-trifluoromethylphenylsulfonyl)pyrazole (Compound No. 5.8)

Following the procedure of Example 1, there were obtained 202 mg (yield 74.4%) of the title compound, as an oily substance.

Nuclear Magnetic Resonance Spectrum (CDCl$_3$, 270 MHz), δ ppm: 8.43 (1H, doublet, J=8.2 Hz); 8.18 (1H, doublet, J=2.9 Hz); 7.85 (1H, doublet, J=2.3 Hz); 7.76 (1H, doublet of doublets, J=2.3 & 8.2 Hz); 6.91 (1H, doublet, J=2.9 Hz); 3.42 (4H, broad quartet, J=7.0 Hz); 1.12 (6H, broad).

1-(Diethylcarbamoyl)-3-(4-bromo-2-trifluoromethylphenylsulfonyl)pyrazole (Compound No. 5.9)

Following the procedure of Example 1, there were obtained 129 mg (yield 36.5%) of the title compound, melting at 60°–62° C.

1-(Diethylcarbamoyl)-3-(4-bromo-2-trifluoromethylphenylthio)pyrazole (Compound No. 5.10)

Following the procedure of Example 1, there were obtained 265 mg (yield 48.0%) of the title compound, as an oily substance.

Nuclear Magnetic Resonance Spectrum (CDCl$_3$, 200 MHz), δ ppm: 8.17 (1H, doublet, J=2.7 Hz); 7.72 (1H, doublet, J=2.2 Hz); 7.62 (1H, doublet, J=8.4 Hz); 7.38 (1H, doublet of doublets, J=2.2 & 2.6 Hz); 6.36 (1H, doublet, J=2.7 Hz); 3.56 (4H, quartet, J=7.0 Hz); 1.20 (6H, triplet, J=7.0 Hz).

1-(Diethylcarbamoyl)-3-(2-chloro-4-methylphenylsulfonyl)pyrazole (Compound No. 5.11)

Following the procedure of Example 1, there were obtained 391 mg (yield 36.7%) of the title compound, melting at 89°–91° C.

1-(Diethylcarbamoyl)-3-(2-chloro-4-methylphenylthio)pyrazole (Compound No. 5.12)

Following the procedure of Example 1, there were obtained 477 mg (yield 41.3%) of the title compound, as an oily substance.

Nuclear Magnetic Resonance Spectrum (CDCl$_3$, 200 MHz), δ ppm: 8.15 (1H, doublet, J=2.5 Hz); 7.27–7.21 (2H, multiplet); 7.01–6.97 (1H, multiplet); 6.30 (1H, doublet, J=2.5 Hz); 3.56 (4H, quartet, J=7.0 Hz); 1.20 (6H, triplet, J=7.0 Hz).

1-(Diethylcarbamoyl)-3-(4-chloro-2-methylphenylsulfonyl)pyrazole (Compound No. 5.13)

Following the procedure of Example 1, there were obtained 271 mg (yield 61.5%) of the title compound, melting at 62°–65° C.

1-(Diethylcarbamoyl)-3-(4-chloro-2-methylphenylthio)pyrazole (Compound No. 5.14)

Following the procedure of Example 1, there were obtained 1.24 g (yield 64.5%) of the title compound, as an oily substance.

Nuclear Magnetic Resonance Spectrum (CDCl$_3$, 200 MHz), δ ppm: 8.11 (1H, doublet, J=2.7 Hz); 7.33 (1H, doublet, J=6.2 Hz); 7.24 (1H, doublet, J=2.5 Hz); 7.12 (1H, doublet of doublets, J=6.2 & 2.5 Hz); 6.18 (1H, doublet, J=2.7 Hz); 3.52 (4H, quartet, J=7.0 Hz); 2.39 (3H, singlet); 1.16 (6H, triplet, J=7.0 Hz).

1-(Diethylcarbamoyl)-3-(2,4-dimethylphenylsulfonyl)-pyrazole (Compound No. 5.15)

Following the procedure of Example 1, there were obtained 188 mg (yield 44.9%) of the title compound, melting at 57°–59° C.

1-(Diethylcarbamoyl)-3-(2,4-dimethylphenylthio)-pyrazole (Compound No. 5.16)

Following the procedure of Example 1, there were obtained 471 mg (yield 56.8%) of the title compound, as an oily substance.

Nuclear Magnetic Resonance Spectrum (CDCl$_3$, 200 MHz), δ ppm: 8.70 (1H, doublet, J=2.7 Hz); 7.36 (1H, doublet, J=7.7 Hz); 7.07–6.95 (2H, multiplet); 6.08 (1H, doublet, J=2.7 Hz); 3.54 (4H, quartet, J=7.0 Hz); 2.38 (3H, singlet); 2.32 (3H, singlet); 1.17 (6H, triplet, J=7.0 Hz).

1-(Diethylcarbamoyl)-3-(4-methoxy-2-methylphenylsulfonyl)pyrazole (Compound No. 5.17)

Following the procedure of Example 1, there were obtained 108 mg (yield 68.2%) of the title compound, as an oily substance.

Nuclear Magnetic Resonance Spectrum (CDCl$_3$, 200 MHz), δ ppm: 8.16 (1H, doublet, J=2.8 Hz); 8.12 (1H, doublet, J=8.8 Hz); 6.87 (1H, doublet of doublets, J=8.8 & 2.6 Hz); 6.83 (1H, doublet, J=2.8 Hz); 6.76 (1H, doublet, J=2.6 Hz); 3.85 (3H, singlet); 3.47 (4H, quartet, J=7.0 Hz); 2.55 (3H, singlet); 1.30–1.05 (6H, broad).

1-(Diethylcarbamoyl)-3-(4-methoxy-2-methylphenylthio)pyrazole (Compound No. 5.18)

Following the procedure of Example 1, there were obtained 269 mg (yield 68.9%) of the title compound, as an oily substance.

Nuclear Magnetic Resonance Spectrum (CDCl$_3$, 200 MHz), δ ppm: 8.04 (1H, doublet, J=2.8 Hz); 7.5 (1H, doublet, J=8.5 Hz); 6.8 (1H, doublet, J=2.7 Hz); 6.75 (1H, doublet of doublets, J=8.5 & 2.7 Hz); 6.0 (1H, doublet, J=2.8 Hz); 3.8 (3H, singlet); 3.58 (4H, quartet, J=7.0 Hz); 2.4 (3H, singlet); 1.16 (6H, triplet, J=7.0 Hz).

1-(Diethylcarbamoyl)-3-(4-bromo-2-chlorophenylsulfonyl)pyrazole (Compound No. 5.19)

Following the procedure of Example 1, there were obtained 192 mg (yield 63.1%) of the title compound, melting at 109°–110° C.

1-(Diethylcarbamoyl)-3-(4-bromo-2-chlorophenylthio)-pyrazole (Compound No, 5.20)

Following the procedure of Example 1, there were obtained 355 mg (yield 67.9%) of the title compound, as an oily substance.

Nuclear Magnetic Resonance Spectrum (CDCl$_3$, 200 MHz), δ ppm: 8.19 (1H, doublet, J=2.6 Hz); 7.56 (1H, doublet, J=2.0 Hz); 7.28 (1H, doublet of doublets, J=8.5 & 2.0 Hz); 7.07 (1H, doublet, J=8.5 Hz); 6.39 (1H, doublet, J=2.6 Hz); 3.56 (4H, quartet, J=7.0 Hz); 1.21 (6H, triplet, J=7.0 Hz).

1-(Dimethylcarbamoyl)-3-(2,4-difluorophenylthio)-4-chloropyrazole (Compound No. 5.25)

Following the procedure of Example 3, there were obtained 174 mg (yield 47.3%) of the title compound, as an oily substance.

Nuclear Magnetic Resonance Spectrum (CDCl$_3$, 200 MHz), δ ppm: 8.09 (1H, singlet); 7.47–7.39 (1H, multiplet); 6.93–6.82 (2H, multiplet); 3.13 (6H, singlet).

1-(Dimethylcarbamoyl)-3-(2,4-difluorophenylsulfonyl)-4-chloropyrazole (Compound No. 5.26)

Following the procedure of Example 3, there were obtained 148 mg (yield 47.3%) of the title compound, as an oily substance.

Nuclear Magnetic Resonance Spectrum (CDCl$_3$, 200 MHz), δ ppm: 8.24–8.12 (1H, multiplet); 8.14 (1H, singlet); 7.16–7.06 (1H, multiplet); 6.99–6.89 (1H, multiplet); 3.22 (3H, broad); 3.17 (3H, broad).

1-(N-Ethyl-N-methylcarbamoyl)-3-(2,4-difluorophenylthio)-4-chloropyrazole (Compound No. 5.27)

Following the procedure of Example 3, there were obtained 185 mg (yield 46.1%) of the title compound, as an oily substance.

Nuclear Magnetic Resonance Spectrum (CDCl$_3$, 200 MHz), δ ppm: 8.10 (1H, singlet); 7.52–7.41 (1H, multiplet); 6.93–6.83 (2H, multiplet); 3.50 (2H, quartet, J=7.0 Hz); 3.08 (3H, singlet); 1.10 (3H, broad).

1-(N-Ethyl-N-methylcarbamoyl)-3-(2,4-difluorophenylsulfonyl)-4-chloropyrazole (Compound No. 5.28)

Following the procedure of Example 3, there were obtained 152 mg (yield 43.8%) of the title compound, melting at 77°–79° C.

1-(Diethylcarbamoyl)-3-(2,4-difluorophenylthio)-4-chloropyrazole (Compound No. 5.29)

Following the procedure of Example 3, there were obtained 657 mg (yield 57.1%) of the title compound, melting at 84°–86° C.

1-(Diethylcarbamoyl)-3-(2,4-difluorophenylsulfonyl)-4-chloropyrazole (Compound No. 5.30)

Following the procedure of Example 3, there were obtained 554 mg (yield 54.9%) of the title compound, melting at 99°–100° C.

1(N-Ethyl-N-propylcarbamoyl)-3-(2,4-difluorophenylthio)-4-chloropyrazole (Compound No. 5.31)

Following the procedure of Example 3, there were obtained 198 mg (yield 45.0%) of the title compound, melting at 60°–64° C.

1(N-Ethyl-N-propylcarbamoyl)-3-(2,4-difluorophenylsulfonyl)-4-chloropyrazole (Compound No. 5.32)

Following the procedure of Example 3, there were obtained 162 mg (yield 41.4%) of the title compound, as an oily substance.

Nuclear Magnetic Resonance Spectrum (CDCl$_3$, 200 MHz), δ ppm: 8.23–8.12 (1H, multiplet); 8.16 (1H, singlet); 7.15–7.05 (1H, multiplet); 6.99–6.88 (2H, multiplet); 3.54–3.36 (4H, multiplet); 1.73–1.61 (2H, multiplet); 1.22 (3H, broad); 0.91 (3H, broad).

1-(Dipropylcarbamoyl)-3-(2,4-difluorophenylthio)-chloropyrazole (Compound No. 5.33)

Following the procedure of Example 3, there were obtained 197 mg (yield 43.8%) of the title compound, as an oily substance.

Nuclear Magnetic Resonance Spectrum (CDCl$_3$, 200 MHz), δ ppm: 8.11 (1H, singlet); 7.52–7.40 (1H, multiplet); 6.93–6.83 (2H, multiplet); 3.39 (4H, broad triplet, J=7.5 Hz); 1.66–1.50 (4H, multiplet); 0.81 (6H, broad).

1-(Dipropylcarbamoyl)-3-(2,4,difluorophenylsulfonyl)-4-chloropyrazole (Compound No. 5.34)

Following the procedure of Example 3, there were obtained 179 mg (yield 43.8%) of the title compound, as an oily substance.

Nuclear Magnetic Resonance Spectrum (CDCl$_3$, 200 MHz), δ ppm: 8.23–8.12 (1H, multiplet); 8.17 (1H, singlet); 7.15–7.05 (1H, multiplet); 6.99–6.88 (1H, multiplet); 3.93 (4H, broad); 1.65 (4H, broad); 0.90 (6H, broad).

1(N-Butyl-N-methylcarbamoyl)-3-(2,4-difluorophenylthio)-4-chloropyrazole (Compound No. 5.35)

Following the procedure of Example 3, there were obtained 199 mg (yield 46.1%) of the title compound, as an oily substance.

Nuclear Magnetic Resonance Spectrum (CDCl$_3$, 200 MHz), δ ppm: 8.10 (1H, singlet); 7.50–7.39 (1H, multiplet); 6.93–6.82 (2H, multiplet); 3.48 (2H, broad triplet, J=7.4 Hz); 3.10 (3H, singlet); 1.60–1.53 (2H, multiplet); 1.26–1.19 (2H, multiplet); 0.90 (3H, broad triplet, J=7.2 Hz).

1(N-Butyl-N-methylcarbamoyl)-3-(2,4-difluorophenylsulfonyl)-4-chloropyrazole (Compound No. 5.36)

Following the procedure of Example 3, there were obtained 157 mg (yield 42.4%) of the title compound, as an oily substance.

Nuclear Magnetic Resonance Spectrum (CDCl$_3$, 200 MHz), δ ppm: 8.23–8.12 (1H, multiplet); 8.14 (1H, singlet); 7.15–7.05 (1H, multiplet); 6.98–6.88 (1H, multiplet); 3.56 (3H, broad); 3.19 (2H, broad); 1.77–1.54 (2H, multiplet); 1.43–1.21 (2H, multiplet); 0.93 (3H, broad).

1-(Diethylcarbamoyl)-3-(2-chloro-4-methylphenylthio)-4-chloropyrazole (Compound No. 5.37)

Following the procedure of Example 4, there were obtained 403 mg (yield 38.9%) of the title compound, as an oily substance.

Nuclear Magnetic Resonance Spectrum (CDCl$_3$, 200 MHz), δ ppm: 8.16 (1H, singlet); 7.26 (1H, doublet, J=1.4 Hz); 7.17 (1H, doublet, J=8.1 Hz); 7.00 (1H, doublet of doublets, J=8.1 & 1.4 Hz); 3.50 (4H, broad quartet, J=6.6 Hz); 2.32 (3H, singlet); 1.15 (6H, broad triplet, J=6.6 Hz).

1-(Diethylcarbamoyl)-3-(2-chloro-4-methylphenylsulfonyl)-4-chloropyrazole (Compound No. 5.38)

Following the procedure of Example 4, there were obtained 167 mg (yield 38.9%) of the title compound, melting at 105°–107° C.

1-(Diethylcarbamoyl)-3-(4-chloro-2-methylphenylsulfonyl)-4-chloropyrazole (Compound No. 5.39)

Following the procedure of Example 4, there were obtained 154 mg (yield 27.7%) of the title compound, melting at 84°–85° C.

1-(Diethylcarbamoyl)-3-(4-bromo-2-fluorophenylsulfonyl)-4-chloropyrazole (Compound No. 5.40)

Following the procedure of Example 4, there were obtained 103 mg (yield 65.3%) of the title compound, as an oily substance.

Nuclear Magnetic Resonance Spectrum (CDCl$_3$, 200 MHz), δ ppm: 8.17 (1H, singlet); 8.00 (1H, triplet, J=8.5 Hz); 7.53 (1H, doubled doublet of doublets, J=8.5, 1.8 & 0.8 Hz); 7.39 (1H, doublet of doublets, J=9.0 & 1.8 Hz); 3.51 (4H, broad quartet, J=6.4 Hz); 1.30–1.15 (6H, broad).

1-(Diethylcarbamoyl)-3-(4-chloro-2-trifluoromethylphenylthio)-4-chloropyrazole (Compound No. 5.41)

Following the procedure of Example 3, there were obtained 265 mg (yield 42.6%) of the title compound, as an oily substance.

Nuclear Magnetic Resonance Spectrum (CDCl$_3$, 200 MHz), δ ppm: 8.17 (1H, singlet); 7.69 (1H, doublet, J=2.1 Hz); 7.40 (1H, doublet of doublets, J=8.4 & 2.1 Hz); 7.29 (1H, doublet, J=8.4 Hz); 2.55 (4H, multiplet); 1.17 (6H, multiplet).

1-(Diethylcarbamoyl)-3-(4-chloro-2-trifluoromethylphenylsulfonyl)-4-chloropyrazole (Compound No. 5.42)

Following the procedure of Example 3, there were obtained 184 mg (yield 28.5%) of the title compound, as an oily substance.

Nuclear Magnetic Resonance Spectrum (CDCl$_3$, 200 MHz), δ ppm: 8.47 (1H, doublet, J=8.6 Hz); 8.15 (1H, singlet); 7.83 (1H, doublet of doublets, J=8.6 & 1.6 Hz); 7.71 (1H, doublet, J=1.6 Hz); 3.5–3.3 (4H, broad); 1.4–0.8 (6H, broad).

1-[N-(4-Chlorophenyl)-N-methylcarbamoyl]-3-(4-chloro-2-trifluoromethylphenylsulfonyl)-4-chloropyrazole (Compound No. 5.59)

Following the procedure of Example 3, there were obtained 137 mg (yield 29.6%) of the title compound, as an oily substance.

Nuclear Magnetic Resonance Spectrum (CDCl$_3$, 200 MHz), δ ppm: 8.16 (1H, singlet); 8.07 (1H, doublet, J=8.4 Hz); 7.83–7.65 (2H, multiplet); 7.11–7.01 (2H, multiplet); 6.80–6.71 (2H, multiplet); 3.36 (3H, singlet).

1-(Diethylcarbamoyl)-3-(2,4-difluorophenylthio)-4-bromopyrazole (Compound No. 5.69)

Following the procedure of Example 5, there were obtained 480 mg (yield 71.8%) of the title compound, melting at 95°–96° C.

1-(Diethylcarbamoyl)-3-(2,4-difluorophenylsulfonyl)-4-bromopyrazole (Compound No. 5.70)

Following the procedure of Example 5, there were obtained 375 mg (yield 69.7%) of the title compound, melting at 95°–97° C.

1-(Diethylcarbamoyl)-3-(2-chloro-4-methylphenylthio)-4-bromopyrazole (Compound No. 5.71)

Following the procedure of Example 4, there were obtained 727 mg (yield 63.8%) of the title compound, as an oily substance.

Nuclear Magnetic Resonance Spectrum (CDCl$_3$, 200 MHz), δ ppm: 8.19 (1H, singlet); 7.27–7.26 (1H, multiplet); 7.18 (1H, doublet, J=8.0 Hz); 7.02–6.98 (1H, multiplet); 3.49 (4H, broad quartet, J=7.1 Hz); 2.32 (3H, singlet); 1.13 (6H, broad).

1-(Diethylcarbamoyl)-3-(2-chloro-4-methylphenylsulfonyl)-4-bromopyrazole (Compound No. 5.72)

Following the procedure of Example 4, there were obtained 164 mg (yield 60.0%) of the title compound, melting at 98°–100° C.

1-(Diethylcarbamoyl)-3-(4-chloro-2-methylphenylsulfonyl)-4-bromopyrazole (Compound No. 5.73)

Following the procedure of Example 5, there were obtained 273 mg (yield 51.1%) of the title compound, melting at 94°–95° C.

1-(Diethylcarbamoyl)-3-(2-chloro-4-methylphenylsulfonyl)-4-fluoropyrazole (Compound No. 5.74)

Following the procedure of Example 7, there were obtained 16 mg (yield 3.0%) of the title compound, as an oily substance.

Nuclear Magnetic Resonance Spectrum (CDCl$_3$, 200 MHz), δ ppm: 8.03 (1H, doublet, J=8.1 Hz); 7.97 (1H, doublet, J=4.7 Hz); 7.37 (1H, doublet, J=8.1 Hz); 7.20 (1H, singlet); 3.47 (4H, broad quartet, J=7.0 Hz); 2.41 (3H, singlet); 1.30–1.10 (6H, multiplet).

1-(Diethylcarbamoyl)-3-(4-chloro-2-trifluoromethylphenylsulfonyl)-4-fluoropyrazole (Compound No. 5.75)

Following the procedure of Example 7, there were obtained 27 mg (yield 4.3%) of the title compound, as an oily substance.

Nuclear Magnetic Resonance Spectrum (CDCl$_3$, 200 MHz), δ ppm: 8.48 (1H, doublet, J=8.5 Hz); 7.98 (1H, doublet, J=4.7 Hz); 7.83 (1H, doublet of doublets, J=8.5 & 2.1 Hz); 7.71 (1H, doublet, J=2.1 Hz); 3.45 (4H, quartet, J=7.0 Hz); 1.30–1.06 (6H, broad ).

1-(Diethylcarbamoyl)-3-(2,4-difluorophenylsulfonyl)-4-fluoropyrazole (Compound No. 5.76)

Following the procedure of Example 19, there were obtained 50 mg (yield 4.5%) of the title compound, melting at 74°–76° C.

1-(Diethylcarbamoyl)-3-(2,4-difluorophenylthio)-4-fluoropyrazole (Compound No. 5.107)

Following the procedure of Example 19, there were obtained 68 mg (yield 6.5%) of the title compound, as an oily substance.

Nuclear Magnetic Resonance Spectrum CDCl$_3$, 200 MHz), δ ppm: 7.97 (1H, doublet, J=5.0 Hz); 7.84–7.46 (2H, multiplet); 6.91–6.83 (2H, multiplet); 3.50 (4H, quartet, J=7.0 Hz); 1.16 (6H, triplet, J=7.0 Hz).

1-(Diethylcarbamoyl)-3-(2-fluoro-5-methylphenylsulfonyl)pyrazole (Compound No. 6.1)

Following the procedure of Example 1, there were obtained 123 mg (yield 40.3%) of the title compound, as an oily substance.

Nuclear Magnetic Resonance Spectrum (CDCl$_3$, 200 MHz), δ ppm: 8.18 (1H, doublet, J=3.1 Hz); 7.89 (1H, doublet of doublets, J=2.2 & 3.1 Hz); 7.45–7.37 (1H, multiplet); 7.13 (1H, triplet, J=9.0 Hz); 6.95 (1H, doublet, J=3.1 Hz); 3.49 (4H, quartet, J=7.0 Hz); 2.41 (3H, singlet); 1.45–1.08 (6H, broad).

1-(Diethylcarbamoyl)-3-(2-fluoro-5-methylphenylthio)-pyrazole (Compound No. 6.2)

Following the procedure of Example 1, there were obtained 153 mg (yield 40.3%) of the title compound, as an oily substance.

Nuclear Magnetic Resonance Spectrum (CDCl$_3$, 200 MHz), δ ppm: 8.11 (1H, doublet, J=2.7 Hz); 7.27–7.22 (1H, multiplet); 7.14–7.06 (1H, multiplet); 6.99 (1H, triplet, J=8.6 Hz); 6.26 (1H, doublet, J=2.7 Hz); 3.54 (4H, quartet, J=7.0 Hz); 2.29 (3H, singlet); 1.18 (6H, triplet, J=7.0 Hz).

1-(Diethylcarbamoyl)-3-(2,5-dichlorophenylsulfonyl)-pyrazole (Compound No. 6.3)

Following the procedure of Example 1, there were obtained 390 mg (yield 39.5%) of the title compound, melting at 62°–66° C.

1-(Diethylcarbamoyl)-3-(2,5-dichlorophenylthio)-pyrazole Compound No. 6.4)

Following the procedure of Example 1, there were obtained 531 mg (yield 44.9%) of the title compound, melting at 62°–64° C.

1-(Diethylcarbamoyl)-3-(2-chloro-5-trifluoromethylphenylthio)pyrazole (Compound No. 6.5)

Following the procedure of Example 1, there were obtained 613 mg (yield 64.6%) of the title compound, as an oily substance.

Nuclear Magnetic Resonance Spectrum (CDCl$_3$, 200 MHz), δ ppm: 8.23 (1H, doublet, J=2.7 Hz); 7.53–7.37 (3H, multiplet); 6.46 (1H, doublet, J=2.7 Hz); 3.56 (4H, quartet, J=6.9 Hz); 1.21 (6H, triplet, J=6.9 Hz).

1-(Diethylcarbamoyl)-3-(2-chloro-5-trifluoromethylphenylsulfonyl)pyrazole (Compound No. 6.6)

Following the procedure of Example 1, there were obtained 208 mg (yield 59.4%) of the title compound, as an oily substance.

Nuclear Magnetic Resonance Spectrum (CDCl$_3$, 200 MHz), δ ppm: 8.61 (1H, doublet, J=2.0 Hz); 8.22 (1H, doublet, J=2.7 Hz); 7.82 (1H, doublet of doublets, J=8.4 & 2.0 Hz); 7.63 (1H, doublet, J=8.4 Hz); 7.03 (1H, doublet, J=2.7 Hz); 3.43 (4H, doublet, J=7.0 Hz); 1.35–1.00 (6H, broad).

1-(Diethylcarbamoyl)-3-(5-chloro-2-methylphenylthio)pyrazole (Compound No. 6.7)

Following the procedure of Example 1, there were obtained 750 mg (yield 75.7%) of the title compound, as an oily substance.

Nuclear Magnetic Resonance Spectrum (CDCl$_3$, 200 MHz), δ ppm: 8.15 (1H, doublet, J=2.8 Hz); 7.32 (1H, broad singlet); 7.15 (2H, doublet, J=1.3 Hz); 6.27 (1H, doublet, J=2.8 Hz); 3.55 (4H, broad quartet, J=7.0 Hz); 2.38 (3H, singlet); 1.19 (6H, broad triplet, J=7.0 Hz).

1-(Diethylcarbamoyl)-3-(5-chloro-2-methylphenylsulfonyl)pyrazole (Compound No. 6.8)

Following the procedure of Example 1, there were obtained 197 mg (yield 75.7%) of the title compound, as an oily substance.

Nuclear Magnetic Resonance Spectrum (CDCl$_3$, 200 MHz), δ ppm: 8.19 (1H, doublet, J=2.3 Hz); 8.18 (1H, doublet, J=2.3 Hz); 7.47 (1H, doublet of doublets, J=2.3 & 8.1 Hz); 7.22 (1H, doublet, J=8.1 Hz); 6.89 (1H, doublet, J=2.3 Hz); 3.47 (4H, broad quartet, J=7.0 Hz); 2.54 (3H, singlet); 1.18 (6H, broad).

1-(Diethylcarbamoyl)-3-(2,5-dimethylphenylthio)-pyrazole (Compound No. 6.9)

Following the procedure of Example 1, there were obtained 914 mg (yield 74.0%) of the title compound, as an oily substance.

Nuclear Magnetic Resonance Spectrum (CDCl$_3$, 200 MHz), δ ppm: 8.09 (1H, doublet, J=2.6 Hz); 7.24 (1H, broad singlet); 7.14–7.01 (2H, multiplet); 6.14 (1H, doublet, J=2.6 Hz); 3.55 (4H, broad quartet, J=6.8 Hz); 2.37 (3H, singlet); 2.27 (3H, singlet); 1.18 (6H, broad triplet, J=6.8).

1-(Diethylcarbamoyl)-3-(2,5-dimethylphenylsulfonyl)-pyrazole (Compound No. 6.10)

Following the procedure of Example 1, there were obtained 186 mg (yield 68.1%) of the title compound, as an oily substance.

Nuclear Magnetic Resonance Spectrum (CDCl$_3$, 270 MHz), δ ppm: 8.17 (1H, doublet, J=2.6 Hz); 7.99 (1H, broad singlet); 7.32–7.30 (1H, multiplet); 7.16 (1H, doublet, J=8.1 Hz); 6.86 (1H, doublet, J=2.6 Hz); 3.46 (4H, broad quartet, J=7.0 Hz); 2.53 (3H, singlet); 2.40 (3H, singlet); 1.16 (6H, broad ).

1-(Diethylcarbamoyl)-3-(2-methoxy-5-methylphenylsulfonyl)pyrazole (Compound No. 6.11)

Following the procedure of Example 1, there were obtained 139 mg (yield 70.6%) of the title compound, as an oily substance.

Nuclear Magnetic Resonance Spectrum (CDCl$_3$, 200 MHz), δ ppm: 8.14 (1H, doublet, J=2.7 Hz); 7.95 (1H, doublet, J=2.2 Hz); 7.37 (1H, doublet of doublets, J=2.2 & 2.7 Hz); 6.93 (1H, doublet, J=2.7 Hz); 6.85 (1H, doublet, J=8.4 Hz); 3.76 (3H, singlet); 3.47 (4H, quartet, J=7.0 Hz); 2.36 (3H, singlet); 1.45–1.00 (6H, broad).

1-(Diethylcarbamoyl)-3-(2-methoxy-5-methylphenylthio)pyrazole (Compound No. 6.12)

Following the procedure of Example 1, there were obtained 330 mg (yield 70.6%) of the title compound, as an oily substance.

Nuclear Magnetic Resonance Spectrum (CDCl$_3$, 200 MHz), δ ppm: 8.12 (1H, doublet, J=2.4 Hz); 7.09–7.03 (2H, multiplet); 6.80 (1H, doublet, J=8.3 Hz); 6.25 (1H, doublet, J=2.4 Hz); 3.84 (3H, singlet); 3.58 (4H, quartet, J=7.0 Hz); 2.23 (3H, singlet); 1.21 (6H, triplet, J=7.0 Hz).

1-(Diethylcarbamoyl)-3-(5-chloro-2-methoxyphenylthio)pyrazole (Compound No. 6.13)

Following the procedure of Example 1, there were obtained 133 mg (yield 45.7%) of the title compound, as an oily substance.

Nuclear Magnetic Resonance Spectrum (CDCl₃, 200 MHz), δ ppm: 8.17 (1H, doublet, J=2.7 Hz); 7.20–7.15 (2H, multiplet); 6.82 –6.78 (1H, multiplet); 6.37 (1H, doublet, J=2.7 Hz); 3.87 (3H, singlet); 3.59 (4H, quartet, J=7.0 Hz); 1.23 (6H, triplet, J=7.0 Hz).

1-(Diethylcarbamoyl)-3-(5-chloro-2-methoxyphenylsulfonyl)pyrazole (Compound No. 6.14)

Following the procedure of Example 1, there were obtained 123 mg (yield 45.7%) of the title compound, as an oily substance.

Nuclear Magnetic Resonance Spectrum (CDCl₃, 200 MHz), δ ppm: 8.16 (1H, doublet, J=2.7 Hz); 8.13 (1H, doublet, J=2.7 Hz); 7.53 (1H, doublet of doublets, J=2.7 & 8.8 Hz); 6.95 (1H, doublet, J=2.7 Hz); 6.90 (1H, doublet, J=8.8 Hz); 3.80 (3H, singlet); 3.47 (4H, quartet, J=7.0 Hz); 1.38–1.05 (6H, broad).

1-(Diethylcarbamoyl)-3-(2-chloro-5-methoxyphenylthio)pyrazole (Compound No. 6.15)

Following the procedure of Example 1, there were obtained 289 mg (yield 89.0%) of the title compound, as an oily substance.

Nuclear Magnetic Resonance Spectrum (CDCl₃, 200 MHz), δ ppm: 8.18 (1H, doublet, J=2.8 Hz); 7.29 (1H, doublet, J=9.9 Hz); 6.76 (1H, doublet, J=2.8 Hz); 6.71 (1H, doublet of doublets, J=9.9 & 2.8 Hz); 6.39 (1H, doublet, J=2.8 Hz); 3.70 (3H, singlet); 3.58 (4H, broad quartet, J=6.9 Hz); 1.22 (6H, triplet, J=6.9 Hz).

1-(Diethylcarbamoyl)-3-(2-chloro-5-methoxyphenylsulfonyl)pyrazole (Compound No. 6.16)

Following the procedure of Example 1, there were obtained 224 mg (yield 85.4%) of the title compound, as an oily substance.

Nuclear Magnetic Resonance Spectrum (CDCl₃, 200 MHz), δ ppm: 8.18 (1H, doublet, J=2.7 Hz); 7.84 (1H, doublet, J=3.0 Hz); 7.35 (1H, doublet, J=8.8 Hz); 7.08 (1H, doublet of doublets, J=3.0, 8.8 Hz); 6.98 (1H, doublet, J=2.7 Hz); 3.88 (3H, singlet); 3.43 (4H, broad quartet, J=7.0 Hz); 1.14 (6H, broad).

1-(Diethylcarbamoyl)-3-(2,5-dibromophenylsulfonyl)pyrazole (Compound No. 6.17)

Following the procedure of Example 1, there were obtained 144 mg (yield 21.0%) of the title compound, as an oily substance.

Nuclear Magnetic Resonance Spectrum (CDCl₃, 200 MHz), δ ppm: 8.50 (1H, doublet, J=2.1 Hz); 8.20 (1H, doublet, J=2.5 Hz); 7.58–7.56 (2H, multiplet); 7.01 (1H, doublet, J=2.1 Hz); 3.43 (4H, quartet, J=7.0 Hz); 1.35–0.90 (6H, broad).

1-(Diethylcarbamoyl)-3-(2.5-difluorophenylthio)pyrazole (Compound No. 6.18)

Following the procedure of Example 1, there were obtained 134 mg (yield 55.7%) of the title compound, as an oily substance.

Nuclear Magnetic Resonance Spectrum (CDCl₃, 200 MHz), δ ppm: 8.17 (1H, doublet, J=2.6 Hz); 7.11–6.90 (3H, multiplet); 6.38 (1H, doublet, J=2.6 Hz); 3.56 (4H, quartet, J=7.0 Hz); 1.21 (6H, triplet, J=7.0 Hz).

1-(Diethylcarbamoyl)-3-(2,5-difluorophenylsulfonyl)pyrazole (Compound. No. 6.19)

Following the procedure of Example 1, there were obtained 109 mg (yield 48.4%) of the title compound, as an oily substance.

Nuclear Magnetic Resonance Spectrum (CDCl₃, 200 MHz), δ ppm: 8.21 (1H, doublet, J=2.8 Hz); 7.82 (1H, doubled doublet of doublets, J=5.2, 3.2 & 2.2 Hz); 7.37–7.29 (1H, multiplet); 7.21–7.10 (1H, multiplet); 6.98 (1H, doublet, J=2.8 Hz); 3.50 (4H, quartet, J=7.0 Hz); 1.22 (6H, multiplet).

1-(Diethylcarbamoyl)-3-(2,5,dichlorophenylsulfonyl)-4-fluoropyrazole (Compound No. 6.60)

Following the procedure of Example 19, there were obtained 12 mg (yield 2.0%) of the title compound, as an oily substance.

Nuclear Magnetic Resonance Spectrum CDCl₃, 200 MHz), δ ppm: 8.14 (1H, doublet, J=2.4 Hz); 8.00 (1H, doublet, J=4.7 Hz); 7.45 (1H, doublet of doublets, J=8.4 & 2.4 Hz); 7.31 (1H, doublet, J=8.4 Hz); 3.50–3.37 (4H, multiplet); 1.30–1.08 (6H, broad).

1-(Diethylcarbamoyl)-3-(2,5-dimethylphenylsulfonyl)-4-fluoropyrazole (Compound No. 6.61)

Following the procedure of Example 7, there were obtained 16 mg (yield 3.1%) of the title compound, melting at 96°–97°

1-(Diethylcarbamoyl)-3-(2-chloro-5-trifluoromethylphenylsulfonyl)-4-fluoropyrazole (Compound No. 6.62)

Following the procedure of Example 7, there were obtained 49 mg (yield 4.7%) of the title compound, as an oily substance.

Nuclear Magnetic Resonance Spectrum (CDCl₃, 200 MHz), δ ppm: 8.60 (1H, doublet, J=1.5 Hz); 8.05 (1H, doublet, J=4.7 Hz); 7.85 (1H, doublet of doublets, J=8.5 & 1.5 Hz); 7.66 (1H, doublet, J=8.5 Hz); 3.45 (4H, quartet, J=7.2 Hz); 1.20–1.07 (6H, broad).

1-(Diethylcarbamoyl)-3-(5-chloro-2-methylphenylsulfonyl)-4-fluoropyrazole (Compound No. 6.63)

Following the procedure of Example 7, there were obtained 12 mg (yield 3.3%) of the title compound, as an oily substance.

Nuclear Magnetic Resonance Spectrum (CDCl₃, 200 MHz), δ ppm: 8.18 (1H, doublet, J=2.2 Hz); 8.02 (1H, doublet, J=4.7 Hz); 7.50 (1H, doublet of doublets, J=2.2 & 8.1 Hz); 7.25 (1H, doublet, J=8.1 Hz); 3.48 (4H, broad quartet, J=7.1 Hz); 2.58 (3H, singlet); 1.22 (6H, broad triplet, J=7.1 Hz).

1-(Diethylcarbamoyl)-3-(2-fluoro-5-methylphenylsulfonyl)-4-fluoropyrazole (Compound No. 6.66)

Following the procedure of Example 19, there were obtained 35 mg (yield 3.9%) of the title compound, as an oily substance.

Nuclear Magnetic Resonance Spectrum CDCl₃, 200 MHz), δ ppm: 8.02 (1H, doublet, J=4.7 Hz); 7.89 (1H, doublet of doublets, J=6.6 & 2.0 Hz); 7.44 (1H, doublet of doublets of doublets, J=8.5, 4.9 & 2.0 Hz); 7.07 (1H, triplet, J=8.5 Hz); 3.50 (4H, broad quartet, J=7.0 Hz); 2.42 (3H, singlet); 1.22 (6H, triplet, J=7.0 Hz).

1-(Diethylcarbamoyl)-3-(2-chloro-5-methoxyphenylsulfonyl)-4-fluoropyrazole (Compound No. 6.70)

Following the procedure of Example 19, there were obtained 52 mg (yield 4.7%) of the title compound, as an oily substance.

Nuclear Magnetic Resonance Spectrum CDCl₃, 200 MHz), δ ppm: 8.02 (1H, doublet, J=4.7 Hz); 7.83 (1H, doublet, J=3.1 Hz); 7.38 (1H, doublet, J=8.8 Hz); 7.10 (1H, doublet of doublets, J=8.8 & 3.1 Hz); 3.89 (3H, singlet); 3.47 (4H, quartet, J=7.0 Hz); 1.31–1.04 (6H, broad).

1-(Diethylcarbamoyl)-3-(2,5-dichlorophenylsulfonyl)-4-chloropyrazole (Compound No. 6.101)

Following the procedure of Example 5, there were obtained 85 mg (yield 31.5%) of the title compound, melting at 97°–98° C.

1-(Diethylcarbamoyl)-3-(2,5-dimethylphenylsulfonyl)-4-chloropyrazole (Compound No. 6.102)

Following the procedure of Example 4, there were obtained 201 mg (yield 23.7%) of the title compound, melting at 108°–108.5° C.

1-(Diethylcarbamoyl)-3-(2-chloro-5-trifluoromethylphenylsulfonyl)-4-chloropyrazole (Compound No. 6.103)

Following the procedure of Example 3, there were obtained 63 mg (yield 9.6%) of the title compound, melting at 80°–81.5° C.

1-(Diethylcarbamoyl)-3-(5-chloro-2-methylphenylsulfonyl)-4-chloropyrazole (Compound No. 6.104)

Following the procedure of Example 4, there were obtained 203 mg (yield 14.4%) of the title compound, melting at 59°–63° C.

1-(Diethylcarbamoyl)-3-(2-chloro-5-methoxyphenylthio)-4chloropyrazole (Compound No. 6.105)

Following the procedure of Example 4, there were obtained 222 mg (yield 38.0%) of the title compound, as an oily substance.

Nuclear Magnetic Resonance Spectrum (CDCl$_3$, 200 MHz), δ ppm: 8.20 (1H, singlet); 7.30 (1H, doublet of doublets, J=1.0 & 8.0 Hz); 6.77 (1H, multiplet); 6.73 (1H, doublet, J=8.0 Hz); 3.72 (3H, singlet); 3.53 (4H, broad quartet, J=6.7 Hz); 1.18 (6H, broad triplet, J=6.7 Hz).

1-(Diethylcarbamoyl).3-(2-chloro-5-methoxyphenylsulfonyl)-4-chloropyrazole (Compound No. 6.106)

Following the procedure of Example 4, there were obtained 180 mg (yield 35.3%) of the title compound, as an oily substance.

Nuclear Magnetic Resonance Spectrum (CDCl$_3$, 200 MHz), δ ppm: 8.15 (1H, singlet); 7.86 (1H, doublet, J=3.0 Hz); 7.37 (1H, doublet, J=8.8 Hz); 7.11 (1H, doublet of doublets, J=3.0 & 8.8 Hz); 3.89 (3H, singlet); 3.48 (4H, broad quartet, J=6.9 Hz); 1.24 (6H, broad).

1-(Diethylcarbamoyl)-3-(2-fluoro-5-methylphenylthio)-4-chloropyrazole (Compound No. 6.108)

Following the procedure of Example 4, there were obtained 323 mg (yield 61.8%) of the title compound, as an oily substance.

Nuclear Magnetic Resonance Spectrum (CDCl$_3$, 200 MHz), δ ppm: 8.12 (1H, singlet); 7.22–6.93 (3H, multiplet); 3.47 (4H, quartet, J=7.0 Hz); 2.28 (3H, singlet); 1.12 (6H, triplet, J=7.0 Hz).

1-(Diethylcarbamoyl)-3-(2-fluoro-5-methylphenylsulfonyl)-4-chloropyrazole (Compound No. 6.109)

Following the procedure of Example 4, there were obtained 251 mg (yield 49.5%) of the title compound, as an oily substance.

Nuclear Magnetic Resonance Spectrum (CDCl$_3$, 200 MHz), δ ppm: 8.15 (1H, singlet); 7.94–7.83 (1H, multiplet); 7.49–7.39 (1H, multiplet); 7.10–6.92 (1H, multiplet); 3.60–3.38 (4H, broad); 2.43 (3H, singlet); 1.30–1.06 (6H, broad).

1-(Diethylcarbamoyl)-3-(2,5-difluorophenylthio)-4-chloropyrazole (Compound No. 6.110)

Following the procedure of Example 3, there were obtained 218 mg (yield 38.2%) of the title compound, as an oily substance.

Nuclear Magnetic Resonance Spectrum (CDCl$_3$, 200 MHz), δ ppm: 8.18 (1H, singlet); 6.92–7.13 (3H, multiplet); 3.52 (4H, quartet, J=7.0 Hz); 1.18 (6H, triplet, J=7.0 Hz).

1-(Diethylcarbamoyl)-3-(3,5-difluorophenylsulfonyl)-4-chloropyrazole (Compound No. 6.111)

Following the procedure of Example 3, there were obtained 112 mg (yield 20.2%) of the title compound, as an oily substance.

Nuclear Magnetic Resonance Spectrum (CDCl$_3$, 200 MHz), δ ppm: 8.17 (1H, singlet); 7.88–7.80 (1H, multiplet); 7.42–7.31 (1H, multiplet); 7.23–7.12 (1H, multiplet); 3.6–3.4 (4H, multiplet); 1.3–1.2 (6H, multiplet).

1-(Diethylcarbamoyl)-3-(5-chloro-2-methoxyphenylsulfonyl)-4-chloropyrazole (Compound No. 6.112)

Following the procedure of Example 5, there were obtained 80 mg (yield 17.8%) of the title compound, melting at 94°–95° C.

1-(Diethylcarbamoyl)-3-(2-chloro-5-trifluoromethylphenylsulfonyl)-4-bromopyrazole (Compound No. 6.115)

Following the procedure of Example 3, there were obtained 140 mg (yield 9.4%) of the title compound, as an oily substance.

Nuclear Magnetic Resonance Spectrum (CDCl$_3$, 200 MHz), δ ppm: 8.49 (1H, doublet, J=1.9 Hz); 8.21 (1H, singlet); 7.74 (1H, doublet of doublets, J=1.9 & 8.4 Hz); 7.52 (1H, doublet, J=8.4 Hz); 3.45 (4H, quartet, J=6.9 Hz); 1.19 (6H, broad).

1-(Diethylcarbamoyl)-3-(2,5-dichlorophenylsulfonyl)-4-bromopyrazole (Compound No. 6.117)

Following the procedure of Example 5, there were obtained 132 mg (yield 55.0%) of the title compound, melting at 100°–102° C.

1-(Diethylcarbamoyl)-3-(2-fluoro-5-methylphenylthio)-4-bromopyrazole (Compound No. 6.118)

Following the procedure of Example 4, there were obtained 178 mg (yield 29.1%) of the title compound, as an oily substance.

Nuclear Magnetic Resonance Spectrum (CDCl$_3$, 200 MHz), δ ppm: 8.16 (1H, singlet); 7.24–6.94 (3H, multiplet); 3.46 (4H, quartet, J=7.0 Hz); 2.29 (3H, singlet); 1.21–1.00 (6H, broad).

1-(Diethylcarbamoyl)-3-(2-fluoro-5-methylphenylsulfonyl)-4-bromopyrazole (Compound No. 6.119)

Following the procedure of Example 4, there were obtained 147 mg (yield 25.9%) of the title compound, melting at 93°–95° C.

1-(Diethylcarbamoyl)-3-(5-chloro-2-methylphenylthio)-4-bromopyrazole (Compound No. 6.120)

Following the procedure of Example 4, there were obtained 482 mg (yield 39.8%) of the title compound, melting at 74°–76° C.

1-(Diethylcarbamoyl)-3-(5-chloro-2-methylphenylsulfonyl)-4-bromopyrazole (Compound No. 6.121)

Following the procedure of Example 4, there were obtained 359 mg (yield 39.8%) of the title compound, melting at 115°–117° C.

1-(Diethylcarbamoyl)-3-(2,5-dichlorophenylsulfonyl)-4-allylpyrazole (Compound No. 6.126)

Following the procedure of Example 4, there were obtained 41 mg (yield 6.5%) of the title compound, as an oily substance.

Nuclear Magnetic Resonance Spectrum (CDCl$_3$, 200 MHz), δ ppm: 8.11 (1H, doublet, J=2.5 Hz); 7.98 (1H, singlet); 7.41 (1H, doublet of doublets, J=2.5 & 8.5 Hz); 7.28 (1H, doublet, J=8.5 Hz); 5.99–5.83 (1H, multiplet); 5.17–5.08 (2H, multiplet); 3.55–3.27 (6H, multiplet); 1.01 (6H, broad).

1-(Diethylcarbamoyl)-3-(2,5-dichlorophenylthio)-4-cyanopyrazole (Compound No. 6.144)

Following the procedure of Example 6, there were obtained 140 mg (yield 19.4%) of the title compound, melting at 93°–96° C.

1-(Diethylcarbamoyl)-3-(2,5-dichlorophenylsulfonyl)-4-cyanopyrazole (Compound No. 6.145)

Following the procedure of Example 6, there were obtained 50 mg (yield 8.0%) of the title compound, melting at 101°–104° C.

1-(Diethylcarbamoyl)-3-(2-chloro-5-trifluoromethylphenylthio)-4-cyanopyrazole (Compound No. 6.147)

Following the procedure of Example 14, there were obtained 167 mg (yield 22.9%) of the title compound, as an oily substance.

Nuclear Magnetic Resonance Spectrum (CDCl$_3$, 200 MHz), δ ppm: 8.58 (1H, singlet); 7.74 (1H, singlet); 7.63–7.56 (2H, multiplet); 3.47 (4H, quartet, J=7.0 Hz); 1.25–1.00 (6H, multiplet).

1-(Diethylcarbamoyl)-3-(2-chloro-5-trifluoromethylphenylsulfonyl)-4-cyanopyrazole (Compound No. 6.148)

Following the procedure of Example 14, there were obtained 129 mg (yield 18.3%) of the title compound, as an oily substance.

Nuclear Magnetic Resonance Spectrum (CDCl$_3$, 200 MHz), δ ppm: 8.65 (1H, doublet, J=2.0 Hz); 8.62 (1H, singlet); 7.88 (1H, doublet of doublets, J=8.4 & 2.0 Hz); 7.68 (1H, doublet, J=8.4 Hz); 3.46 (4H, quartet, J=7.0 Hz); 1.33–1.07 (6H, multiplet).

Ethyl 1-(diethylcarbamoyl)-3-(2,5-dichlorophenylthio)-pyrazole-4-carboxylate (Compound No. 6.150)

Following the procedure of Example 9, there were obtained 172 mg (yield 16.4%) of the title compound, as an oily substance.

Nuclear Magnetic Resonance Spectrum (CDCl$_3$, 200 MHz), δ ppm: 8.63 (1H, singlet); 7.66 (1H, doublet, J=2.5 Hz); 7.42 (1H, doublet, J=8.5 Hz); 7.29 (1H, doublet of doublets, J=2.5 & 8.5 Hz); 4.35 (2H, quartet, J=7.2 Hz); 3.40 (4H, quartet, J=7.0 Hz); 1.36 (3H, triplet, J=7.2 Hz); 1.30–0.73 (6H, broad).

Ethyl 1-(diethylcarbamoyl)-3-(2,5,dichlorophenylsulfonyl)pyrazole-4-carboxylate (Compound No. 6.151)

Following the procedure of Example 9, there were obtained 149 mg (yield 15.0%) of the title compound, as an oily substance.

Nuclear Magnetic Resonance Spectrum (CDCl$_3$, 200 MHz), δ ppm: 8.68 (1H, singlet); 8.35 (1H, doublet, J=2.5 Hz); 7.55 (1H, doublet of doublets, J=2.5 & 8.5 Hz); 7.43 (1H, doublet, J=8.5 Hz); 4.32 (2H, quartet, J=7.0 Hz); 3.47 (4H, quartet, J=7.0 Hz); 1.34 (3H, triplet, J=7.0 Hz); 1.32–1.17 (3H, broad); 1.12–0.96 (3H, broad).

1-(Diethylcarbamoyl)-3-(2,5-dichlorophenylthio)-4-methylthiopyrazole (Compound No. 6.159)

Following the procedure of Example 9, there were obtained 128 mg (yield 13.8%) of the title compound, as an oily substance.

Nuclear Magnetic Resonance Spectrum (CDCl$_3$, 200 MHz), δ ppm: 8.15 (1H, singlet); 7.33 (1H, doublet, J=9.1 Hz); 7.16–7.11 (2H, multiplet); 3.54 (4H, quartet, J=6.8 Hz); 2.36 (3H, singlet); 1.19 (6H, triplet, J=6.8 Hz).

1-(Diethylcarbamoyl)-3-(2,5-dichlorophenylsulfonyl)-4-methylsulfonylpyrazole (Compound No. 6.160)

Following the procedure of Example 9, there were obtained 88 mg (yield 10.8%) of the title compound, melting at 55°–60° C.

1-(Diethylcarbamoyl)-3-(2-chloro-5-methoxyphenylsulfonyl)-4-fluoropyrazole (Compound No. 6.172)

Following the procedure of Example 19, there were obtained 22 mg (yield 3.4%) of the title compound, as an oily substance.

Nuclear Magnetic Resonance Spectrum CDCl$_3$, 200 MHz), δ ppm: 8.06 (1H, doublet, J=5.1 Hz); 7.31–7.26 (1H, multiplet); 6.74–6.69 (2H, multiplet); 3.72 (3H, singlet); 3.56 (4H, quartet, J=7.0 Hz); 1.22 (6H, triplet, J=7.0 Hz).

1-(Diethylcarbamoyl)-3-(2-fluoro-5-methylphenylthio)-4-fluoropyrazole (Compound No. 6.173)

Following the procedure of Example 9, there were obtained 39 mg (yield 4.7%) of the title compound, as an oily substance.

Nuclear Magnetic Resonance Spectrum CDCl$_3$, 200 MHz), δ ppm: 7.98 (1H, doublet, J=5.1 Hz); 7.18 (1H, doublet, J=7.5 Hz); 7.09–6.92 (2H, multiplet); 3.52 (4H, quartet, J=7.0 Hz); 2.28 (3H, singlet); 1.18 (6H, triplet, J=7.0 Hz).

1-(Diethylcarbamoyl)-3-(2,6-difluorophenylsulfonyl)-pyrazole (Compound No. 7.1)

Following the procedure of Example 1, there were obtained 97 mg (yield 69.3%) of the title compound, as an oily substance.

Nuclear Magnetic Resonance Spectrum (CDCl$_3$, 200 MHz), δ ppm: 8.21 (1H, doublet, J=2.6 Hz); 7.65–7.51 (1H, multiplet); 7.02 (2H, triplet, J=8.4 Hz); 6.97 (1H, doublet, J=2.6 Hz); 3.49 (4H, quartet, J=7.0 Hz); 1.45–1.05 (6H, broad).

1-(Diethylcarbamoyl)-3-(6-chloro-2-fluorophenylsulfonyl)pyrazole (Compound No. 7.2)

Following the procedure of Example 1, there were obtained 519 mg (yield 86.4%) of the title compound, as an oily substance.

Nuclear Magnetic Resonance Spectrum (CDCl$_3$, 200 MHz), δ ppm: 8.21 (1H, doublet, J=2.5 Hz); 7.55–7.42 (1H, multiplet); 7.34–7.30 (1H, multiplet); 7.19–7.09 (1H, multiplet); 6.98 (1H, doublet, J=2.5 Hz); 3.47 (4H, quartet, J=7.0 Hz); 1.4–1.0 (6H, broad).

1-(Diethylcarbamoyl)-3-(6-chloro-2-fluorophenylthio)-pyrazole (Compound No. 7.3)

Following the procedure of Example 1, there were obtained 1.38 g (yield 87.3%) of the title compound, melting at 30° C.

1-(Diethylcarbamoyl)-3-2,6-dichlorophenylsulfonyl)-pyrazole (Compound No. 7.4)

Following the procedure of Example 1, there were obtained 111 mg (yield 78.6%) of the title compound, as an oily substance.

Nuclear Magnetic Resonance Spectrum (CDCl$_3$, 200 MHz), δ ppm: 8.20 (1H, doublet, J=2.8 Hz); 7.47–7.34 (3H, multiplet); 6.99 (1H, doublet, J=2.8 Hz); 3.43 (4H, quartet, J=7.0 Hz); 1.40–0.88 (6H, broad).

1-(Diethylcarbamoyl)-3-(2,6-dibromophenylsulfonyl)-pyrazole (Compound No. 7.6)

Following the procedure of Example 1, there were obtained 88 mg (yield 93.0%) of the title compound, as an oily substance.

Nuclear Magnetic Resonance Spectrum (CDCl$_3$, 200 MHz), δ ppm: 8.23 (1H, doublet, J=2.7 Hz); 7.76 (2H, doublet, J=8.0 Hz); 7.43 (1H, triplet, J=8.0 Hz); 7.03 (1H, doublet, J=2.7 Hz); 3.44 (4H, quartet, J=7.0 Hz); 1.40–0.90 (6H, broad).

1-(Diethylcarbamoyl)-3-(2,6-dimethylphenylsulfonyl)-pyrazole (Compound No. 7.7)

Following the procedure of Example 1, there were obtained 189 mg (yield 64.9%) of the title compound, melting at 91°-92° C.

1-(Diethylcarbamoyl)-3-(2,6-dimethylphenylthio)-pyrazole (Compound No. 7.9)

Following the procedure of Example 1, there were obtained 134 mg (yield 72.9%) of the title compound, as an oily substance.

Nuclear Magnetic Resonance Spectrum (CDCl$_3$, 200 MHz), δ ppm: 8.04 (1H, doublet, J=2.8 Hz); 7.19–7.10 (3H, multiplet); 5.96 (1H, doublet, J=2.8 Hz); 3.48 (4H, broad quartet, J=7.0 Hz); 2.48 (6H, singlet); 1.11 (6H, broad triplet, J=7.0 Hz).

1-(Diethylcarbamoyl)-3-(2-fluoro-6-methoxyphenylthio)pyrazole (Compound No. 7.13)

Following the procedure of Example 1, there were obtained 769 mg (yield 71.3%) of the title compound, as an oily substance.

Nuclear Magnetic Resonance Spectrum (CDCl$_3$, 200 MHz), δ ppm: 8.04 (1H, doublet, J=2.8 Hz); 7.35 (1H, triplet of doublets, J=8.4 & 6.5 Hz); 6.83–6.73 (2H, multiplet); 6.12 (1H, doublet, J=2.8 Hz); 3.86 (3H, singlet); 3.49 (4H, broad quartet, J=7.0 Hz); 1.12 (3H, broad triplet, J=7.0 Hz).

1-(Diethylcarbamoyl)-3-(2-fluoro-6-methoxyphenylsulfonyl)pyrazole (Compound No. 7.14)

Following the procedure of Example 1, there were obtained 117 mg (yield 71.3%) of the title compound, as an oily substance.

Nuclear Magnetic Resonance Spectrum (CDCl$_3$, 200 MHz), δ ppm: 8.16 (1H, doublet, J=2.6 Hz); 7.50 (1H, triplet of doublets, J=6.0 & 5.8 Hz); 6.93 (1H, doublet, J=2.6 Hz); 6.85–6.73 (2H, multiplet); 3.80 (3H, singlet); 3.48 (4H, broad quartet, J=7.0 Hz); 1.35–1.05 (6H, broad).

1-(Diethylcarbamoyl)-3-(2-methyl-6-isopropylphenylsulfonyl)pyrazole (Compound No. 7.15)

Following the procedure of Example 1, there were obtained 447 mg (yield 69.8%) of the title compound, as an oily substance.

Nuclear Magnetic Resonance Spectrum (CDCl$_3$, 200 MHz), δ ppm: 8.20 (1H, doublet, J=2.6 Hz); 7.45–7.32 (2H, multiplet); 7.14–7.10 (1H, multiplet); 6.87 (1H, doublet, J=2.6 Hz); 4.15 (1H, septet, J=6.7 Hz); 3.44 (4H, quartet, J=7.0 Hz); 2.74 (3H, singlet); 1.14 (6H, doublet, J=6.7 Hz); 1.3–0.9 (6H, broad).

1-(Diethylcarbamoyl)-3-(2-methyl-6-isopropylphenylthio)pyrazole (Compound No. 7.16)

Following the procedure of Example 1, there were obtained 1.00 g (yield 74.3%) of the title compound, as an oily substance.

Nuclear Magnetic Resonance Spectrum (CDCl$_3$, 200 MHz), δ ppm: 8.03 (1H, doublet, J=2.8 Hz); 7.33–7.11 (3H, multiplet); 5.93 (1H, doublet, J=2.8 Hz); 3.81 (1H, septet, J=7.0 Hz); 3.47 (4H, quartet, J=7.0 Hz); 2.45 (3H, singlet); 1.18 (6H, broad).

1-(Diethylcarbamoyl)-3-(2-chloro-6-methylphenylsulfonyl)pyrazole (Compound No. 7.17)

Following the procedure of Example 1, there were obtained 793 mg (yield 42.1%) of the title compound, melting at 83°-83.5° C.

1-(Diethylcarbamoyl)-3-(2-methoxy-6-methylphenylsulfonyl)pyrazole (Compound No. 7.20)

Following the procedure of Example 1, there were obtained 343 mg (yield 32.9%) of the title compound, melting at 93°-94° C.

1-(Diethylcarbamoyl)-3-(2-methoxy-6-methylphenylthio)pyrazole (Compound No. 7.21)

Following the procedure of Example 1, there were obtained 381 mg (yield 34.3%) of the title compound, as an oily substance.

Nuclear Magnetic Resonance Spectrum (CDCl$_3$, 200 MHz), δ ppm: 8.02 (1H, doublet, J=2.6 Hz); 7.27 (1H, triplet, J=8.0 Hz); 6.92 (1H, broad doublet, J=8.0 Hz); 6.80 (1H, broad doublet, J=8.0 Hz); 5.99 (1H, doublet, J=2.6 Hz); 3.83 (3H, singlet); 3.50 (4H, broad quartet, J=7.0 Hz); 2.47 (3H, singlet); 1.12 (6H, triplet, J=7.0 Hz).

1-(Diethylcarbamoyl)-3-(2,6-diethylphenylsulfonyl)pyrazole (Compound No. 7.22)

Following the procedure of Example 1, there were obtained 308 mg (yield 72.0%) of the title compound, as an oily substance.

Nuclear Magnetic Resonance Spectrum (CDCl$_3$, 200 MHz), δ ppm: 8.20 (1H, doublet, J=2.9 Hz); 7.42 (1H, triplet, J=8.1 Hz); 7.20 (2H, doublet, J=7.7 Hz); 6.88 (1H, doublet, J=2.9 Hz); 3.43 (4H, quartet, J=7.0 Hz); 3.08 (4H, quartet, J=7.3 Hz); 1.26 (6H, triplet, J=7.3 Hz); 1.40–0.90 (6H, broad).

1-(Diethylcarbamoyl)-3-(2,6-diethylphenylthio)pyrazole (Compound No. 7.23)

Following the procedure of Example 1, there were obtained 1.21 g (yield 77.4%) of the title compound, as an oily substance.

Nuclear Magnetic Resonance Spectrum (CDCl$_3$, 200 MHz), δ ppm: 8.01 (1H, doublet, J=2.9 Hz); 7.30 (1H, doublet, J=2.0 Hz); 7.18 (1H, singlet); 7.14 (1H, doublet, J=2.0 Hz); 5.93 (1H, doublet, J=2.9 Hz); 3.46 (4H, quartet, J=7.0 Hz); 2.88 (4H, quartet, J=7.4 Hz); 1.17 (6H, triplet, J=7.4 Hz); 1.08 (6H, triplet, J=7.0 Hz).

1-(Diethylcarbamoyl)-3-(2,6-diisopropylphenylsulfonyl)pyrazole (Compound No. 7.24)

Following the procedure of Example 1, there were obtained 20 mg (yield 5.7%) of the title compound, as an oily substance.

Nuclear Magnetic Resonance Spectrum (CDCl$_3$, 200 MHz), δ ppm: 8.22 (1H, doublet, J=2.9 Hz); 8.09–7.89 (1H, multiplet); 7.65–7.30 (2H, multiplet); 6.86 (1H, doublet, J=2.9 Hz); 4.24 (2H, septet, J=6.7 Hz); 3.45 (4H, quartet, J=7.0 Hz); 1.35–0.90 (6H, multiplet); 1.19 (12H, doublet, J=6.7 Hz).

1-(N-Methyl-N-phenylcarbamoyl)-3-(6-ethyl-2-methylphenylthio)pyrazole (Compound No. 7.75)

Following the procedure of Example 1, there were obtained 246 mg (yield 40.5%) of the title compound, as an oily substance.

Nuclear Magnetic Resonance Spectrum (CDCl$_3$, 270 MHz), δ ppm: 7.87 (1H, doublet, J=2.9 Hz); 7.26–7.00 (8H, multiplet); 5.74 (1H, doublet, J=2.9 Hz); 3.47 (3H, singlet); 2.75 (2H, quartet, J=7.5 Hz); 2.25 (3H, singlet); 1.11 (3H, triplet, J=7.5 Hz).

1-(N-Methyl-N-phenylcarbamoyl)-3-(2-ethyl-6-methylphenylsulfonyl)pyrazole (Compound No. 7.76)

Following the procedure of Example 1, there were obtained 224 mg (yield 19.4%) of the title compound, melting at 94°-96° C.

1-(Diethylcarbamoyl)-3-(2-chloro-6-methylphenylsulfonyl)-5-allylpyrazole (Compound No. 7.91)

Following the procedure of Example 15, there were obtained 62 mg (yield 13.8%) of the title compound, as an oily substance.

Nuclear Magnetic Resonance Spectrum (CDCl$_3$, 200 MHz), δ ppm: 7.37–7.32 (1H, multiplet); 7.25–7.18 (2H, multiplet); 5.95–5.74 (1H, multiplet); 5.87 (1H, singlet); 5.14–5.04 (2H, multiplet); 3.56–3.51 (2H, multiplet); 3.33 (4H, broad); 2.52 (3H, singlet); 1.10 (6H, broad).

1-(Diethylcarbamoyl)-3-(2,6-dichlorophenylsulfonyl)-5-(methoxymethyl)pyrazole (Compound No. 7.93)

Following the procedure of Example 15, there were obtained 151 mg (yield 37.3%) of the title compound, melting at 71°–73° C.

1-(Diethylcarbamoyl)-3-(2.6-difluorophenylthio)-5-(methoxymethyl)pyrazole (Compound No. 7.94)

Following the procedure of Example 15, there were obtained 95 mg (yield 52.7%) of the title compound, as an oily substance.

Nuclear Magnetic Resonance Spectrum (CDCl$_3$, 200 MHz), δ ppm: 7.39–7.28 (1H, multiplet); 6.97 (2H, doublet of doublets, J=8.4 & 6.6 Hz); 6.23 (1H, singlet); 4.61 (2H, singlet); 3.45–3.25 (4H, broad); 3.39 (3H, singlet); 1.30–0.98 (6H, broad).

1-(Diethylcarbamoyl)-3-(2,6-difluorophenylsulfonyl)-5-(methoxyethyl)pyrazole (Compound No. 7.95)

Following the procedure of Example 15, there were obtained 69 mg (yield 38.4%) of the title compound, as an oily substance.

Nuclear Magnetic Resonance Spectrum (CDCl$_3$, 200 MHz), δ ppm: 7.63–7.49 (1H, multiplet); 7.00 (2H, triplet, J=8.4 Hz); 6.94 (1H, singlet); 4.64 (2H, singlet); 3.46 (2H, quartet, J=7.0 Hz); 3.41 (3H, singlet); 3.21 (2H, quartet, J=6.9 Hz); 1.26 (3H, triplet, J=6.9 Hz); 1.12 (3H, triplet, J=7.0 Hz).

1-(Diethylcarbamoyl): 3-(2-ethyl-6-methylphenylthio)-5-(methylthio)pyrazole (Compound No. 7.96)

Following the procedure of Example 15, there were obtained 65 mg (yield 27.6%) of the title compound, as an oily substance.

Nuclear Magnetic Resonance Spectrum (CDCl$_3$, 200 MHz), δ ppm: 7.24–7.11 (3H, multiplet); 5.72 (1H, singlet); 3.38 (4H, quartet, J=7.0 Hz); 2.90 (2H, quartet, J=7.5 Hz); 2.45 (3H, singlet); 2.35 (3H, singlet); 1.19 (3H, triplet, J=7.5 Hz); 1.2–1.0 (6H, multiplet).

1-(Diethylcarbamoyl)-3-(2-chloro-6-methylphenylsulfonyl)-5-(ethylsulfonyl)pyrazole (Compound No. 7.97)

Following the procedure of Example 15, there were obtained 144 mg (yield 42.8%) of the title compound, melting at 92°–93.5° C.

1-(Diethylcarbamoyl)-3-(2-chloro-6-methylphenylthio)-5-(ethylthio)pyrazole (Compound No. 7.98)

Following the procedure of Example 15, there were obtained 55 mg (yield 53.5%) of the title compound, as an oily substance.

Nuclear Magnetic Resonance Spectrum (CDCl$_3$, 200 MHz), δ ppm: 7.35–7.33 (1H, multiplet); 7.26–7.19 (2H, multiplet); 5.94 (1H, singlet); 3.36 (4H, quartet, J=7.3 Hz); 2.85 (2H, quartet, J=7.3 Hz); 2.52 (3H, singlet); 1.31 (3H, triplet, J=7.3 Hz); 1.20–0.97 (6H, broad).

1-(Diethylcarbamoyl)-3-(2-ethyl-6-methylphenylsulfonyl)-5-cyanopyrazole (Compound No. 7.99)

Following the procedure of Example 16, there were obtained 72 mg (yield 14.6%) of the title compound, as an oily substance.

Nuclear Magnetic Resonance Spectrum (CDCl$_3$, 200 MHz) δ ppm: 7.42 (1H, singlet); 7.42 (1H, doublet of doublets, J=7.6 & 7.3 Hz); 7.23 (1H, doublet, J=7.6 Hz); 7.17 (1H, doublet, J=7.3 Hz); 3.53–3.22 (4H, broad); 3.08 (2H, quartet, J=7.4 Hz); 2.66 (3H, singlet); 1.29 (3H, triplet, J=7.4 Hz); 1.40–0.95 (6H, broad).

1-(Diethylcarbamoyl)-3-(2-chloro-6-methylphenylsulfonyl)-5-cyanopyrazole (Compound No. 7.100)

Following the procedure of Example 15, there were obtained 130 mg (yield 28.7%) of the title compound, melting at 92°–93° C.

1-(Diethylcarbamoyl)-3-(2-ethyl-6-methylphenylsulfonyl)-5-chloropyrazole (Compound No. 7.103)

Following the procedure of Example 16, there were obtained 72 mg (yield 14.6%) of the title compound, as an oily substance.

Nuclear Magnetic Resonance Spectrum (CDCl$_3$, 200 MHz), δ ppm: 7.38 (1H, triplet, J=6.6 Hz); 7.17 (2H, doublet, J=6.6 Hz); 6.79 (1H, singlet); 3.47 (2H, quartet, J=7.3 Hz); 3.10 (4H, broad quartet, J=7.4 Hz); 2.67 (3H, singlet); 1.28 (3H, triplet, J=7.3 Hz); 1.26 (3H, triplet, J=7.4 Hz); 1.03 (3H, triplet, J=7.3 Hz).

1-(Diethylcarbamoyl)-3-(2,6-dimethylphenylsulfonyl)-4-fluoropyrazole (Compound No. 7.112)

Following the procedure of Example 7, there were obtained 31 mg (yield 6.1%) of the title compound, as an oily substance.

Nuclear Magnetic Resonance Spectrum (CDCl$_3$, 200 MHz), δ ppm: 8.02 (1H, doublet, J=4.5 Hz); 7.35–7.31 (1H, multiplet); 7.16 (2H, doublet, J=7.1 Hz); 3.48 (4H, quartet, J=7.0 Hz); 2.71 (6H, singlet); 1.03–1.08 (6H, broad).

1-(Diethylcarbamoyl)-3-(2-ethyl-6-methylphenylsulfonyl)-4-fluoropyrazole (Compound No. 7.113)

Following the procedure of Example 7, there were obtained 12 mg (yield 3.5%) of the title compound, as an oily substance.

Nuclear Magnetic Resonance Spectrum (CDCl$_3$, 200 MHz), δ ppm: 8.02 (1H, doublet, J=4.7 Hz); 7.40 (1H, triplet, J=7.6 Hz); 7.22 (1H, doublet, J=7.6 Hz); 7.15 (1H, doublet, J=7.6 Hz); 3.46 (4H, quartet, J=7.0 Hz); 3.13 (2H, quartet, J=7.4 Hz); 2.70 (3H, singlet); 1.31–1.08 (9H, multiplet). 1-(Diethylcarbamoyl)-3-(2,6-diethylphenylsulfonyl)-4-fluoropyrazole (Compound No. 7.114)

Following the procedure of Example 7, there were obtained 14 mg (yield 1.9%) of the title compound, as an oily substance.

Nuclear Magnetic Resonance Spectrum (CDCl$_3$, 200 MHz), δ ppm: 8.02 (1H, doublet, J=4.7 Hz); 7.48–7.41 (1H, multiplet); 7.21 (2H, doublet, J=7.6 Hz); 3.45 (4H, quartet, J=7.0 Hz); 3.11 (4H, quartet, J=7.3 Hz); 1.27 (6H, triplet, J=7.3 Hz); 1.35–1.03 (6H, broad).

1-(Diethylcarbamoyl)-3-(2-chloro-6-methylphenylsulfonyl)-4-fluoropyrazole (Compound No. 7.115)

Following the procedure of Example 7, there were obtained 44 mg (yield 11.1%) of the title compound, as an oily substance.

Nuclear Magnetic Resonance Spectrum (CDCl$_3$, 200 MHz), δ ppm: 8.01 (1H, doublet, J=4.7 Hz); 7.43–7.23 (3H, multiplet); 3.48–3.38 (4H, multiplet); 2.83 (3H, singlet); 1.35–0.9 (6H, multiplet).

1-(Diethylcarbamoyl)-3-(2,6-difluorophenylsulfonyl)-4-fluoropyrazole (Compound No. 7.119)

Following the procedure of Example 19, there were obtained 32 mg (yield 2.9%) of the title compound, as an oily substance.

Nuclear Magnetic Resonance Spectrum CDCl$_3$, 200 MHz), δ ppm: 8.04 (1H, doublet, J=4.7 Hz); 7.65–7.54 (1H, multiplet); 7.10–6.99 (2H, multiplet); 3.50 (4H, broad ); 1.22 (6H, triplet, J=6.9 Hz).

1-(Diethylcarbamoyl)-3-(2-methyl-6-methoxyphenylsulfonyl)-4-fluoropyrazole (Compound No. 7.120)

Following the procedure of Example 7, there were obtained 20 mg (yield 2.6%) of the title compound, as an oily substance.

Nuclear Magnetic Resonance Spectrum CDCl$_3$, 200 MHz), δ ppm: 7.98 (1H, doublet, J=4.8 Hz); 7.40 (1H, triplet, J=8.0 Hz); 6.89 (1H, doublet, J=8.0 Hz); 6.81

(1H, doublet, J=8.0 Hz); 3.78 (3H, singlet); 3.47 (4H, quartet, J=7.0 Hz); 2.79 (3H, singlet); 1.19 (6H, triplet, J=7.0 Hz).

1-(Diethylcarbamoyl)-3-(2-chloro-6-fluorophenylsulfonyl)-4-fluoropyrazole (Compound No. 7.121)

Following the procedure of Example 19, there were obtained 44 mg (yield 4.6%) of the title compound, as an oily substance.

Nuclear Magnetic Resonance Spectrum CDCl$_3$, 200 MHz), δ ppm: 8.04 (1H, doublet, J=4.7 Hz); 7.58–7.44 (1H, multiplet); 7.36–7.11 (2H, multiplet); 3.48 (4H, quartet, J=6.8 Hz); 1.25 (6H, broad).

1-(Diethylcarbamoyl)-3-(2-isopropyl-6-methylphenylsulfonyl)-4-fluoropyrazole (Compound No. 7.122)

Following the procedure of Example 19, there were obtained 47 mg (yield 4.4%) of the title compound, melting at 85°–86° C.

1-(Dimethylcarbamoyl)-3-(2,6-dimethylphenylsulfonyl)-4-fluoropyrazole (Compound No. 7.126)

Following the procedure of Example 7, there were obtained 24 mg (yield 14.5%) of the title compound, as an oily substance.

Nuclear Magnetic Resonance Spectrum CDCl$_3$, 200 MHz), δ ppm: 7.99 (1H, doublet, J=4.7 Hz); 7.34 (1H, triplet, J=7.0 Hz); 7.15 (2H, doublet, J=7.0 Hz); 3.30–3.08 (6H, broad); 2.72 (6H, singlet).

1(N-Ethyl-N-propylcarbamoyl)-3-(2,6-dimethylphenylsulfonyl)-4-fluoropyrazole (Compound No. 7.142)

Following the procedure of Example 7, there were obtained 22 mg (yield 11.9%) of the title compound, melting at 68°–70° C.

1-(Dipropylcarbamoyl)-3-(2,6-dimethylphenylsulfonyl)-4-fluoropyrazole (Compound No. 7.150)

Following the procedure of Example 7, there were obtained 15 mg (yield 5.8%) of the title compound, melting at 66°–67° C.

1-(Diethylcarbamoyl)-3-(2,6-dimethylphenylthio)-4-chloropyrazole (Compound No. 7.166)

Following the procedure of Example 4, there were obtained 188 mg (yield 30.3%) of the title compound, melting at 95°–96° C.

1-(Diethylcarbamoyl)-3-(2,6-dimethylphenylsulfonyl)-4-chloropyrazole (Compound No. 7.167)

Following the procedure of Example 4, there were obtained 169 mg (yield 27.5%) of the title compound, melting at 78°–78.5° C.

1-(Diethylcarbamoyl)-3-(2-chloro-6-methylphenylthio)-4-chloropyrazole (Compound No. 7.172)

Following the procedure of Example 5, there were obtained 180 mg (yield 54.6%) of the title compound, melting at 85°–87° C.

1-(Diethylcarbamoyl)-3-(2-chloro-6-methylphenylsulfonyl)-4-chloropyrazole (Compound No. 7.173)

Following the procedure of Example 5, there were obtained 94 mg (yield 32.7%) of the title compound, melting at 88°–89° C.

1-(Dimethylcarbamoyl)-3-(2-methoxy-6-methylphenylthio)-4-chloropyrazole (Compound No. 7.174)

Following the procedure of Example 3, there were obtained 216 mg (yield 52.3%) of the title compound, as an oily substance.

Nuclear Magnetic Resonance Spectrum (CDCl$_3$, 200 MHz), δ ppm: 8.01 (1H, singlet); 7.25 (1H, triplet, J=8.0 Hz); 6.71 (1H, broad doublet, J=8.0 Hz); 6.76 (1H, broad doublet, J=8.0 Hz); 3.78 (3H, singlet); 3.05 (6H, singlet); 2.48 (3H, singlet).

1-(Dimethylcarbamoyl)-3-(2-methoxy-6-methylphenylsulfonyl)-4-chloropyrazole (Compound No. 7.175)

Following the procedure of Example 3, there were obtained 158 mg (yield 47.6%) of the title compound, melting at 116°–117° C.

1-(N-Ethyl-N-methylcarbamoyl)-3-(2-methoxy-6-methylphenylthio)-4-chloropyrazole (Compound No. 7.176)

Following the procedure of Example 3, there were obtained 227 mg (yield 50.2%) of the title compound, melting at 68°–71° C.

1(N-Ethyl-N-methylcarbamoyl)-3-(2-methoxy-6-methylphenylsulfonyl)-4-chloropyrazole (Compound No. 7.177)

Following the procedure of Example 3, there were obtained 179 mg (yield 50.2%) of the title compound, as an oily substance.

Nuclear Magnetic Resonance Spectrum (CDCl$_3$, 200 MHz), δ ppm: 8.09 (1H, singlet); 7.41 (1H, broad triplet, J=8.0 Hz); 6.90 (1H, broad doublet, J=8.0 Hz); 6.80 (1H, broad doublet, J=8.0 Hz); 3.71 (3H, singlet); 3.54 (2H, broad quartet, J=7.2 Hz); 3.11 (3H, broad ); 2.81 (3H, singlet); 1.23 (3H, broad).

1-(Diethylcarbamoyl)-3-(2-methoxy-6-methylphenylthio)-4-chloropyrazole (Compound No. 7.178)

Following the procedure of Example 3, there were obtained 706 mg (yield 41.8%) of the title compound, melting at 90°–91.5° C.

1-(Diethylcarbamoyl)-3-(2-methoxy-6-methylphenylsulfonyl)-4-chloropyrazole (Compound No. 7.179)

Following the procedure of Example 3, there were obtained 157 mg (yield 41.3%) of the title compound, melting at 93°–94° C.

1(N-Ethyl-N-propylcarbamoyl)-3-(2-methoxy-6-methylphenylthio)-4-chloropyrazole (Compound No. 7.181)

Following the procedure of Example 3, there were obtained 230 mg (yield 49.6%) of the title compound, melting at 90°–92° C.

1-(N-Ethyl-N-propylcarbamoyl)-3-(2-methoxy-6-methylphenylsulfonyl)-4-chloropyrazole (Compound No. 7.182)

Following the procedure of Example 3, there were obtained 193 mg (yield 49.6%) of the title compound, melting at 113°–115° C.

1-(Dipropylcarbamoyl)-3-(2-methoxy-6-methylphenylthio)-4-chloropyrazole (Compound No. 7.183)

Following the procedure of Example 3, there were obtained 246 mg (yield 50.2%) of the title compound, melting at 92°–94° C.

1-(Dipropylcarbamoyl)-3-(2-methoxy-6-methylphenylsulfonyl)-4-chloropyrazole (Compound No. 7.184)

Following the procedure of Example 3, there were obtained 208 mg (yield 50.2%) of the title compound, melting at 93°–96° C.

1(N-Butyl-N-methylcarbamoyl)-3-(2-methoxy-6-methyl-phenylthio)-4-chloropyrazole (Compound No. 7.185)

Following the procedure of Example 3, there were obtained 232 mg (yield 50.2%) of the title compound, as an oily substance.

Nuclear Magnetic Resonance Spectrum (CDCl$_3$, 200 MHz), δ ppm: 8.03 (1H, singlet); 7.25 (1H, triplet, J=8.0 Hz); 6.89 (1H, broad doublet, J=8.0 Hz); 6.76 (1H, broad doublet, J=8.0 Hz); 3.79 (3H, singlet); 3.47 (3H, singlet); 3.41 (2H, broad triplet, J=7.5 Hz); 3.01 (3H, singlet); 1.45 (2H, broad); 1.15 (2H, broad); 0.85 (3H, broad triplet, J=6.6 Hz).

1(N-Butyl-N-methylcarbamoyl)-3-(2-methoxy-6-methylphenylsulfonyl)-4-chloropyrazole (Compound No. 7.186)

Following the procedure of Example 3, there were obtained 182 mg (yield 50.2%) of the title compound, as an oily substance.

Nuclear Magnetic Resonance Spectrum (CDCl$_3$, 200 MHz), δ ppm: 8.09 (1H, singlet); 7.41 (1H, triplet, J=8.0 Hz); 6.90 (1H, broad doublet, J=8.0 Hz); 6.80 (1H, broad doublet, J=8.0 Hz); 3.70 (3H, singlet); 3.48 (2H, broad triplet, J=7.2 Hz); 3.14 (3H, broad); 2.80 (3H, singlet); 1.60 (2H, broad); 1.25 (2H, broad); 0.91 (3H, broad).

1-(Diethylcarbamoyl)-3-(2-chloro-6-fluorophenylthio)-4-chloropyrazole (Compound No. 7.187)

Following the procedure of Example 4, there were obtained 132 mg (yield 61.1%) of the title compound, melting at 72°-73° C.

1-(Diethylcarbamoyl)-3-(2-chloro-6-fluorophenylsulfonyl)-4-chloropyrazole (Compound No. 7.188)

Following the procedure of Example 4, there were obtained 121 mg (yield 60.5%) of the title compound, melting at 90°-91° C.

1-(Diethylcarbamoyl)-3-(2,6-difluorophenylthio)-4-chloropyrazole (Compound No. 7.189)

Following the procedure of Example 3, there were obtained 333 mg (yield 30.0%) of the title compound, melting at 56°-57° C.

1-(Diethylcarbamoyl)-3-(2,6-difluorophenylsulfonyl)-4-chloropyrazole (Compound No. 7.190)

Following the procedure of Example 3, there were obtained 291 mg (yield 27.9%) of the title compound, as an oily substance.

Nuclear Magnetic Resonance Spectrum (CDCl$_3$, 200 MHz), δ ppm: 8.17 (1H, singlet); 7.66-7.55 (1H, multiplet); 7.10-7.00 (2H, multiplet); 3.51 (4H, quartet, J=7.0 Hz); 1.30-1.19 (6H, broad).

1-(Diethylcarbamoyl)-3-(2-fluoro-6-methoxyphenylsulfonyl)-4-chloropyrazole (Compound No. 7.191)

Following the procedure of Example 3, there were obtained 55 mg (yield 56.4%) of the title compound, melting at 102°-103° C.

1-(Diethylcarbamoyl)-3-(2,6-dimethylphenylsulfonyl)-4-bromopyrazole (Compound No. 7.211)

Following the procedure of Example 4, there were obtained 548 mg (yield 19.7%) of the title compound, melting at 70°-72° C.

1-(Diethylcarbamoyl)-3-(2,6-dimethylphenylthio)-4-bromopyrazole (Compound No. 7.212)

Following the procedure of Example 4, there were obtained 677 mg (yield 24.1%) of the title compound, melting at 103°-105° C.

1-(Diethylcarbamoyl)-3-(2-ethyl-6-methylphenylsulfonyl)-4-bromopyrazole (Compound No. 7.213)

Following the procedure of Example 4, there were obtained 129 mg (yield 20.7%) of the title compound, melting at 63°-64° C.

1-(Diethylcarbamoyl)-3-(2-chloro-6-methylphenylsulfonyl)-4-bromopyrazole (Compound No. 7.215)

Following the procedure of Example 4, there were obtained 1.73 g (yield 26.9%) of the title compound, melting at 99°-100° C.

1-(Diethylcarbamoyl)-3-(2-chloro-6-methylphenylthio)-4-bromopyrazole (Compound No. 7.216)

Following the procedure of Example 4, there were obtained 2.11 g (yield 34.0%) of the title compound, melting at 96°-99° C.

1-(Diethylcarbamoyl)-3-(2-chloro-6-fluorophenylthio)-4-bromopyrazole (Compound No. 7.217)

Following the procedure of Example 4, there were obtained 143 mg (yield 30.4%) of the title compound, melting at 82°-83° C.

1-(Diethylcarbamoyl)-3-(2-chloro-6-fluorophenylsulfonyl)-4-bromopyrazole (Compound No. 7.218)

Following the procedure of Example 4, there were obtained 93 mg (yield 27.3%) of the title compound, melting at 108°-109° C.

1-(Diethylcarbamoyl)-3-(2-methoxy-6-methylphenylthio)-4-bromopyrazole (Compound No. 7.219)

Following the procedure of Example 5, there were obtained 882 mg (yield 46.1%) of the title compound, melting at 88°-92° C.

1-(Diethylcarbamoyl)-3-(2-methoxy-6-methylphenylsulfonyl)-4-bromopyrazole (Compound No. 7.220)

Following the procedure of Example 5, there were obtained 180 mg (yield 46.1%) of the title compound, melting at 142°-146° C.

1-(Diethylcarbamoyl)-3-(2,6-difluorophenylsulfonyl)-4-bromopyrazole (Compound No. 7.221)

Following the procedure of Example 3, there were obtained 79 mg (yield 7.6%) of the title compound, as an oily substance.

Nuclear Magnetic Resonance Spectrum (CDCl$_3$, 200 MHz), δ ppm: 8.21 (1H, singlet); 7.68-7.48 (1H, multiplet); 7.09-7.01 (2H, multiplet); 3.51 (4H, quartet, J=7.0 Hz); 1.29-1.13 (6H, broad).

1-(Diethylcarbamoyl)-3-(2-isopropyl-6-methylphenylthio)-4-iodopyrazole (Compound No. 7.222)

Following the procedure of Example 4, there were obtained 265 mg (yield 88.4%) of the title compound, as an oily substance.

Nuclear Magnetic Resonance Spectrum (CDCl$_3$, 200 MHz), δ ppm: 8.16 (1H, singlet); 7.32-7.10 (3H, multiplet); 3.74 (1H, septet, J=6.9 Hz); 3.28 (4H, quartet, J=7.0 Hz); 2.41 (3H, singlet); 1.18 (6H, doublet, J=6.9 Hz); 1.2-0.6 (6H, broad).

1-(Diethylcarbamoyl)-3-(2-isopropyl-6-methylphenylsulfonyl)-4-iodopyrazole (Compound No. 7.223)

Following the procedure of Example 4, there were obtained 1.06 g (yield 76.0%) of the title compound, as an oily substance.

Nuclear Magnetic Resonance Spectrum (CDCl$_3$, 200 MHz), δ ppm: 8.25 (1H, singlet); 7.48-7.32 (2H, multiplet); 7.13 (1H, doublet, J=8.0 Hz); 4.01 (1H, septet, J=6.8 Hz); 3.42 (4H, quartet, J=7.0 Hz); 2.75 (3H, singlet); 1.10 (6H, doublet, J=6.8 Hz); 1.4-0.8 (6H, broad).

1-(Diethylcarbamoyl)-3-(2-ethyl-6-methylphenylsulfonyl)-4-methylpyrazole (Compound No. 7.231)

Following the procedure of Example 14, there were obtained 53 mg (yield 6.1%) of the title compound, as an oily substance.

Nuclear Magnetic Resonance Spectrum (CDCl$_3$, 200 MHz), δ ppm: 7.96 (1H, broad quartet, J=1.0 Hz); 7.38 (1H, triplet, J=7.6 Hz); 7.21-7.11 (2H, multiplet); 3.37 (4H, quartet, J=7.0 Hz); 3.07 (2H, quartet, J=7.4 Hz); 2.62 (3H, singlet); 2.32 (3H, doublet, J=1.0 Hz); 1.24 (3H, triplet, J=7.4 Hz); 0.87 (6H, broad).

1-(Diethylcarbamoyl)-3-(2-ethyl-6-methylphenylsulfonyl)-4-ethylpyrazole (Compound No. 7.234)

Following the procedure of Example 14, there were obtained 197 mg (yield 24.2%) of the title compound, as an oily substance.

Nuclear Magnetic Resonance Spectrum (CDCl$_3$, 200 MHz), δ ppm: 7.99 (1H, triplet, J=1.0 Hz); 7.38 (1H, triplet, J=7.8 Hz); 7.21–7.11 (2H, multiplet); 3.36 (4H, broad quartet, J=7.0 Hz); 3.06 (2H, quartet, J=7.4 Hz); 2.80 (2H, doublet of quartets, J=1.0 & 7.5 Hz); 2.60 (3H, singlet); 1.30–1.20 (6H, multiplet); 0.85 (6H, broad).

1-(Diethylcarbamoyl)-3-(2-chloro-6-methylphenylsulfonyl)-4-allylpyrazole (Compound No. 7.235)

Following the procedure of Example 14, there were obtained 70 mg (yield 13.2%) of the title compound, as an oily substance.

Nuclear Magnetic Resonance Spectrum (CDCl$_3$, 200 MHz), δ ppm: 7.96 (1H, singlet); 7.35 (1H, doublet, J=6.3 Hz); 7.34 (1H, triplet, J=6.3 Hz); 7.24 (1H, doublet, J=6.3 Hz); 6.05–5.91 (1H, multiplet); 5.30–5.10 (2H, multiplet); 3.57 (2H, doublet, J=6.7 Hz); 3.36 (4H, quartet, J=6.7 Hz); 2.82 (3H, singlet); 1.13 (3H, broad); 0.89 (3H, broad).

1-(Diethylcarbamoyl)-3-(2,6-diethylphenylsulfonyl)-4-allylpyrazole (Compound No. 7.236)

Following the procedure of Example 14, there were obtained 69 mg (yield 12.4%) of the title compound, as an oily substance.

Nuclear Magnetic Resonance Spectrum (CDCl$_3$, 200 MHz), δ ppm: 7.98 (1H, singlet); 7.43 (1H, triplet, J=7.7 Hz); 7.19 (2H, doublet, J=7.7 Hz); 6.05–5.91 (1H, multiplet); 5.30–5.10 (2H, multiplet); 3.56 (2H, doublet, J=6.9 Hz); 3.34 (4H, quartet, J=6.9 Hz); 3.03 (4H, quartet, J=7.4 Hz); 1.23 (6H, triplet, J=6.9 Hz); 1.10 (6H, broad).

1-(Diethylcarbamoyl)-3-(2-ethyl-6-methylphenylsulfonyl)-4-allylpyrazole (Compound No. 7.237)

Following the procedure of Example 14, there were obtained 42 mg (yield 10.4%) of the title compound, as an oily substance.

Nuclear Magnetic Resonance Spectrum (CDCl$_3$, 200 MHz), δ ppm: 7.98 (1H, singlet); 7.38 (1H, triplet, J=7.5 Hz); 7.19 (1H, doublet, J=7.5 Hz); 7.12 (1H, doublet, J=7.5 Hz); 6.09–5.90 (1H, multiplet); 5.20–5.09 (2H, multiplet); 3.53 (2H, doublet, J=6.4 Hz); 3.35 (4H, quartet, J=7.7 Hz); 3.06 (2H, quartet, J=7.3 Hz); 1.23 (3H, triplet, J=7.3 Hz); 0.96 (6H, broad).

1-(Diethylcarbamoyl)-3-(2-ethyl-6-methylphenylsulfonyl)-4-(methoxymethyl)pyrazole (Compound No. 7.241)

Following the procedure of Example 14, there were obtained 23 mg (yield 12.0%) of the title compound, as an oily substance.

Nuclear Magnetic Resonance Spectrum (CDCl$_3$, 200 MHz), δ ppm: 8.19 (1, singlet); 7.39 (1H, triplet, J=7.7 Hz); 7.17 (2H, doublet, J=7.7 Hz); 4.67 (2H, singlet); 3.43 (3H, singlet); 3.36 (4H, quartet, J=7.0 Hz); 3.07 (2H, quartet, J=7.4 Hz); 2.61 (3H, singlet); 1.24 (3H, triplet, J=7.4 Hz); 1.05–0.70 (6H, broad).

1-(Diethylcarbamoyl)-3-(2,6-diethylphenylthio)-4-cyanopyrazole (Compound No. 7.254)

Following the procedure of Example 14, there were obtained 134 mg (yield 30.3%) of the title compound, melting at 50°–51° C.

1-(Diethylcarbamoyl)-3-(2,6-diethylphenylsulfonyl)-4-cyanopyrazole (Compound No. 7.255)

Following the procedure of Example 14, there were obtained 117 mg (yield 28.2%) of the title compound, melting at 79°–80° C.

1-(Diethylcarbamoyl)-3-(2-chloro-6-methylphenylthio)-4-cyanopyrazole (Compound No. 7.256)

Following the procedure of Example 14, there were obtained 127 mg (yield 29.3%) of the title compound, melting at 82°–85° C.

1-(Diethylcarbamoyl)-3-(2-chloro-6-methylphenylsulfonyl)-4-cyanopyrazole (Compound No. 7.257)

Following the procedure of Example 14, there were obtained 105 mg (yield 27.9%) of the title compound, melting at. 120°–123° C.

Ethyl 1-(diethylcarbamoyl)-3-(2-ethyl-6-methylphenylthio)pyrazole-4-carboxylate (Compound No. 7.262)

Following the procedure of Example 14, there were obtained 137 mg (yield 20.9%) of the title compound, as an oily substance.

Nuclear Magnetic Resonance Spectrum (CDCl$_3$, 200 MHz), δ ppm: 8.60 (1H, singlet); 7.23–7.10 (3H, multiplet); 4.37 (2H, quartet, J=7.0 Hz); 3.50–3.18 (4H, broad); 2.86 (2H, quartet, J=7.4 Hz); 2.43 (3H, singlet); 1.39 (3H, triplet, J=7.0 Hz); 1.15 (6H, triplet, J=7.4 Hz); 0.70–0.50 (3H, broad).

Ethyl 1-(diethylcarbamoyl)-3-(2-ethyl-6-methylphenylsulfonyl)pyrazole-4-carboxylate (Compound No. 7.263)

Following the procedure of Example 14, there were obtained 122 mg (yield 19.5%) of the title compound, as an oily substance.

Nuclear Magnetic Resonance Spectrum (CDCl$_3$, 200 MHz), δ ppm: 8.70 (1H, singlet); 7.39 (1H, triplet, J=7.6 Hz); 7.22–7.12 (2H, multiplet); 4.35 (2H, quartet, J=7.1 Hz); 3.48–3.24 (4H, broad); 3.02 (2H, quartet, J=7.4 Hz); 2.60 (3H, singlet); 1.36 (3H, triplet, J=7.1 Hz); 1.22 (3H, triplet, J=7.4 Hz); 1.27–1.13 (3H, broad); 0.82–0.65 (3H, broad).

Ethyl 1-(diethylcarbamoyl)-3-(2,6-diethylphenylthio)pyrazole-4-carboxylate (Compound No. 7.264)

Following the procedure of Example 14, there were obtained 259 mg (yield 43.7%) of the title compound, as an oily substance.

Nuclear Magnetic Resonance Spectrum (CDCl$_3$, 200 MHz), δ ppm: 8.60 (1H, singlet); 7.31–7.13 (3H, multiplet); 4.37 (2H, quartet, J=7.0 Hz); 3.37–3.18 (4H, broad); 2.84 (4H, quartet, J=7.6 Hz); 1.39 (3H, triplet, J=7.0 Hz); 1.16 (6H, triplet, J=7.6 Hz); 0.65–0.40 (6H, broad).

Ethyl 1-(diethylcarbamoyl)-3-(2,6-diethylphenylsulfonyl)pyrazole-4-carboxylate (Compound No. 7.265)

Following the procedure of Example 14, there were obtained 138 mg (yield 38.1%) of the title compound, melting at 87°–88° C.

Ethyl 1-(diethylcarbamoyl)-3-(2-chloro-6-methylphenylthio)pyrazole-4-carboxylate (Compound No. 7.266)

Following the procedure of Example 14, there were obtained 210 mg (yield 35.8%) of the title compound, melting at 103°–105° C.

Ethyl 1-(diethylcarbamoyl)-3-(2-chloro-6-methylphenyl sulfonyl)pyrazole-4-carboxylate (Compound No. 7.267)

Following the procedure of Example 14, there were obtained 186 mg (yield 32.2%) of the title compound, as an oily substance.

Nuclear Magnetic Resonance Spectrum (CDCl$_3$, 200 MHz), δ ppm: 8.67 (1H, singlet); 7.42–7.24 (3H, multiplet); 4.28 (2H, quartet, J=7.1 Hz); 3.45 (4H, quartet, J=7.0 Hz); 2.83 (3H, singlet); 1.31 (3H, triplet, J=7.1 Hz); 1.32–1.13 (3H, broad); 1.08–0.88 (3H, broad).

1-(Diethylcarbamoyl)-3-(2,6-diethylphenylthio)-4-methylthiopyrazole (Compound No. 7.268)

Following the procedure of Example 14, there were obtained 235 mg (yield 45.1%) of the title compound, as an oily substance.

Nuclear Magnetic Resonance Spectrum (CDCl$_3$, 200 MHz), δ ppm: 8.09 (1H, singlet); 7.27–7.13 (3H, multiplet); 3.29 (4H, quartet, J=6.7 Hz); 2.40 (3H, singlet); 2.85 (4H, quartet, J=7.4 Hz); 1.17 (6H, triplet, J=7.4 Hz); 1.10–0.50 (6H, broad).

1-(Diethylcarbamoyl)-3-(2-ethyl-6-methylphenylthio)-4-methylthiopyrazole (Compound No. 7.269)

Following the procedure of Example 14, there were obtained 144 mg (yield 21.3%) of the title compound, as an oily substance.

Nuclear Magnetic Resonance Spectrum (CDCl$_3$, 200 MHz), δ ppm: 8.09 (1H, singlet); 7.26–7.10 (3H, multiplet); 3.30 (4H, quartet, J=6.9 Hz); 2.88 (2H, quartet, J=7.4 Hz); 2.43 (3H, singlet); 2.39 (3H, singlet); 1.17 (3H, triplet, J=7.4 Hz); 1.12–0.84 (6H, broad).

1-(Diethylcarbamoyl)-3-(2-chloro-6-methylphenylthio)-4-methylthiopyrazole (Compound No. 7.270)

Following the procedure of Example 14, there were obtained 206 mg (yield 41.6%) of the title compound, melting at 75°–78° C.

1-(Diethylcarbamoyl)-3-(2,6-diethylphenylsulfonyl)-4methylsulfonylpyrazole (Compound No. 7.271)

Following the procedure of Example 14, there were obtained 206 mg (yield 39.7%) of the title compound, melting at 183°–187° C.

1-(Diethylcarbamoyl)-3-(2-ethyl-6-methylphenylsulfonyl)-4-methylsulfonylpyrazole (Compound No. 7.272)

Following the procedure of Example 14, there were obtained 111 mg (yield 19.6%) of the title compound, melting at 154°–157° C.

1-(Diethylcarbamoyl)-3-(2-chloro-6-methylphenylsulfonyl)-4-methylsulfonylpyrazole (Compound No. 7.273)

Following the procedure of Example 14, there were obtained 159 mg (yield 32.5%) of the title compound, melting at 157°–160° C.

1-(Diethylcarbamoyl)-3-(2-ethyl-6-methylphenylthio)-4-difluoromethylpyrazole (Compound No. 7.300)

Following the procedure of Example 13, there were obtained 224 mg (yield 30.2%) of the title compound, as an oily substance.

Nuclear Magnetic Resonance Spectrum (CDCl$_3$, 200 MHz), δ ppm: 8.30 (1H, triplet, J=1.8 Hz); 7.27–7.10 (3H, multiplet); 6.61 (1H, triplet, J=55.5 Hz); 3.32 (4H, quartet, J=7.0 Hz); 2.88 (2H, quartet, J=7.5 Hz); 2.42 (3H, singlet); 1.17 (3H, triplet, J=7.5 Hz); 1.11–0.72 (6H, multiplet).

1-(Diethylcarbamoyl)-3-(2-ethyl-6-methylphenylsulfonyl)-4-difluoromethylpyrazole (Compound No. 7.301)

Following the procedure of Example 13, there were obtained 135 mg (yield 27.2%) of the title compound, as an oily substance.

Nuclear Magnetic Resonance Spectrum (CDCl$_3$, 200 MHz), δ ppm: 8.45 (1H, singlet); 7.41 (1H, triplet, J=7.6 Hz); 7.24–6.90 (3H, multiplet); 3.45–3.30 (4H, multiplet); 3.07 (2H, quartet, J=7.3 Hz); 2.62 (3H, singlet); 1.25 (3H, triplet, J=7.3 Hz); 1.21–0.84 (6H, multiplet).

1-(Diethylcarbamoyl)-3-(2-ethyl-6-methylphenylthio-4-(dimethylcarbamoyl)pyrazole (Compound No. 7.311)

Following the procedure of Example 14, there were obtained 139 mg (yield 8.7%) of the title compound, as an oily substance.

Nuclear Magnetic Resonance Spectrum (CDCl$_3$, 200 MHz), δ ppm: 8.28 (1H, singlet); 7.26–7.09 (3H, multiplet); 3.30 (4H, quartet, J=7.0 Hz); 3.13 (6H, singlet); 2.88 (2H, quartet, J=7.5 Hz); 2.43 (3H, singlet); 1.16 (6H, triplet, J=7.0 Hz); 0.85–0.55 (3H, broad).

1-(Diethylcarbamoyl)-3-(2-ethyl-6-methylphenylsulfonyl)-4-(dimethylcarbamoyl)pyrazole (Compound No. 7.312)

Following the procedure of Example 14, there were obtained 121 mg (yield 7.5%) of the title compound, as an oily substance.

Nuclear Magnetic Resonance Spectrum (CDCl$_3$, 200 MHz), δ ppm: 8.22 (1H, singlet); 7.38 (1H, triplet, J=7.6 Hz); 7.21–7.11 (2H, multiplet); 3.39 (4H, quartet, J=7.0 Hz); 3.15–3.03 (2H, multiplet); 3.11 (3H, singlet); 3.02 (3H, singlet); 2.63 (3H, singlet); 1.26 (3H, triplet, J=7.5 Hz); 1.30–0.85 (6H, broad).

1-(Diethylcarbamoyl)-3-(2-chloro-6-methylphenylsulfonyl)-4-bromo-5-methylthiopyrazole (Compound No. 7.330)

Following the procedure of Example 16, there were obtained 136 mg (yield 10.5%) of the title compound, as an oily substance.

Nuclear Magnetic Resonance Spectrum (CDCl$_3$, 200 MHz), δ ppm: 7.44–7.24 (3H, multiplet); 3.51 (2H, quartet, J=7.2 Hz); 3.03 (2H, quartet, J=7.1 Hz); 2.97 (2H, quartet, J=7.4 Hz); 2.87 (3H, singlet); 1.30 (3H, triplet, J=7.2 Hz); 1.24 (3H, triplet, J=7.4 Hz); 1.04 (3H, triplet, J=7.1 Hz).

1-(Diethylcarbamoyl)-3-(2,6-difluorophenylthio)-4-fluoropyrazole (Compound No. 7.331)

Following the procedure of Example 19, there were obtained 49 mg (yield 4.9%) of the title compound, as an oily substance.

Nuclear Magnetic Resonance Spectrum CDCl$_3$, 200 MHz), δ ppm: 7.94 (1H, doublet, J=4.8 Hz); 7.40–7.29 (1H, multiplet); 6.96 (2H, doublet of doublets, J=8.4 & 6.3 Hz); 3.46 (4H, quartet, J=7.0 Hz); 1.12 (6H, triplet, J=7.0 Hz).

1-(Diethylcarbamoyl)-3-(2-chloro-6-fluorophenylthio)-4-fluoropyrazole (Compound No. 7.332)

Following the procedure of Example 19, there were obtained 60 mg (yield 6.8%) of the title compound, as an oily substance.

Nuclear Magnetic Resonance Spectrum CDCl$_3$, 200 MHz), δ ppm: 7.95 (1H, doublet, J=5.8 Hz); 7.92–7.26 (2H, multiplet); 7.08–7.01 (1H, multiplet); 3.44 (4H, quartet, J=7.0 Hz); 1.09 (6H, broad).

1-(Diethylcarbamoyl)-3-(2-isopropyl-6-methylphenylthio)-4-fluoropyrazole (Compound No. 7.333)

Following the procedure of Example 19, there were obtained 67 mg (yield 6.9%) of the title compound, as an oily substance.

Nuclear Magnetic Resonance Spectrum CDCl$_3$, 200 MHz), δ ppm: 7.92 (1H, doublet, J=5.1 Hz); 7.26–7.08 (3H, multiplet); 3.86 (1H, septet, J=6.9 Hz); 3.37 (4H, quartet, J=7.0 Hz); 2.47 (3H, singlet); 1.19 (3H, singlet); 1.16 (3H, singlet); 0.98 (6H, broad).

1(N-Ethyl-N-propylcarbamoyl)-3-(2,6-dimethylphenylthio)-4-fluoropyrazole (Compound No. 7.334)

Following the procedure of Example 7, there were obtained 25 mg (yield 14.5%) of the title compound, melting at 49°–52° C.

1-(Dipropylcarbamoyl)-3-(2,6-dimethylphenylthio)-4-fluoropyrazole (Compound No. 7.335)

Following the procedure of Example 7, there were obtained 28 mg (yield 11.6%) of the title compound, melting at 40°–43° C.

1-(Dimethylcarbamoyl)-3-(2,6-difluorophenylsulfonyl)-4-chloropyrazole (Compound No. 7.336)

Following the procedure of Example 3, there were obtained 17 mg (yield 13.9%) of the title compound, as an oily substance.

Nuclear Magnetic Resonance Spectrum CDCl₃, 200 MHz), δ ppm: 8.15 (1H, singlet); 7.69–7.54 (1H, multiplet); 7.26–6.98 (2H, multiplet); 3.28–3.10 (6H, broad).

1-(Dimethylcarbamoyl)-3-(2,6-difluorophenylthio)-4-chloropyrazole (Compound No. 7.337)

Following the procedure of Example 3, there were obtained 25 mg (yield 21.1%) of the title compound, as an oily substance.

Nuclear Magnetic Resonance Spectrum CDCl₃, 200 MHz), δ ppm: 8.05 (1H, singlet); 7.44–7.29 (1H, multiplet); 7.01–6.92 (2H, multiplet); 3.08 (6H, singlet).

1(N-Ethyl-N-propylcarbamoyl)-3-(2,6-difluorophenylsulfonyl)-4-chloropyrazole (Compound No. 7.338)

Following the procedure of Example 3, there were obtained 20 mg (yield 15.2%) of the title compound, melting at 70°–72° C.

1(N-Ethyl-N-propylcarbamoyl)-3-(2,6-difluorophenylthio)-4-chloropyrazole (Compound No. 7.339)

Following the procedure of Example 3, there were obtained 26 mg (yield 19.5%) of the title compound, as an oily substance.

Nuclear Magnetic Resonance Spectrum CDCl₃, 200 MHz), δ ppm: 8.08 (1H, singlet); 7.43–7.32 (1H, multiplet); 7.00–6.92 (2H, multiplet); 3.44 (2H, quartet, J=7.1 Hz); 3.33 (2H, triplet, J=7.1 Hz); 1.75–1.48 (2H, multiplet); 1.03–0.95 (3H, broad); 0.95–0.65 (3H, broad).

1-(Dipropylcarbamoyl)-3-(2,6-difluorophenylsulfonyl)-4-chloropyrazole (Compound No. 7.340)

Following the procedure of Example 3, there were obtained 29 mg (yield 9.8%) of the title compound, melting at 85°–87° C.

1-(Diethylcarbamoyl)-3-(3-chloro-4-fluorophenylsulfonyl)pyrazole (Compound No. 8.1)

Following the procedure of Example 1, there were obtained 391 mg (yield 75.2%) of the title compound, as an oily substance.

Nuclear Magnetic Resonance Spectrum (CDCl₃, 200 MHz), δ ppm: 8.18 (1H, doublet, J=2.6 Hz); 8.12 (1H, doublet of doublets, J=2.2 & 6.6 Hz); 7.98–7.90 (1H, multiplet); 7.31 (1H, triplet, J=8.4 Hz); 6.68 (1H, doublet, J=2.6 Hz); 3.49 (4H, quartet, J=7.0 Hz); 1.24 (6H, triplet, J=7.0 Hz).

1-(Diethylcarbamoyl)-3-(3-chloro-4-fluorophenylthio)-pyrazole (Compound No. 8.2)

Following the procedure of Example 1, there were obtained 443 mg (yield 79.2%) of the title compound, as an oily substance.

Nuclear Magnetic Resonance Spectrum (CDCl₃, 200 MHz), δ ppm: 8.14 (1H, doublet, J=2.5 Hz); 7.53 (1H, doublet of doublets, J=2.2 & 6.8 Hz); 7.37–7.30 (1H, multiplet); 7.10 (1H, triplet, J=8.7 Hz); 6.28 (1H, doublet, J=2.5 Hz); 3.56 (4H, J=7.0 Hz); 1.21 (6H, triplet, J=7.0 Hz).

1-(Diethylcarbamoyl)-3-(3-chloro-4-methoxyphenylthio)pyrazole (Compound No. 8.3)

Following the procedure of Example 1, there were obtained 791 mg (yield 51.4%) of the title compound, as an oily substance.

Nuclear Magnetic Resonance Spectrum (CDCl₃, 200 MHz), δ ppm: 8.09 (1H, doublet, J=2.7 Hz); 7.55 (1H, doublet, J=2.2 Hz); 7.38 (1H, doublet of doublets, J=2.2 & 8.5 Hz); 6.87 (1H, doublet, J=8.5 Hz); 6.18 (1H, doublet, J=2.7 Hz); 3.89 (3H, singlet); 3.55 (4H, quartet, J=7.0 Hz); 1.19 (6H, triplet, J=7.0 Hz).

1-(Diethylcarbamoyl)-3-(3-chloro-4-methoxyphenylsulfonyl)pyrazole (Compound No. 8.4)

Following the procedure of Example 1, there were obtained 214 mg (yield 50.4%) of the title compound, melting at 91°–92° C.

1-(Diethylcarbamoyl)-3-(3,4-dichlorophenylsulfonyl)-pyrazole (Compound No. 8.5)

Following the procedure of Example 1, there were obtained 239 mg (yield 55.1%) of the title compound, as an oily substance.

Nuclear Magnetic Resonance Spectrum (CDCl₃, 200 MHz), δ ppm: 8.17 (1H, doublet, J=2.9 Hz); 8.11 (1H, doublet, J=2.1 Hz); 7.85 (1H, doublet of doublets, J=2.1 & 8.4 Hz); 7.62 (1H, doublet, J=2.9 Hz); 3.49 (4H, quartet, J=7.0 Hz); 1.23 (6H, triplet, J=7.0 Hz).

1-(Diethylcarbamoyl),3-(3,4-dichlorophenylthio)-pyrazole (Compound No. 8.6)

Following the procedure of Example 1, there were obtained 1.02 g (yield 56.2%) of the title compound, as an oily substance.

Nuclear Magnetic Resonance Spectrum (CDCl₃, 200 MHz), δ ppm: 8.16 (1H, doublet, J=2.6 Hz); 7.49 (1H, doublet, J=2.1 Hz); 7.36 (2H, doublet, J=8.4 Hz); 7.22 (1H, doublet of doublets, J=2.1 & 8.4 Hz); 6.34 (1H, doublet, J=2.6 Hz); 3.56 (4H, quartet, J=7.0 Hz); 1.22 (6H, triplet, J=7.0 Hz).

1-(Diethylcarbamoyl)-3-(3,4-dimethylphenylsulfonyl)-pyrazole (Compound No. 8.7)

Following the procedure of Example 1, there were obtained 208 mg (yield 42.2%) of the title compound, melting at 85°–86° C.

1-(Diethylcarbamoyl)-3-(3,4-dimethylphenylthio)-pyrazole (Compound No. 8.8)

Following the procedure of Example 1, there were obtained 381 mg (yield 45.4%) of the title compound, as an oily substance.

Nuclear Magnetic Resonance Spectrum (CDCl₃, 200 MHz), δ ppm: 8.08 (1H, doublet, J=2.7 Hz); 7.26–7.06 (3H, multiplet); 6.18 (1H, doublet, J=2.7 Hz); 3.58 (4H, quartet, J=7.0 Hz); 2.24 (3H, singlet); 2.23 (3H, singlet); 1.21 (6H, triplet, J=7.0 Hz).

1-(Diethylcarbamoyl)-3-(4-bromo-3-methylphenylsulfonyl)pyrazole (Compound. No. 8.9)

Following the procedure of Example 1, there were obtained 196 mg (yield 45.8%) of the title compound, melting at 59°–60° C.

1-(Diethylcarbamoyl)-3-(4-bromo-3-methylphenylthio)pyrazole (Compound No. 8.10)

Following the procedure of Example 1, there were obtained 855 mg (yield 50.8%) of the title compound, as an oily substance.

Nuclear Magnetic Resonance Spectrum (CDCl₃, 200 MHz), δ ppm: 8.12 (1H, doublet, J=3.0 Hz); 7.45 (1H, doublet, J=8.2 Hz); 7.30 (1H, doublet, J=2.2 Hz); 7.10 (1H, doublet of doublets, J=2.2 & 8.2 Hz); 6.26 (1H, doublet, J=3.0 Hz); 3.56 (4H, quartet, J=7.0 Hz); 2.35 (3H, singlet); 1.21 (6H, triplet, J=7.0 Hz).

1-(Diethylcarbamoyl)-3-(4-fluoro-3-trifluoromethylphenylthio)pyrazole (Compound No. 8.11)

Following the procedure of Example 1, there were obtained 392 mg (yield 71.1%) of the title compound, as an oily substance.

Nuclear Magnetic Resonance Spectrum (CDCl₃, 200 MHz), δ ppm: 8.15 (1H, doublet, J=2.7 Hz); 7.76–7.71 (1H, multiplet); 7.67–7.59 (1H, multiplet); 7.17 (1H, triplet, J=9.5 Hz); 6.31 (1H, doublet, J=2.7 Hz); 3.54 (4H, quartet, J=7.0 Hz); 1.89 (6H, triplet, J=7.0 Hz).

1-(Diethylcarbamoyl)-3-(4-fluoro-3-trifluoromethylphenylsulfonyl)pyrazole (Compound No. 8.12)

Following the procedure of Example 1, there were obtained 213 mg (yield 65.4%) of the title compound, as an oily substance.

Nuclear Magnetic Resonance Spectrum (CDCl$_3$, 200 MHz), δ ppm: 8.36–8.18 (2H, multiplet); 8.10 (1H, doublet, J=2.8 Hz); 7.40 (1H, triplet, J=8.8 Hz); 6.91 (1H, doublet, J=2.8 Hz); 3.49 (4H, quartet, J=7.0 Hz); 1.22 (6H, triplet, J=7.0 Hz).

1-(Diethylcarbamoyl)-3-(3,4-dichlorophenylthio)-4-chloropyrazole (Compound No. 8.16)

Following the procedure of Example 5, there were obtained 220 mg (yield 22.9%) of the title compound, as an oily substance.

Nuclear Magnetic Resonance Spectrum (CDCl$_3$, 200 MHz), δ ppm: 8.17 (1H, singlet); 7.50 (1H, doublet, J=2.1 Hz); 7.37 (1H, doublet, J=8.4 Hz); 7.22 (1H, doublet of doublets, J=2.1 & 8.4 Hz); 3.54 (4H, quartet, J=7.0 Hz); 1.20 (6H, triplet, J=7.0 Hz).

1-(Diethylcarbamoyl)-3-(3,4-dichlorophenylsulfonyl)-4-chloropyrazole (Compound No. 8.17)

Following the procedure of Example 5, there were obtained 173 mg (yield 20.2%) of the title compound, melting at 113°–115.5° C.

1-(Dimethylcarbamoyl)-3-(4-fluoro-3-trifluoromethylphenylsulfonyl)-4-chloropyrazole (Compound No. 8.18)

Following the procedure of Example 3, there were obtained 123 mg (yield 78.6%) of the title compound, as an oily substance.

Nuclear Magnetic Resonance Spectrum (CDCl$_3$, 200 MHz), δ ppm: 8.38–8.26 (2H, multiplet); 8.13 (1H, singlet); 7.42 (1H, triplet, J=8.8 Hz); 3.19 (6H, broad singlet).

1(N-Ethyl-N-methylcarbamoyl)-3-(4-fluoro-3-trifluoromethylphenylsulfonyl)-4-chloropyrazole (Compound No. 8.19)

Following the procedure of Example 3, there were obtained 116 mg (yield 33.3%) of the title compound, as an oily substance.

Nuclear Magnetic Resonance Spectrum (CDCl$_3$, 200 MHz), δ ppm: 8.37–8.26 (2H, multiplet); 8.15 (1H, singlet); 7.42 (1H, triplet, J=9.2 Hz); 3.54 (2H, quartet, J=7.2 Hz); 3.15 (3H, broad); 1.25 (3H, triplet, J=7.2 Hz).

1-(Diethylcarbamoyl)-3-(4-fluoro-3-trifluoromethylphenylthio)-4-chloropyrazole (Compound No. 8.20)

Following the procedure of Example 3, there were obtained 219 mg (yield 52.8%) of the title compound, as an oily substance.

Nuclear Magnetic Resonance Spectrum (CDCl$_3$, 200 MHz), δ ppm: 8.16 (1H, singlet); 7.76–7.72 (1H, multiplet); 7.68–7.61 (1H, multiplet); 7.25–7.13 (1H, multiplet); 3.50 (4H, broad quartet, J=6.8 Hz); 1.15 (6H, broad triplet, J=6.8 Hz).

1-(Diethylcarbamoyl)-3-(4-fluoro-3-trifluoromethylphenylsulfonyl)-4-chloropyrazole (Compound No. 8.21)

Following the procedure of Example 3, there were obtained 196 mg (yield 52.8%) of the title compound, melting at 75°–77° C.

1-(Diethylcarbamoyl)-3-(3-chloro-4-fluorophenylthio)-4-chloropyrazole (Compound No. 8.22)

Following the procedure of Example 4, there were obtained 141 mg (yield 54.8%) of the title compound, as an oily substance.

Nuclear Magnetic Resonance Spectrum (CDCl$_3$, 200 MHz), δ ppm: 8.14 (1H, singlet); 7.53 (1H, doublet of doublets, J=6.8 & 2.3 Hz); 7.34 (1H, doubled doublet of doublets, J=8.7, 4.4 & 2.3 Hz); 7.09 (1H, triplet, J=8.7 Hz); 3.51 (4H, quartet, J=7.0 Hz); 1.18 (6H, triplet, J=7.0 Hz).

1-(Diethylcarbamoyl)-3-(3-chloro-4-fluorophenylsulfonyl)-4-chloropyrazole (Compound No. 8.23)

Following the procedure of Example 4, there were obtained 132 mg (yield 53.7%) of the title compound, as an oily substance.

Nuclear Magnetic Resonance Spectrum (CDCl$_3$, 200 MHz), δ ppm: 8.14 (1H, singlet); 8.13 (1H, doublet of doublets, J=6.6 & 2.4 Hz); 7.98 (1H, doubled doublet of doublets, J=8.6, 4.4 & 2.2 Hz); 7.33 (1H, triplet, J=8.6 Hz); 3.50 (4H, quartet, J=7.0 Hz); 1.24 (6H, triplet, J=7.0 Hz).

1-(Diethylcarbamoyl)-3-(3,4-difluorophenylsulfonyl)-4-chloropyrazole (Compound No. 8.24)

Following the procedure of Example 3, there were obtained 385 mg (yield 37.9%) of the title compound, as a gum-like substance.

Nuclear Magnetic Resonance Spectrum (CDCl$_3$, 200 MHz), δ ppm: 8.14 (1H, singlet); 7.95–7.83 (2H, multiplet); 7.37 (1H, doublet of triplets, J=7.0 & 9.3 Hz); 3.51 (4H, broad quartet); 1.25 (6H, triplet, J=7.0 Hz).

1-(Diethylcarbamoyl)-3-(4-fluoro-3-trifluoromethylphenylthio)-4-bromopyrazole (Compound No. 8.26)

Following the procedure of Example 3, there were obtained 306 mg (yield 12.8%) of the title compound, as an oily substance.

Nuclear Magnetic Resonance Spectrum (CDCl$_3$, 200 MHz), δ ppm: 8.19 (1H, singlet); 7.75 (1H, doublet of doublets, J=2.2 & 7.0 Hz); 7.68–7.62 (1H, multiplet); 7.18 (1H, triplet, J=9.2 Hz); 3.48 (4H, quartet, J=7.0 Hz); 1.14 (6H, triplet, J=7.0 Hz).

1-(Diethylcarbamoyl)-3-(4-fluoro-3-trifluoromethylphenylsulfonyl)-4-bromopyrazole (Compound No. 8.27)

Following the procedure of Example 3, there were obtained 204 mg (yield 11.9%) of the title compound, melting at 67°–69° C.

1-(Diethylcarbamoyl)-3-(3,4-dichlorophenylthio)-4-bromopyrazole (Compound No. 8.28)

Following the procedure of Example 5, there were obtained 222 mg (yield 26.4%) of the title compound, as an oily substance.

Nuclear Magnetic Resonance Spectrum (CDCl$_3$, 200 MHz), δ ppm: 8.20 (1H, singlet); 7.51 (1H, doublet, J=2.2 Hz); 7.38 (1H, doublet, J=8.4 Hz); 7.23 (1H, doublet of doublets, J=2.2 & 8.4 Hz); 3.52 (4H, quartet, J=7.0 Hz); 1.19 (6H, triplet, J=7.0 Hz).

1-(Diethylcarbamoyl)-3-(3,4-dichlorophenylsulfonyl)-4-bromopyrazole (Compound No. 8.29)

Following the procedure of Example 5, there were obtained 158 mg (yield 20.9%) of the title compound, melting at 128°–129° C.

1-(Diethylcarbamoyl)-3-(3-chloro-4-fluorophenylthio)-4-bromopyrazole (Compound No. 8.30)

Following the procedure of Example 4, there were obtained 164 mg (yield 52.8%) of the title compound, as an amorphous product.

Nuclear Magnetic Resonance Spectrum (CDCl$_3$, 200 MHz), δ ppm: 8.18 (1H, singlet); 7.53 (1H, doublet of doublets, J=6.7 & 2.3 Hz); 7.34 (1H, doubled doublet of doublets, J=8.6, 4.5 & 2.3 Hz); 7.10 (1H, triplet, J=8.6 Hz); 3.50 (4H, quartet, J=7.0 Hz); 1.16 (6H, triplet, J=7.0 Hz).

1-(Diethylcarbamoyl)-3-(3-chloro-4-fluorophenylsulfonyl)-4-bromopyrazole (Compound No. 8.31)

Following the procedure of Example 4, there were obtained 149 mg (yield 52.2%) of the title compound, melting at 73°-74° C.

1-(Diethylcarbamoyl)-3-(4-fluoro-3-trifluoromethylphenylsulfonyl)-4-fluoropyrazole (Compound No. 8.32)

Following the procedure of Example 7, there were obtained 15 mg (yield 5.7%) of the title compound, melting at 117°-119° C.

1-(Diethylcarbamoyl)-3-(3,4-dichlorophenylsulfonyl)-4-fluoropyrazole (Compound No. 8.34)

Following the procedure of Example 7, there were obtained 8 mg (yield 0.6%) of the title compound, melting at 58°-60° C.

1-(Diethylcarbamoyl)-3-(3-chloro-4-fluorophenylsulfonyl)-4-fluoropyrazole (Compound No. 8.35)

Following the procedure of Example 19, there were obtained 47 mg (yield 5.2%) of the title compound, melting at 75°-78° C.

1-(Diethylcarbamoyl)-3-(3-chloro-4-fluorophenylthio)-4-fluoropyrazole (Compound No. 8.57)

Following the procedure of Example 19, there were obtained 65 mg (yield 7.1%) of the title compound, as an oily substance.

Nuclear Magnetic Resonance Spectrum (CDCl$_3$, 200 MHz), δ ppm: 8.00 (1H, doublet, J=5.1 Hz); 7.51 (1H, doublet, J=6.8 Hz); 7.36-7.28 (1H, multiplet); 7.08 (1H, triplet, J=6.8 Hz); 3.55 (4H, quartet, J=7.0 Hz); 1.22 (6H, triplet, J=7.0 Hz).

1-(Diethylcarbamoyl)-3-(3,5-dichlorophenylsulfonyl)pyrazole (Compound No. 9.1)

Following the procedure of Example 1, there were obtained 221 mg (yield 84.5%) of the title compound, melting at 86°-87° C.

1-(Diethylcarbamoyl)-3-(3,5-dichlorophenylthio)pyrazole (Compound No. 9.3)

Following the procedure of Example 1, there were obtained 877 mg (yield 89.0%) of the title compound, as an oily substance.

Nuclear Magnetic Resonance Spectrum (CDCl$_3$, 200 MHz), δ ppm: 8.19 (1H, doublet, J=2.8 Hz); 7.26-7.21 (3H, multiplet); 6.40 (1H, doublet, J=2.8 Hz); 3.50-3.40 (4H, broad quartet); 1.25 (6H, triplet, J=7.0 Hz).

1-(Diethylcarbamoyl)-3-(3,5-dibromophenylsulfonyl)pyrazole (Compound No. 9.4)

Following the procedure of Example 1, there were obtained 383 mg (yield 70.2%) of the title compound, melting at 97°-98° C.

1-(Diethylcarbamoyl)-3-(3,5-dibromophenylthio)pyrazole (Compound No. 9.5)

Following the procedure of Example 1, there were obtained 491 mg (yield 73.9%) of the title compound, as an oily substance.

Nuclear Magnetic Resonance Spectrum (CDCl$_3$, 200 MHz), δ ppm: 8.18 (1H, doublet, J=2.6 Hz); 7.52 (1H, triplet, J=1.6 Hz); 7.44 (2H, doublet, J=1.6 Hz); 6.39 (1H, doublet, J=2.6 Hz); 3.59 (4H, quartet, J=7.0 Hz); 1.24 (6H, triplet, J=7.0 Hz).

1-(Diethylcarbamoyl)-3-(3,5-dimethylphenylsulfonyl)pyrazole (Compound No. 9.6)

Following the procedure of Example 1, there were obtained 451 mg (yield 61.1%) of the title compound, melting at 71°-73° C.

1-(Diethylcarbamoyl)-3-(3,5-dimethylphenylthio)pyrazole (Compound No. 9.7)

Following the procedure of Example 1, there were obtained 514 mg (yield 63.0%) of the title compound, as an oily substance.

Nuclear Magnetic Resonance Spectrum (CDCl$_3$, 200 MHz), δ ppm: 8.11 (1H, doublet, J=2.6 Hz); 7.07 (2H, broad singlet); 6.90 (1H, broad singlet); 6.25 (1H, doublet, J=2.6 Hz); 3.59 (4H, quartet, J=7.0 Hz); 2.28 (6H, singlet); 1.23 (6H, triplet, J=7.0 Hz).

1-(Diethylcarbamoyl)-3-(3,5-difluorophenylsulfonyl)pyrazole (Compound No. 9.8)

Following the procedure of Example 1, there were obtained 302 mg (yield 54.1%) of the title compound, melting at 73°-74° C.

1-(Diethylcarbamoyl)-3-(3,5-difluorophenylthio)pyrazole (Compound No. 9.9)

Following the procedure of Example 1, there were obtained 377 mg (yield 60.8%) of the title compound, as an oily substance.

Nuclear Magnetic Resonance Spectrum (CDCl$_3$, 200 MHz), δ ppm: 8.19 (1H, doublet, J=2.7 Hz); 7.26-6.83 (2H, multiplet); 6.71-6.61 (1H, multiplet); 6.42 (1H, doublet, J=2.7 Hz); 3.59 (4H, quartet, J=7.0 Hz); 1.24 (6H, triplet, J=7.0 Hz).

1-(Diethylcarbamoyl)-3-(3,5-dimethoxyphenylthio)pyrazole (Compound No. 9.10)

Following the procedure of Example 1, there were obtained 200 mg (yield 52.6%) of the title compound, as an oily substance.

Nuclear Magnetic Resonance Spectrum (CDCl$_3$, 200 MHz), δ ppm: 8.13 (1H, doublet, J=2.7 Hz); 6.53 (2H, doublet, J=2.2 Hz); 6.35 (1H, triplet, J=2.2 Hz); 6.32 (1H, doublet, J=2.7 Hz); 3.75 (6H, singlet); 3.69 (4H, quartet, J=7.0 Hz); 1.24 (6H, triplet, J=7.0 Hz).

1-(Diethylcarbamoyl)-3-(3,5-dimethoxyphenylsulfonyl)pyrazole (Compound No. 9.11)

Following the procedure of Example 1, there were obtained 182 mg (yield 49.9%) of the title compound, as an oily substance.

Nuclear Magnetic Resonance Spectrum (CDCl$_3$, 200 MHz), δ ppm: 8.15 (1H, doublet, J=2.7 Hz); 7.15 (2H, doublet, J=2.0 Hz); 6.85 (1H, doublet, J=2.7 Hz); 6.65 (1H, triplet, J=2.0 Hz); 3.83 (6H, singlet); 3.50 (4H, quartet, J=7.0 Hz); 1.23 (6H, triplet, J=7.0 Hz).

1-(Methylcarbamoyl)-3-(3,5-dichlorophenylthio)pyrazole Compound No. 9.13)

Following the procedure of Example 1, there were obtained 2.22 g (yield 75.7%) of the title compound, as a gum-like substance.

Nuclear Magnetic Resonance Spectrum (CDCl$_3$, 200 MHz), δ ppm: 8.27 (1H, doublet, J=2.6 Hz); 7.24-7.18 (3H, multiplet); 7.03 (1H, broad ); 6.42 (1H, doublet, J=2.6 Hz); 3.03 (3H, doublet, J=5.1 Hz).

1-(Dipropylcarbamoyl)-3-(3,5-dichlorophenylsulfonyl)pyrazole (Compound No. 9.14)

Following the procedure of Example 2, there were obtained 131 mg (yield 33.9%) of the title compound, melting at 58°-60° C.

1(N-Ethyl-N-propylcarbamoyl)-3-(3,5-dichlorophenylsulfonyl)pyrazole (Compound No. 9.18)

Following the procedure of Example 2, there were obtained 165 mg (yield 45.7%) of the title compound, melting at 47°-50° C.

1-(Dimethylcarbamoyl)-3-(3,5-dichlorophenylsulfonyl)pyrazole (Compound No. 9.22)

Following the procedure of Example 2, there were obtained 229 mg (yield 68.5%) of the title compound, as an oily substance.

Nuclear Magnetic Resonance Spectrum (CDCl$_3$, 200 MHz), δ ppm: 8.16 (1H, doublet, J=2.8 Hz); 7.90 (2H, doublet, J=1.9 Hz); 7.58 (1H, triplet, J=1.9 Hz); 6.88 (1H, doublet, J=2.8 Hz); 3.28-3.10 (6H, broad).

1(N-Ethyl-N-methylcarbamoyl)-3-(3,5-dichlorophenyl-sulfonyl)pyrazole (Compound No. 9.26)

Following the procedure of Example 2, there were obtained 131 mg (yield 37.1%) of the title compound, as an oily substance.

Nuclear Magnetic Resonance Spectrum (CDCl$_3$, 200 MHz), δ ppm: 8.18 (1H, doublet, J=2.8 Hz); 7.91-7.90 (2H, multiplet); 7.59 (1H, triplet, J=1.9 Hz); 6.89 (1H, doublet, J=2.8 Hz); 3.54 (2H, quartet, J=7.0 Hz); 3.14-3.08 (3H, broad); 1.27 (3H, triplet, J=7.0 Hz).

1(N-Butyl-N-methylcarbamoyl)-3-(3,5-dichlorophenyl-sulfonyl)pyrazole (Compound No. 9.27)

Following the procedure of Example 2, there were obtained 131 mg (yield 34.7%) of the title compound, as an oily substance.

Nuclear Magnetic Resonance Spectrum (CDCl$_3$, 200 MHz), δ ppm: 8.18 (1H, doublet, J=2.6 Hz); 7.90 (2H, doublet, J=2.7 Hz); 7.61-7.58 (1H, multiplet); 6.89 (1H, doublet, J=2.6 Hz); 3.56-3.48 (2H, multiplet); 3.19-3.10 (3H, broad); 1.69-1.60 (2H, multiplet); 1.36-1.27 (2H, broad); 1.03-0.90 (3H, multiplet).

1-(Diallylcarbamoyl)-3-(3,5-dichlorophenylsulfonyl)-pyrazole (Compound No. 9.34)

Following the procedure of Example 2, there were obtained 92 mg (yield 23.4%) of the title compound, as an oily substance.

Nuclear Magnetic Resonance Spectrum (CDCl$_3$, 200 MHz), δ ppm: 8.21 (1H, doublet, J=2.6 Hz); 7.91-7.88 (2H, multiplet); 7.61-7.59 (1H, multiplet); 6.91 (1H, doublet, J=2.6 Hz); 5.89-5.79 (2H, multiplet); 5.29-5.15 (4H, multiplet); 4.15-4.06 (4H, multiplet).

1-(Pyrrolidin-1-ylcarbonyl)-3-(3,5-dichlorophenylsul-fonyl)pyrazole (Compound No. 9.37)

Following the procedure of Example 2, there were obtained 29 mg (yield 8.1%) of the title compound, melting at 88°-91° C.

1-[N-Methyl-N-(2-methylphenyl)carbamoyl]-3-(3,5-dichlorophenylsulfonyl)pyrazole (Compound No. 9.40)

Following the procedure of Example 2, there were obtained 82 mg (yield 25.8%) of the title compound, melting at 81°-84° C.

1-[N-Methyl-N-(3-methylphenyl)carbamoyl]-3-(3,5-dichlorophenylsulfonyl)pyrazole (Compound No. 9.41)

Following the procedure of Example 2, there were obtained 57 mg (yield 17.8%) of the title compound, as an oily substance.

Nuclear Magnetic Resonance Spectrum (CDCl$_3$, 200 MHz), δ ppm: 8.14 (1H, doublet, J=2.7 Hz); 7.57 (3H, singlet); 7.09 (1H, quartet, J=7.9 Hz); 6.99 (1H, doublet, J=7.3 Hz); 6.81 (1H, doublet, J=2.7 Hz); 6.80-6.76 (2H, broad); 3.47 (3H, singlet); 2.23 (3H, singlet).

1-[N-(2-Chlorophenyl)-N-methylcarbamoyl]-3-(3,5-dichlorophenylsulfonyl)pyrazole (Compound No. 9.42)

Following the procedure of Example 2, there were obtained 26 mg (yield 8.1%) of the title compound, as an oily substance.

Nuclear Magnetic Resonance Spectrum (CDCl$_3$, 200 MHz), δ ppm: 8.25 (1H, doublet, J=1.8 Hz); 7.60-7.59 (2H, multiplet); 7.35-7.21 (5H, multiplet); 6.79 (1H, doublet, J=1.8 Hz); 3.42 (3H, singlet).

1-[N-(3-Chlorophenyl)-N-methylcarbamoyl]-3-(3,5-dichlorophenylsulfonyl)pyrazole (Compound No. 9.43)

Following the procedure of Example 2, there were obtained 155 mg (yield 46.0%) of the title compound, melting at 117°-119° C.

1-[N-(4-Chlorophenyl)-N-methylcarbamoyl]-3-(3,5-dichloro phenylsulfonyl)pyrazole (Compound No. 9.44)

Following the procedure of Example 2, there were obtained 146 mg (yield 43.6%) of the title compound, an oily substance.

Nuclear Magnetic Resonance Spectrum (CDCl$_3$, 200 MHz), δ ppm: 8.18 (1H, doublet, J=2.9 Hz); 7.62 (3H, singlet); 7.22 (2H, doublet, J=8.7 Hz); 6.92 (2H, doublet, J=8.7 Hz); 6.85 (1H, doublet, J=2.9 Hz); 3.45 (3H, singlet).

1-[N-(3-Chlorophenyl)-N-ethylcarbamoyl]-3-(3,5-dichlorophenylsulfonyl)pyrazole (Compound No. 9.45)

Following the procedure of Example 2, there were obtained 167 mg (yield 48.5%) of the title compound, as an oily substance.

Nuclear Magnetic Resonance Spectrum (CDCl$_3$, 200 MHz), δ ppm: 8.19 (1H, doublet, J=2.9 Hz); 7.59 (3H, singlet); 7.21-7.18 (2H, multiplet); 6.92-6.86 (2H, multiplet); 6.84 (1H, doublet, J=2.9 Hz); 3.89 (2H, quartet, J=7.1 Hz); 1.24 (3H, triplet, J=7.1 Hz).

1-[N-(4-Chlorophenyl)-N-isopropylcarbamoyl]-3-(3,5dichlorophenylsulfonyl)pyrazole (Compound No. 9.46)

Following the procedure of Example 2, there were obtained 209 mg (yield 58.1%) of the title compound, melting at 150°-153° C.

1-[N-(5-Chloro-2-pyridyl)-N-methylcarbamoyl]-3-(3,5-dichlorophenylsulfonyl)pyrazole (Compound No. 9.47)

Following the procedure of Example 2, there were obtained 159 mg (yield 46.8%) of the title compound, melting at 103°-106° C.

1-(Diethylcarbamoyl)-3-(3,5-dichlorophenylsulfonyl)-5-chloropyrazole (Compound No. 9.48)

Following the procedure of Example 15, there were obtained 193 mg (yield 60.7%) of the title compound, melting at 93°-94° C.

1-(Diethylcarbamoyl)-3-(3,5-dimethoxyphenylthio)-4-chloropyrazole (Compound No. 9.52)

Following the procedure of Example 3, there were obtained 140 mg (yield 39.2%) of the title compound, as an oily substance.

Nuclear Magnetic Resonance Spectrum (CDCl$_3$, 200 MHz), δ ppm: 8.16 (1H, singlet); 6.53 (2H, doublet, J=2.2 Hz); 6.35 (1H, triplet, J=2.2 Hz); 3.75 (6H, singlet); 3.55 (4H, quartet, J=7.0 Hz); 1.21 (6H, triplet, J=7.0 Hz).

1-(Diethylcarbamoyl)-3-(3,5-dimethoxyphenylsul-fonyl)-4-chloropyrazole (Compound No. 9.53)

Following the procedure of Example 3, there were obtained 91 mg (yield 28.3%) of the title compound, as an oily substance.

Nuclear Magnetic Resonance Spectrum (CDCl$_3$, 200 MHz), δ ppm: 8.12 (1H, singlet); 7.19 (2H, doublet, J=2.2 Hz); 6.68 (1H, triplet, J=2.2 Hz); 3.84 (6H, singlet); 3.51 (4H, broad quartet, J=7.1 Hz); 1.25 (6H, triplet, J=7.1 Hz).

1-(Diethylcarbamoyl)-3-(3,5-difluorophenylthio)-4-chloropyrazole (Compound No. 9.55)

Following the procedure of Example 3, there were obtained 294 mg (yield 36.8%) of the title compound, as an oily substance.

Nuclear Magnetic Resonance Spectrum (CDCl$_3$, 200 MHz), δ ppm: 8.20 (1H, singlet); 6.90-6.81 (2H, multiplet); 6.74-6.63 (1H, multiplet); 3.56 (4H, quartet, J=7.0 Hz); 1.23 (6H, triplet, J=7.0 Hz).

1-(Diethylcarbamoyl)-3-(3,5-difluorophenylsulfonyl)-4-chloropyrazole (Compound No. 9.56)

Following the procedure of Example 3, there were obtained 179 mg (yield 27.6%) of the title compound, as an oily substance.

Nuclear Magnetic Resonance Spectrum (CDCl$_3$, 200 MHz), δ ppm: 8.15 (1H, singlet); 7.63–7.58 (2H, multiplet); 7.15–7.06 (1H, multiplet); 3.51 (4H, quartet, J=7.0 Hz); 1.26 (6H, triplet, J=7.0 Hz).

1-(Diethylcarbamoyl)-3-(3,5-dibromophenylthio)-4-chloropyrazole (Compound No. 9.57)

Following the procedure of Example 4, there were obtained 156 mg (yield 46.5%) of the title compound, as an oily substance.

Nuclear Magnetic Resonance Spectrum (CDCl$_3$, 200 MHz), δ ppm: 8.19 (1H, singlet); 7.55 (1H, triplet, J=1.8 Hz); 7.45 (2H, doublet, J=1.8 Hz); 3.55 (4H, quartet, J=7.0 Hz); 1.22 (6H, triplet, J=7.0 Hz).

1-(Diethylcarbamoyl)-3-(3,5-dibromophenylsulfonyl)-4-chloropyrazole (Compound No. 9.58)

Following the procedure of Example 4, there were obtained 118 mg (yield 38.6%) of the title compound, melting at 83°–84° C.

1-[N-Methyl-N-(2-methylphenyl)carbamoyl]-3-(3,5-dichlorophenylsulfonyl)-4-chloropyrazole (Compound No. 9.59)

Following the procedure of Example 2, there were obtained 18 mg (yield 6.0%) of the title compound, melting at 120°–125° C.

1-[N-Methyl-N-(3-methylphenyl) carbamoyl]-3-(3,5-dichlorophenylsulfonyl)-4-chloropyrazole (Compound No. 9.60)

Following the procedure of Example 2, there were obtained 51 mg (yield 17.6%) of the title compound, melting at 155°–156° C.

1-[N-(2-Chlorophenyl)-N-methylcarbamoyl]-3-(3,5-dichlorophenylsulfonyl)-4-chloropyrazole (Compound No. 9.61)

Following the procedure of Example 2, there were obtained 52 mg (yield 17.1%) of the title compound, melting at 105°–108° C.

1-[N-(3-Chlorophenyl)-N-methylcarbamoyl]-3-dichlorophenylsulfonyl)-4-chloropyrazole (Compound No. 9.62).

Following the procedure of Example 2, there were obtained 65 mg (yield 21.1%) of the title compound, melting at 170°–172° C.

1-[N-(4-Chlorophenyl)-N-methylcarbamoyl]-3-(3,5-dichlorophenylsulfonyl)-4-chloropyrazole (Compound No. 9.63)

Following the procedure of Example 2, there were obtained 42 mg (yield 13.6%) of the title compound, melting at 145°–148° C.

1-[N-(3-Chlorophenyl)-N-ethylcarbamoyl]-3-(3,5-dichlorophenylsulfonyl)-4-chloropyrazole (Compound No. 9.64)

Following the procedure of Example 2, there were obtained 42 mg (yield 13.1%) of the title compound, melting at 167°–170° C.

1-[N-(3-Chlorophenyl)-N-isopropylcarbamoyl]-3-(3,5-dichlorophenylsulfonyl)-4-chloropyrazole (Compound No. 9.65)

Following the procedure of Example 2, there were obtained 140 mg (yield 43.2%) of the title compound, melting at 130°–133° C.

1-[N-(5-Chloro-2-pyridyl)-N-methylcarbamoyl]-3-(3,5-dichlorophenylsulfonyl)-4-chloropyrazole (Compound No. 9.72)

Following the procedure of Example 2, there were obtained 33 mg (yield 10.5%) of the title compound, melting at 143°–145° C.

1-(Diethylcarbamoyl)-3-(3,5-dichlorophenylthio)-4-bromopyrazole (Compound No. 9.76)

Following the procedure of Example 4, there were obtained 2.67 g (yield 71.3%) of the title compound, as an oily substance.

Nuclear Magnetic Resonance Spectrum (CDCl$_3$, 200 MHz), δ ppm: 8.22 (1H, singlet); 7.24 (3H, broad singlet); 3.51 (4H, broad quartet, J=7.0 Hz); 1.21 (6H, broad triplet, J=7.0 Hz).

1-(Diethylcarbamoyl)-3-(3,5-dichlorophenylsulfonyl)-4-bromopyrazole (Compound No. 9.77)

Following the procedure of Example 4, there were obtained 2.48 g (yield 56.4%) of the title compound, melting at 75°–77° C.

1-(Diethylcarbamoyl)-3-(3,5-difluorophenylthio)-4-bromopyrazole (Compound No. 9.80)

Following the procedure of Example 4, there were obtained 1.02 g (yield 42.9%) of the title compound, as an oily substance.

Nuclear Magnetic Resonance Spectrum (CDCl$_3$, 200 MHz), δ ppm: 8.23 (1H, singlet); 6.86 (2H, doublet of triplets, J=2.2 & 5.2 Hz); 6.68 (1H, triplet of triplets, J=2.2 & 8.8 Hz); 3.56 (4H, quartet, J=7.0 Hz); 1.23 (6H, triplet, J=7.0 Hz).

1-(Diethylcarbamoyl)-3-(3,5-difluorophenylsulfonyl)-4-bromopyrazole (Compound No. 9.81)

Following the procedure of Example 4, there were obtained 211 mg (yield 42.0%) of the title compound, as an oily substance.

Nuclear Magnetic Resonance Spectrum (CDCl$_3$, 200 MHz), δ ppm: 8.19 (1H, singlet); 7.83–7.59 (2H, multiplet); 7.10 (1H, triplet of triplets, J=6.0 & 2.4 Hz); 3.50 (4H, quartet, J=7.0 Hz); 1.25 (6H, triplet, J=7.0 Hz).

1-(Diethylcarbamoyl)-3-(3,5-dibromophenylthio)-4-bromopyrazole (Compound No. 9.82)

Following the procedure of Example 4, there were obtained 179 mg (yield 48.7%) of the title compound, as an oily substance.

Nuclear Magnetic Resonance Spectrum (CDCl$_3$, 200 MHz), δ ppm: 8.22 (1H, singlet); 7.55 (1H, triplet, J=1.8 Hz); 7.46 (2H, doublet, J=1.8 Hz); 3.55 (4H, quartet, J=7.0 Hz); 1.22 (6H, triplet, J=7.0 Hz).

1-(Diethylcarbamoyl)-3-(3,5-dibromophenylsulfonyl)-4-bromopyrazole (Compound No. 9.83)

Following the procedure of Example 4, there were obtained 136 mg (yield 40.9%) of the title compound, melting at 86°–87° C.

1-(Diethylcarbamoyl)-3-(3,5-dichlorophenylsulfonyl)-4-fluoropyrazole (Compound No. 9.84)

Following the procedure of Example 7, there were obtained 22 mg (yield 5.6%) of the title compound, as an oily substance.

Nuclear Magnetic Resonance Spectrum (CDCl$_3$, 200 MHz), δ ppm: 8.03 (1H, doublet, J=4.7 Hz); 7.93 (2H, doublet, J=1.8 Hz); 7.63 (1H, triplet, J=1.8 Hz); 3.52 (4H, broad quartet, J=7.0 Hz); 1.26 (6H, triplet, J=7.0 Hz).

1-(Diethylcarbamoyl)-3-(3,5-dimethylphenylsulfonyl)-4-fluoropyrazole (Compound No. 9.85)

Following the procedure of Example 7, there were obtained 97 mg (yield 20.6%) of the title compound, as an oily substance.

Nuclear Magnetic Resonance Spectrum (CDCl$_3$, 200 MHz), δ ppm: 7.97 (1H, doublet, J=4.8 Hz); 7.66 (2H, singlet); 7.27 (1H, singlet); 3.6–3.4 (4H, broad); 2.39 (6H, singlet); 1.25 (6H, triplet, J=7.0 Hz).

1-(Diethylcarbamoyl)-3-(3,5-difluorophenylsulfonyl)-4-fluoropyrazole (Compound No. 9.88)

Following the procedure of Example 7, there were obtained 8 mg (yield 2.0%) of the title compound, as an oily substance.

Nuclear Magnetic Resonance Spectrum (CDCl$_3$, 200 MHz), δ ppm: 8.02 (1H, doublet, J=4.8 Hz); 7.61–7.75 (2H, multiplet); 7.15–7.06 (1H, multiplet); 3.6–3.4 (4H, broad); 1.27 (6H, triplet, J=7.0 Hz).

1-(Diethylcarbamoyl)-3-(3,5-dichlorophenylsulfonyl)-4-methylpyrazole (Compound No. 9.109)

Following the procedure of Example 14, there were obtained 63 mg (yield 17.3%) of the title compound, melting at 87°–89° C.

1-(Diethylcarbamoyl)-3 N-(3,5-dichlorophenylsulfonyl)-4-allylpyrazole (Compound No. 9.111)

Following the procedure of Example 14, there were obtained 67 mg (yield 9.0%) of the title compound, as an oily substance.

Nuclear Magnetic Resonance Spectrum (CDCl$_3$, 200 MHz), δ ppm: 7.97 (1H, singlet); 7.89 (2H, doublet, J=1.8 Hz); 7.59 (1H, triplet, J=1.8 Hz); 6.04–5.84 (1H, multiplet); 5.16–5.04 (2H, multiplet); 3.54 (2H, doublet, J=5.5 Hz); 3.47 (4H, quartet, J=7.0 Hz); 1.21 (6H, triplet, J=7.0 Hz).

1-(Diethylcarbamoyl)-3-(3,5-dichlorophenylthio)-4-(difluoromethyl)pyrazole (Compound No. 9.117)

Following the procedure of Example 13, there were obtained 219 mg (yield 32.2%) of the title compound, as an oily substance.

Nuclear Magnetic Resonance Spectrum (CDCl$_3$, 200 MHz), δ ppm: 8.41 (1H, triplet, J=1.6 Hz); 7.27 (3H, singlet); 6.64 (1H, triplet, J=55.1 Hz); 3.55 (4H, quartet, J=6.8 Hz); 1.22 (6H, triplet, J=6.8 Hz).

1-(Diethylcarbamoyl)-3-(3,5-dichlorophenylsulfonyl)-4-(difluoromethyl)pyrazole (Compound No. 9.118)

Following the procedure of Example 13, there were obtained 203 mg (yield 31.3%) of the title compound, melting at 112°–113° C.

1-(Diethylcarbamoyl)-3-(3,5-dichlorophenylthio)-4-cyanopyrazole (Compound No. 9.122)

Following the procedure of Example 14, there were obtained 170 mg (yield 30.8%) of the title compound, as an oily substance.

Nuclear Magnetic Resonance Spectrum (CDCl$_3$, 200 MHz), δ ppm: 8.57 (1H, singlet); 7.39 (2H, doublet, J=1.8 Hz); 7.34 (1H, triplet, J=1.8 Hz); 3.52 (4H, quartet, J=7.0 Hz); 1.30–1.11 (6H, multiplet).

1-(Diethylcarbamoyl)-3-(3,5-dichlorophenylsulfonyl)-4-cyanopyrazole (Compound No. 9.123)

Following the procedure of Example 14, there were obtained 146 mg (yield 28.0%) of the title compound, melting at 132°–135° C.

1-(Diethylcarbamoyl)-3-(3,5-difluorophenylthio)-4-cyanopyrazole (Compound No. 9.125)

Following the procedure of Example 14, there were obtained 163 mg (yield 26.0%) of the title compound, as an oily substance.

Nuclear Magnetic Resonance Spectrum (CDCl$_3$, 200 MHz), δ ppm: 8.58 (1H, singlet); 7.05–6.96 (2H, multiplet); 6.78 (1H, triplet of triplets, J=8.8 & 2.2 Hz); 3.58–3.48 (4H, multiplet); 1.22 (6H, triplet, J=6.8 Hz).

1-(Diethylcarbamoyl)-3-(3,5-difluorophenylsulfonyl)-4-cyanopyrazole (Compound No. 9.126)

Following the procedure of Example 14, there were obtained 135 mg (yield 22.6%) of the title compound, melting at 117°–118° C.

Ethyl 1-(diethylcarbamoyl)-3-(3,5-dichlorophenylsulfonyl)pyrazole-4-carboxylate (Compound No. 9.127)

Following the procedure of Example 14, there were obtained 121 mg (yield 19.2%) of the title compound, as an oily substance.

Nuclear Magnetic Resonance Spectrum (CDCl$_3$, 200 MHz), δ ppm: 8.65 (1H, singlet); 7.97 (2H, doublet, J=1.8 Hz); 7.63 (1H, triplet, J=1.8 Hz); 4.37 (2H, quartet, J=7.2 Hz); 3.46 (4H, quartet, J=7.0 Hz); 1.37 (3H, triplet, J=7.2 Hz); 1.30–1.02 (6H, broad).

1-(Diethylcarbamoyl)-3-(3,5-dichlorophenylthio)-4-methylthiopyrazole (Compound No. 9.131)

Following the procedure of Example 14, there were obtained 186 mg (yield 40.2%) of the title compound, as an oily substance.

Nuclear Magnetic Resonance Spectrum (CDCl$_3$, 200 MHz), δ ppm: 8.13 (1H, singlet); 7.26–7.22 (3H, multiplet); 3.55 (4H, quartet, J=6.8 Hz); 2.34 (3H, singlet); 1.21 (6H, triplet, J=6.8 Hz).

1-(Diethylcarbamoyl)-3-(3,5-dichlorophenylsulfonyl)-4-methylsulfonylpyrazole (Compound No. 9.132)

Following the procedure of Example 14, there were obtained 103 mg (yield 18.9%) of the title compound, melting at 180°–183° C.

1-(Diethylcarbamoyl)-3-(2,4,6-trimethylphenylsulfonyl)pyrazole (Compound No. 10.1)

Following the procedure of Example 1, there were obtained 335 mg (yield 85.6%) of the title compound, melting at 72°–73° C.

1-(Diethylcarbamoyl)-3-(2,4,6-trimethylphenylthio)pyrazole (Compound No. 10.2)

Following the procedure of Example 1, there were obtained 401 mg (yield 85.6%) of the title compound, as an oily substance.

Nuclear Magnetic Resonance Spectrum (CDCl$_3$, 200 MHz), δ ppm: 8.01 (1H, doublet, J=2.7 Hz); 6.96 (2H, singlet); 5.91 (1H, doublet, J=2.7 Hz); 3.50 (4H, quartet, J=7.0 Hz); 2.43 (6H, singlet); 2.28 (3H, singlet); 1.12 (6H, triplet, J=7.0 Hz).

1-(Dimethylcarbamoyl)-3-(2,4,6-trimethylphenylthio)pyrazole (Compound No. 10.3)

Following the procedure of Example 1, there were obtained 348 mg (yield 74.4%) of the title compound, melting at 79°–80° C.

1-(Dimethylcarbamoyl)-3-(2,4,6-trimethylphenylsulfonyl)pyrazole (Compound No. 10.4)

Following the procedure of Example 1, there were obtained 226 mg (yield 85.6%) of,the title compound, as an oily substance.

Nuclear Magnetic Resonance Spectrum (CDCl$_3$, 200 MHz), δ ppm: 8.14 (1H, doublet, J=2.9 Hz); 6.94 (2H, singlet); 6.83 (1H, doublet, J=2.9 Hz); 3.15 (6H, broad); 2.67 (6H, singlet); 2.29 (3H, singlet).

1-(Diethylcarbamoyl)-3-(4-bromo-2,6-dimethylphenylsulfonyl)pyrazole (Compound No. 10.6)

Following the procedure of Example 1, there were obtained 278 mg (yield 67.1%) of the title compound, melting at 87°–90° C.

1-(Diethylcarbamoyl)-3-(3-chloro-2,6-dimethylphenylthio)pyrazole (Compound No. 10.13)

Following the procedure of Example 1, there were obtained 440 mg (yield 55.4%) of the title compound, as an oily substance.

Nuclear Magnetic Resonance Spectrum (CDCl$_3$, 200 MHz), δ ppm: 8.06 (1H, doublet, J=2.6 Hz); 7.30 (1H, doublet, J=8.0 Hz); 7.08 (1H, doublet, J=8.0 Hz); 6.03 (1H, doublet, J=2.6 Hz); 3.45 (4H, quartet, J=7.0 Hz); 2.58 (3H, singlet); 2.45 (3H, singlet); 1.08 (6H, triplet, J=7.0 Hz).

1-(Diethylcarbamoyl)-3-(3-chloro-2,6-dimethylphenylsulfonyl)pyrazole (Compound No. 10.14)

Following the procedure of Example 1, there were obtained 325 mg (yield 53.2%) of the title compound, melting at 57°–60° C.

1-(Diethylcarbamoyl)-3-(3,5-dichloro-2,6-dimethylphenylthio)pyrazole (Compound No. 10.15)

Following the procedure of Example 1, there were obtained 375 mg (yield 56.0%) of the title compound, as an oily substance.

Nuclear Magnetic Resonance Spectrum (CDCl$_3$, 200 MHz), δ ppm: 8.08 (1H, doublet, J=2.7 Hz); 7.47 (1H, singlet); 6.09 (1H, doublet, J=2.7 Hz); 3.44 (4H, quartet, J=7.0 Hz); 2.56 (6H, singlet); 1.08 (6H, triplet, J=7.0 Hz).

1-(Diethylcarbamoyl)-3-(3,5-dichloro-2,6-dimethylphenylsulfonyl)pyrazole (Compound No. 10.16)

Following the procedure of Example 1, there were obtained 271 mg (yield 52.1%) of the title compound, melting at 87°–90° C.

1-(Diethylcarbamoyl)-3-(4-chloro-2-fluoro-5-methoxyphenylthio)pyrazole (Compound No. 10.17)

Following the procedure of Example 1, there were obtained 191 mg (yield 79.1%) of the title compound, as an oily substance.

Nuclear Magnetic Resonance Spectrum (CDCl$_3$, 200 MHz), δ ppm: 8.12 (1H, doublet, J=2.7 Hz); 7.18 (1H, doublet, J=8.1 Hz); 7.00 (1H, doublet, J=6.3 Hz); 6.28 (1H, doublet, J=2.7 Hz); 3.83 (3H, singlet); 3.53 (4H, broad quartet, J=7.0 Hz); 1.18 (6H, triplet, J=7.0 Hz).

1-(Diethylcarbamoyl)-3-(4-chloro-2-fluoro-5-methoxyphenylsulfonyl)pyrazole (Compound No. 10.18)

Following the procedure of Example 1, there were obtained 151 mg (yield 71.1%) of the title compound, as an oily substance.

Nuclear Magnetic Resonance Spectrum (CDCl$_3$, 200 MHz), δ ppm: 8.19 (1H, doublet, J=2.5 Hz); 7.58 (1H, doublet, J=5.9 Hz); 7.24 (1H, doublet, J=8.7 Hz); 6.95 (1H, doublet, J=2.5 Hz); 3.97 (3H, singlet); 3.49 (4H, broad quartet, J=7.0 Hz); 1.21 (6H, broad triplet, J=7.0 Hz).

1-(Diethylcarbamoyl)-3-(4-chloro-3,5-dimethoxyphenylsulfonyl)pyrazole (Compound No. 10.19)

Following the procedure of Example 1, there were obtained 21 mg (yield 5.2%) of the title compound, melting at 148°–151° C.

1-(Diethylcarbamoyl)-3-(2-chloro-3,5-dimethoxyphenylsulfonyl)pyrazole (Compound No. 10.20)

Following the procedure of Example 1, there were obtained 91 mg (yield 20.2%) of the title compound, as an oily substance.

Nuclear Magnetic Resonance Spectrum (CDCl$_3$, 200 MHz), δ ppm: 8.17 (1H, doublet, J=2.9 Hz); 7.48 (1H, doublet, J=2.9 Hz); 6.98 (1H, doublet, J=2.9 Hz); 6.74 (1H, doublet, J=2.9 Hz); 3.90 (3H, singlet); 3.88 (3H, singlet); 3.44 (4H, quartet, J=7.1 Hz); 1.16 (6H, multiplet).

1-(Diethylcarbamoyl)-3-(2-bromo-3,5-dimethoxyphenylsulfonyl)pyrazole (Compound No. 10.21)

Following the procedure of Example 1, there were obtained 55 mg (yield 15.3%) of the title compound, as an oily substance.

Nuclear Magnetic Resonance Spectrum (CDCl$_3$, 200 MHz), δ ppm: 8.17 (1H, doublet, J=2.6 Hz); 7.57 (1H, doublet, J=2.8 Hz); 7.00 (1H, doublet, J=2.8 Hz); 6.71 (1H, doublet, J=2.6 Hz); 3.91 (3H, singlet); 3.89 (3H, singlet); 3.42 (4H, quartet, J=7.0 Hz); 1.15 (6H, multiplet).

1-(Diethylcarbamoyl),3-(3-chloro-2,4,6-trimethylphenylsulfonyl)pyrazole (Compound No. 10.22)

Following the procedure of Example 1, there were obtained 132 mg (yield 30.2%) of the title compound, melting at 89°–90° C.

1-(Diethylcarbamoyl)-3-(2,6-dichloro-3-methylphenylsulfonyl)pyrazole (Compound No. 10.23)

Following the procedure of Example 1, there were obtained 164 mg (yield 22.1%) of the title compound, melting at 63°–64° C.

1-(Diethylcarbamoyl)-3-(2,6-dichloro-3-methylphenylthio)pyrazole (Compound No. 10.24)

Following the procedure of Example 1, there were obtained 634 mg (yield 29.4%) of the title compound, as an oily substance.

Nuclear Magnetic Resonance Spectrum (CDCl$_3$, 200 MHz), δ ppm: 8.07 (1H, doublet, J=2.6 Hz); 7.32 (1H, doublet, J=8.1 Hz); 7.24 (1H, doublet, J=8.1 Hz); 6.18 (1H, doublet, J=2.6 Hz); 3.45 (4H, quartet, J=7.0 Hz); 2.38 (3H, singlet); 1.09 (6H, broad).

1-(Diethylcarbamoyl)-3-(2,3,4,5,6-pentafluorophenylsulfonyl)pyrazole (Compound No. 10.25)

Following the procedure of Example 1, there were obtained 377 mg (yield 73.6%) of the title compound, as an oily substance.

Nuclear Magnetic Resonance Spectrum (CDCl$_3$, 200 MHz), δ ppm: 8.28 (1H, doublet, J=3.0 Hz); 6.99 (1H, doublet, J=3.0 Hz); 3.60–3.40 (4H, multiplet); 1.29–1.13 (6H, multiplet).

1-(Diethylcarbamoyl)-3-(2,3,4,5,6-pentafluorophenylthio)pyrazole (Compound No. 10.26)

Following the procedure of Example 1, there were obtained 531 mg (yield 82.7%) of the title compound, as an oily substance.

Nuclear Magnetic Resonance Spectrum (CDCl$_3$, 200 MHz), δ ppm: 8.11 (1H, doublet, J=2.7 Hz); 6.33 (1H, doublet, J=2.7 Hz); 3.49 (4H, quartet, J=7.0 Hz); 1.15 (6H, triplet, J=7.0 Hz).

1-(Ethylcarbamoyl)-3-(2,4,6-trimethylphenylsulfonyl)pyrazole (Compound No. 10.40)

Following the procedure of Example 2, there were obtained 470 mg (yield 85.6%) of the title compound, as an oily substance.

Nuclear Magnetic Resonance Spectrum (CDCl$_3$, 200 MHz), δ ppm: 8.25 (1H, doublet, J=2.8 Hz); 7.03 (1H, broad); 6.97 (2H, singlet); 6.78 (1H, doublet, J=2.8 Hz); 3.45 (2H, multiplet); 2.68 (6H, singlet); 2.31 (3H, singlet); 1.26 (3H, triplet, J=7.2 Hz).

1(N-Ethyl-N-methylcarbamoyl)-3-(2,4,6,-trimethylphenylsulfonyl)pyrazole (Compound No. 10.41)

Following the procedure of Example 2, there were obtained 235 mg (yield 75.3%) of the title compound, as an oily substance.

Nuclear Magnetic Resonance Spectrum (CDCl$_3$, 200 MHz), δ ppm: 8.16 (1H, doublet, J=2.8 Hz); 6.94 (2H, singlet); 6.85 (1H, doublet, J=2.8 Hz); 3.50 (2H, quartet, J=7.2 Hz); 3.10 (3H, broad); 2.66 (6H, singlet); 2.29 (3H, singlet); 1.22 (3H, broad).

1-[N-(2-Bromoethyl)-N-ethylcarbamoyl]-3-(2,4,6-trimethylphenylsulfonyl)pyrazole (Compound No. 10.42)

Following the procedure of Example 2, there were obtained 48 mg (yield 18.0%) of the title compound, as an oily substance.

Nuclear Magnetic Resonance Spectrum (CDCl$_3$, 200 MHz), δ ppm: 7.50 (1H, doublet, J=1.9 Hz); 7.01 (2H, singlet); 6.55 (1H, doublet, J=1.9 Hz); 4.60 (2H, triplet, J=7.4 Hz); 4.51 (2H, quartet, J=7.4 Hz); 3.54 (2H, triplet, J=7.4 Hz); 2.60 (6H, singlet); 2.34 (3H, singlet); 1.45 (3H, triplet, J=7.4 Hz).

1-(Pyrrolidin-1-ylcarbonyl)-3-(2,4,6-trimethylphenylsulfonyl)pyrazole (Compound No. 10.45)

Following the procedure of Example 2, there were obtained 222 mg (yield 68.4%) of the title compound, as an oily substance.

Nuclear Magnetic Resonance Spectrum (CDCl$_3$, 200 MHz), δ ppm: 8.27 (1H, doublet, J=2.7 Hz); 6.95 (2H, singlet); 6.83 (1H, doublet, J=2.7 Hz); 3.82 (2H, triplet, J=6.7 Hz); 3.63 (2H, triplet, J=6.7 Hz); 2.69 (6H, singlet); 2.29 (3H, singlet); 1.90 (4H, broad).

1(N-Ethyl-N-propylcarbamoyl)-3-(2,4,6-trimethylphenylsulfonyl)pyrazole (Compound No. 10.47)

Following the procedure of Example 2, there were obtained 187 mg (yield 54.8%) of the title compound, melting at 69°–70° C.

1-(N-Butyl-N-methylcarbamoyl)-3-(2,4,6-trimethylphenylsulfonyl)pyrazole (Compound No. 10.48)

Following the procedure of Example 2, there were obtained 255 mg (yield 75.3%) of the title compound, as an oily substance.

Nuclear Magnetic Resonance Spectrum (CDCl$_3$, 200 MHz), δ ppm: 8.15 (1H, doublet, J: 2.6 Hz); 6.94 (2H, singlet); 6.85 (1H, doublet, J=2.6 Hz); 3.45 (2H, triplet, J=7.6 Hz); 3.12 (4H, broad); 2.65 (6H, singlet); 2.29 (3H, singlet); 1.56 (3H, broad); 0.87 (3H, broad).

1-(Diallylcarbamoyl)-3-(2,4,6-trimethylphenylsulfonyl)pyrazole (Compound No. 10.50)

Following the procedure of Example 2, there were obtained 269 mg (yield 77.0%) of the title compound, as an oily substance.

Nuclear Magnetic Resonance Spectrum (CDCl$_3$, 200 MHz), δ ppm: 8.18 (1H, doublet, J=8.2 Hz); 6.94 (2H, singlet); 6.87 (1H, doublet, J=8.2 Hz); 5.75 (2H, broad); 5.29 (4H, broad); 4.03 (4H, broad); 2.63 (6H, singlet); 2.29 (3H, singlet).

1-(Diethylcarbamoyl)-3-(4-iodo-3,5-dimethoxyphenylsulfonyl)pyrazole (Compound No. 10.51)

Following the procedure of Example 1, there were obtained 37 mg (yield 3.3%) of the title compound, melting at 120°–122° C.

1-(Diethylcarbamoyl)-3-(2-iodo-3,5-dimethoxyphenylsulfonyl)pyrazole (Compound No. 10.52)

Following the procedure of Example 1, there were obtained 25 mg (yield 3.7%) of the title compound, as an oily substance.

Nuclear Magnetic Resonance Spectrum (CDCl$_3$, 200 MHz), δ ppm: 8.18 (1H, doublet, J=2.6 Hz); 7.67 (1H, doublet, J=2.8 Hz); 7.03 (1H, doublet, J=2.8 Hz); 6.60 (1H, doublet, J=2.6 Hz); 3.91 (3H, singlet); 3.89 (3H, singlet); 3.40 (4H, quartet, J=7.0 Hz); 1.80–1.50 (6H, broad).

1-(Dimethylcarbamoyl)-3-(2,4,6-trimethylphenylsulfonyl)-4-chloropyrazole (Compound No. 10.53)

Following the procedure of Example 2, there were obtained 165 mg (yield 71.6%) of the title compound, melting at 52°–60° C.

1-(N-Ethyl-N-methylcarbamoyl)-3-(2,4,6-trimethylphenylsulfonyl)-4-chloropyrazole (Compound No. 10.54)

Following the procedure of Example 2, there were obtained 156 mg (yield 62.3%) of the title compound, melting at 119°–120° C.

1-(N-Ethyl-N-propylcarbamoyl)-3-(2,4,6-trimethylphenylsulfonyl)-4-chloropyrazole (Compound No. 10.57)

Following the procedure of Example 2, there were obtained 154 mg (yield 58.6%) of the title compound, melting at 108°–110° C.

1-(Dipropylcarbamoyl)-3-(2,4,6-trimethylphenylsulfonyl)-4-chloropyrazole (Compound No. 10.58)

Following the procedure of Example 2, there were obtained 150 mg (yield 62.3%) of the title compound, melting at 103°–105° C.

1(N-Butyl-N-methylcarbamoyl)-3-(2,4,6-trimethylphenylsulfonyl)-4-chloropyrazole (Compound No. 10.59)

Following the procedure of Example 2, there were obtained 143 mg (yield 57.7%) of the title compound, melting at 69°–71.5° C.

1(N-Methoxy-N-methylcarbamoyl)-3-(2,4,6-trimethylphenylsulfonyl)-4-chloropyrazole (Compound No. 10.60)

Following the procedure of Example 2, there were obtained 212 mg (yield 53.0%) of the title compound, melting at 105°–107° C.

1-(Diethylcarbamoyl)-3-(3-chloro-2,6-dimethylphenylthio)-4-chloropyrazole (Compound No. 10.61)

Following the procedure of Example 4, there were obtained 381 mg (yield 39.1%) of the title compound, as an oily substance.

Nuclear Magnetic Resonance Spectrum (CDCl$_3$, 200 MHz), δ ppm: 8.09 (1H, singlet); 7.30 (1H, doublet, J=8.3 Hz); 7.07 (1H, doublet, J=8.3 Hz); 3.33 (4H, quartet, J=7.0 Hz); 2.57 (3H, singlet); 2.45 (3H, singlet); 1.08–0.87 (6H, broad).

1-(Diethylcarbamoyl)-3-(3-chloro-2,6-dimethylphenylsulfonyl)-4-chloropyrazole (Compound No. 10.62)

Following the procedure of Example 4, there were obtained 254 mg (yield 34.0%) of the title compound, melting at 103°–105° C.

1-(Diethylcarbamoyl)-3-(3,5-dichloro-2,6-dimethylphenylthio)-4-chloropyrazole (Compound No. 10.63)

Following the procedure of Example 4, there were obtained 454 mg (yield 37.8%) of the title compound, melting at 90°–93° C.

1-(Diethylcarbamoyl)-3-(3,5-dichloro-2,6-dimethylphenylsulfonyl)-4-chloropyrazole (Compound No. 10.64)

Following the procedure of Example 4, there were obtained 301 mg (yield 31.8%) of the title compound, melting at 108°–110° C.

1-(Diethylcarbamoyl)-3-(4-bromo-2,6-dimethylphenylthio)-4-chloropyrazole (Compound No. 10.65)

Following the procedure of Example 4, there were obtained 396 mg (yield 43.3%) of the title compound, melting at 88°–90° C.

1-(Diethylcarbamoyl)-3-(4-bromo-2,6-dimethylphenylsulfonyl)-4-chloropyrazole (Compound No. 10.66)

Following the procedure of Example 4, there were obtained 340 mg (yield 37.6%) of the title compound, melting at 106°–108° C.

1-(Diethylcarbamoyl)-3-(2,4,6-trichlorophenylsulfonyl)-4-chloropyrazole (Compound No. 10.67)

Following the procedure of Example 4, there were obtained 81 mg (yield 14.3%) of the title compound, melting at 114°–117° C.

1-(Diethylcarbamoyl)-3-(2,4,5-trichlorophenylsulfonyl)-4-chloropyrazole (Compound No. 10.68)

Following the procedure of Example 4, there were obtained 325 mg (yield 56.4%) of the title compound, melting at 112°–113° C.

1-(Diethylcarbamoyl)-3-(4-chloro-2-fluoro-5-methoxyphenylthio)-4-chloropyrazole (Compound No. 10.69)

Following the procedure of Example 4, there were obtained 191 mg (yield 51.0%) of the title compound, as an oily substance.

Nuclear Magnetic Resonance Spectrum (CDCl$_3$, 200 MHz), δ ppm: 8.13 (1H, singlet); 7.18 (1H, doublet, J=8.1 Hz); 6.99 (1H, doublet, J=6.3 Hz); 3.84 (3H, singlet); 3.48 (4H, broad quartet, J=7.0 Hz); 1.13 (6H, broad triplet, J=7.0 Hz).

1-(Diethylcarbamoyl)-3-(4-chloro-2-fluoro-5-methoxyphenylsulfonyl)-4-chloropyrazole (Compound No. 10.70)

Following the procedure of Example 4, there were obtained 161 mg (yield 50.0%) of the title compound, melting at 124°–125° C.

1-(Diethylcarbamoyl)-3-(4-chloro-2-fluoro-5-isopropoxyphenylthio)-4-chloropyrazole (Compound No. 10.72)

Following the procedure of Example 3, there were obtained 198 mg (yield 45.6%) of the title compound, as an oily substance.

Nuclear Magnetic Resonance Spectrum (CDCl$_3$, 200 MHz), δ ppm: 8.14 (1H, singlet); 7.16 (1H, doublet, J=8.3 Hz); 7.00 (1H, doublet, J=6.5 Hz); 4.41 (1H, septet, J=6.1 Hz); 3.48 (4H, broad quartet, J=6.9 Hz); 1.33 (6H, doublet, J=6.1 Hz); 1.14 (6H, broad triplet, J=6.9 Hz).

1-(Diethylcarbamoyl)-3-(4-chloro-2-fluoro-5-isopropoxyphenylsulfonyl)-4-chloropyrazole (Compound No. 10.73)

Following the procedure of Example 3, there were obtained 142 mg (yield 40.0%) of the title compound, melting at 92°–94° C.

1-(Diethylcarbamoyl)-3-(3-chloro-2,4,6-trimethylphenylsulfonyl)-4-chloropyrazole (Compound No. 10.74)

Following the procedure of Example 3, there were obtained 169 mg (yield 41.7%) of the title compound, melting at 104°–105° C.

1-(Diethylcarbamoyl)-3-(3,5-dichloro-2,4,6-trimethylphenylsulfonyl)pyrazole (Compound No. 10.75)

Following the procedure of Example 3, there were obtained 56 mg (yield 37.1%) of the title compound, melting at 140° C.

1-(Diethylcarbamoyl)-3-(3,5-dichloro-2,4,6-trimethylphenylsulfonyl)-4-chloropyrazole (Compound No. 10.76)

Following the procedure of Example 3, there were obtained 38 mg (yield 14.3%) of the title compound, melting at 144°–145° C.

1-(Diethylcarbamoyl)-3-(2,6-dichloro-3-methylphenylsulfonyl)-4-chloropyrazole (Compound No. 10.77)

Following the procedure of Example 5, there were obtained 80 mg (yield 44.8%) of the title compound, melting at 74°–75° C.

1-(Diethylcarbamoyl)-3-(3,5-dichloro-2,4,6-trimethylphenylthio)pyrazole (Compound No. 10.79)

Following the procedure of Example 1, there were obtained 82 mg (yield 41.7%) of the title compound, melting at 63°–65° C.

1-(Diethylcarbamoyl)-3-(3,5-dichloro-2,4,6-trimethylphenylthio)-4-chloropyrazole (Compound No. 10.80)

Following the procedure of Example 1, there were obtained 68 mg (yield 17.1%) of the title compound, melting at 85°–89° C.

1-(Dimethylcarbamoyl)-3-(2,4,6-trimethylphenylsulfonyl)-4-fluoropyrazole (Compound No. 10.83)

Following the procedure of Example 7, there were obtained 51 mg (yield 21.9%) of the title compound, as an amorphous product.

Nuclear Magnetic Resonance Spectrum (CDCl$_3$, 200 MHz), δ ppm: 8.01 (1H, doublet, J=4.8 Hz); 6.97 (2H, singlet); 3.2 (6H, broad); 2.67 (6H, singlet); 1.58 (3H, singlet).

1-(N-Ethyl-N-methylcarbamoyl)-3-(2,4,6-trimethylphenylsulfonyl)-4-fluoropyrazole (Compound No. 10.84)

Following the procedure of Example 7, there were obtained 51 mg (yield 18.4%) of the title compound, as an oily substance.

Nuclear Magnetic Resonance Spectrum (CDCl$_3$, 200 MHz), δ ppm: 7.98 (1H, doublet, J=4.8 Hz); 6.96 (2H, singlet); 3.53 (2H, quartet, J=7.0 Hz); 3.12 (3H, broad); 2.67 (6H, singlet); 2.30 (3H, singlet); 1.20 (3H, broad).

1-(N-Ethyl-N-propylcarbamoyl)-3-(2,4,6-trimethylphenylsulfonyl)-4-fluoropyrazole (Compound No. 10.86)

Following the procedure of Example 7, there were obtained 45 mg (yield 18.1%) of the title compound, as an amorphous product.

Nuclear Magnetic Resonance Spectrum (CDCl$_3$, 200 MHz), δ ppm: 8.00 (1H, doublet, J=4.8 Hz); 6.96 (2H, singlet); 3.6–3.3 (4H, multiplet); 2.66 (6H, singlet); 2.30 (3H, singlet); 1.76–1.53 (2H, multiplet); 1.18 (3H, broad); 0.86 (3H, broad).

1-(Diethylcarbamoyl)-3-(2,6-dichloro-3-methylphenylsulfonyl)-4-fluoropyrazole (Compound No. 10.87)

Following the procedure of Example 7, there were obtained 29 mg (yield 4.5%) of the title compound, melting at 77°–79° C.

1-(Diethylcarbamoyl)-3-(3,5-dichloro-2,4,6-trimethylphenylsulfonyl)-4-fluoropyrazole (Compound No. 10.89)

Following the procedure of Example 7, there were obtained 10 mg (yield 3.7%) of the title compound, melting at 70°–72° C.

1-(Diethylcarbamoyl)-3, (3-chloro-2,6-dimethylphenylsulfonyl)-4-fluoropyrazole (Compound No. 10.90)

Following the procedure of Example 7, there were obtained 36 mg (yield 4.5%) of the title compound, as an oily substance.

Nuclear Magnetic Resonance Spectrum (CDCl$_3$, 200 MHz), δ ppm: 8.04 (1H, doublet, J=5.7 Hz); 7.50 (1H, doublet, J=7.9 Hz); 7.12 (1H, doublet, J=7.9 Hz); 3.48 (4H, quartet, J=7.1 Hz); 2.73 (6H, singlet); 1.13 (6H, broad).

1-(Diethylcarbamoyl)-3-(2,4,6-trimethylphenylthio)-4-bromopyrazole (Compound No. 10.116)

Following the procedure of Example 5, there were obtained 455 mg (yield 78.7%) of the title compound, melting at 87°–88° C.

1-(Diethylcarbamoyl)-3-(2,4,6-trimethylphenylsulfonyl)-4-bromopyrazole (Compound No. 10.117)

Following the procedure of Example 5, there were obtained 439 mg (yield 78.7%) of the title compound, melting at 111°–113° C.

1-(Diethylcarbamoyl)-3-(4-bromo-3,3-dimethyl)phenylsulfonyl)-4-bromopyrazole (Compound No. 10.118)

Following the procedure of Example 5, there were obtained 44 mg (yield 3.8%) of the title compound, melting at 123°–125° C.

1-(Diethylcarbamoyl)-3-(2,4,6-trichlorophenylsulfonyl)-4-bromopyrazole (Compound No. 10.119)

Following the procedure of Example 5, there were obtained 23 mg (yield 13.5%) of the title compound, melting at 105°–108° C.

1-(Diethylcarbamoyl)-3-(2,6-dichloro-3-methylphenylsulfonyl)-4-bromopyrazole (Compound No. 10.120)

Following the procedure of Example 5, there were obtained 131 mg (yield 14.7%) of the title compound, as an amorphous product.

Nuclear Magnetic Resonance Spectrum (CDCl$_3$, 200 MHz), δ ppm: 8.20 (1H, singlet); 7.39 (2H, singlet); 3.45 (4H, quartet, J=7.0 Hz); 2.40 (3H, singlet); 1.4–0.8 (6H, broad).

1-(Diethylcarbamoyl)N-3-(2,4,6-trimethylphenylthio)-4-cyanopyrazole (Compound No. 10.140)

Following the procedure of Example 14, there were obtained 148 mg (yield 40.6%) of the title compound, melting at 96°–100° C.

1-(Diethylcarbamoyl)-3-(2,4,6-trimethylphenylsulfonyl)-4-cyanopyrazole (Compound No. 10.141)

Following the procedure of Example 14, there were obtained 129 mg (yield 39.4%) of the title compound, melting at 145 149° C.

1-(Diethylcarbamoyl)-3-(2,4,6-trimethylphenylsulfonyl)-4,5-dichloropyrazole (Compound No. 10.158)

Following the procedure of Example 16, there were obtained 137 mg (yield 41.0%) of the title compound, melting at 78°–80° C.

1-(Diethylcarbamoyl)-3-(2,4,6-trimethylphenylsulfonyl)-4-chloro-5-cyanopyrazole (Compound No. 10.159)

Following the procedure of Example 16, there were obtained 133 mg (yield 38.2%) of the title compound, melting at 119°–121° C.

1-(Diethylcarbamoyl)-3-(2,4,6-trichlorophenylsulfonyl)pyrazole (Compound No. 10.160)

Following the procedure of Example 1, there were obtained 261 mg (yield 42.8%) of the title compound, melting at 116°–117° C.

1-(Diethylcarbamoyl)-3-(2-pyridylsulfonyl)pyrazole (Compound No. 11.1)

Following the procedure of Example 1, there were obtained 316 mg (yield 53.0%) of the title compound, as an oily substance.

Nuclear Magnetic Resonance Spectrum (CDCl$_3$, 200 MHz), δ ppm: 8.72 (1H, doublet of doublets, J=4.8 & 1.1 Hz); 8.26 (1H, doublet of doublets, J=7.8 & 1.1 Hz); 8.18 (1H, doublet, J=2.8 Hz); 7.98 (1H, triplet of doublets, J=7.8 & 1.1 Hz); 7.54 (1H, doubled doublet of doublets, J=7.8, 4.8 a 1.1 Hz); 7.12 (1H, doublet, J=2.8 Hz); 3.42 (4H, quartet, J=7.0 Hz); 1.26–1.16 (6H, broad).

1-(Diethylcarbamoyl)-3-(2-pyridylthio)pyrazole (Compound No. 11.2)

Following the procedure of Example 1, there were obtained 1.42 g (yield 56.4%) of the title compound, as an oily substance.

Nuclear Magnetic Resonance Spectrum (CDCl$_3$, 200 MHz), δ ppm: 8.44 (1H, doublet of doublets, J=5.8 & 2.8 Hz); 8.23 (1H, doublet, J=2.8 Hz); 7.51 (1H, triplet of doublets, J=8.2 & 1.9 Hz); 7.13–7.02 (2H, multiplet); 6.55 (1H, doublet, J=2.8 Hz); 3.62 (4H, quartet, J=7.0 Hz); 1.26 (6H, triplet, J=7.0 Hz).

1-(Diethylcarbamoyl)-3-(5-chloro-2-pyridylsulfonyl)-pyrazole (Compound No. 11.4)

Following the procedure of Example 1, there were obtained 164 mg (yield 31.6%) of the title compound, melting at 82°–87° C.

1-(Diethylcarbamoyl)-3-(5-bromo-2-pyridylthio)-pyrazole (Compound No. 11.7)

Following the procedure of Example 1, there were obtained 1.03 g (yield 25.7%) of the title compound, as an oily substance.

Nuclear Magnetic Resonance Spectrum (CDCl$_3$, 200 MHz), δ ppm: 8.49 (1H, doublet, J=2.2 Hz); 8.23 (1H, doublet, J=2.6 Hz); 7.63 (1H, doublet of doublets, J=8.8 & 2.2 Hz); 7.01 (1H, doublet, J=8.8 Hz); 6.55 (1H, doublet, J=2.6 Hz); 3.61 (4H, quartet, J=7.0 Hz); 1.26 (6H, triplet, J=7.0 Hz).

1-(Diethylcarbamoyl)-3-(5-bromo-2-pyridylsulfonyl)-pyrazole (Compound No. 11.8)

Following the procedure of Example 1, there were obtained 206 mg (yield 23.9%) of the title compound, melting at 80°–83° C.

1-(Diethylcarbamoyl)-3-(3-chloro-2-pyridylthio)-pyrazole (Compound No. 11.9)

Following the procedure of Example 1, there were obtained 233 mg (yield 33.1%) of the title compound, as an oily substance.

Nuclear Magnetic Resonance Spectrum (CDCl$_3$, 200 MHz), δ ppm: 8.24 (1H, doublet of doublets, J=4.7 & 1.5 Hz); 8.23 (1H, doublet, J=2.6 Hz); 7.60 (1H, doublet of doublets, J=7.9 & 1.5 Hz); 7.02 (1H, doublet of doublets, J=7.9 & 4.7 Hz); 6.60 (1H, doublet, J=2.6 Hz); 3.62 (4H, quartet, J=7.1 Hz); 1.26 (6H, triplet, J=7.1 Hz).

1-(Diethylcarbamoyl)-3-(3-chloro-2-pyridylsulfonyl)-pyrazole (Compound No. 11.10)

Following the procedure of Example 1, there were obtained 133 mg (yield 20.2%) of the title compound, melting at 105.5°–106.5° C.

1-(Diethylcarbamoyl)-3-(6-methyl-2-pyridylthio)-pyrazole (Compound No. 11.11)

Following the procedure of Example 1, there were obtained 270 mg (yield 46.2%) of the title compound, as an oily substance.

Nuclear Magnetic Resonance Spectrum (CDCl$_3$, 200 MHz), δ ppm: 8.21 (1H, doublet, J=2.7 Hz); 7.42 (1H, triplet, J=7.8 Hz); 6.93 (1H, doublet, J=7.8 Hz); 6.89 (1H, doublet, J=7.8 Hz); 6.54 (1H, doublet, J=2.7 Hz); 3.62 (4H, quartet, J=7.0 Hz); 2.53 (3H, singlet); 1.26 (6H, singlet).

1-(Diethylcarbamoyl)-3-(6-methyl-2-pyridylsulfonyl)-pyrazole (Compound No. 11.12)

Following the procedure of Example 1, there were obtained 160 mg (yield 34.7%) of the title compound, as an oily substance.

Nuclear Magnetic Resonance Spectrum (CDCl$_3$, 200 MHz), δ ppm: 8.17 (1H, doublet, J=2.7 Hz); 8.06 (1H, doublet, J=7.6 Hz); 7.83 (1H, triplet, J=7.6 Hz); 7.36 (1H, doublet, J=7.6 Hz); 7.01 (1H, doublet, J=2.7 Hz); 3.50 (4H, quartet, J=7.0 Hz); 2.60 (3H, singlet); 1.29–1.15 (6H, multiplet).

1-(Diethylcarbamoyl)-3-(3-trifluoromethyl-2-pyridylthio)pyrazole (Compound No. 11.13)

Following the procedure of Example 1, there were obtained 283 mg (yield 49.9%) of the title compound, as an oily substance.

Nuclear Magnetic Resonance Spectrum (CDCl$_3$, 200 MHz), δ ppm: 8.47 (1H, doublet, J=4.4 Hz); 8.21 (1H, doublet, J=2.6 Hz); 7.90 (1H, doublet, J=8.0 Hz); 7.17

(1H, doublet of doublets, J=8.0 & 4.4 Hz); 6.55 (1H, doublet, J=2.6 Hz); 3.61 (4H, quartet, J=7.0 Hz); 1.24 (6H, triplet, J=7.0 Hz).

1-(Diethylcarbamoyl)-3-(3-trifluoromethyl-2-pyridylsulfonyl)pyrazole (Compound No. 11.14)

Following the procedure of Example 1, there were obtained 201 mg (yield 36.9%) of the title compound, melting at 88°-89° C.

1-(Diethylcarbamoyl)3-(5-trifluoromethyl-2pyridylthio)pyrazole (Compound No. 11.15)

Following the procedure of Example 1, there were obtained 888 mg (yield 20.9%) of the title compound, as an oily substance.

Nuclear Magnetic Resonance Spectrum (CDCl$_3$, 200 MHz), δ ppm: 8.66 (1H, doublet, J=1.8 Hz); 8.27 (1H, doublet, J=2.6 Hz); 7.70 (1H, doublet of doublets, J=8.1 & 1.8 Hz); 7.15 (1H, doublet, J=8.1 Hz); 6.60 (1H, doublet, J=2.6 Hz); 3.62 (4H, quartet, J=7.2 Hz); 1.28 (6H, triplet, J=7.2 Hz).

1-(Diethylcarbamoyl)-3-(5-trifluoromethyl-2-pyridylsulfonyl)pyrazole (Compound No. 11.16)

Following the procedure of Example 1, there were obtained 432 mg (yield 10.0%) of the title compound, melting at 81°-85° C.

1-(Diethylcarbamoyl)-3-(3-chloro-5-trifluoromethyl-2-pyridylsulfonyl)pyrazole (Compound No. 11.17)

Following the procedure of Example 3, there were obtained 210 mg (yield 40.9%) of the title compound, as an oily substance.

Nuclear Magnetic Resonance Spectrum (CDCl$_3$, 200 MHz), δ ppm: 8.74 (1H, doublet, J=1.8 Hz); 8.27 (1H, doublet, J=2.8 Hz); 8.14 (1H, doublet, J=1.8 Hz); 7.02 (1H, doublet, J=2.8 Hz); 3.53 (4H, quartet, J=7.0 Hz); 1.26 (6H, triplet, J=7.0 Hz).

1-(Diethylcarbamoyl)-3-(5-chloro-2-pyridylthio)-4-chloropyrazole (Compound No. 11.18)

Following the procedure of Example 3, there were obtained 154 mg (yield 23.5%) of the title compound, as an oily substance.

Nuclear Magnetic Resonance Spectrum (CDCl$_3$, 200 MHz), δ ppm: 8.39 (1H, doublet, J=2.2 Hz); 8.24 (1H, singlet); 7.52 (1H, doublet of doublets, J=8.6 & 2.2 Hz); 7.04 (1H, doublet, J=8.6 Hz); 3.59 (4H, quartet, J=7.0 Hz); 1.26 (6H, triplet, J=7.0 Hz).

1-(Diethylcarbamoyl)-3-(5-chloro-2-pyridylsulfonyl)-4-chloropyrazole (Compound No. 11.19)

Following the procedure of Example 3, there were obtained 119 mg (yield 19.0%) of the title compound, melting at 139°-142° C.

1-(Dimethylcarbamoyl)-3-(3-trifluoromethyl-2-pyridylthio)-4-chloropyrazole (Compound No. 11.20)

Following the procedure of Example 4, there were obtained 137 mg (yield 44.5%) of the title compound, melting at 104°-108° C.

1-(Dimethylcarbamoyl)-3-(3-trifluoromethyl-3-sulfonyl)-4-chloropyrazole (Compound No. 11.21)

Following the procedure of Example 4, there were obtained 111 mg (yield 37.8%) of the title compound, as an oily substance.

Nuclear Magnetic Resonance Spectrum (CDCl$_3$, 200 MHz), δ ppm: 8.69 (1H, doublet of doublets, J=4.7 & 1.1 Hz); 8.27 (1H, doublet of doublets, J=8.1 & 1.1 Hz); 8.22 (1H, singlet); 7.67 (1H, doublet of doublets, J=8.1 & 4.7 Hz); 3.10-3.30 (6H, multiplet).

1(N-Ethyl-N-methylcarbamoyl)-3-(3-trifluoromethyl-2-pyridylthio)-4-chloropyrazole (Compound No. 11.22)

Following the procedure of Example 4, there were obtained 195 mg (yield 56.7%) of the title compound, melting at 73°-75° C.

1(N-Ethyl-N-methylcarbamoyl)-3-(3-trifluoromethyl-2-pyridylsulfonyl)-4-chloropyrazole (Compound No. 11.23)

Following the procedure of Example 4, there were obtained 151 mg (yield 47.1%) of the title compound, as an oily substance.

Nuclear Magnetic Resonance Spectrum (CDCl$_3$, 200 MHz), δ ppm: 8.69 (1H, doublet of doublets, J=4.5 & 0.8 Hz); 8.27 (1H, doublet of doublets, J=7.7 & 0.8 Hz); 8.21 (1H, singlet); 7.67 (1H, doublet of doublets, J=7.7 & 4.5 Hz); 3.54-3.62 (2H, multiplet); 3.14-3.25 (3H, multiplet); 1.27 (3H, triplet, J=7.0 Hz).

1-(Diethylcarbamoyl)-3-(3-trifluoromethyl-2-pyridylthio)-4-chloropyrazole (Compound No. 11.24)

Following the procedure of Example 4, there were obtained 306 mg (yield 61.0%) of the title compound, as an oily substance.

Nuclear Magnetic Resonance Spectrum (CDCl$_3$, 200 MHz), δ ppm: 8.45 (1H, doublet, J=4.7 Hz); 8.22 (1H, singlet); 7.90 (1H, doublet, J=8.1 Hz); 7.18 (1H, doublet of doublets, J=8.1 & 4.7 Hz); 3.60 (4H, quartet, J=7.0 Hz); 1.26 (6H, triplet, J=7.0 Hz).

1-(Diethylcarbamoyl)-3-(3-trifluoromethyl-2-pyridylsulfonyl)-4-chloropyrazole (Compound No. 11.25)

Following the procedure of Example 4, there were obtained 212 mg (yield 45.1%) of the title compound, melting at 125°-126.5° C.

1-(Diethylcarbamoyl)-3-(5-trifluoromethyl-2-pyridylthio)-4-chloropyrazole (Compound No. 11.26)

Following the procedure of Example 3, there were obtained 346 mg (yield 25.2%) of the title compound, as an oily substance.

Nuclear Magnetic Resonance Spectrum (CDCl$_3$, 200 MHz), δ ppm: 8.66 (1H, doublet, J=2.2 Hz); 8.28 (1H, singlet); 7.74 (1H, doublet of doublets, J=8.1 & 2.2 Hz); 7.14 (1H, doublet, J=8.1 Hz); 3.60 (4H, quartet, J=7.0 Hz); 1.27 (6H, triplet, J=7.0 Hz).

1-(Diethylcarbamoyl)-3-(5-trifluoromethyl-2-pyridylsulfonyl)-4-chloropyrazole (Compound No. 11.27)

Following the procedure of Example 3, there were obtained 227 mg (yield 17.9%) of the title compound, melting at 98°-99° C.

1-(Diethylcarbamoyl)-3-(3-chloro-5-trifluoromethyl-2-pyridylthio)-4-chloropyrazole (Compound No. 11.28)

Following the procedure of Example 3, there were obtained 171 mg (yield 52.9%) of the title compound, as an oily substance.

Nuclear Magnetic Resonance Spectrum (CDCl$_3$, 200 MHz), δ ppm: 8.44 (1H, doublet, J=1.8 Hz); 8.26 (1H, singlet); 7.82 (1H, doublet, J=1.8 Hz); 3.61 (4H, quartet, J=7.0 Hz); 1.27 (6H, triplet, J=7.0 Hz).

1-(Diethylcarbamoyl)-3-(3-chloro-5-trifluoromethyl-2-pyridylsulfonyl)-4-chloropyrazole (Compound No. 11.29)

Following the procedure of Example 3, there were obtained 127 mg (yield 44.4%) of the title compound, as an oily substance.

Nuclear Magnetic Resonance Spectrum (CDCl$_3$, 200 MHz), δ ppm: 8.71 (1H, doublet, J=1.7 Hz); 8.25 (1H, singlet); 8.17 (1H, doublet, J=1.7 Hz); 3.56-3.50 (4H, multiplet); 1.26 (6H, triplet, J=7.0 Hz).

1-(Diethylcarbamoyl)-3-(3-trifluoromethyl-2-pyridylthio)-4-bromopyrazole (Compound No. 11.30)

Following the procedure of Example 4, there were obtained 204 mg (yield 31.7%) of the title compound, as an oily substance.

Nuclear Magnetic Resonance Spectrum (CDCl$_3$, 200 MHz), δ ppm: 8.45 (1H, doublet, J=4.4 Hz); 8.25 (1H, singlet); 7.90 (1H, doublet, J=7.7 Hz); 7.17 (1H, doublet of doublets, J=7.7 & 4.4 Hz); 3.60 (4H, quartet, J=7.0 Hz); 1.25 (6H, triplet, J=7.0 Hz).

1-(Diethylcarbamoyl)-3-(3-trifluoromethyl-2-pyridylsulfonyl)-4-bromopyrazole (Compound No. 11.31)

Following the procedure of Example 4, there were obtained 60 mg (yield 10.5%) of the title compound, melting at 111°–115° C.

1-(Diethylcarbamoyl)-3-(3-chloro-5-trifluoromethyl-2-pyridylsulfonyl)-4-bromopyrazole (Compound No. 11.32)

Following the procedure of Example 4, there were obtained 38 mg (yield 6.3%) of the title compound, as an oily substance.

Nuclear Magnetic Resonance Spectrum (CDCl$_3$, 200 MHz), δ ppm: 8.72 (1H, singlet); 8.29 (1H, doublet, J=1.7 Hz); 8.16 (1H, doublet, J=1.7 Hz); 3.62–3.47 (4H, multiplet); 1.26 (6H, triplet, J=7.3 Hz).

1-(Diethylcarbamoyl)-3-(3-trifluoromethyl-2-pyridylsulfonyl)-4-fluoropyrazole (Compound No. 11.34)

Following the procedure of Example 19, there were obtained 27 mg (yield 2.5%) of the title compound, melting at 105°–106 ° C.

1-(Diethylcarbamoyl)-3-(5-chloro-2-pyridylsulfonyl)-4-fluoropyrazole (Compound No. 11.35)

Following the procedure of Example 19, there were obtained 36 mg (yield 3.6%) of the title compound, melting at 81°–82° C.

1-(Diethylcarbamoyl)-3-(3-trifluoromethyl-2-pyridylthio)-4-fluoropyrazole (Compound No. 11.57)

Following the procedure of Example 19, there were obtained 43 mg (yield 4.3%) of the title compound, as an oily substance.

Nuclear Magnetic Resonance Spectrum CDCl$_3$, 200 MHz), δ ppm: 8.45 (1H, doublet, J=4.7 Hz); 8.07 (1H, doublet, J=5.1 Hz); 7.89 (1H, doublet, J=7.0 Hz); 7.17 (1H, doublet of doublets, J=7.0 & 5.1 Hz); 3.60 (4H, quartet, J=7.0 Hz); 1.26 (6H, triplet, J=7.0 Hz).

1-(Diethylcarbamoyl)-3-(5-chloro-2-pyridylthio)-4-fluoropyrazole (Compound No. 11.58)

Following the procedure of Example 19, there were obtained 32 mg (yield 3.6%) of the title compound, as an oily substance.

Nuclear Magnetic Resonance Spectrum CDCl$_3$, 200 MHz), δ ppm: 8.37 (1H, doublet, J=2.5 Hz); 8.10 (1H, doublet, J=5.1 Hz); 7.51 (1H, doublet of doublets, J=8.5 & 2.5 Hz); 7.07 (1H, doublet, J=8.5 Hz); 3.60 (4H, quartet, J=7.0 Hz); 1.26 (6H, triplet, J=7.0 Hz).

1-(Diethylcarbamoyl)-3-(4,6-dimethyl-2-pyrimidinylthio)pyrazole (Compound No. 12.1)

Following the procedure of Example 1, there were obtained 680 mg (yield 28.1%) of the title compound, melting at 59°–60° C.

1-(Diethylcarbamoyl)-3-(4,6-dimethyl-2-pyrimidinylsulfonyl)pyrazole (Compound No. 12.2)

Following the procedure of Example 1, there were obtained 528 mg (yield 24.7%) of the title compound, melting at 88°–90° C. The preparation of various agrochemical compositions is now illustrated. In the following, all parts and percentages are by weight. The mesh sizes given are based on the Tyler standard.

PREPARATION 1

Wettable powders

A mixture comprising 25% of Compound No. 1.4, 2.5% of sodium dodecylbenzenesulfonate, 2.5% of calcium ligninsulfonate and 70% of diatomaceous earth was well mixed and pulverized to make a wettable powder.

PREPARATION 2

Emulsifiable concentrates

A mixture comprising 30% of Compound No. 2.105, 2.68% of calcium dodecylbenzenesulfonate, 4.92% of polyoxyethylene alkyl ether, 0.4% of calcium polyoxyethylene nonylphenyl ether phosphate and 62% of xylene was well mixed to make an emulsifiable concentrate.

PREPARATION 3

Granules

A mixture comprising 5% of Compound No. 3.12, 1% of white carbon, 5% of calcium ligninsulfonate, 20% of bentonite and 69% of clay was mixed and pulverized. The resulting mixture was then well mixed with water, kneaded, granulated and dried to make granules.

PREPARATION 4

Wettable powders

A mixture comprising 10% of Compound No. 4.46, 1% of polyoxyethylene octylphenyl ether, 5% of sodium salt of a condensation product of N-naphthalenesulfonic acid and formalin, 20% of diatomaceous earth and 64% of clay was homogeneously mixed and pulverized to make a wettable powder.

PREPARATION 5

Wettable powders

A mixture comprising 25% of Compound No. 5.6, 2.5% of sodium dodecylbenzenesulfonate, 2.5% of calcium ligninsulfonate and 70% of diatomaceous earth was mixed and pulverized to make a wettable powder.

PREPARATION 6

Emulsifiable concentrates

A mixture comprising 15% of Compound No. 5.13, 35% of cyclohexanone, 2.61% of calcium dodecylbenzenesulfonate, 3.96% of polyoxyethylene distyrenylated methylphenyl ether, 1.87% of polyoxyethylene alkyl ether, 0.26% of calcium polyoxyethylene nonylphenyl phosphate, 1.3% of xylene and 40% of mesitylene was homogeneously dissolved to make an emulsifiable concentrate.

PREPARATION 7

Emulsifiable concentrates

A mixture comprising 30% of Compound No. 6.104, 2.61% of calcium dodecylbenzenesulfonate, 3.96% of polyoxyethylene distyrenylated methylphenyl ether, 1.87% of polyoxyethylene alkyl ether, 0.26% of calcium polyoxyethylene nonylphenyl phosphate and 61.3% of xylene was well mixed to make an emulsifiable concentrate.

PREPARATION 8

Granules

A mixture comprising 5% of Compound No. 7.20, 2% of sodium laurylsulfate, 5% of sodium ligninsulfonate, 2% of the sodium salt of carboxymethyl cellulose, 66% of calcium carbonate and 20% of bentonite was homogeneously mixed and pulverized. To 100 parts of the resulting mixture were added 20 parts of water. The mixture was kneaded, granulated using a extruding granulator, dried and sieved out by passing through a 14-mesh sieve and a 32-mesh sieve to make granules.

PREPARATION 9

Granules

A mixture comprising 5% of Compound No. 7.112, 30% of bentonite, 62.5% of talc, 2% of sodium ligninsulfonate, 0.35% of sodium dioctylsulfosuccinate, 0.075% of propylene glycol and 0.075% of water was homogeneously mixed and pulverized. To 100 parts of the resulting mixture were added 20 parts of water. The mixture was kneaded, granulated using a extruding granulator, dried and sieved out by passing through a 14-mesh sieve and a 32-mesh sieve to make granules.

PREPARATION 10

Granules

A mixture comprising 4% of Compound No. 7.221, 30% of bentonite, 63% of clay, 1% of poly(vinyl alcohol) and 2% of sodium alkylbenzenesulfonate was homogeneously mixed and pulverized. To 100 parts of the resulting mixture were added 20 parts of water. The mixture was kneaded, granulated using a extruding granulator, dried and sieved out by passing through a 14-mesh sieve and a 32-mesh sieve to make granules.

PREPARATION 11

Granules

A mixture comprising 4% of Compound No. 8.32, 35% of bentonite, 58% of talc, 2% of sodium alkylnaphthalenesulfonate and 1% of sodium dioctylsulfosuccinate was homogeneously mixed and pulverized. To 100 parts of the resulting mixture were added 20 parts of water. The mixture was kneaded, granulated using a extruding granulator, dried and sieved out by passing through a 14-mesh sieve and a 32-mesh sieve to make granules.

PREPARATION 12

Granules

A mixture comprising 5% of Compound No. 9.18, 1% of white carbon, 5% of calcium ligninsulfonate, 84% of clay and 5% of sodium salt of carboxymethyl cellulose was mixed and pulverized. To the resulting mixture was added water, and the mixture was kneaded, granulated and dried to make granules.

PREPARATION 13

Wettable powders

A mixture comprising 80% of Compound No. 10.58, 3% of sodium dodecylbenzenesulfonate, 2% of sodium alkylnaphthalenesulfonate, 2% of sodium ligninsulfonate, 3% of synthetic amorphous silica and 10% of kaolinite was mixed, pulverized by using an air mill, again mixed and packaged.

PREPARATION 14

Granules

A mixture comprising 15% of the wettable powders of Preparation Example 13, 50% of kaolin clay, 25% of talc and 10% of sodium ligninsulfonate was mixed in a rotatory mixer or a running floor mixer and granulated by spraying with water. After attaining 1.0–0.15 mm diameter for most of the granules, the granules were picked out and dried, and those having a diameter of 1.0–0.15 mm were collected by passing through a sieve. Over-sized granules were pulverized to make granules having a diameter of 1.0–0.15 mm.

PREPARATION 15

Wettable granules

A mixture comprising 80% of Compound No. 11.14, 1.25% of the sodium salt of a specific poly(carboxylic acid)polymer, 3.75% of water, 3% of sodium dodecylbenzenesulfonate, 7% of dextrin and 5% of titanium oxide was mixed and pulverized using an air mill. The resulting mixture was placed in a rotatory mixer or a running floor mixer and granulated by spraying water. After attaining 1.0–0.15 mm in diameter for most of the granules, the granules were collected, dried and sieved. Over-sized granules were pulverized to make granules having a diameter of 1.0–0.15 mm.

PREPARATION 16

Aqueous suspensions

A mixture comprising 25 parts of Compound No. 10.87, 0.7 part of sodium dioctylsulfosuccinate, 0.15 part of propylene glycol, 10 parts of calcium ligninsulfonate, 44.15 parts of water and 10 parts of propylene glycol was pulverized in a ball mill, a sand mill or a roller mill until the diameter of solid particles reduced to not more than 5 microns. A mixture of 90 parts of the pulverized slurry thus obtained and 10 parts of an aqueous 0.05% (w/w) solution of xanthan gum was mixed to make an aqueous suspension.

PREPARATION 17

Liquors

A mixture comprising 30% of Compound No. 10.160, 30% of dimethylformamide and 40% of 3-methyl-3-methoxybutanol was stirred to make a liquor.

BIOLOGICAL ACTIVITY

The activity of the compounds of the invention is further demonstrated by the following biological Test Examples.

Test Example 1

Pre-emergence application to a paddy field

Soil taken from a paddy field was placed in a pot having a surface area of 100 square centimeters. Seeds broken from dormancy of *Echinochloa oryzicola* Vasing. and *Scirpus juncoides* Roxb. subsp. hotarui (Ohwi) T. Koyama were mixed in the outer layer of soil at a height of 1 cm and tubers broken from dormancy of *Cyperus serotinus* Rottb. and *Eleocharis kuroguwai* Ohwi and *Eleocharis acicularis* (L) Roem. et Schult. var. longiseta Sven. were planted in the pots. Paddy-rice plants at the two-leaf stage were then transplanted to each of the same pots under flooded conditions, and allowed to vegetate in a greenhouse. After 3 days, soil application under flooded conditions was carried out using the necessary quantity of the wettable powder, prepared as described in Preparation 1, to achieve the desired concentration of active compound. After 21 days, a survey was conducted of all of the plants (weeds as well as rice plants) according to the following criteria. The results are reported in Table 13.

0: an inhibitory rate of growth  0–10%

| | | |
|---|---|---|
| 1: an inhibitory rate of growth | 11–30% |
| 2: an inhibitory rate of growth | 31–50% |
| 3: an inhibitory rate of growth | 51–70% |
| 4: an inhibitory rate of growth | 71–90% |
| 5: an inhibitory rate of growth | 91–100% |

Test Example 2

Following the method of Test Example 1, seeds of *Echinochloa oryzicola* Vasing. were sown and seedlings of paddy-rice plants at the two-leaf stage were planted in the same pot. After 3 days and at the two-leaf stage of *Echinochloa oryzicola*, soil application under flooded conditions was carried out using the necessary quantity of the wettable powder, prepared as described in Preparation 1, to achieve the desired concentration of active compound. After 21 days, a survey of the plants was carried out. The results are reported in Table 14, in which the left hand columns report the results after 3 days and the right hand columns report the results at the two leaf stage. The criteria for judgement is same as that of Test Example 1.

In addition to the compounds of the invention, we also tested, under precisely the same conditions, two compounds from the prior art European Patent Specification No. 7 990. These two compounds are methyl 1-acetyl-3-phenylthio-5-methylpyrazole-4-carboxylate (the compound of Example 181 of the prior patent), which is identified as "Compound A" in the following Tables, and methyl 1-phenoxycarbonyl-3-phenylthio-5-methylpyrazole-4-carboxylate (the compound of Example 187 of the prior patent), which is identified as "Compound B" in the following Tables.

The compounds of the invention are all identified by the numbers assigned to them previously in Tables 1 to 12.

In Tables 13 and 14, the abbrebiations used denote the following:

EO: *Echinochloa oryzicola* Vasing.;
BL: broad-lieved weeds;
SJ: *Scirpus juncoides* Roxb. subsp. hotarui (Ohwi) T. Koyama;
EA: *Eleocharis acicularis* (L) Roem. et Schult. var. longiseta Sven.;
CS: *Cyperus serotinus* Rottb.;
EK: *Eleocharis kuroguwai* Ohwi; and
OS: paddy-rice plant.

TABLE 13

| Cpd. No. | Dose (g/a) | EO | BL | SJ | EA | CS | EK | OS |
|---|---|---|---|---|---|---|---|---|
| 1.1 | 20 | 5 | 5 | 5 | 5 | 5 | 4 | 0 |
| 1.2 | 20 | 5 | 5 | 4 | 4 | 4 | 4 | 0 |
| 1.4 | 20 | 5 | 5 | 5 | 5 | 5 | 5 | 0 |
| 1.5 | 20 | 5 | 5 | 4 | 4 | 4 | 4 | 0 |
| 1.6 | 20 | 5 | 5 | 5 | 5 | 5 | 5 | 0 |
| 1.7 | 20 | 5 | 5 | 5 | 5 | 5 | 5 | 0 |
| 1.8 | 20 | 5 | 5 | 5 | 5 | 5 | 5 | 0 |
| 1.9 | 20 | 5 | 4 | 4 | 4 | 4 | 4 | 0 |
| 1.10 | 20 | 5 | 5 | 5 | 5 | 5 | 5 | 0 |
| 1.11 | 20 | 5 | 5 | 4 | 4 | 4 | 4 | 0 |
| 1.12 | 20 | 5 | 4 | 4 | 4 | 3 | 3 | 0 |
| 1.13 | 20 | 5 | 4 | 4 | 3 | 4 | 3 | 0 |
| 1.14 | 20 | 5 | 5 | 4 | 4 | 5 | 4 | 0 |
| 1.15 | 20 | 5 | 5 | 5 | 5 | 5 | 5 | 0 |
| 1.16 | 20 | 5 | 5 | 5 | 5 | 5 | 5 | 0 |
| 1.17 | 20 | 5 | 5 | 4 | 4 | 5 | 4 | 0 |
| 1.18 | 20 | 5 | 4 | 4 | 4 | 3 | 3 | 0 |
| 1.19 | 20 | 5 | 5 | 5 | 5 | 5 | 5 | 0 |
| 1.20 | 20 | 5 | 4 | 4 | 4 | 5 | 4 | 0 |
| 1.21 | 20 | 5 | 5 | 5 | 4 | 5 | 5 | 0 |

TABLE 13-continued

| Cpd. No. | Dose (g/a) | EO | BL | SJ | EA | CS | EK | OS |
|---|---|---|---|---|---|---|---|---|
| 1.22 | 20 | 5 | 4 | 4 | 4 | 4 | 4 | 0 |
| 1.23 | 20 | 5 | 5 | 5 | 5 | 5 | 5 | 0 |
| 1.24 | 20 | 5 | 4 | 4 | 4 | 5 | 4 | 0 |
| 1.26 | 20 | 5 | 4 | 4 | 4 | 4 | 3 | 0 |
| 1.27 | 20 | 5 | 5 | 5 | 5 | 4 | 4 | 0 |
| 1.37 | 20 | 5 | 5 | 5 | 5 | 5 | 5 | 0 |
| 1.38 | 20 | 5 | 5 | 5 | 5 | 5 | 5 | 0 |
| 1.40 | 20 | 5 | 5 | 5 | 5 | 5 | 5 | 0 |
| 1.56 | 20 | 5 | 5 | 4 | 5 | 3 | 4 | 0 |
| 1.57 | 20 | 5 | 5 | 5 | 5 | 5 | 5 | 0 |
| 1.58 | 20 | 5 | 4 | 5 | 5 | 4 | 5 | 0 |
| 1.59 | 20 | 5 | 4 | 4 | 4 | 4 | 4 | 0 |
| 1.60 | 20 | 5 | 4 | 4 | 5 | 4 | 4 | 0 |
| 1.79 | 20 | 5 | 4 | 5 | 5 | 4 | 5 | 0 |
| 1.80 | 20 | 5 | 4 | 5 | 4 | 4 | 4 | 0 |
| 1.81 | 20 | 5 | 5 | 5 | 5 | 5 | 5 | 0 |
| 2.1 | 20 | 5 | 5 | 5 | 5 | 5 | 5 | 0 |
| 2.2 | 20 | 5 | 4 | 4 | 4 | 4 | 4 | 0 |
| 2.3 | 20 | 5 | 4 | 4 | 4 | 4 | 4 | 0 |
| 2.4 | 20 | 5 | 5 | 5 | 5 | 5 | 5 | 0 |
| 2.5 | 20 | 5 | 4 | 4 | 4 | 4 | 4 | 0 |
| 2.6 | 20 | 5 | 5 | 5 | 5 | 5 | 5 | 0 |
| 2.7 | 20 | 5 | 5 | 5 | 5 | 5 | 5 | 0 |
| 2.8 | 20 | 5 | 5 | 4 | 4 | 4 | 4 | 0 |
| 2.9 | 20 | 5 | 4 | 4 | 4 | 4 | 4 | 0 |
| 2.10 | 20 | 5 | 5 | 5 | 5 | 5 | 5 | 0 |
| 2.11 | 20 | 5 | 4 | 4 | 5 | 4 | 4 | 0 |
| 2.12 | 20 | 5 | 5 | 5 | 5 | 5 | 5 | 0 |
| 2.13 | 20 | 5 | 5 | 5 | 5 | 5 | 5 | 0 |
| 2.14 | 20 | 5 | 4 | 4 | 4 | 4 | 4 | 0 |
| 2.15 | 20 | 5 | 5 | 4 | 4 | 4 | 4 | 0 |
| 2.16 | 20 | 5 | 5 | 5 | 5 | 5 | 5 | 0 |
| 2.18 | 20 | 5 | 4 | 4 | 4 | 4 | 4 | 0 |
| 2.19 | 20 | 5 | 5 | 5 | 5 | 4 | 4 | 0 |
| 2.21 | 20 | 5 | 5 | 4 | 5 | 4 | 4 | 0 |
| 2.22 | 20 | 5 | 4 | 5 | 4 | 4 | 4 | 0 |
| 2.41 | 20 | 5 | 5 | 4 | 5 | 4 | 5 | 0 |
| 2.42 | 20 | 5 | 5 | 5 | 5 | 5 | 5 | 0 |
| 2.43 | 20 | 5 | 5 | 4 | 5 | 4 | 3 | 0 |
| 2.44 | 20 | 5 | 5 | 4 | 5 | 4 | 5 | 0 |
| 2.45 | 20 | 5 | 5 | 4 | 5 | 5 | 5 | 0 |
| 2.46 | 20 | 5 | 5 | 4 | 5 | 5 | 4 | 0 |
| 2.50 | 20 | 5 | 5 | 5 | 5 | 5 | 4 | 0 |
| 2.51 | 20 | 5 | 5 | 4 | 4 | 4 | 4 | 0 |
| 2.52 | 20 | 5 | 5 | 5 | 5 | 4 | 5 | 0 |
| 2.53 | 20 | 5 | 4 | 4 | 4 | 4 | 5 | 0 |
| 2.54 | 20 | 5 | 5 | 4 | 4 | 4 | 4 | 0 |
| 2.56 | 20 | 5 | 5 | 5 | 5 | 5 | 5 | 0 |
| 2.58 | 20 | 5 | 5 | 4 | 4 | 4 | 5 | 0 |
| 2.59 | 20 | 5 | 5 | 5 | 5 | 5 | 5 | 0 |
| 2.60 | 20 | 5 | 4 | 4 | 4 | 4 | 3 | 0 |
| 2.61 | 20 | 5 | 5 | 4 | 4 | 4 | 4 | 0 |
| 2.64 | 20 | 5 | 5 | 5 | 5 | 5 | 5 | 0 |
| 2.65 | 20 | 5 | 5 | 5 | 5 | 5 | 5 | 0 |
| 2.66 | 20 | 5 | 5 | 5 | 5 | 5 | 5 | 0 |
| 2.68 | 20 | 5 | 5 | 5 | 5 | 5 | 5 | 0 |
| 2.83 | 20 | 5 | 5 | 5 | 5 | 5 | 5 | 0 |
| 2.97 | 20 | 5 | 4 | 4 | 4 | 4 | 3 | 0 |
| 2.98 | 20 | 5 | 4 | 5 | 5 | 5 | 4 | 0 |
| 2.104 | 20 | 5 | 5 | 4 | 5 | 4 | 4 | 0 |
| 2.105 | 20 | 5 | 5 | 5 | 5 | 5 | 5 | 0 |
| 2.120 | 20 | 5 | 4 | 5 | 4 | 4 | 4 | 0 |
| 2.121 | 20 | 5 | 4 | 5 | 4 | 4 | 4 | 0 |
| 3.1 | 20 | 5 | 5 | 5 | 5 | 5 | 5 | 0 |
| 3.2 | 20 | 5 | 4 | 4 | 4 | 4 | 4 | 0 |
| 3.3 | 20 | 5 | 5 | 5 | 5 | 5 | 5 | 0 |
| 3.4 | 20 | 5 | 4 | 4 | 4 | 5 | 4 | 0 |
| 3.5 | 20 | 5 | 5 | 4 | 5 | 4 | 4 | 0 |
| 3.6 | 20 | 5 | 5 | 5 | 5 | 5 | 5 | 0 |
| 3.7 | 20 | 5 | 4 | 4 | 4 | 4 | 4 | 0 |
| 3.8 | 20 | 5 | 4 | 4 | 4 | 4 | 4 | 0 |
| 3.9 | 20 | 5 | 5 | 5 | 5 | 5 | 5 | 0 |
| 3.10 | 20 | 5 | 4 | 4 | 4 | 4 | 4 | 0 |
| 3.11 | 20 | 5 | 5 | 5 | 5 | 5 | 5 | 0 |
| 3.12 | 20 | 5 | 5 | 5 | 5 | 5 | 5 | 0 |
| 3.14 | 20 | 5 | 4 | 4 | 4 | 4 | 3 | 0 |
| 3.15 | 20 | 5 | 5 | 5 | 5 | 5 | 5 | 0 |
| 3.16 | 20 | 5 | 5 | 5 | 5 | 5 | 5 | 0 |
| 3.17 | 20 | 5 | 4 | 4 | 4 | 4 | 4 | 0 |
| 3.18 | 20 | 5 | 5 | 5 | 5 | 5 | 5 | 0 |
| 3.19 | 20 | 5 | 4 | 4 | 4 | 4 | 4 | 0 |

TABLE 13-continued

| Cpd. No. | Dose (g/a) | EO | BL | SJ | EA | CS | EK | OS |
|---|---|---|---|---|---|---|---|---|
| 3.20 | 20 | 5 | 5 | 5 | 5 | 5 | 5 | 0 |
| 3.21 | 20 | 5 | 4 | 4 | 4 | 4 | 4 | 0 |
| 3.29 | 20 | 4 | 4 | 3 | 4 | 3 | 3 | 0 |
| 3.30 | 20 | 3 | 4 | 3 | 4 | 3 | 3 | 0 |
| 3.32 | 20 | 4 | 4 | 3 | 4 | 3 | 3 | 0 |
| 3.33 | 20 | 4 | 4 | 3 | 4 | 3 | 3 | 0 |
| 3.34 | 20 | 5 | 5 | 5 | 5 | 4 | 4 | 0 |
| 4.1 | 20 | 5 | 5 | 5 | 5 | 5 | 5 | 0 |
| 4.2 | 20 | 5 | 4 | 4 | 4 | 4 | 4 | 0 |
| 4.3 | 20 | 5 | 5 | 5 | 5 | 5 | 5 | 0 |
| 4.4 | 20 | 5 | 5 | 4 | 4 | 4 | 4 | 0 |
| 4.5 | 20 | 5 | 5 | 5 | 5 | 5 | 5 | 0 |
| 4.6 | 20 | 5 | 4 | 4 | 4 | 4 | 4 | 0 |
| 4.7 | 20 | 5 | 5 | 5 | 5 | 5 | 5 | 0 |
| 4.8 | 20 | 5 | 4 | 4 | 4 | 5 | 4 | 0 |
| 4.42 | 20 | 5 | 5 | 5 | 5 | 4 | 4 | 0 |
| 4.43 | 20 | 5 | 5 | 5 | 5 | 5 | 5 | 0 |
| 4.44 | 20 | 5 | 5 | 5 | 5 | 4 | 4 | 0 |
| 4.45 | 20 | 5 | 5 | 5 | 5 | 5 | 5 | 0 |
| 4.46 | 20 | 5 | 5 | 5 | 5 | 5 | 5 | 0 |
| 4.47 | 20 | 5 | 5 | 5 | 5 | 4 | 4 | 0 |
| 4.48 | 20 | 5 | 5 | 5 | 5 | 5 | 5 | 0 |
| 4.49 | 20 | 5 | 5 | 5 | 5 | 4 | 4 | 0 |
| 4.50 | 20 | 5 | 5 | 5 | 5 | 5 | 5 | 0 |
| 4.51 | 20 | 5 | 5 | 5 | 5 | 4 | 4 | 0 |
| 4.52 | 20 | 5 | 5 | 5 | 5 | 5 | 5 | 0 |
| 4.56 | 20 | 5 | 5 | 5 | 5 | 5 | 5 | 0 |
| 4.58 | 20 | 5 | 5 | 5 | 5 | 5 | 5 | 0 |
| 4.61 | 20 | 5 | 5 | 5 | 4 | 4 | 4 | 0 |
| 4.62 | 20 | 5 | 5 | 5 | 5 | 4 | 4 | 0 |
| 4.64 | 20 | 5 | 4 | 5 | 5 | 4 | 5 | 0 |
| 4.65 | 20 | 5 | 5 | 5 | 5 | 5 | 5 | 0 |
| 4.66 | 20 | 5 | 5 | 5 | 5 | 5 | 5 | 0 |
| 4.67 | 20 | 5 | 5 | 5 | 5 | 5 | 5 | 0 |
| 4.69 | 20 | 5 | 5 | 5 | 5 | 5 | 5 | 0 |
| 4.102 | 20 | 4 | 3 | 3 | 3 | 3 | 3 | 0 |
| 4.107 | 20 | 5 | 4 | 4 | 4 | 5 | 4 | 0 |
| 4.112 | 20 | 4 | 3 | 3 | 3 | 3 | 3 | 0 |
| 4.133 | 20 | 5 | 5 | 5 | 5 | 4 | 4 | 0 |
| 4.134 | 20 | 5 | 5 | 5 | 5 | 5 | 5 | 0 |
| 5.1 | 20 | 5 | 5 | 5 | 5 | 5 | 5 | 0 |
| 5.2 | 20 | 5 | 4 | 3 | 4 | 4 | 3 | 0 |
| 5.3 | 20 | 5 | 5 | 5 | 5 | 5 | 5 | 0 |
| 5.5 | 20 | 5 | 5 | 5 | 5 | 5 | 5 | 0 |
| 5.6 | 20 | 5 | 5 | 5 | 5 | 5 | 5 | 0 |
| 5.7 | 20 | 5 | 4 | 4 | 4 | 4 | 3 | 0 |
| 5.8 | 20 | 5 | 5 | 5 | 5 | 5 | 5 | 0 |
| 5.9 | 20 | 5 | 5 | 5 | 5 | 5 | 5 | 0 |
| 5.11 | 20 | 5 | 5 | 5 | 5 | 5 | 5 | 0 |
| 5.12 | 20 | 5 | 4 | 4 | 4 | 4 | 3 | 0 |
| 5.13 | 20 | 5 | 5 | 5 | 5 | 5 | 5 | 0 |
| 5.14 | 20 | 5 | 4 | 4 | 4 | 3 | 3 | 0 |
| 5.15 | 20 | 5 | 5 | 5 | 5 | 5 | 5 | 0 |
| 5.16 | 20 | 5 | 4 | 4 | 4 | 3 | 3 | 0 |
| 5.17 | 20 | 5 | 5 | 5 | 5 | 5 | 5 | 0 |
| 5.18 | 20 | 5 | 5 | 5 | 4 | 4 | 4 | 0 |
| 5.19 | 20 | 5 | 5 | 5 | 5 | 5 | 5 | 0 |
| 5.20 | 20 | 5 | 5 | 4 | 4 | 4 | 4 | 0 |
| 5.25 | 20 | 5 | 5 | 4 | 4 | 4 | 4 | 0 |
| 5.26 | 20 | 5 | 5 | 5 | 5 | 5 | 4 | 0 |
| 5.27 | 20 | 5 | 5 | 5 | 5 | 4 | 4 | 0 |
| 5.28 | 20 | 5 | 5 | 5 | 5 | 5 | 5 | 0 |
| 5.29 | 20 | 5 | 5 | 5 | 5 | 4 | 4 | 0 |
| 5.30 | 20 | 5 | 5 | 5 | 5 | 5 | 5 | 0 |
| 5.31 | 20 | 5 | 5 | 5 | 4 | 4 | 4 | 0 |
| 5.32 | 20 | 5 | 5 | 5 | 5 | 5 | 5 | 0 |
| 5.33 | 20 | 5 | 5 | 5 | 4 | 4 | 4 | 0 |
| 5.34 | 20 | 5 | 5 | 5 | 5 | 5 | 5 | 0 |
| 5.35 | 20 | 5 | 5 | 4 | 4 | 4 | 4 | 0 |
| 5.36 | 20 | 5 | 5 | 5 | 5 | 5 | 4 | 0 |
| 5.37 | 20 | 5 | 5 | 5 | 4 | 4 | 4 | 0 |
| 5.38 | 20 | 5 | 5 | 5 | 5 | 5 | 5 | 0 |
| 5.39 | 20 | 5 | 5 | 5 | 5 | 5 | 5 | 0 |
| 5.40 | 20 | 5 | 5 | 5 | 5 | 5 | 4 | 0 |
| 5.41 | 20 | 5 | 5 | 4 | 4 | 4 | 4 | 0 |
| 5.42 | 20 | 5 | 5 | 5 | 5 | 4 | 5 | 0 |
| 5.59 | 20 | 5 | 5 | 4 | 4 | 4 | 4 | 0 |
| 5.69 | 20 | 5 | 5 | 4 | 4 | 4 | 4 | 0 |
| 5.70 | 20 | 5 | 5 | 5 | 5 | 4 | 5 | 0 |
| 5.71 | 20 | 5 | 5 | 5 | 4 | 4 | 4 | 0 |
| 5.72 | 20 | 5 | 5 | 5 | 5 | 5 | 5 | 0 |
| 5.73 | 20 | 5 | 5 | 5 | 4 | 4 | 4 | 0 |
| 5.74 | 20 | 5 | 5 | 5 | 5 | 5 | 5 | 0 |
| 5.75 | 20 | 5 | 5 | 5 | 5 | 5 | 5 | 0 |
| 5.76 | 20 | 5 | 5 | 5 | 5 | 5 | 5 | 0 |
| 5.107 | 20 | 5 | 4 | 5 | 4 | 4 | 4 | 0 |
| 6.1 | 20 | 5 | 5 | 5 | 5 | 5 | 5 | 0 |
| 6.2 | 20 | 5 | 5 | 4 | 4 | 4 | 4 | 0 |
| 6.3 | 20 | 5 | 5 | 5 | 5 | 5 | 5 | 0 |
| 6.4 | 20 | 5 | 4 | 4 | 4 | 4 | 4 | 0 |
| 6.5 | 20 | 5 | 4 | 4 | 4 | 3 | 3 | 0 |
| 6.6 | 20 | 5 | 5 | 5 | 5 | 5 | 5 | 0 |
| 6.7 | 20 | 5 | 5 | 4 | 4 | 4 | 4 | 0 |
| 6.8 | 20 | 5 | 5 | 5 | 5 | 5 | 5 | 0 |
| 6.9 | 20 | 5 | 4 | 4 | 4 | 4 | 4 | 0 |
| 6.10 | 20 | 5 | 5 | 5 | 5 | 5 | 5 | 0 |
| 6.11 | 20 | 5 | 5 | 5 | 5 | 5 | 5 | 0 |
| 6.12 | 20 | 5 | 4 | 4 | 4 | 4 | 4 | 0 |
| 6.13 | 20 | 5 | 5 | 4 | 4 | 4 | 4 | 0 |
| 6.14 | 20 | 5 | 5 | 5 | 5 | 5 | 4 | 0 |
| 6.15 | 20 | 5 | 5 | 5 | 4 | 4 | 4 | 0 |
| 6.16 | 20 | 5 | 5 | 5 | 5 | 4 | 4 | 0 |
| 6.17 | 20 | 5 | 5 | 5 | 5 | 5 | 5 | 0 |
| 6.18 | 20 | 5 | 5 | 5 | 4 | 4 | 4 | 0 |
| 6.19 | 20 | 5 | 5 | 5 | 5 | 5 | 5 | 0 |
| 6.60 | 20 | 5 | 5 | 5 | 5 | 5 | 5 | 0 |
| 6.61 | 20 | 5 | 5 | 5 | 5 | 5 | 5 | 0 |
| 6.62 | 20 | 5 | 5 | 5 | 5 | 5 | 5 | 0 |
| 6.63 | 20 | 5 | 5 | 5 | 5 | 5 | 5 | 0 |
| 6.66 | 20 | 5 | 5 | 5 | 5 | 5 | 5 | 0 |
| 6.70 | 20 | 5 | 5 | 5 | 5 | 5 | 5 | 0 |
| 6.101 | 20 | 5 | 5 | 5 | 5 | 5 | 5 | 0 |
| 6.102 | 20 | 5 | 5 | 4 | 5 | 5 | 5 | 0 |
| 6.103 | 20 | 5 | 5 | 4 | 5 | 4 | 5 | 0 |
| 6.104 | 20 | 5 | 5 | 5 | 5 | 5 | 5 | 0 |
| 6.105 | 20 | 5 | 5 | 5 | 4 | 4 | 4 | 0 |
| 6.106 | 20 | 5 | 5 | 5 | 5 | 5 | 5 | 0 |
| 6.108 | 20 | 5 | 5 | 5 | 4 | 4 | 4 | 0 |
| 6.109 | 20 | 5 | 5 | 5 | 5 | 5 | 5 | 0 |
| 6.110 | 20 | 5 | 5 | 4 | 4 | 4 | 4 | 0 |
| 6.111 | 20 | 5 | 5 | 5 | 5 | 5 | 5 | 0 |
| 6.112 | 20 | 5 | 5 | 5 | 5 | 5 | 4 | 0 |
| 6.114 | 20 | 5 | 4 | 5 | 5 | 5 | 5 | 0 |
| 6.115 | 20 | 5 | 5 | 5 | 5 | 5 | 5 | 0 |
| 6.116 | 20 | 5 | 5 | 4 | 4 | 4 | 4 | 0 |
| 6.117 | 20 | 5 | 5 | 4 | 4 | 5 | 5 | 0 |
| 6.118 | 20 | 5 | 5 | 4 | 4 | 4 | 4 | 0 |
| 6.119 | 20 | 5 | 5 | 5 | 5 | 5 | 4 | 0 |
| 6.120 | 20 | 5 | 4 | 4 | 4 | 4 | 4 | 0 |
| 6.121 | 20 | 5 | 5 | 4 | 4 | 4 | 4 | 0 |
| 6.126 | 20 | 5 | 4 | 4 | 4 | 3 | 3 | 0 |
| 6.144 | 20 | 5 | 5 | 5 | 4 | 4 | 4 | 0 |
| 6.145 | 20 | 5 | 5 | 5 | 5 | 5 | 5 | 0 |
| 6.147 | 20 | 5 | 5 | 4 | 4 | 4 | 4 | 0 |
| 6.148 | 20 | 5 | 5 | 5 | 5 | 5 | 5 | 0 |
| 6.150 | 20 | 4 | 3 | 3 | 3 | 3 | 3 | 0 |
| 6.151 | 20 | 5 | 4 | 4 | 4 | 5 | 5 | 0 |
| 6.159 | 20 | 5 | 5 | 4 | 4 | 4 | 4 | 0 |
| 6.160 | 20 | 5 | 5 | 5 | 4 | 5 | 5 | 0 |
| 6.172 | 20 | 5 | 4 | 5 | 4 | 4 | 4 | 0 |
| 6.173 | 20 | 5 | 4 | 5 | 4 | 4 | 4 | 0 |
| 7.1 | 20 | 5 | 5 | 5 | 5 | 5 | 5 | 0 |
| 7.2 | 20 | 5 | 5 | 5 | 5 | 5 | 5 | 0 |
| 7.3 | 20 | 5 | 4 | 5 | 4 | 4 | 4 | 0 |
| 7.4 | 20 | 5 | 5 | 5 | 5 | 5 | 5 | 0 |
| 7.6 | 20 | 5 | 5 | 5 | 5 | 5 | 5 | 0 |
| 7.7 | 20 | 5 | 5 | 5 | 5 | 5 | 5 | 0 |
| 7.9 | 20 | 5 | 5 | 4 | 4 | 5 | 4 | 0 |
| 7.10 | 20 | 5 | 5 | 5 | 5 | 5 | 5 | 0 |
| 7.12 | 20 | 5 | 5 | 5 | 5 | 5 | 5 | 0 |
| 7.13 | 20 | 5 | 4 | 4 | 4 | 4 | 4 | 0 |
| 7.14 | 20 | 5 | 5 | 5 | 4 | 4 | 4 | 0 |
| 7.15 | 20 | 5 | 5 | 5 | 5 | 5 | 5 | 0 |
| 7.16 | 20 | 5 | 4 | 4 | 4 | 5 | 4 | 0 |
| 7.17 | 20 | 5 | 5 | 5 | 5 | 5 | 5 | 0 |
| 7.19 | 20 | 5 | 4 | 4 | 4 | 4 | 4 | 0 |
| 7.20 | 20 | 5 | 5 | 5 | 5 | 5 | 5 | 0 |
| 7.21 | 20 | 5 | 4 | 5 | 4 | 4 | 4 | 0 |
| 7.22 | 20 | 5 | 5 | 5 | 5 | 5 | 5 | 0 |
| 7.23 | 20 | 5 | 4 | 4 | 4 | 4 | 3 | 0 |
| 7.24 | 20 | 5 | 5 | 5 | 5 | 5 | 5 | 0 |
| 7.75 | 20 | 5 | 5 | 5 | 5 | 5 | 5 | 0 |

TABLE 13-continued

| Cpd. No. | Dose (g/a) | EO | BL | SJ | EA | CS | EK | OS |
|---|---|---|---|---|---|---|---|---|
| 7.76 | 20 | 5 | 5 | 5 | 5 | 5 | 5 | 0 |
| 7.90 | 20 | 5 | 4 | 5 | 4 | 4 | 4 | 0 |
| 7.91 | 20 | 5 | 5 | 5 | 5 | 4 | 5 | 0 |
| 7.93 | 20 | 5 | 5 | 5 | 5 | 5 | 4 | 0 |
| 7.95 | 20 | 5 | 5 | 5 | 5 | 5 | 5 | 0 |
| 7.96 | 20 | 5 | 5 | 5 | 5 | 5 | 5 | 0 |
| 7.97 | 20 | 5 | 5 | 4 | 4 | 5 | 5 | 0 |
| 7.99 | 20 | 5 | 5 | 4 | 4 | 4 | 5 | 0 |
| 7.100 | 20 | 5 | 5 | 4 | 5 | 5 | 5 | 0 |
| 7.103 | 20 | 5 | 5 | 5 | 4 | 5 | 5 | 0 |
| 7.112 | 20 | 5 | 5 | 5 | 5 | 5 | 5 | 0 |
| 7.113 | 20 | 5 | 5 | 5 | 5 | 5 | 5 | 0 |
| 7.114 | 20 | 5 | 5 | 5 | 5 | 5 | 5 | 0 |
| 7.115 | 20 | 5 | 5 | 5 | 5 | 5 | 5 | 0 |
| 7.119 | 20 | 5 | 5 | 5 | 5 | 5 | 5 | 0 |
| 7.120 | 20 | 5 | 5 | 5 | 5 | 5 | 5 | 0 |
| 7.121 | 20 | 5 | 5 | 5 | 5 | 5 | 5 | 0 |
| 7.122 | 20 | 5 | 5 | 5 | 5 | 5 | 5 | 0 |
| 7.126 | 20 | 5 | 5 | 5 | 5 | 5 | 5 | 0 |
| 7.142 | 20 | 5 | 5 | 5 | 5 | 5 | 5 | 0 |
| 7.150 | 20 | 5 | 5 | 5 | 5 | 5 | 5 | 0 |
| 7.166 | 20 | 5 | 5 | 5 | 4 | 4 | 4 | 0 |
| 7.167 | 20 | 5 | 5 | 5 | 5 | 5 | 5 | 0 |
| 7.168 | 20 | 5 | 5 | 5 | 5 | 5 | 5 | 0 |
| 7.169 | 20 | 5 | 5 | 5 | 4 | 5 | 5 | 0 |
| 7.172 | 20 | 5 | 5 | 5 | 4 | 4 | 4 | 0 |
| 7.173 | 20 | 5 | 5 | 5 | 5 | 5 | 5 | 0 |
| 7.174 | 20 | 5 | 5 | 4 | 4 | 4 | 4 | 0 |
| 7.175 | 20 | 5 | 5 | 5 | 5 | 5 | 5 | 0 |
| 7.176 | 20 | 5 | 5 | 4 | 4 | 4 | 4 | 0 |
| 7.177 | 20 | 5 | 5 | 5 | 5 | 5 | 5 | 0 |
| 7.178 | 20 | 5 | 5 | 5 | 5 | 4 | 4 | 0 |
| 7.179 | 20 | 5 | 5 | 5 | 5 | 5 | 5 | 0 |
| 7.181 | 20 | 5 | 5 | 4 | 4 | 4 | 4 | 0 |
| 7.182 | 20 | 5 | 5 | 5 | 5 | 4 | 4 | 0 |
| 7.183 | 20 | 5 | 4 | 4 | 4 | 4 | 4 | 0 |
| 7.184 | 20 | 5 | 5 | 5 | 5 | 4 | 4 | 0 |
| 7.185 | 20 | 5 | 4 | 4 | 4 | 4 | 4 | 0 |
| 7.186 | 20 | 5 | 5 | 5 | 4 | 4 | 4 | 0 |
| 7.187 | 20 | 5 | 5 | 4 | 4 | 4 | 4 | 0 |
| 7.188 | 20 | 5 | 5 | 5 | 5 | 5 | 5 | 0 |
| 7.189 | 20 | 5 | 5 | 5 | 4 | 4 | 4 | 0 |
| 7.190 | 20 | 5 | 5 | 5 | 5 | 5 | 5 | 0 |
| 7.191 | 20 | 5 | 5 | 5 | 5 | 5 | 5 | 0 |
| 7.211 | 20 | 5 | 5 | 4 | 5 | 4 | 5 | 0 |
| 7.212 | 20 | 5 | 5 | 4 | 4 | 4 | 4 | 0 |
| 7.213 | 20 | 5 | 5 | 5 | 5 | 5 | 5 | 0 |
| 7.215 | 20 | 5 | 5 | 5 | 5 | 5 | 5 | 0 |
| 7.216 | 20 | 5 | 5 | 5 | 5 | 5 | 5 | 0 |
| 7.217 | 20 | 5 | 5 | 4 | 4 | 4 | 4 | 0 |
| 7.218 | 20 | 5 | 5 | 5 | 5 | 5 | 5 | 0 |
| 7.219 | 20 | 5 | 4 | 4 | 4 | 4 | 4 | 0 |
| 7.220 | 20 | 5 | 4 | 5 | 5 | 5 | 5 | 0 |
| 7.221 | 20 | 5 | 5 | 5 | 5 | 5 | 5 | 0 |
| 7.222 | 20 | 5 | 5 | 5 | 5 | 5 | 5 | 0 |
| 7.223 | 20 | 5 | 5 | 5 | 5 | 5 | 5 | 0 |
| 7.231 | 20 | 5 | 5 | 4 | 5 | 4 | 4 | 0 |
| 7.234 | 20 | 5 | 3 | 3 | 3 | 4 | 3 | 0 |
| 7.235 | 20 | 4 | 4 | 3 | 3 | 3 | 3 | 0 |
| 7.236 | 20 | 4 | 3 | 3 | 3 | 3 | 3 | 0 |
| 7.237 | 20 | 5 | 4 | 3 | 3 | 4 | 3 | 0 |
| 7.241 | 20 | 4 | 4 | 3 | 3 | 3 | 3 | 0 |
| 7.246 | 20 | 5 | 4 | 4 | 3 | 3 | 3 | 0 |
| 7.247 | 20 | 5 | 5 | 4 | 5 | 4 | 5 | 0 |
| 7.252 | 20 | 5 | 5 | 5 | 5 | 5 | 4 | 0 |
| 7.253 | 20 | 5 | 5 | 4 | 4 | 4 | 4 | 0 |
| 7.254 | 20 | 5 | 5 | 5 | 4 | 4 | 4 | 0 |
| 7.255 | 20 | 5 | 5 | 4 | 4 | 4 | 4 | 0 |
| 7.256 | 20 | 5 | 5 | 5 | 4 | 4 | 4 | 0 |
| 7.257 | 20 | 5 | 5 | 5 | 5 | 5 | 5 | 0 |
| 7.258 | 20 | 5 | 5 | 5 | 5 | 4 | 4 | 0 |
| 7.259 | 20 | 5 | 5 | 5 | 5 | 5 | 5 | 0 |
| 7.262 | 20 | 4 | 3 | 3 | 3 | 3 | 3 | 0 |
| 7.266 | 20 | 4 | 3 | 3 | 3 | 3 | 3 | 0 |
| 7.267 | 20 | 5 | 4 | 4 | 4 | 5 | 4 | 0 |
| 7.268 | 20 | 4 | 3 | 3 | 3 | 3 | 3 | 0 |
| 7.269 | 20 | 4 | 4 | 4 | 3 | 3 | 3 | 0 |
| 7.270 | 20 | 4 | 4 | 3 | 3 | 3 | 3 | 0 |
| 7.271 | 20 | 5 | 4 | 4 | 4 | 4 | 4 | 0 |
| 7.272 | 20 | 5 | 4 | 4 | 4 | 4 | 4 | 0 |
| 7.273 | 20 | 5 | 4 | 4 | 4 | 5 | 5 | 0 |
| 7.286 | 20 | 5 | 4 | 4 | 4 | 4 | 3 | 0 |
| 7.300 | 20 | 5 | 4 | 4 | 4 | 4 | 4 | 0 |
| 7.301 | 20 | 5 | 4 | 4 | 5 | 4 | 5 | 0 |
| 7.329 | 20 | 5 | 5 | 5 | 5 | 5 | 5 | 0 |
| 7.330 | 20 | 4 | 4 | 3 | 3 | 3 | 3 | 0 |
| 7.331 | 20 | 5 | 4 | 5 | 4 | 4 | 4 | 0 |
| 7.332 | 20 | 5 | 4 | 5 | 4 | 4 | 4 | 0 |
| 7.333 | 20 | 5 | 4 | 5 | 4 | 4 | 4 | 0 |
| 7.334 | 20 | 5 | 4 | 5 | 4 | 4 | 4 | 0 |
| 7.335 | 20 | 5 | 4 | 5 | 4 | 4 | 4 | 0 |
| 7.336 | 20 | 5 | 5 | 5 | 5 | 5 | 5 | 0 |
| 7.337 | 20 | 5 | 4 | 5 | 4 | 4 | 4 | 0 |
| 7.338 | 20 | 5 | 5 | 5 | 5 | 5 | 5 | 0 |
| 7.339 | 20 | 5 | 4 | 5 | 4 | 4 | 4 | 0 |
| 7.340 | 20 | 5 | 5 | 5 | 5 | 5 | 5 | 0 |
| 8.1 | 20 | 5 | 5 | 5 | 5 | 5 | 5 | 0 |
| 8.2 | 20 | 5 | 4 | 5 | 4 | 4 | 4 | 0 |
| 8.3 | 20 | 5 | 4 | 5 | 4 | 4 | 4 | 0 |
| 8.4 | 20 | 5 | 5 | 5 | 5 | 5 | 5 | 0 |
| 8.5 | 20 | 5 | 5 | 5 | 5 | 5 | 5 | 0 |
| 8.6 | 20 | 5 | 4 | 4 | 4 | 4 | 4 | 0 |
| 8.7 | 20 | 5 | 5 | 5 | 5 | 5 | 5 | 0 |
| 8.8 | 20 | 5 | 4 | 4 | 4 | 3 | 5 | 0 |
| 8.9 | 20 | 5 | 5 | 5 | 5 | 5 | 5 | 0 |
| 8.10 | 20 | 5 | 4 | 4 | 4 | 4 | 4 | 0 |
| 8.11 | 20 | 5 | 4 | 4 | 4 | 3 | 4 | 0 |
| 8.12 | 20 | 5 | 5 | 5 | 5 | 5 | 5 | 0 |
| 8.16 | 20 | 5 | 4 | 4 | 4 | 3 | 4 | 0 |
| 8.17 | 20 | 5 | 5 | 5 | 5 | 4 | 5 | 0 |
| 8.18 | 20 | 5 | 5 | 5 | 5 | 4 | 4 | 0 |
| 8.19 | 20 | 5 | 5 | 5 | 5 | 4 | 4 | 0 |
| 8.20 | 20 | 5 | 4 | 4 | 4 | 4 | 4 | 0 |
| 8.21 | 20 | 5 | 5 | 5 | 4 | 5 | 5 | 0 |
| 8.22 | 20 | 5 | 4 | 4 | 4 | 4 | 4 | 0 |
| 8.23 | 20 | 5 | 5 | 5 | 5 | 4 | 5 | 0 |
| 8.24 | 20 | 5 | 5 | 5 | 5 | 5 | 5 | 0 |
| 8.26 | 20 | 5 | 4 | 4 | 4 | 4 | 4 | 0 |
| 8.27 | 20 | 5 | 5 | 5 | 5 | 4 | 5 | 0 |
| 8.28 | 20 | 5 | 4 | 4 | 4 | 4 | 4 | 0 |
| 8.29 | 20 | 5 | 4 | 4 | 4 | 4 | 5 | 0 |
| 8.30 | 20 | 5 | 5 | 4 | 4 | 4 | 4 | 0 |
| 8.31 | 20 | 5 | 5 | 5 | 5 | 4 | 5 | 0 |
| 8.32 | 20 | 5 | 5 | 5 | 5 | 5 | 5 | 0 |
| 8.34 | 20 | 5 | 5 | 5 | 5 | 5 | 5 | 0 |
| 8.35 | 20 | 5 | 5 | 5 | 5 | 5 | 5 | 0 |
| 8.57 | 20 | 5 | 4 | 5 | 4 | 4 | 4 | 0 |
| 9.1 | 20 | 5 | 5 | 5 | 5 | 5 | 5 | 0 |
| 9.3 | 20 | 5 | 4 | 4 | 4 | 4 | 4 | 0 |
| 9.4 | 20 | 5 | 5 | 5 | 5 | 5 | 5 | 0 |
| 9.5 | 20 | 5 | 4 | 4 | 4 | 4 | 4 | 0 |
| 9.6 | 20 | 5 | 5 | 5 | 5 | 5 | 5 | 0 |
| 9.7 | 20 | 5 | 4 | 4 | 4 | 3 | 4 | 0 |
| 9.8 | 20 | 5 | 5 | 5 | 5 | 5 | 5 | 0 |
| 9.9 | 20 | 5 | 4 | 4 | 4 | 4 | 3 | 0 |
| 9.11 | 20 | 5 | 5 | 5 | 5 | 5 | 5 | 0 |
| 9.13 | 20 | 5 | 3 | 3 | 3 | 3 | 3 | 0 |
| 9.14 | 20 | 5 | 5 | 4 | 5 | 5 | 4 | 0 |
| 9.18 | 20 | 5 | 5 | 5 | 5 | 5 | 5 | 0 |
| 9.22 | 20 | 5 | 5 | 5 | 5 | 5 | 5 | 0 |
| 9.26 | 20 | 5 | 5 | 5 | 5 | 5 | 5 | 0 |
| 9.27 | 20 | 5 | 5 | 5 | 5 | 5 | 5 | 0 |
| 9.34 | 20 | 5 | 5 | 5 | 5 | 5 | 5 | 0 |
| 9.37 | 20 | 5 | 5 | 4 | 4 | 5 | 4 | 0 |
| 9.40 | 20 | 5 | 4 | 4 | 3 | 3 | 3 | 0 |
| 9.41 | 20 | 5 | 5 | 4 | 5 | 4 | 5 | 0 |
| 9.43 | 20 | 5 | 4 | 4 | 5 | 4 | 5 | 0 |
| 9.44 | 20 | 5 | 5 | 4 | 5 | 4 | 5 | 0 |
| 9.45 | 20 | 5 | 4 | 4 | 4 | 4 | 4 | 0 |
| 9.46 | 20 | 5 | 4 | 4 | 4 | 4 | 5 | 0 |
| 9.47 | 20 | 4 | 3 | 3 | 3 | 3 | 3 | 0 |
| 9.48 | 20 | 5 | 5 | 4 | 4 | 5 | 5 | 0 |
| 9.49 | 20 | 5 | 5 | 5 | 5 | 5 | 5 | 0 |
| 9.52 | 20 | 5 | 4 | 4 | 4 | 4 | 4 | 0 |
| 9.53 | 20 | 5 | 5 | 4 | 5 | 4 | 4 | 0 |
| 9.55 | 20 | 5 | 5 | 4 | 4 | 4 | 4 | 0 |
| 9.56 | 20 | 5 | 5 | 5 | 5 | 5 | 5 | 0 |
| 9.57 | 20 | 5 | 4 | 4 | 4 | 4 | 4 | 0 |
| 9.58 | 20 | 5 | 5 | 4 | 5 | 4 | 5 | 0 |
| 9.59 | 20 | 4 | 3 | 3 | 3 | 3 | 3 | 0 |
| 9.60 | 20 | 5 | 4 | 3 | 3 | 3 | 3 | 0 |
| 9.61 | 20 | 5 | 4 | 4 | 4 | 4 | 5 | 0 |

TABLE 13-continued

| Cpd. No. | Dose (g/a) | EO | BL | SJ | EA | CS | EK | OS |
|---|---|---|---|---|---|---|---|---|
| 9.76 | 20 | 5 | 4 | 4 | 4 | 4 | 4 | 0 |
| 9.77 | 20 | 5 | 5 | 5 | 5 | 5 | 5 | 0 |
| 9.80 | 20 | 5 | 4 | 4 | 4 | 4 | 4 | 0 |
| 9.81 | 20 | 5 | 4 | 4 | 5 | 4 | 4 | 0 |
| 9.82 | 20 | 5 | 4 | 4 | 4 | 4 | 4 | 0 |
| 9.83 | 20 | 5 | 5 | 4 | 4 | 4 | 4 | 0 |
| 9.84 | 20 | 5 | 5 | 5 | 5 | 5 | 5 | 0 |
| 9.85 | 20 | 5 | 5 | 5 | 5 | 5 | 5 | 0 |
| 9.88 | 20 | 5 | 5 | 5 | 5 | 5 | 5 | 0 |
| 9.109 | 20 | 5 | 5 | 4 | 5 | 4 | 5 | 0 |
| 9.111 | 20 | 5 | 4 | 4 | 3 | 3 | 3 | 0 |
| 9.117 | 20 | 5 | 4 | 3 | 3 | 3 | 3 | 0 |
| 9.118 | 20 | 5 | 4 | 4 | 4 | 4 | 5 | 0 |
| 9.122 | 20 | 5 | 5 | 4 | 4 | 4 | 4 | 0 |
| 9.123 | 20 | 5 | 5 | 4 | 5 | 5 | 5 | 0 |
| 9.125 | 20 | 5 | 5 | 4 | 4 | 4 | 4 | 0 |
| 9.126 | 20 | 5 | 5 | 5 | 5 | 5 | 5 | 0 |
| 9.127 | 20 | 5 | 5 | 4 | 5 | 5 | 4 | 0 |
| 9.132 | 20 | 5 | 4 | 3 | 3 | 3 | 3 | 0 |
| 10.1 | 20 | 5 | 5 | 5 | 5 | 5 | 5 | 0 |
| 10.2 | 20 | 5 | 4 | 4 | 4 | 4 | 3 | 0 |
| 10.3 | 20 | 5 | 5 | 5 | 5 | 4 | 4 | 0 |
| 10.4 | 20 | 5 | 5 | 5 | 5 | 5 | 5 | 0 |
| 10.6 | 20 | 5 | 5 | 5 | 5 | 4 | 5 | 0 |
| 10.13 | 20 | 5 | 5 | 5 | 5 | 4 | 3 | 0 |
| 10.14 | 20 | 5 | 5 | 5 | 5 | 5 | 4 | 0 |
| 10.15 | 20 | 5 | 4 | 4 | 4 | 4 | 3 | 0 |
| 10.16 | 20 | 5 | 5 | 4 | 4 | 4 | 4 | 0 |
| 10.17 | 20 | 5 | 4 | 4 | 4 | 4 | 4 | 0 |
| 10.18 | 20 | 5 | 5 | 4 | 4 | 4 | 4 | 0 |
| 10.19 | 20 | 5 | 5 | 4 | 4 | 4 | 5 | 0 |
| 10.20 | 20 | 5 | 5 | 4 | 4 | 4 | 5 | 0 |
| 10.21 | 20 | 5 | 5 | 4 | 4 | 4 | 4 | 0 |
| 10.22 | 20 | 5 | 5 | 5 | 4 | 4 | 4 | 0 |
| 10.23 | 20 | 5 | 5 | 5 | 5 | 5 | 5 | 0 |
| 10.24 | 20 | 5 | 4 | 4 | 4 | 4 | 4 | 0 |
| 10.25 | 20 | 5 | 5 | 5 | 5 | 5 | 5 | 0 |
| 10.26 | 20 | 5 | 4 | 4 | 4 | 3 | 3 | 0 |
| 10.40 | 20 | 5 | 4 | 3 | 3 | 3 | 3 | 0 |
| 10.41 | 20 | 5 | 5 | 5 | 5 | 5 | 5 | 0 |
| 10.42 | 20 | 5 | 4 | 3 | 3 | 3 | 3 | 0 |
| 10.45 | 20 | 5 | 5 | 5 | 5 | 4 | 4 | 0 |
| 10.46 | 20 | 5 | 5 | 5 | 5 | 5 | 5 | 0 |
| 10.47 | 20 | 5 | 5 | 4 | 5 | 5 | 5 | 0 |
| 10.48 | 20 | 5 | 5 | 4 | 5 | 4 | 4 | 0 |
| 10.50 | 20 | 5 | 5 | 5 | 5 | 5 | 5 | 0 |
| 10.53 | 20 | 5 | 5 | 5 | 5 | 5 | 5 | 0 |
| 10.54 | 20 | 5 | 5 | 5 | 5 | 5 | 5 | 0 |
| 10.55 | 20 | 5 | 5 | 4 | 4 | 4 | 4 | 0 |
| 10.56 | 20 | 5 | 5 | 5 | 5 | 5 | 5 | 0 |
| 10.57 | 20 | 5 | 5 | 5 | 5 | 5 | 5 | 0 |
| 10.58 | 20 | 5 | 5 | 5 | 5 | 5 | 5 | 0 |
| 10.59 | 20 | 5 | 5 | 5 | 5 | 5 | 5 | 0 |
| 10.60 | 20 | 4 | 3 | 3 | 3 | 3 | 3 | 0 |
| 10.61 | 20 | 5 | 4 | 4 | 4 | 4 | 4 | 0 |
| 10.62 | 20 | 5 | 5 | 5 | 5 | 5 | 4 | 0 |
| 10.63 | 20 | 5 | 4 | 4 | 4 | 4 | 4 | 0 |
| 10.64 | 20 | 5 | 5 | 5 | 5 | 4 | 4 | 0 |
| 10.65 | 20 | 5 | 4 | 4 | 4 | 4 | 4 | 0 |
| 10.66 | 20 | 5 | 5 | 5 | 5 | 5 | 5 | 0 |
| 10.67 | 20 | 5 | 5 | 5 | 5 | 4 | 5 | 0 |
| 10.68 | 20 | 5 | 5 | 5 | 5 | 4 | 5 | 0 |
| 10.69 | 20 | 5 | 4 | 4 | 4 | 4 | 4 | 0 |
| 10.70 | 20 | 5 | 5 | 5 | 5 | 5 | 4 | 0 |
| 10.72 | 20 | 5 | 4 | 4 | 4 | 4 | 4 | 0 |
| 10.73 | 20 | 5 | 5 | 5 | 5 | 4 | 4 | 0 |
| 10.74 | 20 | 5 | 5 | 5 | 4 | 4 | 4 | 0 |
| 10.75 | 20 | 5 | 5 | 5 | 5 | 5 | 4 | 0 |
| 10.76 | 20 | 5 | 5 | 5 | 5 | 5 | 5 | 0 |
| 10.77 | 20 | 5 | 5 | 5 | 5 | 5 | 5 | 0 |
| 10.79 | 20 | 5 | 4 | 4 | 4 | 4 | 3 | 0 |
| 10.80 | 20 | 5 | 4 | 4 | 4 | 4 | 4 | 0 |
| 10.83 | 20 | 5 | 5 | 5 | 5 | 5 | 5 | 0 |
| 10.84 | 20 | 5 | 5 | 5 | 5 | 5 | 5 | 0 |
| 10.85 | 20 | 5 | 5 | 5 | 5 | 5 | 5 | 0 |
| 10.86 | 20 | 5 | 5 | 5 | 5 | 5 | 5 | 0 |
| 10.87 | 20 | 5 | 5 | 5 | 5 | 5 | 5 | 0 |
| 10.89 | 20 | 5 | 5 | 5 | 5 | 5 | 5 | 0 |
| 10.90 | 20 | 5 | 5 | 5 | 5 | 5 | 5 | 0 |
| 10.92 | 20 | 5 | 5 | 5 | 5 | 5 | 5 | 0 |
| 10.116 | 20 | 5 | 4 | 4 | 4 | 4 | 4 | 0 |
| 10.117 | 20 | 5 | 5 | 5 | 5 | 5 | 4 | 0 |
| 10.118 | 20 | 5 | 5 | 5 | 5 | 4 | 5 | 0 |
| 10.119 | 20 | 5 | 5 | 5 | 5 | 4 | 5 | 0 |
| 10.120 | 20 | 5 | 5 | 4 | 5 | 4 | 4 | 0 |
| 10.140 | 20 | 5 | 4 | 4 | 4 | 4 | 4 | 0 |
| 10.141 | 20 | 5 | 5 | 5 | 5 | 5 | 4 | 0 |
| 10.158 | 20 | 5 | 5 | 5 | 5 | 4 | 4 | 0 |
| 10.159 | 20 | 5 | 5 | 5 | 5 | 4 | 4 | 0 |
| 10.161 | 20 | 5 | 4 | 5 | 4 | 4 | 4 | 0 |
| 11.1 | 20 | 5 | 5 | 5 | 5 | 5 | 5 | 0 |
| 11.2 | 20 | 5 | 4 | 4 | 4 | 4 | 4 | 0 |
| 11.4 | 20 | 5 | 5 | 5 | 5 | 5 | 5 | 0 |
| 11.7 | 20 | 5 | 4 | 4 | 4 | 4 | 3 | 0 |
| 11.8 | 20 | 5 | 5 | 5 | 5 | 5 | 5 | 0 |
| 11.9 | 20 | 5 | 4 | 4 | 4 | 4 | 4 | 0 |
| 11.10 | 20 | 5 | 5 | 5 | 5 | 5 | 5 | 0 |
| 11.11 | 20 | 5 | 4 | 4 | 4 | 4 | 3 | 0 |
| 11.12 | 20 | 5 | 5 | 5 | 5 | 5 | 5 | 0 |
| 11.13 | 20 | 5 | 4 | 4 | 4 | 4 | 4 | 0 |
| 11.14 | 20 | 5 | 5 | 5 | 5 | 5 | 5 | 0 |
| 11.15 | 20 | 5 | 4 | 4 | 4 | 4 | 4 | 0 |
| 11.16 | 20 | 5 | 5 | 5 | 5 | 5 | 5 | 0 |
| 11.17 | 20 | 5 | 4 | 4 | 4 | 4 | 3 | 0 |
| 11.18 | 20 | 5 | 4 | 4 | 4 | 4 | 4 | 0 |
| 11.19 | 20 | 5 | 5 | 5 | 5 | 5 | 5 | 0 |
| 11.20 | 20 | 5 | 4 | 4 | 4 | 4 | 4 | 0 |
| 11.21 | 20 | 5 | 5 | 5 | 5 | 5 | 4 | 0 |
| 11.22 | 20 | 5 | 4 | 4 | 4 | 4 | 4 | 0 |
| 11.23 | 20 | 5 | 5 | 5 | 5 | 5 | 5 | 0 |
| 11.24 | 20 | 5 | 4 | 5 | 4 | 4 | 4 | 0 |
| 11.25 | 20 | 5 | 5 | 5 | 5 | 5 | 5 | 0 |
| 11.26 | 20 | 5 | 4 | 4 | 4 | 4 | 4 | 0 |
| 11.27 | 20 | 5 | 5 | 5 | 5 | 4 | 5 | 0 |
| 11.28 | 20 | 5 | 4 | 4 | 3 | 3 | 3 | 0 |
| 11.29 | 20 | 5 | 5 | 4 | 4 | 4 | 4 | 0 |
| 11.30 | 20 | 5 | 4 | 4 | 4 | 4 | 4 | 0 |
| 11.31 | 20 | 5 | 5 | 5 | 5 | 4 | 5 | 0 |
| 11.32 | 20 | 5 | 4 | 4 | 3 | 3 | 3 | 0 |
| 11.34 | 20 | 5 | 5 | 5 | 5 | 5 | 5 | 0 |
| 11.35 | 20 | 5 | 5 | 5 | 5 | 5 | 5 | 0 |
| 11.57 | 20 | 5 | 4 | 5 | 4 | 4 | 4 | 0 |
| 11.58 | 20 | 5 | 4 | 5 | 4 | 4 | 4 | 0 |
| 12.2 | 20 | 5 | 5 | 5 | 5 | 5 | 5 | 0 |
| Cpd. A | 20 | 3 | 5 | 0 | 0 | 0 | 0 | 0 |
| Cpd. B | 20 | 5 | 5 | 1 | 0 | 0 | 0 | 0 |

TABLE 14

| Cpd. No. | Dose (g/a) | EO | OS | EO | OS |
|---|---|---|---|---|---|
| 1.1 | 10 | 5 | 0 | 5 | 0 |
| 1.1 | 5 | 5 | 0 | 5 | 0 |
| 1.2 | 10 | 5 | 0 | 5 | 0 |
| 1.2 | 5 | 5 | 0 | 4 | 0 |
| 1.4 | 10 | 5 | 0 | 5 | 0 |
| 1.4 | 5 | 5 | 0 | 5 | 0 |
| 1.5 | 10 | 5 | 0 | 4 | 0 |
| 1.5 | 5 | 5 | 0 | 4 | 0 |
| 1.6 | 10 | 5 | 0 | 5 | 0 |
| 1.6 | 5 | 5 | 0 | 5 | 0 |
| 1.7 | 10 | 5 | 0 | 5 | 0 |
| 1.7 | 5 | 5 | 0 | 5 | 0 |
| 1.8 | 10 | 5 | 0 | 5 | 0 |
| 1.8 | 5 | 5 | 0 | 5 | 0 |
| 1.9 | 10 | 5 | 0 | 5 | 0 |
| 1.9 | 5 | 5 | 0 | 4 | 0 |
| 1.10 | 10 | 5 | 0 | 5 | 0 |
| 1.10 | 5 | 5 | 0 | 5 | 0 |
| 1.11 | 10 | 5 | 0 | 4 | 0 |
| 1.11 | 5 | 5 | 0 | 4 | 0 |
| 1.13 | 10 | 5 | 0 | 4 | 0 |
| 1.13 | 5 | 4 | 0 | 3 | 0 |
| 1.14 | 10 | 5 | 0 | 5 | 0 |
| 1.14 | 5 | 5 | 0 | 4 | 0 |
| 1.15 | 10 | 5 | 0 | 5 | 0 |
| 1.15 | 5 | 5 | 0 | 5 | 0 |
| 1.16 | 10 | 5 | 0 | 5 | 0 |
| 1.16 | 5 | 5 | 0 | 5 | 0 |
| 1.17 | 10 | 5 | 0 | 5 | 0 |
| 1.17 | 5 | 5 | 0 | 5 | 0 |

TABLE 14-continued

| Cpd. No. | Dose (g/a) | EO | OS | EO | OS |
|---|---|---|---|---|---|
| 1.18 | 10 | 5 | 0 | 4 | 0 |
| 1.18 | 5 | 5 | 0 | 4 | 0 |
| 1.19 | 10 | 5 | 0 | 5 | 0 |
| 1.19 | 5 | 5 | 0 | 5 | 0 |
| 1.20 | 10 | 5 | 0 | 4 | 0 |
| 1.20 | 5 | 4 | 0 | 4 | 0 |
| 1.21 | 10 | 5 | 0 | 5 | 0 |
| 1.21 | 5 | 5 | 0 | 5 | 0 |
| 1.22 | 10 | 5 | 0 | 4 | 0 |
| 1.22 | 5 | 4 | 0 | 4 | 0 |
| 1.23 | 10 | 5 | 0 | 5 | 0 |
| 1.23 | 5 | 5 | 0 | 5 | 0 |
| 1.24 | 10 | 5 | 0 | 4 | 0 |
| 1.24 | 5 | 4 | 0 | 4 | 0 |
| 1.26 | 10 | 5 | 0 | 3 | 0 |
| 1.26 | 5 | 4 | 0 | 3 | 0 |
| 1.27 | 10 | 5 | 0 | 5 | 0 |
| 1.27 | 5 | 5 | 0 | 4 | 0 |
| 1.37 | 10 | 5 | 0 | 5 | 0 |
| 1.37 | 5 | 5 | 0 | 5 | 0 |
| 1.38 | 10 | 5 | 0 | 5 | 0 |
| 1.38 | 5 | 5 | 0 | 5 | 0 |
| 1.40 | 10 | 5 | 0 | 5 | 0 |
| 1.40 | 5 | 5 | 0 | 5 | 0 |
| 1.56 | 10 | 5 | 0 | 4 | 0 |
| 1.56 | 5 | 4 | 0 | 4 | 0 |
| 1.57 | 10 | 5 | 0 | 5 | 0 |
| 1.57 | 5 | 5 | 0 | 5 | 0 |
| 1.58 | 10 | 5 | 0 | 5 | 0 |
| 1.58 | 5 | 5 | 0 | 5 | 0 |
| 1.59 | 10 | 5 | 0 | 4 | 0 |
| 1.59 | 5 | 4 | 0 | 3 | 0 |
| 1.60 | 10 | 5 | 0 | 4 | 0 |
| 1.60 | 5 | 4 | 0 | 4 | 0 |
| 1.79 | 10 | 5 | 0 | 5 | 0 |
| 1.79 | 5 | 5 | 0 | 4 | 0 |
| 1.80 | 10 | 5 | 0 | 4 | 0 |
| 1.80 | 5 | 4 | 0 | 3 | 0 |
| 1.81 | 10 | 5 | 0 | 5 | 0 |
| 1.81 | 5 | 5 | 0 | 5 | 0 |
| 2.1 | 10 | 5 | 0 | 5 | 0 |
| 2.1 | 5 | 5 | 0 | 5 | 0 |
| 2.2 | 10 | 5 | 0 | 4 | 0 |
| 2.2 | 5 | 4 | 0 | 4 | 0 |
| 2.3 | 10 | 5 | 0 | 4 | 0 |
| 2.3 | 5 | 4 | 0 | 4 | 0 |
| 2.4 | 10 | 5 | 0 | 5 | 0 |
| 2.4 | 5 | 5 | 0 | 5 | 0 |
| 2.5 | 10 | 5 | 0 | 4 | 0 |
| 2.5 | 5 | 4 | 0 | 4 | 0 |
| 2.6 | 10 | 5 | 0 | 5 | 0 |
| 2.6 | 5 | 5 | 0 | 5 | 0 |
| 2.7 | 10 | 5 | 0 | 5 | 0 |
| 2.7 | 5 | 5 | 0 | 5 | 0 |
| 2.8 | 10 | 5 | 0 | 4 | 0 |
| 2.8 | 5 | 4 | 0 | 4 | 0 |
| 2.9 | 10 | 5 | 0 | 5 | 0 |
| 2.9 | 5 | 4 | 0 | 4 | 0 |
| 2.10 | 10 | 5 | 0 | 5 | 0 |
| 2.10 | 5 | 5 | 0 | 5 | 0 |
| 2.11 | 10 | 5 | 0 | 4 | 0 |
| 2.11 | 5 | 4 | 0 | 3 | 0 |
| 2.12 | 10 | 5 | 0 | 5 | 0 |
| 2.12 | 5 | 5 | 0 | 5 | 0 |
| 2.13 | 10 | 5 | 0 | 5 | 0 |
| 2.13 | 5 | 5 | 0 | 5 | 0 |
| 2.14 | 10 | 5 | 0 | 4 | 0 |
| 2.14 | 5 | 4 | 0 | 4 | 0 |
| 2.15 | 10 | 5 | 0 | 4 | 0 |
| 2.15 | 5 | 4 | 0 | 3 | 0 |
| 2.16 | 10 | 5 | 0 | 5 | 0 |
| 2.16 | 5 | 5 | 0 | 5 | 0 |
| 2.18 | 10 | 5 | 0 | 4 | 0 |
| 2.18 | 5 | 4 | 0 | 3 | 0 |
| 2.19 | 10 | 5 | 0 | 5 | 0 |
| 2.19 | 5 | 5 | 0 | 4 | 0 |
| 2.21 | 10 | 5 | 0 | 3 | 0 |
| 2.21 | 5 | 4 | 0 | 3 | 0 |
| 2.22 | 10 | 5 | 0 | 5 | 0 |
| 2.22 | 5 | 5 | 0 | 3 | 0 |
| 2.41 | 10 | 5 | 0 | 4 | 0 |
| 2.41 | 5 | 4 | 0 | 3 | 0 |
| 2.42 | 10 | 5 | 0 | 5 | 0 |
| 2.42 | 5 | 5 | 0 | 5 | 0 |
| 2.43 | 10 | 5 | 0 | 4 | 0 |
| 2.43 | 5 | 5 | 0 | 3 | 0 |
| 2.44 | 10 | 5 | 0 | 4 | 0 |
| 2.44 | 5 | 4 | 0 | 4 | 0 |
| 2.45 | 10 | 5 | 0 | 5 | 0 |
| 2.45 | 5 | 5 | 0 | 5 | 0 |
| 2.46 | 10 | 5 | 0 | 4 | 0 |
| 2.46 | 5 | 4 | 0 | 3 | 0 |
| 2.50 | 10 | 5 | 0 | 5 | 0 |
| 2.50 | 5 | 5 | 0 | 4 | 0 |
| 2.51 | 10 | 5 | 0 | 4 | 0 |
| 2.51 | 5 | 4 | 0 | 3 | 0 |
| 2.52 | 10 | 5 | 0 | 5 | 0 |
| 2.52 | 5 | 5 | 0 | 5 | 0 |
| 2.53 | 10 | 5 | 0 | 4 | 0 |
| 2.53 | 5 | 5 | 0 | 4 | 0 |
| 2.54 | 10 | 5 | 0 | 5 | 0 |
| 2.54 | 5 | 5 | 0 | 4 | 0 |
| 2.56 | 10 | 5 | 0 | 5 | 0 |
| 2.56 | 5 | 4 | 0 | 4 | 0 |
| 2.58 | 10 | 5 | 0 | 4 | 0 |
| 2.58 | 5 | 4 | 0 | 3 | 0 |
| 2.59 | 10 | 5 | 0 | 5 | 0 |
| 2.59 | 5 | 5 | 0 | 5 | 0 |
| 2.60 | 10 | 5 | 0 | 4 | 0 |
| 2.60 | 5 | 4 | 0 | 3 | 0 |
| 2.61 | 10 | 5 | 0 | 4 | 0 |
| 2.61 | 5 | 5 | 0 | 3 | 0 |
| 2.64 | 10 | 5 | 0 | 5 | 0 |
| 2.64 | 5 | 5 | 0 | 5 | 0 |
| 2.65 | 10 | 5 | 0 | 5 | 0 |
| 2.65 | 5 | 5 | 0 | 5 | 0 |
| 2.66 | 10 | 5 | 0 | 5 | 0 |
| 2.66 | 5 | 5 | 0 | 5 | 0 |
| 2.68 | 10 | 5 | 0 | 5 | 0 |
| 2.68 | 5 | 5 | 0 | 5 | 0 |
| 2.83 | 10 | 5 | 0 | 5 | 0 |
| 2.83 | 5 | 5 | 0 | 5 | 0 |
| 2.97 | 10 | 5 | 0 | 4 | 0 |
| 2.97 | 5 | 4 | 0 | 3 | 0 |
| 2.98 | 10 | 5 | 0 | 5 | 0 |
| 2.98 | 5 | 5 | 0 | 4 | 0 |
| 2.104 | 10 | 5 | 0 | 4 | 0 |
| 2.104 | 5 | 4 | 0 | 3 | 0 |
| 2.105 | 10 | 5 | 0 | 5 | 0 |
| 2.105 | 5 | 5 | 0 | 5 | 0 |
| 2.120 | 10 | 5 | 0 | 4 | 0 |
| 2.120 | 5 | 4 | 0 | 3 | 0 |
| 2.121 | 10 | 5 | 0 | 4 | 0 |
| 2.121 | 5 | 4 | 0 | 3 | 0 |
| 3.1 | 10 | 5 | 0 | 5 | 0 |
| 3.1 | 5 | 5 | 0 | 5 | 0 |
| 3.2 | 10 | 5 | 0 | 4 | 0 |
| 3.2 | 5 | 4 | 0 | 4 | 0 |
| 3.3 | 10 | 5 | 0 | 5 | 0 |
| 3.3 | 5 | 5 | 0 | 5 | 0 |
| 3.4 | 10 | 5 | 0 | 4 | 0 |
| 3.4 | 5 | 4 | 0 | 3 | 0 |
| 3.5 | 10 | 5 | 0 | 3 | 0 |
| 3.5 | 5 | 4 | 0 | 3 | 0 |
| 3.6 | 10 | 5 | 0 | 5 | 0 |
| 3.6 | 5 | 5 | 0 | 5 | 0 |
| 3.7 | 10 | 5 | 0 | 4 | 0 |
| 3.7 | 5 | 4 | 0 | 3 | 0 |
| 3.8 | 10 | 5 | 0 | 3 | 0 |
| 3.8 | 5 | 4 | 0 | 3 | 0 |
| 3.9 | 10 | 5 | 0 | 5 | 0 |
| 3.9 | 5 | 5 | 0 | 5 | 0 |
| 3.10 | 10 | 5 | 0 | 4 | 0 |
| 3.10 | 5 | 4 | 0 | 3 | 0 |
| 3.11 | 10 | 5 | 0 | 5 | 0 |
| 3.11 | 5 | 5 | 0 | 5 | 0 |
| 3.12 | 10 | 5 | 0 | 5 | 0 |
| 3.12 | 5 | 5 | 0 | 5 | 0 |
| 3.14 | 10 | 5 | 0 | 4 | 0 |
| 3.14 | 5 | 5 | 0 | 4 | 0 |
| 3.15 | 10 | 5 | 0 | 5 | 0 |
| 3.15 | 5 | 5 | 0 | 5 | 0 |

TABLE 14-continued

| Cpd. No. | Dose (g/a) | EO | OS | EO | OS |
|---|---|---|---|---|---|
| 3.16 | 10 | 5 | 0 | 5 | 0 |
| 3.16 | 5 | 5 | 0 | 5 | 0 |
| 3.17 | 10 | 5 | 0 | 4 | 0 |
| 3.17 | 5 | 4 | 0 | 3 | 0 |
| 3.18 | 10 | 5 | 0 | 5 | 0 |
| 3.18 | 5 | 5 | 0 | 5 | 0 |
| 3.19 | 10 | 5 | 0 | 4 | 0 |
| 3.19 | 5 | 4 | 0 | 4 | 0 |
| 3.20 | 10 | 5 | 0 | 5 | 0 |
| 3.20 | 5 | 5 | 0 | 5 | 0 |
| 3.21 | 10 | 5 | 0 | 4 | 0 |
| 3.21 | 5 | 5 | 0 | 3 | 0 |
| 3.34 | 10 | 5 | 0 | 4 | 0 |
| 3.34 | 5 | 4 | 0 | 3 | 0 |
| 4.1 | 10 | 5 | 0 | 5 | 0 |
| 4.1 | 5 | 5 | 0 | 5 | 0 |
| 4.2 | 10 | 5 | 0 | 4 | 0 |
| 4.2 | 5 | 5 | 0 | 4 | 0 |
| 4.3 | 10 | 5 | 0 | 5 | 0 |
| 4.3 | 5 | 5 | 0 | 5 | 0 |
| 4.4 | 10 | 5 | 0 | 4 | 0 |
| 4.4 | 5 | 5 | 0 | 3 | 0 |
| 4.5 | 10 | 5 | 0 | 5 | 0 |
| 4.5 | 5 | 5 | 0 | 5 | 0 |
| 4.6 | 10 | 5 | 0 | 4 | 0 |
| 4.6 | 5 | 5 | 0 | 4 | 0 |
| 4.7 | 10 | 5 | 0 | 5 | 0 |
| 4.7 | 5 | 5 | 0 | 5 | 0 |
| 4.8 | 10 | 5 | 0 | 4 | 0 |
| 4.8 | 5 | 4 | 0 | 3 | 0 |
| 4.42 | 10 | 5 | 0 | 4 | 0 |
| 4.42 | 5 | 4 | 0 | 4 | 0 |
| 4.43 | 10 | 5 | 0 | 5 | 0 |
| 4.43 | 5 | 5 | 0 | 5 | 0 |
| 4.44 | 10 | 5 | 0 | 4 | 0 |
| 4.44 | 5 | 4 | 0 | 4 | 0 |
| 4.45 | 10 | 5 | 0 | 5 | 0 |
| 4.45 | 5 | 5 | 0 | 5 | 0 |
| 4.46 | 10 | 5 | 0 | 5 | 0 |
| 4.46 | 5 | 5 | 0 | 5 | 0 |
| 4.47 | 10 | 5 | 0 | 4 | 0 |
| 4.47 | 5 | 4 | 0 | 4 | 0 |
| 4.48 | 10 | 5 | 0 | 5 | 0 |
| 4.48 | 5 | 5 | 0 | 5 | 0 |
| 4.49 | 10 | 5 | 0 | 4 | 0 |
| 4.49 | 5 | 4 | 0 | 4 | 0 |
| 4.50 | 10 | 5 | 0 | 5 | 0 |
| 4.50 | 5 | 5 | 0 | 5 | 0 |
| 4.51 | 10 | 5 | 0 | 4 | 0 |
| 4.51 | 5 | 4 | 0 | 4 | 0 |
| 4.52 | 10 | 5 | 0 | 5 | 0 |
| 4.52 | 5 | 5 | 0 | 5 | 0 |
| 4.56 | 10 | 5 | 0 | 5 | 0 |
| 4.56 | 5 | 5 | 0 | 5 | 0 |
| 4.58 | 10 | 5 | 0 | 5 | 0 |
| 4.58 | 5 | 5 | 0 | 5 | 0 |
| 4.61 | 10 | 5 | 0 | 4 | 0 |
| 4.61 | 5 | 4 | 0 | 3 | 0 |
| 4.62 | 10 | 5 | 0 | 5 | 0 |
| 4.62 | 5 | 5 | 0 | 4 | 0 |
| 4.64 | 10 | 5 | 0 | 5 | 0 |
| 4.64 | 5 | 5 | 0 | 3 | 0 |
| 4.65 | 10 | 5 | 0 | 5 | 0 |
| 4.65 | 5 | 5 | 0 | 5 | 0 |
| 4.66 | 10 | 5 | 0 | 5 | 0 |
| 4.66 | 5 | 5 | 0 | 5 | 0 |
| 4.67 | 10 | 5 | 0 | 5 | 0 |
| 4.67 | 5 | 5 | 0 | 5 | 0 |
| 4.69 | 10 | 5 | 0 | 5 | 0 |
| 4.69 | 5 | 5 | 0 | 5 | 0 |
| 4.107 | 10 | 5 | 0 | 4 | 0 |
| 4.107 | 5 | 4 | 0 | 4 | 0 |
| 4.133 | 10 | 5 | 0 | 4 | 0 |
| 4.133 | 5 | 4 | 0 | 4 | 0 |
| 4.134 | 10 | 5 | 0 | 5 | 0 |
| 4.134 | 5 | 5 | 0 | 5 | 0 |
| 5.1 | 10 | 5 | 0 | 5 | 0 |
| 5.1 | 5 | 5 | 0 | 5 | 0 |
| 5.2 | 10 | 5 | 0 | 4 | 0 |
| 5.2 | 5 | 5 | 0 | 4 | 0 |
| 5.3 | 10 | 5 | 0 | 5 | 0 |
| 5.3 | 5 | 5 | 0 | 5 | 0 |
| 5.5 | 10 | 5 | 0 | 5 | 0 |
| 5.5 | 5 | 5 | 0 | 5 | 0 |
| 5.6 | 10 | 5 | 0 | 5 | 0 |
| 5.6 | 5 | 5 | 0 | 5 | 0 |
| 5.7 | 10 | 5 | 0 | 4 | 0 |
| 5.7 | 5 | 4 | 0 | 3 | 0 |
| 5.8 | 10 | 5 | 0 | 5 | 0 |
| 5.8 | 5 | 5 | 0 | 5 | 0 |
| 5.9 | 10 | 5 | 0 | 5 | 0 |
| 5.9 | 5 | 5 | 0 | 5 | 0 |
| 5.11 | 10 | 5 | 0 | 5 | 0 |
| 5.11 | 5 | 5 | 0 | 5 | 0 |
| 5.12 | 10 | 5 | 0 | 4 | 0 |
| 5.12 | 5 | 4 | 0 | 4 | 0 |
| 5.13 | 10 | 5 | 0 | 5 | 0 |
| 5.13 | 5 | 5 | 0 | 5 | 0 |
| 5.14 | 10 | 5 | 0 | 4 | 0 |
| 5.14 | 5 | 4 | 0 | 3 | 0 |
| 5.15 | 10 | 5 | 0 | 5 | 0 |
| 5.15 | 5 | 5 | 0 | 5 | 0 |
| 5.16 | 10 | 5 | 0 | 4 | 0 |
| 5.16 | 5 | 5 | 0 | 3 | 0 |
| 5.17 | 10 | 5 | 0 | 5 | 0 |
| 5.17 | 5 | 5 | 0 | 5 | 0 |
| 5.18 | 10 | 5 | 0 | 4 | 0 |
| 5.18 | 5 | 4 | 0 | 3 | 0 |
| 5.19 | 10 | 5 | 0 | 5 | 0 |
| 5.19 | 5 | 5 | 0 | 5 | 0 |
| 5.20 | 10 | 5 | 0 | 4 | 0 |
| 5.20 | 5 | 4 | 0 | 3 | 0 |
| 5.25 | 10 | 5 | 0 | 4 | 0 |
| 5.25 | 5 | 4 | 0 | 3 | 0 |
| 5.26 | 10 | 5 | 0 | 5 | 0 |
| 5.26 | 5 | 5 | 0 | 4 | 0 |
| 5.27 | 10 | 5 | 0 | 4 | 0 |
| 5.27 | 5 | 4 | 0 | 4 | 0 |
| 5.28 | 10 | 5 | 0 | 5 | 0 |
| 5.28 | 5 | 5 | 0 | 5 | 0 |
| 5.29 | 10 | 5 | 0 | 4 | 0 |
| 5.29 | 5 | 4 | 0 | 4 | 0 |
| 5.30 | 10 | 5 | 0 | 5 | 0 |
| 5.30 | 5 | 5 | 0 | 5 | 0 |
| 5.31 | 10 | 5 | 0 | 4 | 0 |
| 5.31 | 5 | 4 | 0 | 4 | 0 |
| 5.32 | 10 | 5 | 0 | 5 | 0 |
| 5.32 | 5 | 5 | 0 | 5 | 0 |
| 5.33 | 10 | 5 | 0 | 4 | 0 |
| 5.33 | 5 | 4 | 0 | 4 | 0 |
| 5.34 | 10 | 5 | 0 | 5 | 0 |
| 5.34 | 5 | 5 | 0 | 5 | 0 |
| 5.35 | 10 | 5 | 0 | 4 | 0 |
| 5.35 | 5 | 4 | 0 | 3 | 0 |
| 5.36 | 10 | 5 | 0 | 5 | 0 |
| 5.36 | 5 | 5 | 0 | 5 | 0 |
| 5.37 | 10 | 5 | 0 | 4 | 0 |
| 5.37 | 5 | 4 | 0 | 4 | 0 |
| 5.38 | 10 | 5 | 0 | 5 | 0 |
| 5.38 | 5 | 5 | 0 | 5 | 0 |
| 5.39 | 10 | 5 | 0 | 5 | 0 |
| 5.39 | 5 | 5 | 0 | 5 | 0 |
| 5.40 | 10 | 5 | 0 | 5 | 0 |
| 5.40 | 5 | 5 | 0 | 5 | 0 |
| 5.41 | 10 | 5 | 0 | 4 | 0 |
| 5.41 | 5 | 4 | 0 | 3 | 0 |
| 5.42 | 10 | 5 | 0 | 5 | 0 |
| 5.42 | 5 | 5 | 0 | 4 | 0 |
| 5.59 | 10 | 5 | 0 | 4 | 0 |
| 5.59 | 5 | 4 | 0 | 3 | 0 |
| 5.69 | 10 | 5 | 0 | 4 | 0 |
| 5.69 | 5 | 4 | 0 | 3 | 0 |
| 5.70 | 10 | 5 | 0 | 5 | 0 |
| 5.70 | 5 | 5 | 0 | 5 | 0 |
| 5.71 | 10 | 5 | 0 | 4 | 0 |
| 5.71 | 5 | 4 | 0 | 3 | 0 |
| 5.72 | 10 | 5 | 0 | 5 | 0 |
| 5.72 | 5 | 5 | 0 | 5 | 0 |
| 5.73 | 10 | 5 | 0 | 5 | 0 |
| 5.73 | 5 | 5 | 0 | 4 | 0 |
| 5.74 | 10 | 5 | 0 | 5 | 0 |
| 5.74 | 5 | 5 | 0 | 5 | 0 |

TABLE 14-continued

| Cpd. No. | Dose (g/a) | EO | OS | EO | OS |
|---|---|---|---|---|---|
| 5.75 | 10 | 5 | 0 | 5 | 0 |
| 5.75 | 5 | 5 | 0 | 5 | 0 |
| 5.76 | 10 | 5 | 0 | 5 | 0 |
| 5.76 | 5 | 5 | 0 | 5 | 0 |
| 5.107 | 10 | 5 | 0 | 4 | 0 |
| 5.107 | 5 | 4 | 0 | 3 | 0 |
| 6.1 | 10 | 5 | 0 | 5 | 0 |
| 6.1 | 5 | 5 | 0 | 5 | 0 |
| 6.2 | 10 | 5 | 0 | 4 | 0 |
| 6.2 | 5 | 4 | 0 | 3 | 0 |
| 6.3 | 10 | 5 | 0 | 5 | 0 |
| 6.3 | 5 | 5 | 0 | 5 | 0 |
| 6.4 | 10 | 5 | 0 | 4 | 0 |
| 6.4 | 5 | 5 | 0 | 4 | 0 |
| 6.5 | 10 | 5 | 0 | 4 | 0 |
| 6.5 | 5 | 5 | 0 | 4 | 0 |
| 6.6 | 10 | 5 | 0 | 5 | 0 |
| 6.6 | 5 | 5 | 0 | 5 | 0 |
| 6.7 | 10 | 5 | 0 | 4 | 0 |
| 6.7 | 5 | 4 | 0 | 3 | 0 |
| 6.8 | 10 | 5 | 0 | 5 | 0 |
| 6.8 | 5 | 5 | 0 | 5 | 0 |
| 6.9 | 10 | 5 | 0 | 4 | 0 |
| 6.9 | 5 | 4 | 0 | 3 | 0 |
| 6.10 | 10 | 5 | 0 | 5 | 0 |
| 6.10 | 5 | 5 | 0 | 5 | 0 |
| 6.11 | 10 | 5 | 0 | 5 | 0 |
| 6.11 | 5 | 5 | 0 | 5 | 0 |
| 6.12 | 10 | 5 | 0 | 4 | 0 |
| 6.12 | 5 | 4 | 0 | 3 | 0 |
| 6.13 | 10 | 5 | 0 | 4 | 0 |
| 6.13 | 5 | 4 | 0 | 3 | 0 |
| 6.14 | 10 | 5 | 0 | 5 | 0 |
| 6.14 | 5 | 5 | 0 | 4 | 0 |
| 6.15 | 10 | 5 | 0 | 4 | 0 |
| 6.15 | 5 | 4 | 0 | 3 | 0 |
| 6.16 | 10 | 5 | 0 | 5 | 0 |
| 6.16 | 5 | 5 | 0 | 4 | 0 |
| 6.17 | 10 | 5 | 0 | 5 | 0 |
| 6.17 | 5 | 5 | 0 | 5 | 0 |
| 6.18 | 10 | 5 | 0 | 4 | 0 |
| 6.18 | 5 | 4 | 0 | 4 | 0 |
| 6.19 | 10 | 5 | 0 | 5 | 0 |
| 6.19 | 5 | 5 | 0 | 5 | 0 |
| 6.60 | 10 | 5 | 0 | 5 | 0 |
| 6.60 | 5 | 5 | 0 | 5 | 0 |
| 6.61 | 10 | 5 | 0 | 5 | 0 |
| 6.61 | 5 | 5 | 0 | 5 | 0 |
| 6.62 | 10 | 5 | 0 | 5 | 0 |
| 6.62 | 5 | 5 | 0 | 5 | 0 |
| 6.63 | 10 | 5 | 0 | 5 | 0 |
| 6.63 | 5 | 5 | 0 | 5 | 0 |
| 6.66 | 10 | 5 | 0 | 5 | 0 |
| 6.66 | 5 | 5 | 0 | 5 | 0 |
| 6.70 | 10 | 5 | 0 | 5 | 0 |
| 6.70 | 5 | 5 | 0 | 5 | 0 |
| 6.101 | 10 | 5 | 0 | 5 | 0 |
| 6.101 | 5 | 5 | 0 | 5 | 0 |
| 6.102 | 10 | 5 | 0 | 5 | 0 |
| 6.102 | 5 | 5 | 0 | 4 | 0 |
| 6.103 | 10 | 5 | 0 | 5 | 0 |
| 6.103 | 5 | 5 | 0 | 4 | 0 |
| 6.104 | 10 | 5 | 0 | 5 | 0 |
| 6.104 | 5 | 5 | 0 | 5 | 0 |
| 6.105 | 10 | 5 | 0 | 4 | 0 |
| 6.105 | 5 | 4 | 0 | 4 | 0 |
| 6.106 | 10 | 5 | 0 | 5 | 0 |
| 6.106 | 5 | 5 | 0 | 5 | 0 |
| 6.108 | 10 | 5 | 0 | 4 | 0 |
| 6.108 | 5 | 4 | 0 | 4 | 0 |
| 6.109 | 10 | 5 | 0 | 5 | 0 |
| 6.109 | 5 | 5 | 0 | 5 | 0 |
| 6.110 | 10 | 5 | 0 | 4 | 0 |
| 6.110 | 5 | 4 | 0 | 4 | 0 |
| 6.111 | 10 | 5 | 0 | 4 | 0 |
| 6.111 | 5 | 5 | 0 | 3 | 0 |
| 6.112 | 10 | 5 | 0 | 5 | 0 |
| 6.112 | 5 | 5 | 0 | 4 | 0 |
| 6.114 | 10 | 5 | 0 | 5 | 0 |
| 6.114 | 5 | 5 | 0 | 4 | 0 |
| 6.115 | 10 | 5 | 0 | 5 | 0 |
| 6.115 | 5 | 5 | 0 | 4 | 0 |
| 6.116 | 10 | 5 | 0 | 4 | 0 |
| 6.116 | 5 | 4 | 0 | 3 | 0 |
| 6.117 | 10 | 5 | 0 | 5 | 0 |
| 6.117 | 5 | 5 | 0 | 3 | 0 |
| 6.118 | 10 | 5 | 0 | 4 | 0 |
| 6.118 | 5 | 4 | 0 | 3 | 0 |
| 6.119 | 10 | 5 | 0 | 5 | 0 |
| 6.119 | 5 | 5 | 0 | 4 | 0 |
| 6.120 | 10 | 5 | 0 | 4 | 0 |
| 6.120 | 5 | 4 | 0 | 4 | 0 |
| 6.121 | 10 | 5 | 0 | 4 | 0 |
| 6.121 | 5 | 4 | 0 | 3 | 0 |
| 6.126 | 10 | 5 | 0 | 4 | 0 |
| 6.126 | 5 | 4 | 0 | 3 | 0 |
| 6.144 | 10 | 5 | 0 | 4 | 0 |
| 6.144 | 5 | 4 | 0 | 3 | 0 |
| 6.145 | 10 | 5 | 0 | 5 | 0 |
| 6.145 | 5 | 5 | 0 | 5 | 0 |
| 6.147 | 10 | 5 | 0 | 4 | 0 |
| 6.147 | 5 | 4 | 0 | 3 | 0 |
| 6.148 | 10 | 5 | 0 | 5 | 0 |
| 6.148 | 5 | 5 | 0 | 5 | 0 |
| 6.151 | 10 | 5 | 0 | 4 | 0 |
| 6.151 | 5 | 4 | 0 | 3 | 0 |
| 6.159 | 10 | 5 | 0 | 4 | 0 |
| 6.159 | 5 | 5 | 0 | 4 | 0 |
| 6.160 | 10 | 5 | 0 | 4 | 0 |
| 6.160 | 5 | 4 | 0 | 3 | 0 |
| 6.172 | 10 | 5 | 0 | 4 | 0 |
| 6.172 | 5 | 4 | 0 | 3 | 0 |
| 6.173 | 10 | 5 | 0 | 4 | 0 |
| 6.173 | 5 | 4 | 0 | 3 | 0 |
| 7.1 | 10 | 5 | 0 | 5 | 0 |
| 7.1 | 5 | 5 | 0 | 5 | 0 |
| 7.2 | 10 | 5 | 0 | 5 | 0 |
| 7.2 | 5 | 5 | 0 | 5 | 0 |
| 7.3 | 10 | 5 | 0 | 4 | 0 |
| 7.3 | 5 | 4 | 0 | 3 | 0 |
| 7.4 | 10 | 5 | 0 | 5 | 0 |
| 7.4 | 5 | 5 | 0 | 5 | 0 |
| 7.6 | 10 | 5 | 0 | 5 | 0 |
| 7.6 | 5 | 5 | 0 | 5 | 0 |
| 7.7 | 10 | 5 | 0 | 5 | 0 |
| 7.7 | 5 | 5 | 0 | 5 | 0 |
| 7.9 | 10 | 5 | 0 | 5 | 0 |
| 7.9 | 5 | 5 | 0 | 4 | 0 |
| 7.10 | 10 | 5 | 0 | 5 | 0 |
| 7.10 | 5 | 5 | 0 | 5 | 0 |
| 7.12 | 10 | 5 | 0 | 5 | 0 |
| 7.12 | 5 | 5 | 0 | 5 | 0 |
| 7.13 | 10 | 5 | 0 | 4 | 0 |
| 7.13 | 5 | 4 | 0 | 3 | 0 |
| 7.14 | 10 | 5 | 0 | 5 | 0 |
| 7.14 | 5 | 5 | 0 | 4 | 0 |
| 7.15 | 10 | 5 | 0 | 5 | 0 |
| 7.15 | 5 | 5 | 0 | 5 | 0 |
| 7.16 | 10 | 5 | 0 | 4 | 0 |
| 7.16 | 5 | 4 | 0 | 3 | 0 |
| 7.17 | 10 | 5 | 0 | 5 | 0 |
| 7.17 | 5 | 5 | 0 | 5 | 0 |
| 7.19 | 10 | 5 | 0 | 4 | 0 |
| 7.19 | 5 | 4 | 0 | 3 | 0 |
| 7.20 | 10 | 5 | 0 | 5 | 0 |
| 7.20 | 5 | 5 | 0 | 5 | 0 |
| 7.21 | 10 | 5 | 0 | 4 | 0 |
| 7.21 | 5 | 4 | 0 | 3 | 0 |
| 7.22 | 10 | 5 | 0 | 5 | 0 |
| 7.22 | 5 | 5 | 0 | 5 | 0 |
| 7.23 | 10 | 5 | 0 | 3 | 0 |
| 7.23 | 5 | 4 | 0 | 3 | 0 |
| 7.24 | 10 | 5 | 0 | 5 | 0 |
| 7.24 | 5 | 5 | 0 | 5 | 0 |
| 7.75 | 10 | 5 | 0 | 5 | 0 |
| 7.75 | 5 | 5 | 0 | 5 | 0 |
| 7.76 | 10 | 5 | 0 | 5 | 0 |
| 7.76 | 5 | 5 | 0 | 5 | 0 |
| 7.90 | 10 | 5 | 0 | 4 | 0 |
| 7.90 | 5 | 4 | 0 | 3 | 0 |
| 7.91 | 10 | 5 | 0 | 4 | 0 |
| 7.91 | 5 | 4 | 0 | 3 | 0 |

TABLE 14-continued

| Cpd. No. | Dose (g/a) | EO | OS | EO | OS |
|---|---|---|---|---|---|
| 7.93 | 10 | 5 | 0 | 3 | 0 |
| 7.93 | 5 | 4 | 0 | 3 | 0 |
| 7.95 | 10 | 5 | 0 | 5 | 0 |
| 7.95 | 5 | 5 | 0 | 5 | 0 |
| 7.96 | 10 | 5 | 0 | 5 | 0 |
| 7.96 | 5 | 5 | 0 | 5 | 0 |
| 7.97 | 10 | 5 | 0 | 4 | 0 |
| 7.97 | 5 | 5 | 0 | 4 | 0 |
| 7.99 | 10 | 5 | 0 | 4 | 0 |
| 7.99 | 5 | 5 | 0 | 3 | 0 |
| 7.100 | 10 | 5 | 0 | 4 | 0 |
| 7.100 | 5 | 5 | 0 | 4 | 0 |
| 7.103 | 10 | 5 | 0 | 4 | 0 |
| 7.103 | 5 | 5 | 0 | 3 | 0 |
| 7.112 | 10 | 5 | 0 | 5 | 0 |
| 7.112 | 5 | 5 | 0 | 5 | 0 |
| 7.113 | 10 | 5 | 0 | 5 | 0 |
| 7.113 | 5 | 5 | 0 | 5 | 0 |
| 7.114 | 10 | 5 | 0 | 5 | 0 |
| 7.114 | 5 | 5 | 0 | 5 | 0 |
| 7.115 | 10 | 5 | 0 | 5 | 0 |
| 7.115 | 5 | 5 | 0 | 5 | 0 |
| 7.119 | 10 | 5 | 0 | 5 | 0 |
| 7.119 | 5 | 5 | 0 | 5 | 0 |
| 7.120 | 10 | 5 | 0 | 5 | 0 |
| 7.120 | 5 | 5 | 0 | 5 | 0 |
| 7.121 | 10 | 5 | 0 | 5 | 0 |
| 7.121 | 5 | 5 | 0 | 5 | 0 |
| 7.122 | 10 | 5 | 0 | 5 | 0 |
| 7.122 | 5 | 5 | 0 | 5 | 0 |
| 7.126 | 10 | 5 | 0 | 5 | 0 |
| 7.126 | 5 | 5 | 0 | 5 | 0 |
| 7.142 | 10 | 5 | 0 | 5 | 0 |
| 7.142 | 5 | 5 | 0 | 5 | 0 |
| 7.150 | 10 | 5 | 0 | 5 | 0 |
| 7.150 | 5 | 5 | 0 | 5 | 0 |
| 7.166 | 10 | 5 | 0 | 4 | 0 |
| 7.166 | 5 | 4 | 0 | 3 | 0 |
| 7.167 | 10 | 5 | 0 | 5 | 0 |
| 7.167 | 5 | 5 | 0 | 5 | 0 |
| 7.168 | 10 | 5 | 0 | 5 | 0 |
| 7.168 | 5 | 5 | 0 | 5 | 0 |
| 7.169 | 10 | 5 | 0 | 5 | 0 |
| 7.169 | 5 | 5 | 0 | 4 | 0 |
| 7.172 | 10 | 5 | 0 | 4 | 0 |
| 7.172 | 5 | 4 | 0 | 3 | 0 |
| 7.173 | 10 | 5 | 0 | 5 | 0 |
| 7.173 | 5 | 5 | 0 | 5 | 0 |
| 7.174 | 10 | 5 | 0 | 4 | 0 |
| 7.174 | 5 | 4 | 0 | 4 | 0 |
| 7.175 | 10 | 5 | 0 | 5 | 0 |
| 7.175 | 5 | 5 | 0 | 5 | 0 |
| 7.176 | 10 | 5 | 0 | 4 | 0 |
| 7.176 | 5 | 4 | 0 | 4 | 0 |
| 7.177 | 10 | 5 | 0 | 5 | 0 |
| 7.177 | 5 | 5 | 0 | 5 | 0 |
| 7.178 | 10 | 5 | 0 | 4 | 0 |
| 7.178 | 5 | 4 | 0 | 4 | 0 |
| 7.179 | 10 | 5 | 0 | 5 | 0 |
| 7.179 | 5 | 5 | 0 | 5 | 0 |
| 7.181 | 10 | 5 | 0 | 4 | 0 |
| 7.181 | 5 | 4 | 0 | 3 | 0 |
| 7.182 | 10 | 5 | 0 | 5 | 0 |
| 7.182 | 5 | 5 | 0 | 4 | 0 |
| 7.183 | 10 | 5 | 0 | 3 | 0 |
| 7.183 | 5 | 4 | 0 | 3 | 0 |
| 7.184 | 10 | 5 | 0 | 5 | 0 |
| 7.184 | 5 | 4 | 0 | 4 | 0 |
| 7.185 | 10 | 5 | 0 | 3 | 0 |
| 7.185 | 5 | 4 | 0 | 3 | 0 |
| 7.186 | 10 | 5 | 0 | 4 | 0 |
| 7.186 | 5 | 4 | 0 | 4 | 0 |
| 7.187 | 10 | 5 | 0 | 4 | 0 |
| 7.187 | 5 | 4 | 0 | 4 | 0 |
| 7.188 | 10 | 5 | 0 | 5 | 0 |
| 7.188 | 5 | 5 | 0 | 5 | 0 |
| 7.189 | 10 | 5 | 0 | 4 | 0 |
| 7.189 | 5 | 4 | 0 | 4 | 0 |
| 7.190 | 10 | 5 | 0 | 5 | 0 |
| 7.190 | 5 | 5 | 0 | 5 | 0 |
| 7.191 | 10 | 5 | 0 | 5 | 0 |
| 7.191 | 5 | 5 | 0 | 5 | 0 |
| 7.211 | 10 | 5 | 0 | 4 | 0 |
| 7.211 | 5 | 5 | 0 | 4 | 0 |
| 7.212 | 10 | 5 | 0 | 5 | 0 |
| 7.212 | 5 | 5 | 0 | 4 | 0 |
| 7.213 | 10 | 5 | 0 | 5 | 0 |
| 7.213 | 5 | 5 | 0 | 5 | 0 |
| 7.215 | 10 | 5 | 0 | 5 | 0 |
| 7.215 | 5 | 5 | 0 | 5 | 0 |
| 7.216 | 10 | 5 | 0 | 4 | 0 |
| 7.216 | 5 | 5 | 0 | 3 | 0 |
| 7.217 | 10 | 5 | 0 | 4 | 0 |
| 7.217 | 5 | 4 | 0 | 3 | 0 |
| 7.218 | 10 | 5 | 0 | 5 | 0 |
| 7.218 | 5 | 5 | 0 | 5 | 0 |
| 7.219 | 10 | 5 | 0 | 4 | 0 |
| 7.219 | 5 | 4 | 0 | 3 | 0 |
| 7.220 | 10 | 5 | 0 | 5 | 0 |
| 7.220 | 5 | 5 | 0 | 5 | 0 |
| 7.221 | 10 | 5 | 0 | 5 | 0 |
| 7.221 | 5 | 5 | 0 | 5 | 0 |
| 7.222 | 10 | 5 | 0 | 5 | 0 |
| 7.222 | 5 | 5 | 0 | 5 | 0 |
| 7.223 | 10 | 5 | 0 | 5 | 0 |
| 7.223 | 5 | 5 | 0 | 5 | 0 |
| 7.231 | 10 | 5 | 0 | 4 | 0 |
| 7.231 | 5 | 4 | 0 | 3 | 0 |
| 7.234 | 10 | 4 | 0 | 3 | 0 |
| 7.234 | 5 | 3 | 0 | 3 | 0 |
| 7.237 | 10 | 4 | 0 | 3 | 0 |
| 7.237 | 5 | 3 | 0 | 3 | 0 |
| 7.246 | 5 | 5 | 0 | 4 | 0 |
| 7.246 | 5 | 4 | 0 | 3 | 0 |
| 7.247 | 10 | 5 | 0 | 5 | 0 |
| 7.247 | 5 | 5 | 0 | 4 | 0 |
| 7.252 | 10 | 5 | 0 | 4 | 0 |
| 7.252 | 5 | 4 | 0 | 4 | 0 |
| 7.253 | 10 | 5 | 0 | 4 | 0 |
| 7.253 | 5 | 4 | 0 | 3 | 0 |
| 7.254 | 10 | 5 | 0 | 4 | 0 |
| 7.254 | 5 | 4 | 0 | 3 | 0 |
| 7.255 | 10 | 5 | 0 | 4 | 0 |
| 7.255 | 5 | 4 | 0 | 3 | 0 |
| 7.256 | 10 | 5 | 0 | 4 | 0 |
| 7.256 | 5 | 4 | 0 | 4 | 0 |
| 7.257 | 10 | 5 | 0 | 5 | 0 |
| 7.257 | 5 | 5 | 0 | 5 | 0 |
| 7.258 | 10 | 5 | 0 | 4 | 0 |
| 7.258 | 5 | 4 | 0 | 4 | 0 |
| 7.259 | 10 | 5 | 0 | 5 | 0 |
| 7.259 | 5 | 5 | 0 | 5 | 0 |
| 7.262 | 10 | 4 | 0 | 3 | 0 |
| 7.262 | 5 | 3 | 0 | 3 | 0 |
| 7.267 | 10 | 5 | 0 | 4 | 0 |
| 7.267 | 5 | 4 | 0 | 4 | 0 |
| 7.269 | 10 | 4 | 0 | 3 | 0 |
| 7.269 | 5 | 3 | 0 | 3 | 0 |
| 7.270 | 10 | 4 | 0 | 3 | 0 |
| 7.270 | 5 | 3 | 0 | 3 | 0 |
| 7.271 | 10 | 4 | 0 | 4 | 0 |
| 7.271 | 5 | 4 | 0 | 3 | 0 |
| 7.272 | 10 | 5 | 0 | 3 | 0 |
| 7.272 | 5 | 3 | 0 | 3 | 0 |
| 7.273 | 10 | 5 | 0 | 4 | 0 |
| 7.273 | 5 | 4 | 0 | 3 | 0 |
| 7.286 | 10 | 5 | 0 | 4 | 0 |
| 7.286 | 5 | 4 | 0 | 3 | 0 |
| 7.300 | 10 | 5 | 0 | 4 | 0 |
| 7.300 | 5 | 3 | 0 | 3 | 0 |
| 7.301 | 10 | 5 | 0 | 4 | 0 |
| 7.301 | 5 | 5 | 0 | 3 | 0 |
| 7.329 | 10 | 5 | 0 | 5 | 0 |
| 7.329 | 5 | 5 | 0 | 5 | 0 |
| 7.331 | 10 | 5 | 0 | 4 | 0 |
| 7.331 | 5 | 4 | 0 | 3 | 0 |
| 7.332 | 10 | 5 | 0 | 4 | 0 |
| 7.332 | 5 | 4 | 0 | 3 | 0 |
| 7.333 | 10 | 5 | 0 | 4 | 0 |
| 7.333 | 5 | 4 | 0 | 3 | 0 |
| 7.334 | 10 | 5 | 0 | 4 | 0 |
| 7.334 | 5 | 4 | 0 | 3 | 0 |

TABLE 14-continued

| Cpd. No. | Dose (g/a) | EO | OS | EO | OS |
|---|---|---|---|---|---|
| 7.335 | 10 | 5 | 0 | 4 | 0 |
| 7.335 | 5 | 4 | 0 | 3 | 0 |
| 7.336 | 10 | 5 | 0 | 5 | 0 |
| 7.336 | 5 | 5 | 0 | 5 | 0 |
| 7.337 | 10 | 5 | 0 | 4 | 0 |
| 7.337 | 5 | 4 | 0 | 3 | 0 |
| 7.338 | 10 | 5 | 0 | 5 | 0 |
| 7.338 | 5 | 5 | 0 | 5 | 0 |
| 7.339 | 10 | 5 | 0 | 4 | 0 |
| 7.339 | 5 | 4 | 0 | 3 | 0 |
| 7.340 | 10 | 5 | 0 | 5 | 0 |
| 7.340 | 5 | 5 | 0 | 5 | 0 |
| 8.1 | 10 | 5 | 0 | 5 | 0 |
| 8.1 | 5 | 5 | 0 | 5 | 0 |
| 8.2 | 10 | 5 | 0 | 4 | 0 |
| 8.2 | 5 | 4 | 0 | 3 | 0 |
| 8.3 | 10 | 5 | 0 | 4 | 0 |
| 8.3 | 5 | 4 | 0 | 3 | 0 |
| 8.4 | 10 | 5 | 0 | 5 | 0 |
| 8.4 | 5 | 5 | 0 | 5 | 0 |
| 8.5 | 10 | 5 | 0 | 5 | 0 |
| 8.5 | 5 | 5 | 0 | 5 | 0 |
| 8.6 | 10 | 5 | 0 | 3 | 0 |
| 8.6 | 5 | 4 | 0 | 3 | 0 |
| 8.7 | 10 | 5 | 0 | 5 | 0 |
| 8.7 | 5 | 5 | 0 | 5 | 0 |
| 8.8 | 10 | 5 | 0 | 4 | 0 |
| 8.8 | 5 | 5 | 0 | 4 | 0 |
| 8.9 | 10 | 5 | 0 | 5 | 0 |
| 8.9 | 5 | 5 | 0 | 5 | 0 |
| 8.10 | 10 | 5 | 0 | 4 | 0 |
| 8.10 | 5 | 4 | 0 | 3 | 0 |
| 8.11 | 10 | 5 | 0 | 4 | 0 |
| 8.11 | 5 | 5 | 0 | 3 | 0 |
| 8.12 | 10 | 5 | 0 | 5 | 0 |
| 8.12 | 5 | 5 | 0 | 5 | 0 |
| 8.16 | 10 | 5 | 0 | 4 | 0 |
| 8.16 | 5 | 4 | 0 | 3 | 0 |
| 8.17 | 10 | 5 | 0 | 5 | 0 |
| 8.17 | 5 | 5 | 0 | 4 | 0 |
| 8.18 | 10 | 5 | 0 | 5 | 0 |
| 8.18 | 5 | 5 | 0 | 4 | 0 |
| 8.19 | 10 | 5 | 0 | 5 | 0 |
| 8.19 | 5 | 5 | 0 | 4 | 0 |
| 8.20 | 10 | 5 | 0 | 4 | 0 |
| 8.20 | 5 | 4 | 0 | 3 | 0 |
| 8.21 | 10 | 5 | 0 | 5 | 0 |
| 8.21 | 5 | 5 | 0 | 4 | 0 |
| 8.22 | 10 | 5 | 0 | 4 | 0 |
| 8.22 | 5 | 4 | 0 | 3 | 0 |
| 8.23 | 10 | 5 | 0 | 5 | 0 |
| 8.23 | 5 | 5 | 0 | 5 | 0 |
| 8.24 | 10 | 5 | 0 | 5 | 0 |
| 8.24 | 5 | 5 | 0 | 5 | 0 |
| 8.27 | 10 | 5 | 0 | 5 | 0 |
| 8.27 | 5 | 5 | 0 | 4 | 0 |
| 8.28 | 10 | 5 | 0 | 4 | 0 |
| 8.28 | 5 | 3 | 0 | 3 | 0 |
| 8.29 | 10 | 5 | 0 | 4 | 0 |
| 8.29 | 5 | 4 | 0 | 4 | 0 |
| 8.30 | 10 | 5 | 0 | 4 | 0 |
| 8.30 | 5 | 4 | 0 | 3 | 0 |
| 8.31 | 10 | 5 | 0 | 5 | 0 |
| 8.31 | 5 | 5 | 0 | 5 | 0 |
| 8.32 | 10 | 5 | 0 | 5 | 0 |
| 8.32 | 5 | 5 | 0 | 5 | 0 |
| 8.34 | 10 | 5 | 0 | 5 | 0 |
| 8.34 | 5 | 5 | 0 | 5 | 0 |
| 8.35 | 10 | 5 | 0 | 5 | 0 |
| 8.35 | 5 | 5 | 0 | 5 | 0 |
| 8.57 | 10 | 5 | 0 | 4 | 0 |
| 8.57 | 5 | 4 | 0 | 3 | 0 |
| 9.1 | 10 | 5 | 0 | 5 | 0 |
| 9.1 | 5 | 5 | 0 | 5 | 0 |
| 9.3 | 10 | 5 | 0 | 4 | 0 |
| 9.3 | 5 | 4 | 0 | 3 | 0 |
| 9.4 | 10 | 5 | 0 | 5 | 0 |
| 9.4 | 5 | 5 | 0 | 5 | 0 |
| 9.5 | 10 | 5 | 0 | 3 | 0 |
| 9.5 | 5 | 4 | 0 | 3 | 0 |
| 9.6 | 10 | 5 | 0 | 5 | 0 |
| 9.6 | 5 | 5 | 0 | 5 | 0 |
| 9.7 | 10 | 5 | 0 | 4 | 0 |
| 9.7 | 5 | 4 | 0 | 3 | 0 |
| 9.8 | 10 | 5 | 0 | 5 | 0 |
| 9.8 | 5 | 5 | 0 | 5 | 0 |
| 9.9 | 10 | 5 | 0 | 4 | 0 |
| 9.9 | 5 | 4 | 0 | 3 | 0 |
| 9.11 | 10 | 5 | 0 | 5 | 0 |
| 9.11 | 5 | 5 | 0 | 5 | 0 |
| 9.14 | 10 | 5 | 0 | 5 | 0 |
| 9.14 | 5 | 5 | 0 | 4 | 0 |
| 9.18 | 10 | 5 | 0 | 5 | 0 |
| 9.18 | 5 | 5 | 0 | 5 | 0 |
| 9.22 | 10 | 5 | 0 | 5 | 0 |
| 9.22 | 5 | 5 | 0 | 5 | 0 |
| 9.26 | 10 | 5 | 0 | 5 | 0 |
| 9.26 | 5 | 5 | 0 | 5 | 0 |
| 9.27 | 10 | 5 | 0 | 5 | 0 |
| 9.27 | 5 | 5 | 0 | 5 | 0 |
| 9.34 | 10 | 5 | 0 | 5 | 0 |
| 9.34 | 5 | 5 | 0 | 5 | 0 |
| 9.37 | 10 | 5 | 0 | 5 | 0 |
| 9.37 | 5 | 5 | 0 | 4 | 0 |
| 9.41 | 10 | 5 | 0 | 4 | 0 |
| 9.41 | 5 | 4 | 0 | 4 | 0 |
| 9.43 | 10 | 5 | 0 | 4 | 0 |
| 9.43 | 5 | 3 | 0 | 3 | 0 |
| 9.44 | 10 | 5 | 0 | 4 | 0 |
| 9.44 | 5 | 4 | 0 | 3 | 0 |
| 9.45 | 10 | 4 | 0 | 3 | 0 |
| 9.45 | 5 | 3 | 0 | 3 | 0 |
| 9.46 | 10 | 4 | 0 | 3 | 0 |
| 9.46 | 5 | 3 | 0 | 3 | 0 |
| 9.48 | 10 | 5 | 0 | 4 | 0 |
| 9.48 | 5 | 5 | 0 | 3 | 0 |
| 9.49 | 10 | 5 | 0 | 5 | 0 |
| 9.49 | 5 | 5 | 0 | 5 | 0 |
| 9.53 | 10 | 5 | 0 | 5 | 0 |
| 9.53 | 5 | 5 | 0 | 4 | 0 |
| 9.55 | 10 | 5 | 0 | 4 | 0 |
| 9.55 | 5 | 4 | 0 | 3 | 0 |
| 9.56 | 10 | 5 | 0 | 5 | 0 |
| 9.56 | 5 | 5 | 0 | 5 | 0 |
| 9.58 | 10 | 5 | 0 | 5 | 0 |
| 9.58 | 5 | 5 | 0 | 4 | 0 |
| 9.76 | 10 | 5 | 0 | 4 | 0 |
| 9.76 | 5 | 4 | 0 | 3 | 0 |
| 9.77 | 10 | 5 | 0 | 5 | 0 |
| 9.77 | 5 | 5 | 0 | 5 | 0 |
| 9.80 | 10 | 5 | 0 | 4 | 0 |
| 9.80 | 5 | 4 | 0 | 3 | 0 |
| 9.81 | 10 | 5 | 0 | 4 | 0 |
| 9.81 | 5 | 5 | 0 | 4 | 0 |
| 9.83 | 10 | 5 | 0 | 5 | 0 |
| 9.83 | 5 | 4 | 0 | 4 | 0 |
| 9.84 | 10 | 5 | 0 | 5 | 0 |
| 9.84 | 5 | 5 | 0 | 5 | 0 |
| 9.85 | 10 | 5 | 0 | 5 | 0 |
| 9.85 | 5 | 5 | 0 | 5 | 0 |
| 9.88 | 10 | 5 | 0 | 5 | 0 |
| 9.88 | 5 | 5 | 0 | 5 | 0 |
| 9.109 | 10 | 5 | 0 | 5 | 0 |
| 9.109 | 5 | 5 | 0 | 4 | 0 |
| 9.111 | 10 | 5 | 0 | 4 | 0 |
| 9.111 | 5 | 4 | 0 | 4 | 0 |
| 9.117 | 10 | 5 | 0 | 4 | 0 |
| 9.117 | 5 | 4 | 0 | 3 | 0 |
| 9.118 | 10 | 5 | 0 | 5 | 0 |
| 9.118 | 5 | 5 | 0 | 3 | 0 |
| 9.122 | 10 | 5 | 0 | 4 | 0 |
| 9.122 | 5 | 4 | 0 | 4 | 0 |
| 9.123 | 10 | 5 | 0 | 5 | 0 |
| 9.123 | 5 | 5 | 0 | 4 | 0 |
| 9.125 | 10 | 5 | 0 | 4 | 0 |
| 9.125 | 5 | 4 | 0 | 4 | 0 |
| 9.126 | 10 | 5 | 0 | 5 | 0 |
| 9.126 | 5 | 5 | 0 | 5 | 0 |
| 9.127 | 10 | 5 | 0 | 5 | 0 |
| 9.127 | 5 | 5 | 0 | 3 | 0 |
| 10.1 | 10 | 5 | 0 | 5 | 0 |
| 10.1 | 5 | 5 | 0 | 5 | 0 |

TABLE 14-continued

| Cpd. No. | Dose (g/a) | EO | OS | EO | OS |
|---|---|---|---|---|---|
| 10.2 | 10 | 5 | 0 | 4 | 0 |
| 10.2 | 5 | 4 | 0 | 4 | 0 |
| 10.3 | 10 | 5 | 0 | 4 | 0 |
| 10.3 | 5 | 4 | 0 | 3 | 0 |
| 10.4 | 10 | 5 | 0 | 5 | 0 |
| 10.4 | 5 | 5 | 0 | 5 | 0 |
| 10.6 | 10 | 5 | 0 | 5 | 0 |
| 10.6 | 5 | 5 | 0 | 5 | 0 |
| 10.13 | 10 | 5 | 0 | 4 | 0 |
| 10.13 | 5 | 4 | 0 | 3 | 0 |
| 10.14 | 10 | 5 | 0 | 5 | 0 |
| 10.14 | 5 | 5 | 0 | 4 | 0 |
| 10.15 | 10 | 5 | 0 | 4 | 0 |
| 10.15 | 5 | 3 | 0 | 3 | 0 |
| 10.16 | 10 | 5 | 0 | 4 | 0 |
| 10.16 | 5 | 4 | 0 | 3 | 0 |
| 10.17 | 10 | 5 | 0 | 4 | 0 |
| 10.17 | 5 | 4 | 0 | 3 | 0 |
| 10.18 | 10 | 5 | 0 | 5 | 0 |
| 10.18 | 5 | 5 | 0 | 4 | 0 |
| 10.19 | 10 | 5 | 0 | 4 | 0 |
| 10.19 | 5 | 4 | 0 | 4 | 0 |
| 10.20 | 10 | 5 | 0 | 4 | 0 |
| 10.20 | 5 | 4 | 0 | 4 | 0 |
| 10.21 | 10 | 5 | 0 | 4 | 0 |
| 10.21 | 5 | 4 | 0 | 4 | 0 |
| 10.22 | 10 | 5 | 0 | 4 | 0 |
| 10.22 | 5 | 4 | 0 | 4 | 0 |
| 10.23 | 10 | 5 | 0 | 5 | 0 |
| 10.23 | 5 | 5 | 0 | 5 | 0 |
| 10.25 | 10 | 5 | 0 | 5 | 0 |
| 10.25 | 5 | 5 | 0 | 5 | 0 |
| 10.41 | 10 | 5 | 0 | 5 | 0 |
| 10.41 | 5 | 5 | 0 | 5 | 0 |
| 10.42 | 10 | 5 | 0 | 4 | 0 |
| 10.42 | 5 | 3 | 0 | 3 | 0 |
| 10.45 | 10 | 5 | 0 | 5 | 0 |
| 10.45 | 5 | 5 | 0 | 4 | 0 |
| 10.46 | 10 | 5 | 0 | 5 | 0 |
| 10.46 | 5 | 5 | 0 | 5 | 0 |
| 10.47 | 10 | 5 | 0 | 5 | 0 |
| 10.47 | 5 | 5 | 0 | 4 | 0 |
| 10.48 | 10 | 5 | 0 | 4 | 0 |
| 10.48 | 5 | 5 | 0 | 4 | 0 |
| 10.50 | 10 | 5 | 0 | 5 | 0 |
| 10.50 | 5 | 5 | 0 | 5 | 0 |
| 10.53 | 10 | 5 | 0 | 5 | 0 |
| 10.53 | 5 | 5 | 0 | 5 | 0 |
| 10.54 | 10 | 5 | 0 | 5 | 0 |
| 10.54 | 5 | 5 | 0 | 5 | 0 |
| 10.55 | 10 | 5 | 0 | 4 | 0 |
| 10.55 | 5 | 4 | 0 | 4 | 0 |
| 10.56 | 10 | 5 | 0 | 5 | 0 |
| 10.56 | 5 | 5 | 0 | 5 | 0 |
| 10.57 | 10 | 5 | 0 | 5 | 0 |
| 10.57 | 5 | 5 | 0 | 4 | 0 |
| 10.58 | 10 | 5 | 0 | 5 | 0 |
| 10.58 | 5 | 5 | 0 | 4 | 0 |
| 10.59 | 10 | 5 | 0 | 5 | 0 |
| 10.59 | 5 | 5 | 0 | 4 | 0 |
| 10.62 | 10 | 5 | 0 | 4 | 0 |
| 10.62 | 5 | 5 | 0 | 4 | 0 |
| 10.63 | 10 | 5 | 0 | 4 | 0 |
| 10.63 | 5 | 4 | 0 | 3 | 0 |
| 10.64 | 10 | 5 | 0 | 4 | 0 |
| 10.64 | 5 | 4 | 0 | 4 | 0 |
| 10.65 | 10 | 5 | 0 | 4 | 0 |
| 10.65 | 5 | 4 | 0 | 3 | 0 |
| 10.66 | 10 | 5 | 0 | 5 | 0 |
| 10.66 | 5 | 5 | 0 | 4 | 0 |
| 10.67 | 10 | 5 | 0 | 5 | 0 |
| 10.67 | 5 | 5 | 0 | 4 | 0 |
| 10.68 | 10 | 5 | 0 | 5 | 0 |
| 10.68 | 5 | 5 | 0 | 4 | 0 |
| 10.69 | 10 | 5 | 0 | 4 | 0 |
| 10.69 | 5 | 4 | 0 | 3 | 0 |
| 10.70 | 10 | 5 | 0 | 4 | 0 |
| 10.70 | 5 | 5 | 0 | 4 | 0 |
| 10.72 | 10 | 5 | 0 | 4 | 0 |
| 10.72 | 5 | 4 | 0 | 3 | 0 |
| 10.73 | 10 | 5 | 0 | 4 | 0 |
| 10.73 | 5 | 5 | 0 | 3 | 0 |
| 10.74 | 10 | 5 | 0 | 4 | 0 |
| 10.74 | 5 | 5 | 0 | 4 | 0 |
| 10.75 | 10 | 5 | 0 | 5 | 0 |
| 10.75 | 5 | 5 | 0 | 4 | 0 |
| 10.76 | 10 | 5 | 0 | 5 | 0 |
| 10.76 | 5 | 5 | 0 | 5 | 0 |
| 10.77 | 10 | 5 | 0 | 5 | 0 |
| 10.77 | 5 | 5 | 0 | 5 | 0 |
| 10.79 | 10 | 5 | 0 | 4 | 0 |
| 10.79 | 5 | 4 | 0 | 3 | 0 |
| 10.80 | 10 | 5 | 0 | 5 | 0 |
| 10.80 | 5 | 5 | 0 | 4 | 0 |
| 10.83 | 10 | 5 | 0 | 5 | 0 |
| 10.83 | 5 | 5 | 0 | 5 | 0 |
| 10.84 | 10 | 5 | 0 | 5 | 0 |
| 10.84 | 5 | 5 | 0 | 5 | 0 |
| 10.85 | 10 | 5 | 0 | 5 | 0 |
| 10.85 | 5 | 5 | 0 | 5 | 0 |
| 10.86 | 10 | 5 | 0 | 4 | 0 |
| 10.86 | 5 | 4 | 0 | 4 | 0 |
| 10.87 | 10 | 5 | 0 | 5 | 0 |
| 10.87 | 5 | 5 | 0 | 5 | 0 |
| 10.89 | 10 | 5 | 0 | 5 | 0 |
| 10.89 | 5 | 5 | 0 | 5 | 0 |
| 10.90 | 10 | 5 | 0 | 5 | 0 |
| 10.90 | 5 | 5 | 0 | 5 | 0 |
| 10.92 | 10 | 5 | 0 | 5 | 0 |
| 10.92 | 5 | 5 | 0 | 5 | 0 |
| 10.116 | 10 | 5 | 0 | 4 | 0 |
| 10.116 | 5 | 4 | 0 | 4 | 0 |
| 10.117 | 10 | 5 | 0 | 5 | 0 |
| 10.117 | 5 | 5 | 0 | 4 | 0 |
| 10.118 | 10 | 5 | 0 | 5 | 0 |
| 10.118 | 5 | 5 | 0 | 4 | 0 |
| 10.119 | 10 | 5 | 0 | 5 | 0 |
| 10.119 | 5 | 5 | 0 | 4 | 0 |
| 10.120 | 10 | 5 | 0 | 4 | 0 |
| 10.120 | 5 | 5 | 0 | 4 | 0 |
| 10.140 | 10 | 5 | 0 | 4 | 0 |
| 10.140 | 5 | 4 | 0 | 3 | 0 |
| 10.141 | 10 | 5 | 0 | 5 | 0 |
| 10.141 | 5 | 5 | 0 | 4 | 0 |
| 10.158 | 10 | 5 | 0 | 5 | 0 |
| 10.158 | 5 | 5 | 0 | 5 | 0 |
| 10.161 | 10 | 5 | 0 | 4 | 0 |
| 10.161 | 5 | 4 | 0 | 3 | 0 |
| 11.1 | 10 | 5 | 0 | 5 | 0 |
| 11.1 | 5 | 5 | 0 | 5 | 0 |
| 11.2 | 10 | 5 | 0 | 4 | 0 |
| 11.2 | 5 | 4 | 0 | 3 | 0 |
| 11.4 | 10 | 5 | 0 | 5 | 0 |
| 11.4 | 5 | 5 | 0 | 5 | 0 |
| 11.8 | 10 | 5 | 0 | 5 | 0 |
| 11.8 | 5 | 5 | 0 | 5 | 0 |
| 11.9 | 10 | 5 | 0 | 4 | 0 |
| 11.9 | 5 | 4 | 0 | 3 | 0 |
| 11.10 | 10 | 5 | 0 | 5 | 0 |
| 11.10 | 5 | 5 | 0 | 4 | 0 |
| 11.12 | 10 | 5 | 0 | 5 | 0 |
| 11.12 | 5 | 5 | 0 | 4 | 0 |
| 11.13 | 10 | 5 | 0 | 4 | 0 |
| 11.13 | 5 | 4 | 0 | 3 | 0 |
| 11.14 | 10 | 5 | 0 | 5 | 0 |
| 11.14 | 5 | 5 | 0 | 4 | 0 |
| 11.15 | 10 | 5 | 0 | 4 | 0 |
| 11.15 | 5 | 4 | 0 | 4 | 0 |
| 11.16 | 10 | 5 | 0 | 5 | 0 |
| 11.16 | 5 | 5 | 0 | 5 | 0 |
| 11.17 | 10 | 5 | 0 | 4 | 0 |
| 11.17 | 5 | 3 | 0 | 3 | 0 |
| 11.18 | 10 | 5 | 0 | 4 | 0 |
| 11.18 | 5 | 4 | 0 | 4 | 0 |
| 11.19 | 10 | 5 | 0 | 5 | 0 |
| 11.19 | 5 | 5 | 0 | 5 | 0 |
| 11.20 | 10 | 5 | 0 | 4 | 0 |
| 11.20 | 5 | 5 | 0 | 3 | 0 |
| 11.21 | 10 | 5 | 0 | 5 | 0 |
| 11.21 | 5 | 5 | 0 | 4 | 0 |
| 11.22 | 10 | 5 | 0 | 4 | 0 |
| 11.22 | 5 | 4 | 0 | 4 | 0 |

TABLE 14-continued

| Cpd. No. | Dose (g/a) | EO | OS | EO | OS |
|---|---|---|---|---|---|
| 11.23 | 10 | 5 | 0 | 5 | 0 |
| 11.23 | 5 | 5 | 0 | 5 | 0 |
| 11.24 | 10 | 5 | 0 | 4 | 0 |
| 11.24 | 5 | 4 | 0 | 4 | 0 |
| 11.25 | 10 | 5 | 0 | 5 | 0 |
| 11.25 | 5 | 5 | 0 | 5 | 0 |
| 11.26 | 10 | 5 | 0 | 4 | 0 |
| 11.26 | 5 | 3 | 0 | 3 | 0 |
| 11.27 | 10 | 5 | 0 | 5 | 0 |
| 11.27 | 5 | 5 | 0 | 4 | 0 |
| 11.29 | 10 | 5 | 0 | 4 | 0 |
| 11.29 | 5 | 4 | 0 | 3 | 0 |
| 11.31 | 10 | 5 | 0 | 5 | 0 |
| 11.31 | 5 | 5 | 0 | 4 | 0 |
| 11.34 | 10 | 5 | 0 | 5 | 0 |
| 11.34 | 5 | 5 | 0 | 5 | 0 |
| 11.35 | 10 | 5 | 0 | 5 | 0 |
| 11.35 | 5 | 5 | 0 | 5 | 0 |
| 11.57 | 10 | 5 | 0 | 4 | 0 |
| 11.57 | 5 | 4 | 0 | 3 | 0 |
| 11.58 | 10 | 5 | 0 | 4 | 0 |
| 11.58 | 5 | 4 | 0 | 3 | 0 |
| 12.2 | 10 | 5 | 0 | 5 | 0 |
| 12.2 | 5 | 5 | 0 | 5 | 0 |
| Cpd. A | 10 | 3 | 0 | 0 | 0 |
| Cpd. A | 5 | 2 | 0 | 0 | 0 |
| Cpd. B | 10 | 4 | 0 | 0 | 0 |
| Cpd. B | 5 | 3 | 0 | 0 | 0 |

We claim:

1. A compound of formula (I):

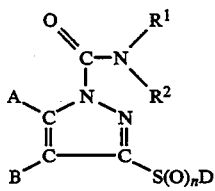

which:

$R^1$ and $R^2$ are independently selected from the group consisting of unsubstituted alkyl groups which have from 1 to 6 carbon atoms;

A is a hydrogen atom,

B is a halogen atom, n is 2, and

D is a group of formula (II) as follows

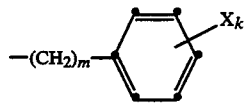

wherein m is 0;

k is 0, 1, 2 or 3, and, where k is 2 or 3, the groups and atoms represented by X may be the same or different; and X is selected from the group consisting of halogen atoms, unsubstituted alkyl groups which have from 1 to 6 carbon atoms, substituted alkyl groups which have from 1 to 6 carbon atoms and which are substituted by at least one substituent selected from the group consisting of substituents (a), defined below, alkoxy groups which have from 1 to 6 carbon atoms, substituted alkoxy groups which have from 1 to 6 carbon atoms and which are substituted by at least one substituent selected from the group consisting of halogen atoms, alkylthio groups which have from 1 to 6 carbon atoms, substituted alklthio groups which have from 1 to 6 carbon atoms and which are substituted by at least one substituent selected from the group consisting of halogen atoms, alkylsulfonyl groups which have from 1 to 6 carbon atoms, substituted alkylsulfonyl groups which have from 1 to 6 carbon atoms and which are substituted by at least one substituent selected from the group consisting of halogen atoms, aryloxy groups in which the aryl part is a carbocyclic aryl group which has from 6 to 14 ring carbon atoms and is unsubstituted or is substituted by at least one substituent selected from the group consisting of substituents (b), defined below, aralkyl groups in which the alkyl part has from 1 to 4 carbon atoms and the aryl part is a carbocyclic aryl group which has from 6 to 14 ring carbon atoms and which is unsubstituted or are substituted by at least one substituent selected from the group consisting of substituents (b), defined below, carboxy groups, nitro groups, and cyano groups;

substituents (a) are selected from the group consisting of halogen atoms and alkoxy groups having from 1 to 6 carbon atoms; and substituents (b) are selected from the group consisting of halogen atoms, alkyl group having from 1 to 6 carbon atoms and alkoxy groups having from 1 to 6 carbon atoms or a salt thereof.

2. The compound of claim 1, wherein each of $R^1$ and $R^2$ is independently selected from the group consisting of an alkyl group having from 1 to 4 carbon atoms.

3. The compound of claim 1, wherein X is a halogen atom;

an alkyl group which has from 1 to 6 carbon atoms and which is unsubstituted or is substituted by at least one substituent selected from the group consisting of substituents (a), defined below;

an alkoxy group which has from 1 to 6 carbon atoms;

an alkoxycarbonyl group having from 2 to 5 carbon atoms; or a cyano group; and substituents (a) are selected from the group consisting of halogen atoms and alkoxy groups having from 1 to 6 carbon atoms.

4. The compound of claim 1, wherein X is a halogen atom;

an alkyl group which has from 1 to 6 carbon atoms and which is unsubstituted or is substituted by from 1 to 3 substituents selected from the group consisting of substituents (a), defined below;

an alkoxy group which has from 1 to 6 carbon atoms; or a cyano group; and substituents (a) are selected from the group consisting of halogen atoms and alkoxy groups having from 1 to 6 carbon atoms.

5. The compound of claim 1, wherein X is a halogen atom;

an alkyl group which has from 1 to 6 carbon atoms and which is unsubstituted or is substituted by from 1 to 3 substituents selected from the group consisting of substituents (a), defined below; or an alkoxy group which has from 1 to 6 carbon atoms; and substituents (a) are selected from the group consisting of halogen atoms and alkoxy groups having from 1 to 6 carbon atoms.

6. The compound of claim 1, wherein:
X represents
a halogen atom,
an unsubstituted alkyl group having from 1 to 6 carbon atoms,
a substituted alkyl group which has from 1 to 6 carbon atoms and which is substituted by from 1 to 3 halogen substituents, or
an alkoxy group having from 1 to 6 carbon atoms;
m is 0;
or a salt thereof.

7. The compound of claim 1, which is 1-(diethylcarbamoyl)-3-(2,6-dimethylphenylsulfonyl)-4-fluoropyrazole.

8. The compound of claim 1, which is 1-(dimethylcarbamoyl)-3-(2,6-dimethylphenylsulfonyl)-4-fluoropyrazole.

9. The compound of claim 1, which is 4-chloro-3-(2-chloro-6-methylphenylsulfonyl)-1-(diethylcarbamoyl)-pyrazole.

10. The compound of claim 1, which is 1-(diethylcarbamoyl)-3-(2,4,6-trimethylphenylsulfonyl)-4-fluoropyrazole.

11. A herbicidal composition comprising an effective amount of a herbicidal agent in admixture with an agriculturally or horticulturally acceptable carrier or diluent, wherein the herbicidal agent is at least one compound selected from the group consisting of compounds of formula (I) and salts thereof, as claimed in claim 1.

12. The composition of claim 11, wherein the herbicidal agent is a compound of formula (I) in which:
X represents
a halogen atom,
an unsubstituted alkyl group having from 1 to 6 carbon atoms,
a substituted alkyl group which has from 1 to 6 carbon atoms and which is substituted by from 1 to 3 substituents selected from the group consisting of substituents (a), defined below,
an alkoxy group having from 1 to 6 carbon atoms,
an alkoxycarbonyl group having from 2 to 7 carbon atoms, or
a cyano group; and
substituents (a) are selected from the group consisting of halogen atoms and alkoxy groups having from 1 to 6 carbon atoms
or a salt thereof.

13. The composition of claim 11, wherein the herbicidal
X represents
a halogen atom,
an unsubstituted alkyl group having from 1 to 6 carbon atoms,
a substituted alkyl group which has from 1 to 6 carbon atoms and which is substituted by from 1 to 3 halogen substituents, or
an alkoxy group having from 1 to 6 carbon atoms;
or a salt thereof.

14. The composition of claim 11, in which said herbicidal agent is selected from the group consisting of:
1-(diethylcarbamoyl)-3-(2,6-dimethylphenylsulfonyl)-4-fluoropyrazole;
1-(dimethylcarbamoyl)-3-(2,6-dimethylphenylsulfonyl)-4-fluoropyrazole;
4-chloro-3-(2-chloro-6-methylphenylsulfonyl)-1-(diethylcarbamoyl)pyrazole; and
1-(diethylcarbamoyl)-3-(2,4,6-trimethylphenylsulfonyl)-4-fluoropyrazole.

15. A method of destroying weeds by administering a herbicidal agent to a locus including said weeds, wherein the herbicidal agent is at least one compound selected from the group consisting of compounds of formula (I) and salts thereof, as claimed in claim 1.

16. The method of claim 15, wherein the herbicidal agent is a compound of formula (I) in which:
X represents
a halogen atom,
an unsubstituted alkyl group having from 1 to 6 carbon atoms,
a substituted alkyl group which has from 1 to 6 carbon atoms and which is substituted by from 1 to 3 substituents selected from the group consisting of substituents (a), defined below, an alkoxy group having from 1 to 6 carbon atoms, an alkoxycarbonyl group having from 2 to 7 carbon atoms, or
a cyano group.

17. The method of claim 15, wherein the herbicidal agent is a compound of formula (I) in which:
X represents
a halogen atom,
an unsubstituted alkyl group having from 1 to 6 carbon atoms,
a substituted alkyl group which has from 1 to 6 carbon atoms and which is substituted by from 1 to 3 halogen substituents, or
an alkoxy group having from 1 to 6 carbon atoms.

18. The method of claim 15, in which said herbicidal agent is selected from the group consisting of:
1-(diethylcarbamoyl)-3-(2,6-dimethylphenylsulfonyl)-4-fluoropyrazole;
1-(dimethylcarbamoyl)-3-(2,6-dimethylphenylsulfonyl)-4-fluoropyrazole;
4-chloro-3-(2-chloro-6-methylphenylsulfonyl)-1-(diethylcarbamoyl)pyrazole; and
1-(diethylcarbamoyl)-3-(2,4,6-trimethylphenylsulfonyl)-4-fluoropyrazole.

19. The compound of claim 1 wherein $R^1$ and $R^2$ are ethyl and B is fluorine.

20. The compound of claim 19 wherein X is alkyl with 1–6 carbon atoms.

21. The compound of claim 20 wherein X is methyl or ethyl.

22. The compound of claim 19 wherein k is 0.

23. The compound of claim 20 wherein k is 1.

24. The compound of claim 20 wherein k is 2.

25. The compound of claim 20 wherein k is 3.

26. The compound of claim 20 wherein X is methyl and k is 2.

27. The compound of claim 20 wherein k is 2 or 3 and at least one X is methyl and one X is ethyl.

28. The compound of claim 1 which is 1(N-diethylcarbamoyl)-3-(2,4,6-trimethylphenylsulfonyl)-4-fluoropyrazole.

29. The compound of claim 1 which is 1(N-ethyl-N-methylcarbamoyl)-3-(2,4,6-trimethylphenylsulfonyl)-4-fluoropyrazole.

30. The compound of claim 1 which is 1-(diethylcarbamoyl)-3-(2-ethyl-6-methylphenylsulfonyl)-4-fluoropyrazole.

31. The compound of claim 1 which is 1-(diethylcarbamoyl)-3-(2,6-diethylphenylsulfonyl)-4-fluoropyrazole.

* * * * *